United States Patent
Shirley et al.

(10) Patent No.: US 8,329,991 B2
(45) Date of Patent: Dec. 11, 2012

(54) TRANSGENIC PLANT WITH INCREASED STRESS TOLERANCE AND YIELD

(75) Inventors: Amber Shirley, Durham, NC (US); Damian Allen, West Lafayette, IN (US); Bryan D. McKersie, Raleigh, NC (US)

(73) Assignee: BASF Plant Science GmbH (DE)

( * ) Notice: Subject to any disclaimer, the term of this patent is extended or adjusted under 35 U.S.C. 154(b) by 160 days.

(21) Appl. No.: 12/531,310

(22) PCT Filed: Mar. 20, 2008

(86) PCT No.: PCT/EP2008/053382
§ 371 (c)(1),
(2), (4) Date: Sep. 15, 2009

(87) PCT Pub. No.: WO2008/116829
PCT Pub. Date: Oct. 2, 2008

(65) Prior Publication Data
US 2010/0257637 A1 Oct. 7, 2010

Related U.S. Application Data

(60) Provisional application No. 60/896,505, filed on Mar. 23, 2007.

(51) Int. Cl.
*C12N 15/29* (2006.01)
*C12N 15/82* (2006.01)
*A01H 5/00* (2006.01)
*C07K 14/415* (2006.01)

(52) U.S. Cl. ........ 800/289; 800/278; 800/290; 800/298; 435/419; 435/468; 530/370; 536/23.6

(58) Field of Classification Search .......... None
See application file for complete search history.

(56) References Cited

U.S. PATENT DOCUMENTS

| | | | | |
|---|---|---|---|---|
| 6,465,718 | B1 * | 10/2002 | Inze et al. | 800/290 |
| 6,670,528 | B1 * | 12/2003 | Shinozaki et al. | 800/298 |
| 2004/0031072 | A1 | 2/2004 | La Rosa | |
| 2004/0216190 | A1 | 10/2004 | Kovalic | |

FOREIGN PATENT DOCUMENTS

| | | | |
|---|---|---|---|
| WO | WO 03/081988 | * | 10/2003 |
| WO | WO 2005/060664 | * | 7/2005 |
| WO | WO 2005/105836 | * | 11/2005 |

OTHER PUBLICATIONS

Oliver, M.J. et al. GenBank Accession No. CN205440, Tor5847 Gametophyte rehydration Library Syntrichia ruralis cDNA, mRNA sequence. Apr. 30, 2004.*
Database EMBL Seq. 409 from Patent WO0216655 27 XP002487162, Accession AX505714, Sep. 27, 2002.
Database UniProt tRNA 2' phosphotransferase-like. 0. sativa, Dec. 7, 2004, Sasaki et al, XP002487163 retrieved from EBI Database accession No. Q5VNV8 abstract.
Database EMBL Physcomitrella patens phosphotransferase, Aug. 29, 2002, Quatrano et al., XP002487164, retrieved from EBI Database accession No. BU052518 abstract.

* cited by examiner

*Primary Examiner* — Cynthia Collins
(74) *Attorney, Agent, or Firm* — Patricia A. McDaniels

(57) ABSTRACT

Polynucleotides are disclosed which are capable of enhancing growth, yield under water-limited conditions, and/or increased tolerance to an environmental stress of a plant transformed to contain such polynucleotides. Also provided are methods of using such polynucleotides and transgenic plants and agricultural products, including seeds, containing such polynucleotides as transgenes.

5 Claims, 4 Drawing Sheets

FIGURE 2A

```
BN50000854   (1)   ---------------------------------------------METDESG----VSLASGPDGRKRRVSYFYEPTI
BN51361834   (1)   ----------------------------------------------------------------MRSKDKISYFYDGDV
EST468       (1)   ----------------------------------------------------------------MPVKDRISYFYDGDV
GM49753757   (1)   ----------------------------------------------------------------MRSKDRIAYFYDGDV
GM50270592   (1)   MHLLKFPRSPSSFGNAFFLVGHHVLDIRVFRKNQRCFRASISCSAVRNGSIEQLSDARLIYSVAP
GM59700314   (1)   ---------------------------------------------------------MLKHDTGNGVFDTGMDP
LU61552369   (1)   ----------------------------------------------------------------MKSKDKISYFYDGDV
os34631911   (1)   ------------------------------------------MDASAGGGGNSLPTAGADGAKRRVCYFYDAEV
ta60089198   (1)   ------------------------------------------MDISAGGGGNSLPTTGADGSKRRVCYFYDAEV
zm59324542   (1)   --------------------------------------------------------MLAHDAGRGVFDSGRDP

BN50000854  (30)   GNYYYGQGHPMKPHRIRMAHSLIVHYNLHRRL------EISRPYLADAADIGRFHSPEYVDFLRS
BN51361834  (16)   GSVYFGPNHPMKPHRLCMTHHLILAYGLHSKM------EVYRPHKAYPIEMAQFHSPDYVEFLQR
EST468      (16)   GSVYFGPNHPMKPHRLCMTNSLVLAYGLHNKM------EIYRPHKAYPVELAQFHSVDYVEFLGR
GM49753757  (16)   GSVYFGAKHPMKPHRLCMTHHLVLSYDLHKKM------EIYRPHKAYPVELAQFHSADYVEFLNR
GM50270592  (66)   SMGHNQESHPESHFRVPAIVNALEEMQLTSKFRGPEVIELQHFEPASVDDIASVHARAYVSGIEK
GM59700314  (18)   GFLEVLEKHPENSDRVKNLVSILKRGPISPYI------SWHLGTPAKIPELFSFHTPEYINELVE
LU61552369  (16)   GSVYFGPNHPMKPHRLCMTHHLVLSYDLHKKM------EIYRPHKAYPVELAQFHSADYVEFLHR
os34631911  (33)   GNYYYGQGHPMKPHRIRMTHALLAHYGLLDQM------QVLKPHPARDRDLCRFHADDYVAFLRS
ta60089198  (33)   GNYYYGQGHPMKPHRIRMTHALLAHYGLLDEM------QVLKPHPARDRDLCRFHADDYVSFLRS
zm59324542  (18)   GFLDVLDQHPENADRVRNMVSILRRGPIAHFL------SWHSGRPAHASELLSFHSSEYIEELVQ

BN50000854  (89)   VSPESVGDSSARNLRRFNVGEDCPVFDGLFEFCRASAGGSIGAAVKLNR-----QDADIAINWGG
BN51361834  (75)   INPENKDL-FPNEMARYNLGEDCPVFEDMFEFCQIYAGATIDAARRLNN-----KLCDIAINWAG
EST468      (75)   ITPESQEK-YAAELIRYNMGEDCPVFDNLFEFCQIYAGGTIDAAHRLNH-----GLCDIAINWAG
GM49753757  (75)   ITPDTQHL-FINELTKYNLGEDCPVFDNLFEFCQIYAGGTIDAARRLNN-----QLCDIAINWAG
GM50270592 (131)   ------SGPTYATATTFQESIVAAGAGLALVDSVVACSKIKGDAPTGFALIR
GM59700314  (77)   VMDQAVEKGLIFLDG-----SGPTYATATTFQESIVAAGAGLALVDSVVACSKIKGDAPTGFALIR
LU61552369  (75)   ITPDTQHL-YRTDLARYNLGEDCPVFENLFEFCQIYAGGTIDAARRLNN-----QLCDIAINWAG
os34631911  (92)   VTPETQQD-QIRALKRFNVGEDCPVFDGLYSFCQTYAGGSVGGAVKLN-----HGHDIAINWAG
ta60089198  (92)   VTPETQQD-QIRALKRFNVGEDCPVFDGLYSFCQTYAGGSVGGAVKLN-----HGHDIAINWAG
zm59324542  (77)   TNATGAKK------K-LCEGTFLNPGSWGAALLAAGTTLSSAKHILD-----GQGNLAYALVR
```

Figure 2B

```
BN50000854   (149)  G-LHHAKKSEASGFCYVNDIVLGILELLKM---FRRVLYIDIDVHHGDGVEEAFYTTDRVMTVSFH
BN51361834   (134)  G-LHHAKKCDASGFCYINDLVLGILELLKH---HPRVLYIDIDVHHGDGVEEAFYTTDRVMTVSFH
EST468       (134)  G-LHHAKKCEASGFCYVNDLVLGILELLKY--HARVLYIDIDIHHGDGVEEAFYLTDRVMTVSFH
GM49753757   (134)  G-LHHAKKCEASGFCYINDLVLGILELLKY--HARVLYIDIDVHHGDGVEEAFYTTDRVMTVSFH
GM50270592   (192)  PPGHHAVPQGPMGFCIFGNVATAARYSQRVHGLKRVFIIDFDVHHGNGTNDAFYDDPDVFFLSFH
GM59700314   (127)  PPGHHAQPSLADGYCFLNNAGLAVQLALDSG--CKKVAVIDIDVHYGNGTAEGFYRSNKVLTISLH
GM59700314   (134)  G-LHHAKKCEASGFCYINDLVLGILELLKY--HARVLYIDIDVHHGDGVEEAFYTTDRVMTVSFH
LU61552369   (150)  G-LHHAKKCEASGFCYVNDIVLAILELLKY--HQRVLYVDIDIHHGDGVEEAFYTTDRVMTVSFH
os34631911   (150)  G-LHHAKKCEASGFCYVNDIVLAILELLKY--HQRVLYVDIDIHHGDGVEEAFYTTDRVMTVSFH
ta60089198   (128)  PPGHHAQPDHADGYCFLNNAGLAVQLALDSG--RAKVAVVDIDVHYGNGTAEGFYRTDTVLTMSLH
zm59324542

BN50000854   (211)  KFGD----FFPGTGHIRDVGAEKGKYYALNVPLNDGMDDESFRSLFRPLIQKVMEVYRPEAVVLQ
BN51361834   (196)  KFGDK---FFPGTGDVKEIGEREGKFYAINVPLRDGIDDSSFNRLFRAIISKVVEIYQPGAIVLQ
EST468       (196)  KFGDY---FFPGTGDVKDVGEREGKYYAINVPLKDGIDDANFIRMFRVVIQKVVEVYQPGAIVLQ
GM49753757   (196)  KYGDS---FFPGTGDAKEIGEREGKFYAINVPLKDGIDDSSFTRLFKTIISKVVETYQPGAIVLQ
GM50270592   (257)  QDGS----YPGTGKFDEVGSGDGEGTTLNLPLPGGSGDTAIRTVFDEVIVPCAQRFKPDIILVS
GM59700314   (191)  MNHGSWGPSHPQSGSVDELGEGEGKFYAINVPLRDGIDDSSFNRLFKTIISKVVEIYQPGAIVLQ
LU61552369   (196)  KFGDL---FFPGTGDVKEIGEREGKFYAINVPLRDGIDDGIDDESYQSLFKPIMGKVMEVFRPGAVVLQ
os34631911   (212)  KFGD----YFPGTGDIRDIGHSKGKYYSLNVPLDDGIDDGIDDESYQSLFKPIMGKVMEIFRPGAVVLQ
ta60089198   (212)  KFGD----YFPGTGDIRDVGHSKGKGIEGEGKGLGYNLNIPLPNGSGDAGYEYAMNELVVPSIDKFQPLLFLV
zm59324542   (192)  MMHGSWGPSHPQSGSVDEIGEGKGLGYNLNIPLPNGSGDAGYEYAMNELVVPSIDKFQPLLFLV
Consensus    (261)  KFGD    FFPGTGDVKEIGE EGKYYALNVPL DGIDDSSF    LFK II KVVEIFQPGAIVLQ
                                                         326                     390

BN50000854   (272)  CGADSLSGDRLGCFNLSVKGHADCLRFLRSYN-----VPLMVLGGGGYTIRNVARCWCYETAVAV
BN51361834   (258)  CGADSLARDRLGCFNLSIDGHAECVKFVKKFN-----IPLLVTGGGGYTKENVARCWTVETGILL
EST468       (258)  CGADSLAGDRLGCFNLSIDGHSECVKFVKKFN-----IPLLVTGGGGYTKENVARCWTVETGVLV
GM49753757   (258)  CGADSLAGDRLGCFNLSIDGHAECVSFVKRFN-----LPLLVTGGGGYTKENVARCWTVETGVLL
GM50270592   (317)  AGYDGHVLDPLANLQYTTGTYYMLASSIKQLAKDLCGGRCVFFLEGGYNLKSLSYSVADTFRALL
GM59700314   (256)  LGQDSNAFDPNGRQCLTMEGYREIGRIVHLLAKRHSAGRLLIVQEGGYHVTYSAYCLHATLEGIL
LU61552369   (258)  CGADSLAGDRLGCFNLSIDGHAECVKFVKKFN-----IPLLVTGGGYTKENVARCWTVETGVLL
os34631911   (273)  CGADSLSGDRLGCFNLSIRGHAECVRFMRSFN-----VPLLLLGGGGYTIRNVARCWCYETGVAL
ta60089198   (273)  CGADSLSGDRLGCFNLSIKGHAECVRFMRSFN-----VPVLLLGGGGYTIRNVARCWCYETGVAL
zm59324542   (257)  VGQDSSAFDPNGRQCLTMEGYHITYSAYCLHATLEGVL
```

Figure 2C

```
BN50000854 (332) GVEPDNKLPYNEYFEYFGPDYTLHVEPG-PMENLNTPKDMERIRNTLLEQLSGLIHAPSVPFQHT
BN51361834 (318) DTELPNEIPDNDYIKYFGPDYSLKIPGG-HIENLNTKSYISTIKAQILDNLRYIQHAPSVQMQEV
EST468     (318) DTELPNEIPDNDYLKYFKPDCTLKTTSGNHMENLNGKTYLSTIKQQVMENLRRIAHAPSVQMHEV
GM49753757 (318) DTELPNEIPQNDYIKYFAPEFSLKVPNG-PIENLNSKSYLSTIKMQVLENLRCIQHAPSVQMQEV
GM50270592 (382) GDRSLASEFDNPNILYEEPSTKVKQAIQKIKHIHSL----------------------------
GM59700314 (321) NLPMPLLADPIAFT--------------------------------------------------
LU61552369 (318) DTELPNEIPENEYIKYFGPDYTLKIPSR-YIENLNSKSYLSSLKVQVMENLRYIQHAPSVQMQEV
os34631911 (333) GHELTDKMPPNEYFEYFGPDYTLHVAPS-NMENKNTRQQLDDIRSRLLDNLSKLRHAPSVQFQER
ta60089198 (333) GHELTDKMPLNEHYEYFGPDYTLHVAPS-NMENKNTHRHLDEIRSRLLENLTKLRHAPSVQFQER
zm59324542 (322) DLEAPLLDDPIAYYPED-DKYTMKVVDMIKSYWKESVPFLKEI---------------------

BN50000854 (396) PPVNRVLDEPEE---------DLEKR---PKPRIWSGTANYESDSDDDEKP
BN51361834 (382) PPDFYIPDFDEDERNP-----DVRVDQRSRDKQIQRDDEYFDGDKDNDAS-
EST468     (383) PPDTYIPEFDEDELNP-----DERMDQHTQDKHIQREEEYYEDNDNDHDM
GM49753757 (382) PPDFYIPEFDEDEQNP-----DERIDQHTQDKHIQRDDEYDGDNDNDQMN
GM50270592 (418) ---------------------------------------------------
GM59700314 (335) ---------------------------------------------------
LU61552369 (382) PPDFYIPDFDEDEQNP-----DERMDQHTRDKQVQRDDEYYDGDNDNDPTD
os34631911 (397) PPEAELPEQDEDQEDPDERHHADSDVEMDDVKPLDDSGRRSSIQNVRVKRESAETDAA-DQDGNR
ta60089198 (397) PPEAEQPEQDEDQENPDERHHADSDVEMDDAKPLEDSERRTSTQGARVKRESAETEVTTDQDGNG
zm59324542 (364) ---------------------------------------------------

BN50000854 (435) LGGFSGING-PTMDRDSTGEDEMEDDSAEPEVDPPSS------
BN51361834 (427) DDS---------------------------------------
EST468     (429) IS----------------------------------------
GM49753757 (428) ------------------------------------------
GM50270592 (418) ------------------------------------------
GM59700314 (335) ------------------------------------------
LU61552369 (428) RS----------------------------------------
os34631911 (461) VAAENTKGTEPAADGVGSSKQTVPTDASAMAIDEPGSLKVEPDNSNKLQDQPSVHQKT-
ta60089198 (462) VASEQVRGPEPVADGVGSSKQNPPIDASPMAIDGPAVVRAEPERSNKLQEQQALHQKP-
zm59324542 (364) ------------------------------------------
```

TRANSGENIC PLANT WITH INCREASED STRESS TOLERANCE AND YIELD

This application is a national stage application under 35 U.S.C. §371 of PCT/EP2008/053382, filed Mar. 20, 2008, which claims benefit of U.S. provisional application Nos. 60/896,505, filed Mar. 23, 2007. The entire contents of each of the above-identified applications are incorporated herein by reference.

Please add the abstract as set forth in the attached supplemental sheet as a separate page.

FIELD OF THE INVENTION

This invention relates generally to transgenic plants which overexpress nucleic acid sequences encoding polypeptides capable of conferring increased stress tolerance and consequently, increased plant growth and crop yield, under normal or abiotic stress conditions. Additionally, the invention relates to novel isolated nucleic acid sequences encoding polypeptides that confer upon a plant increased tolerance under abiotic stress conditions, and/or increased plant growth and/or increased yield under normal or abiotic stress conditions.

BACKGROUND OF THE INVENTION

Abiotic environmental stresses, such as drought, salinity, heat, and cold, are major limiting factors of plant growth and crop yield. Crop yield is defined herein as the number of bushels of relevant agricultural product (such as grain, forage, or seed) harvested per acre. Crop losses and crop yield losses of major crops such as soybean, rice, maize (corn), cotton, and wheat caused by these stresses represent a significant economic and political factor and contribute to food shortages in many underdeveloped countries.

Water availability is an important aspect of the abiotic stresses and their effects on plant growth. Continuous exposure to drought conditions causes major alterations in the plant metabolism which ultimately lead to cell death and consequently to yield losses. Because high salt content in some soils results in less water being available for cell intake, high salt concentration has an effect on plants similar to the effect of drought on plants. Additionally, under freezing temperatures, plant cells lose water as a result of ice formation within the plant. Accordingly, crop damage from drought, heat, salinity, and cold stress, is predominantly due to dehydration.

Because plants are typically exposed to conditions of reduced water availability during their life cycle, most plants have evolved protective mechanisms against dessication caused by abiotic stresses. However, if the severity and duration of dessication conditions are too great, the effects on development, growth, plant size, and yield of most crop plants are profound. Developing plants efficient in water use is therefore a strategy that has the potential to significantly improve human life on a worldwide scale.

Traditional plant breeding strategies are relatively slow and require abiotic stress-tolerant founder lines for crossing with other germplasm to develop new abiotic stress-resistant lines. Limited germplasm resources for such founder lines and incompatibility in crosses between distantly related plant species represent significant problems encountered in conventional breeding. Breeding for tolerance has been largely unsuccessful.

Many agricultural biotechnology companies have attempted to identify genes that could confer tolerance to abiotic stress responses, in an effort to develop transgenic abiotic stress-tolerant crop plants. Although some genes that are involved in stress responses or water use efficiency in plants have been characterized, the characterization and cloning of plant genes that confer stress tolerance and/or water use efficiency remains largely incomplete and fragmented. To date, success at developing transgenic abiotic stress-tolerant crop plants has been limited, and no such plants have been commercialized.

In order to develop transgenic abiotic stress-tolerant crop plants, it is necessary to assay a number of parameters in model plant systems, greenhouse studies of crop plants, and in field trials. For example, water use efficiency (WUE), is a parameter often correlated with drought tolerance. Studies of a plant's response to desiccation, osmotic shock, and temperature extremes are also employed to determine the plant's tolerance or resistance to abiotic stresses. When testing for the impact of the presence of a transgene on a plant's stress tolerance, the ability to standardize soil properties, temperature, water and nutrient availability and light intensity is an intrinsic advantage of greenhouse or plant growth chamber environments compared to the field.

WUE has been defined and measured in multiple ways. One approach is to calculate the ratio of whole plant dry weight, to the weight of water consumed by the plant throughout its life. Another variation is to use a shorter time interval when biomass accumulation and water use are measured. Yet another approach is to use measurements from restricted parts of the plant, for example, measuring only aerial growth and water use. WUE also has been defined as the ratio of $CO_2$ uptake to water vapor loss from a leaf or portion of a leaf, often measured over a very short time period (e.g. seconds/minutes). The ratio of $^{13}C/^{12}C$ fixed in plant tissue, and measured with an isotope ratio mass-spectrometer, also has been used to estimate WUE in plants using $C_3$ photosynthesis.

An increase in WUE is informative about the relatively improved efficiency of growth and water consumption, but this information taken alone does not indicate whether one of these two processes has changed or both have changed. In selecting traits for improving crops, an increase in WUE due to a decrease in water use, without a change in growth would have particular merit in an irrigated agricultural system where the water input costs were high. An increase in WUE driven mainly by an increase in growth without a corresponding jump in water use would have applicability to all agricultural systems. In many agricultural systems where water supply is not limiting, an increase in growth, even if it came at the expense of an increase in water use (i.e. no change in WUE), could also increase yield. Therefore, new methods to increase both WUE and biomass accumulation are required to improve agricultural productivity.

Concomitant with measurements of parameters that correlate with abiotic stress tolerance are measurements of parameters that indicate the potential impact of a transgene on crop yield. For forage crops like alfalfa, silage corn, and hay, the plant biomass correlates with the total yield. For grain crops, however, other parameters have been used to estimate yield, such as plant size, as measured by total plant dry weight, above-ground dry weight, above-ground fresh weight, leaf area, stem volume, plant height, rosette diameter, leaf length, root length, root mass, tiller number, and leaf number. Plant size at an early developmental stage will typically correlate with plant size later in development. A larger plant with a greater leaf area can typically absorb more light and carbon dioxide than a smaller plant and therefore will likely gain a greater weight during the same period. This is in addition to the potential continuation of the micro-environmental or genetic advantage that the plant had to achieve the larger size initially. There is a strong genetic component to plant size and growth rate, and so for a range of diverse genotypes plant size under one environmental condition is likely to correlate with size under another. In this way a standard environment is used to approximate the diverse and dynamic environments encountered at different locations and times by crops in the field.

Harvest index, the ratio of seed yield to above-ground dry weight, is relatively stable under many environmental conditions and so a robust correlation between plant size and grain yield is possible. Plant size and grain yield are intrinsically linked, because the majority of grain biomass is dependent on current or stored photosynthetic productivity by the leaves and stem of the plant. Therefore, selecting for plant size, even at early stages of development, has been used as to screen for plants that may demonstrate increased yield when exposed to field testing. As with abiotic stress tolerance, measurements of plant size in early development, under standardized conditions in a growth chamber or greenhouse, are standard practices to measure potential yield advantages conferred by the presence of a transgene.

There is a need, therefore, to identify additional genes expressed in stress tolerant plants and/or plants that are efficient in water use that have the capacity to confer stress tolerance and/or increased water use efficiency to the host plant and to other plant species. Newly generated stress tolerant plants and/or plants with increased water use efficiency will have many advantages, such as an increased range in which the crop plants can be cultivated, by for example, decreasing the water requirements of a plant species. Other desirable advantages include increased resistance to lodging, the bending of shoots or stems in response to wind, rain, pests, or disease.

SUMMARY OF THE INVENTION

The present inventors have discovered that transforming a plant with certain polynucleotides results in enhancement of the plant's growth and/or response to environmental stress, and accordingly the yield of the agricultural products of the plant is increased, when the polynucleotides are present in the plant as transgenes. The polynucleotides capable of mediating such enhancements have been isolated from *Physcomitrella patens, Brassica napus, Zea mays, Linum usitatissimum, Oryza satvia, Glycine max,* or *Triticum aestivum* and are listed in Table 1, and the sequences thereof are set forth in the Sequence Listing as indicated in Table 1.

TABLE 1

| Gene Name | Gene ID | Organism | Polynucleotide SEQ ID NO | Amino acid SEQ ID NO |
|---|---|---|---|---|
| PpTPT-1 | EST 214 | P. patens | 1 | 2 |
| PpCDC2-1 | EST 280 | P. patens | 3 | 4 |
| PpLRP-1 | EST 298a | P. patens | 5 | 6 |
|  | EST 298b | P. patens | 55 | 56 |
|  | EST 298c | P. patens | 57 | 58 |
| PpRBP-1 | EST 300 | P. patens | 7 | 8 |
| PpPD-1 | EST 362 | P. patens | 9 | 10 |
| PpMSC-1 | EST 378 | P. patens | 11 | 12 |
| PpMBP-1 | EST 398 | P. patens | 13 | 14 |
| PpAK-1 | EST 407 | P. patens | 15 | 16 |
| PpZF-6 | EST 458 | P. patens | 17 | 18 |
| PpCDK-1 | EST 479 | P. patens | 19 | 20 |
| PpZF-7 | EST 520 | P. patens | 21 | 22 |
| PpMFP-1 | EST 544 | P. patens | 23 | 24 |
| PpLRP-2 | EST 545 | P. patens | 25 | 26 |
| PpPPK-1 | EST 549 | P. patens | 27 | 28 |
| PpSRP-1 | EST 554 | P. patens | 29 | 30 |
| PpCBL-1 | EST 321 | P. patens | 31 | 32 |
| PpCBL-2 | EST 416 | P. patens | 33 | 34 |
| PpHD-1 | EST 468 | P. patens | 35 | 36 |
| BnHD-1 | BN51361834 | B. napus | 37 | 38 |
| BnHD-2 | BN50000854 | B. napus | 39 | 40 |
| ZmHD-1 | ZM59324542 | Z. mays | 41 | 42 |
| LuHD-1 | LU61552369 | L. usitatissimum | 43 | 44 |
| OsHD-1 | OS34631911 | O. sativa | 45 | 46 |
| GmHD-1 | GM59700314 | G. max | 47 | 48 |
| GmHD-2 | GM49753757 | G. max | 49 | 50 |
| GmHD-3 | GM50270592 | G. max | 51 | 52 |
| TaHD-1 | TA60089198 | T. aestivum | 53 | 54 |

In one embodiment, the invention provides a transgenic plant transformed with an expression cassette comprising an isolated polynucleotide encoding a tRNA 2'-phosphotransferase.

In another embodiment, the invention provides a transgenic plant transformed with an expression cassette comprising an isolated polynucleotide encoding a cell division control protein kinase.

In another embodiment, the invention provides a transgenic plant transformed with an expression cassette comprising an isolated polynucleotide encoding a leucine-rich repeat protein.

In another embodiment, the invention provides a transgenic plant transformed with an expression cassette comprising an isolated polynucleotide encoding a Ran-binding protein.

In another embodiment, the invention provides a transgenic plant transformed with an expression cassette comprising an isolated polynucleotide encoding a plastid division protein.

In another embodiment, the invention provides a transgenic plant transformed with an expression cassette comprising an isolated polynucleotide encoding a mitochondrial substrate carrier protein.

In another embodiment, the invention provides a transgenic plant transformed with an expression cassette comprising an isolated polynucleotide encoding a MADS-box protein.

In another embodiment, the invention provides a transgenic plant transformed with an expression cassette comprising an isolated polunucleotide encoding an adenosine kinase-1 protein.

In another embodiment, the invention provides a transgenic plant transformed with an expression cassette comprising an isolated polynucleotide encoding a zinc finger-6 protein.

In another embodiment, the invention provides a transgenic plant transformed with an expression cassette comprising an isolated polynucleotide encoding a cyclin-dependent kinase regulatory subunit protein.

In another embodiment, the invention provides a transgenic plant transformed with an expression cassette comprising an isolated polynucleotide encoding a zinc finger-7 protein.

In another embodiment, the invention provides a transgenic plant transformed with an expression cassette comprising an isolated polynucleotide encoding a MAR-binding protein.

In another embodiment, the invention provides a transgenic plant transformed with an expression cassette comprising an polynucleotide encoding a leucine rich repeat receptor protein.

In another embodiment, the invention provides a transgenic plant transformed with an expression cassette comprising an polynucleotide encoding a phytochrome protein kinase protein.

In another embodiment, the invention provides a transgenic plant transformed with an expression cassette comprising an polynucleotide encoding a synaptobrevin protein.

In another embodiment, the invention provides a transgenic plant transformed with an expression cassette comprising an polynucleotide encoding a calcineurin B protein.

In another embodiment, the invention provides a transgenic plant transformed with an expression cassette comprising an polynucleotide encoding a caleosin protein.

In another embodiment, the invention provides a transgenic plant transformed with an expression cassette comprising an polynucleotide encoding a histone deacetylase protein.

In a further embodiment, the invention concerns a seed produced by the transgenic plant of the invention, wherein the seed is true breeding for a transgene comprising the polynucleotide described above. Plants derived from the seed of the invention demonstrate increased tolerance to an environmental stress, and/or increased plant growth, and/or increased yield, under normal or stress conditions as compared to a wild type variety of the plant.

In a still another aspect, the invention concerns products produced by or from the transgenic plants of the invention, their plant parts, or their seeds, such as a foodstuff, feedstuff, food supplement, feed supplement, cosmetic or pharmaceutical.

The invention further provides the isolated polynucleotides identified in Table 1 or in Table 2 below, and polypeptides identified in Table 1. The invention is also embodied in recombinant vector comprising an isolated polynucleotide of the invention.

In yet another embodiment, the invention concerns a method of producing the aforesaid transgenic plant, wherein the method comprises transforming a plant cell with an expression vector comprising an isolated polynucleotide of the invention, and generating from the plant cell a transgenic plant that expresses the polypeptide encoded by thepolynucleotide. Expression of the polypeptide in the plant results in increased tolerance to an environmental stress, and/or growth, and/or yield under normal and/or stress conditions as compared to a wild type variety of the plant.

In still another embodiment, the invention provides a method of increasing a plant's tolerance to an environmental stress, and/or growth, and/or yield. The method comprises the steps of transforming a plant cell with an expression cassette comprising an isolated polynucleotide of the invention, and generating a transgenic plant from the plant cell, wherein the transgenic plant comprises the polynucleotide.

BRIEF DESCRIPTION OF THE DRAWINGS

FIG. 2 shows an alignment of the disclosed amino acids sequences: PpHD-1 (SEQ ID NO:36), BnHD-1 (SEQ ID NO:38), BnHD-2 (SEQ ID NO:40), ZmHD-1 (SEQ ID NO:42), LuHD-1 (SEQ ID NO:44), OsHD-1 (SEQ ID NO:46), GmHD-1 (SEQ ID NO:48), GmHD-2 (SEQ ID NO:50), GmHD-3 (SEQ ID NO:52), and TaHD-1 (SEQ ID NO:54). The alignment was generated using Align X of Vector NTI.

DETAILED DESCRIPTION OF THE PREFERRED EMBODIMENTS

Figure 1:
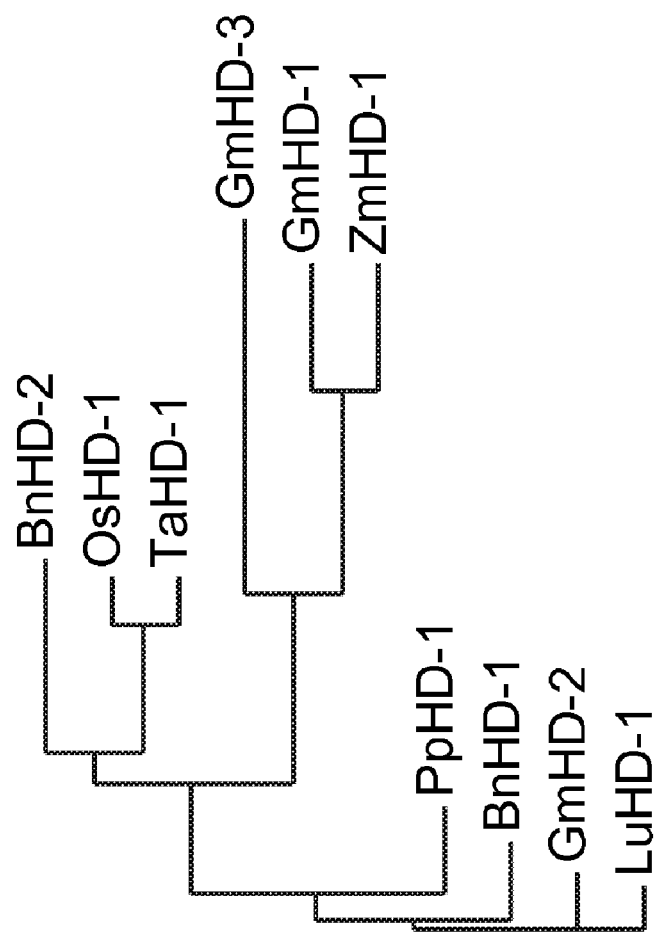
FIG. 1 is a diagram illustrating the phylogenetic relationship among the disclosed PpHD-1 (SEQ ID NO:36), BnHD-1 (SEQ ID NO:38), BnHD-2 (SEQ ID NO:40), ZmHD-1 (SEQ ID NO:42), LuHD-1 (SEQ ID NO:44), OsHD-1 (SEQ ID NO:46), GmHD-1 (SEQ ID NO:48), GmHD-2 (SEQ ID NO:50), GmHD-3 (SEQ ID NO:52), and TaHD-1 (SEQ ID NO:54) amino acid sequences. The diagram was generated using Align X of Vector NTI.

Throughout this application, various publications are referenced. The disclosures of all of these publications and those references cited within those publications in their entireties are hereby incorporated by reference into this application in order to more fully describe the state of the art to which this invention pertains. The terminology used herein is for the purpose of describing specific embodiments only and is not intended to be limiting. As used herein, "a" or "an" can mean one or more, depending upon the context in which it is used. Thus, for example, reference to "a cell" can mean that at least one cell can be used.

In one embodiment, the invention provides a transgenic plant that overexpresses an isolated polynucleotide identified in Table 1, or a homolog thereof. The transgenic plant of the invention demonstrates an increased tolerance to an environmental stress as compared to a wild type variety of the plant. The overexpression of such isolated nucleic acids in the plant may optionally result in an increase in plant growth or in yield of associated agricultural products, under normal or stress conditions, as compared to a wild type variety of the plant. Without wishing to be bound by any theory, the increased tolerance to an environmental stress, increased growth, and/or increased yield of a transgenic plant of the invention is believed to result from an increase in water use efficiency of the plant.

As defined herein, a "transgenic plant" is a plant that has been altered using recombinant DNA technology to contain an isolated nucleic acid which would otherwise not be present in the plant. As used herein, the term "plant" includes a whole plant, plant cells, and plant parts. Plant parts include, but are not limited to, stems, roots, ovules, stamens, leaves, embryos, meristematic regions, callus tissue, gametophytes, sporophytes, pollen, microspores, and the like. The transgenic plant of the invention may be male sterile or male fertile, and may further include transgenes other than those that comprise the isolated polynucleotides described herein.

As used herein, the term "variety" refers to a group of plants within a species that share constant characteristics that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more isolated polynucleotides introduced into a plant variety. As also used herein, the term "wild type variety" refers to a group of plants that are analyzed for comparative purposes as a control plant, wherein the wild type variety plant is identical to the transgenic plant (plant transformed with an isolated polynucleotide in accordance with the invention) with the exception that the wild type variety plant has not been transformed to contain an isolated polynucleotide of the invention.

As defined herein, the term "nucleic acid" and "polynucleotide" are interchangeable and refer to RNA or DNA that is linear or branched, single or double stranded, or a hybrid thereof. The term also encompasses RNA/DNA hybrids. An "isolated" nucleic acid molecule is one that is substantially separated from other nucleic acid molecules which are present in the natural source of the nucleic acid (i.e., sequences encoding other polypeptides). For example, a cloned nucleic acid is considered isolated. A nucleic acid is also considered isolated if it has been altered by human intervention, or placed in a locus or location that is not its natural site, or if it is introduced into a cell by transformation. Moreover, an isolated nucleic acid molecule, such as a cDNA molecule, can be free from some of the other cellular material with which it is naturally associated, or culture medium when produced by recombinant techniques, or chemical precursors or other chemicals when chemically synthesized. While it may optionally encompass untranslated sequence located at both the 3' and 5' ends of the coding region of a gene, it may be preferable to remove the sequences which naturally flank the coding region in its naturally occurring replicon.

As used herein, the term "environmental stress" refers to a sub-optimal condition associated with salinity, drought, nitrogen, temperature, metal, chemical, pathogenic, or oxidative stresses, or any combination thereof. The terms "water use efficiency" and "WUE" refer to the amount of organic matter produced by a plant divided by the amount of water used by the plant in producing it, i.e., the dry weight of a plant in relation to the plant's water use. As used herein, the term "dry weight" refers to everything in the plant other than water, and includes, for example, carbohydrates, proteins, oils, and mineral nutrients.

Any plant species may be transformed to create a transgenic plant in accordance with the invention. The transgenic plant of the invention may be a dicotyledonous plant or a monocotyledonous plant. For example and without limitation, transgenic plants of the invention may be derived from any of the following dicotyledonous plant families: Leguminosae, including plants such as pea, alfalfa and soybean; Umbelliferae, including plants such as carrot and celery; Solanaceae, including the plants such as tomato, potato, aubergine, tobacco, and pepper; Cruciferae, particularly the genus *Brassica*, which includes plant such as oilseed rape, beet, cabbage, cauliflower and broccoli); and *Arabidopsis thaliana*; Compositae, which includes plants such as lettuce; Malvaceae, which includes cotton; Fabaceae, which includes plants such as peanut, and the like. Transgenic plants of the invention may be derived from monocotyledonous plants, such as, for example, wheat, barley, sorghum, millet, rye, triticale, maize, rice, oats, switchgrass, miscanthus, and sugarcane. Transgenic plants of the invention are also embodied as trees such as apple, pear, quince, plum, cherry, peach, nectarine, apricot, papaya, mango, and other woody species including coniferous and deciduous trees such as poplar, pine, sequoia, cedar, oak, willow, and the like. Especially preferred are *Arabidopsis thaliana, Nicotiana tabacum*, oilseed rape, soybean, corn (maize), wheat, linseed, potato and tagetes.

As shown in Table 1, one embodiment of the invention is a transgenic plant transformed with an expression cassette comprising an isolated polynucleotide encoding a tRNA 2'-phosphotransferase polypeptide. In yeast, the RNA 2'-phosphotransferase Tpt1 protein is an essential protein that catalyzes the final step of tRNA splicing. Although this family of proteins is conserved in eukaryotes, bacteria, and archaea, its function has only been well characterized in yeast. tRNA splicing is conserved in all three major kingdoms, but the mechanisms and enzymes involved differ. These differences leave the exact function of RNA 2'-phoshotransferase proteins in plants unclear, although the enzymatic activity has been demonstrated in tobacco nuclear extracts. All of the RNA 2'phosphotransferase family members contain a conserved core domain, exemplified by amino acids 98 to 287 of SEQ ID NO:2, and members from *Escherichia coli, Arabidopsis thaliana, Schizosaccharomyces pombe*, and *Homo sapiens* are capable of complementing the *Saccharomyces cerevisiae* tpt1 mutant, indicating similarity of function.

The transgenic plant of this embodiment may comprise any polynucleotide encoding a tRNA 2'-phosphotransferase. Preferably, the transgenic plant of this embodiment comprises a polynucleotide encoding a tRNA 2'-phosphotransferase having a sequence comprising amino acids 98 to 287 of SEQ ID NO:2. More preferably, the transgenic plant of this embodiment comprises a polynucleotide encoding a tRNA 2'-phosphotransferase having a sequence comprising amino acids 1 to 323 of SEQ ID NO:2.

In another embodiment, the invention provides a transgenic plant transformed with an expression cassette comprising an isolated polynucleotide encoding a cell division control 2 (CDC2) protein kinase. The CDC2 proteins belong to a specific family of cyclin-dependent kinases (CDKs) in plants commonly referred to as the CDKA family. All of the CDKA proteins contain a highly conserved core kinase domain with a PSTAIRE motif that is the principle site for cyclin interaction to form active CDK-cyclin complexes. An exemplary PSTAIRE motif is represented as amino acids 4 to 287 of SEQ ID NO:4. The CDKA proteins are also subject to posttranslational modification. Phosphorylation of the conserved threonine 14 and tyrosine 15 positions inactivates the CDKA, and phosphorylation of the conserved threonine 161 position activates the CDKA. In yeast these CDKs are involved specifically in G1/S and G2/M controls. In plants, CDKA's are proposed to function in both S and M phase progression and to be involved in cell proliferation and maintenance of cell division competence in differentiating tissues. In *Arabidopsis thaliana* for example, a mutation of the CDKA1 gene leads to male gametophytic lethality and impairs seed development by reducing seed size.

The transgenic plant of this embodiment may comprise any polynucleotide encoding a CDC2 protein kinase. Preferably, the transgenic plant of this embodiment comprises a polynucleotide encoding a CDKA protein having a sequence comprising amino acids 4 to 287 of SEQ ID NO:4. More preferably, the transgenic plant of this embodiment comprises a polynucleotide encoding a CDKA protein having a sequence comprising amino acids 1 to 294 of SEQ ID NO:4.

In another embodiment, the invention provides a transgenic plant transformed with an expression cassette comprising an isolated polynucleotide encoding a leucine-rich repeat (LRR) protein. LRRs are typically found in proteins as 20 to 29 amino acids repeats, each containing an 11 amino acid conserved region with the consensus sequence of LXXLX-LXXN/CXL with X as any amino acid and L as valine, leucine, or phenylalanine. The LRR protein of the present invention contains an LRR represented by amino acids 422 to 441 of SEQ ID NO:6. The generally accepted major function of LLRs is to provide a structural scaffold for the formation of protein-protein interactions. LLR-containing proteins are known to be involved in hormone-receptor interactions, enzyme inhibition, cell adhesion, celluar trafficking, plant disease resistance, and bacterial virulence.

The transgenic plant of this embodiment may comprise any polynucleotide encoding an LRR protein having a sequence comprising amino acids 422 to 441 of SEQ ID NO:6. More preferably, the transgenic plant of this embodiment comprises a polynucleotide encoding a LRR protein having a sequence comprising amino acids 1 to 646 of SEQ ID NO:6.

In another embodiment, the invention provides a transgenic plant transformed with an expression cassette comprising an isolated polynucleotide encoding a Ran-binding protein. Ran GTPase (RanGTP) proteins belong to a subfamily of small GTP-binding proteins that are involved in nucleocytoplasmic transport, and are involved in controlling nuclear functions throughout the cell cycle. The Ran binding proteins 1 (RanBP1s) are cytoplasmic proteins that form a complex with the GTP form of RanGTP. The binding domain of RanBP1 s that interacts with RanGTP has been identified and is represented by amino acids 51 to 172 of SEQ ID NO:8. The formation of this RanGTP-RanBP1 complex is key to promoting the initial dissociation of RanGTP from transport factors that are exported from the nucleus to the cytoplasm.

The transgenic plant of this embodiment may comprise any polynucleotide encoding RanBP1 protein having a sequence comprising amino acids 51 to 172 of SEQ ID NO:8. More preferably, the transgenic plant of this embodiment comprises a polynucleotide encoding a RanBP1 protein having a sequence comprising amino acids 1 to 213 of SEQ ID NO:8.

In another embodiment, the invention provides a transgenic plant transformed with an expression cassette comprising an isolated polynucleotide encoding a plastid division protein. The FtsZ plastid division proteins are characterized by domains represented by amino acids 139 to 332 of SEQ ID NO:10. The transgenic plant of this embodiment may comprise any polynucleotide encoding a plastid division protein having a sequence comprising amino acids 139 to 332 of SEQ ID NO:10. More preferably, the transgenic plant of this embodiment comprises a polynucleotide encoding a plastid division protein having a sequence comprising amino acids 1 to 490 of SEQ ID NO:10.

In another embodiment, the invention provides a transgenic plant transformed with an expression cassette comprising an isolated polynucleotide encoding a mitochondrial substrate carrier protein. The mitochondrial substrate carrier proteins are characterized by domains represented by amino acids 1 to 98 of SEQ ID NO:12. The transgenic plant of this embodiment may comprise any polynucleotide encoding a mitochondrial substrate carrier protein having a sequence comprising amino acids 1 to 98 of SEQ ID NO:12. More preferably, the transgenic plant of this embodiment comprises a polynucleotide encoding a mitochondrial substrate carrier protein having a sequence comprising amino acids 1 to 297 of SEQ ID NO:12.

In another embodiment, the invention provides a transgenic plant transformed with an expression cassette comprising an isolated polynucleotide encoding a MADS-box protein. The DNA binding and dimerization domains of SRF-type transcription factors comprise MADS-box domains represented by amino acids 9 to 59 of SEQ ID NO:14. The transgenic plant of this embodiment may comprise any polynucleotide encoding an SRF-type transcription factor protein comprising a MADS-box domain having a sequence comprising amino acids 9 to 59 of SEQ ID NO:14. More preferably, the transgenic plant of this embodiment comprises a polynucleotide encoding a MADS-box protein having a sequence comprising amino acids 1 to 187 of SEQ ID NO:14.

In another embodiment, the invention provides a transgenic plant transformed with an expression cassette comprising an isolated polynucleotide encoding an adenosine kinase-1 (ADK-1) protein. The pfkB family of carbohydrate kinases designated ADK-1 comprise domains represented by amino acids 23 to 339 of SEQ ID NO:16. The transgenic plant of this embodiment may comprise any polynucleotide encoding an ADK-1 protein comprising a domain having a sequence comprising amino acids 23 to 339 of SEQ ID NO:16. More preferably, the transgenic plant of this embodiment comprises a polynucleotide encoding an ADK-1 protein having a sequence comprising amino acids 1 to 343 of SEQ ID NO:16.

In another embodiment, the invention provides a transgenic plant transformed with an expression cassette comprising an isolated polynucleotide encoding a zinc finger-6 (ZF-6) protein. These proteins comprise an IBR domain represented by amino acids 210 to 272 of SEQ ID NO:18. The transgenic plant of this embodiment may comprise any polynucleotide encoding a ZF-6 protein comprising a domain having a sequence comprising amino acids 210 to 272 of SEQ ID NO:18. More preferably, the transgenic plant of this embodiment comprises a polynucleotide encoding a ZF-6 protein having a sequence comprising amino acids 1 to 594 of SEQ ID NO:18.

In another embodiment, the invention provides a transgenic plant transformed with an expression cassette comprising an isolated polynucleotide encoding a cyclin-dependent kinase regulatory subunit (CDK) protein. These proteins comprise a domain represented by amino acids 1 to 72 of SEQ ID NO:20. The transgenic plant of this embodiment may comprise any polynucleotide encoding a CDK protein comprising a domain having a sequence comprising amino acids 1 to 72 of SEQ ID NO:20. More preferably, the transgenic plant of this embodiment comprises a polynucleotide encoding a CDK protein having a sequence comprising amino acids 1 to 91 of SEQ ID NO:20.

In another embodiment, the invention provides a transgenic plant transformed with an expression cassette comprising an isolated polynucleotide encoding a zinc finger-7 (ZF-7) protein. These proteins comprise a $C_3HC4$-type domain represented by amino acids 20 to 60 of SEQ ID NO:22. The transgenic plant of this embodiment may comprise any polynucleotide encoding a ZF-7 protein comprising a domain having a sequence comprising amino acids 20 to 60 of SEQ ID NO:22. More preferably, the transgenic plant of this embodiment comprises a polynucleotide encoding a ZF-7 protein having a sequence comprising amino acids 1 to 347 of SEQ ID NO:22.

In another embodiment, the invention provides a transgenic plant transformed with an expression cassette comprising an isolated polynucleotide encoding a MAR-binding protein. The transgenic plant of this embodiment comprises a polynucleotide encoding a MAR-binding protein having a sequence comprising amino acids 1 to 814 of SEQ ID NO:24.

In another embodiment, the invention provides a transgenic plant transformed with an expression cassette comprising an polynucleotide encoding a leucine rich repeat receptor protein kinase. The LRP-2 protein of the present invention contains several LRRs, represented by amino acids 111 to 133 of SEQ ID NO:26, amino acids 135 to 158 of SEQ ID NO:26, amino acids 160 to 182 of SEQ ID NO:26, and amino acids 184 to 207 of SEQ ID NO:26. The transgenic plant of this embodiment may comprise any polynucleotide encoding an LRP-2 protein having a sequence comprising amino acids 111 to 133 of SEQ ID NO:26, amino acids 135 to 158 of SEQ ID NO:26, amino acids 160 to 182 of SEQ ID NO:26, and amino acids 184 to 207 of SEQ ID NO:26. More preferably, the transgenic plant of this embodiment comprises a polynucleotide encoding a LRR protein having a sequence comprising amino acids 1 to 251 of SEQ ID NO:26.

In another embodiment, the invention provides a transgenic plant transformed with an expression cassette comprising an polynucleotide encoding a phytochrome protein kinase protein. The transgenic plant of this embodiment comprises a polynucleotide encoding a phytochrome protein kinase protein having a sequence comprising amino acids 1 to 689 of SEQ ID NO:28.

In another embodiment, the invention provides a transgenic plant transformed with an expression cassette comprising an polynucleotide encoding a synaptobrevin-related protein.

These proteins comprise a synaptobrevin domain represented by amino acids 127 to 215 of SEQ ID NO:30. The transgenic plant of this embodiment may comprise any polynucleotide encoding a synaptobrevin-related protein comprising a domain having a sequence comprising amino acids 127 to 215 of SEQ ID NO:30. More preferably, the transgenic plant of this embodiment comprises a polynucleotide encoding a synaptobrevin-related protein having a sequence comprising amino acids 1 to 222 of SEQ ID NO:30.

In another embodiment, the invention provides a transgenic plant transformed with an expression cassette comprising an polynucleotide encoding a calcineurin B protein. In plants, a family of proteins has been found that are calcium sensor proteins with similarity to both the regulatory B subunit of calcineurin and neuronal calcium sensors of animals. These proteins have been termed calcineurin B-like proteins (CBL). These CBL proteins contain EF hand motifs that are structurally important for calcium binding and interact specifically with a group of Ser/Thr protein kinases, designated as CBL-interacting protein kinases (CIPK). CIPKs most likely represent targets of calcium sensed and transduced by CBL proteins.

Each EF hand consists of a loop of 12 amino acids flanked by two alpha helices, which binds a single calcium ion via the loop domain. These proteins have also been found to bind magnesium ions. Proteins with four EF hand motifs usually have two structural domains, each formed by a pair of EF hand motifs separated by a flexible linker. Binding of the metal ion to the EF hand protein leads to a conformational change that exposes a hydrophobic surface, which binds to a target sequence. Many EF hand containing proteins also contain a myristoylation site at the N-terminus, with consensus sequence of MGXXXS/T, with X representing any amino acid. Myristoylation at this site promotes protein-protein or protein membrane interaction. This myristoylation site is not present in the EST321 (SEQ ID NO:32) sequence, potentially indicating that the EST321 protein could belong to a different class of EF hand domain containing proteins.

The calcineurin B subunit protein of the present invention contains several EF hand motifs, represented by amino acids 37 to 65 of SEQ ID NO:32, amino acids 106 to 134 of SEQ ID NO:32, and amino acids 142 to 170 of SEQ ID NO:32. The transgenic plant of this embodiment may comprise any polynucleotide encoding a calcineurin B subunit protein having a sequence comprising amino acids 37 to 65 of SEQ ID NO:32, amino acids 106 to 134 of SEQ ID NO:32, and amino acids 142 to 170 of SEQ ID NO:32. More preferably, the transgenic plant of this embodiment comprises a polynucleotide encoding a calcineurin B subunit protein having a sequence comprising amino acids 1 to 182 of SEQ ID NO:32.

In another embodiment, the invention provides a transgenic plant transformed with an expression cassette comprising an polynucleotide encoding a caleosin-related protein. Caleosins are a family of proteins are presumably modulated by calcium-binding and phosphorylation state and are thought to be involved in fusion of membranes and oil bodies. These proteins contain several domains, an N-terminal region with a single calcium ion binding EF-hand motif, a central hydrophobic region with a potential membrane anchor, and a C-terminal region with conserved protein kinase phosphorylation sites. The presence of only a single EF hand motif is unusual for most EF hand containing proteins. It has been postulated that this single EF hand domain may interact with the membrane surface or another protein in order to form the coordinated double EF hand domain interaction found in most other EF hand proteins.

In another embodiment, the invention provides a transgenic plant transformed with an expression cassette comprising an polynucleotide encoding a caleosin-related protein. These proteins comprise a caleosin domain represented by amino acids 26 to 229 of SEQ ID NO:34. The transgenic plant of this embodiment may comprise any polynucleotide encoding a caleosin-related protein comprising a domain having a sequence comprising amino acids 26 to 229 of SEQ ID NO:34. More preferably, the transgenic plant of this embodiment comprises a polynu-cleotide encoding a caleosin-related protein having a sequence comprising amino acids 1 to 239 of SEQ ID NO:34.

In another embodiment, the invention provides a transgenic plant transformed with an expression cassette comprising an polynucleotide encoding a histone deacetylase protein. Nucleosomes consist of histones and DNA, which are essential for packaging DNA into chromosomes. Lysine at the N-terminal ends of core histones are the predominant sites for acetylation and methylation, and histone deacetylases catalyze the removal of the acetyl group from these lysine side chains. Active genes are preferentially associated with highly acetylated histones and inactive genes are associated with hypoacetylated histones. Acetylation results in charge neutralization of histones and weakens histone/DNA contacts. In plants, histone hyperacetylation is correlated with gene activity.

Histones are found to be associated with large multisubunit complexes. Three distinct families of histone deacytelases are found in plants, the RPD3/HDA family, SIR2 family, and the plant specific HD2 family. The RPD3/HDA1 family is found in all eukaryotic organisms, and members possess a complete histone deacetylase domain. Some histone deacetylase proteins possess unique regions outside the histone deacetylase domain that may be important for function and/or specificity of these proteins.

The histone deacetylases of the present invention are characterized by the following domains: from amino acids 6 to 318 of SEQ ID NO:36; from amino acids 6 to 318 of SEQ ID NO:38; from amino acids 20 to 332 of SEQ ID NO:40; from amino acids 8 to 322 of SEQ ID NO:42; from amino acids 6 to 318 of SEQ ID NO:44; from amino acids 23 to 333 of SEQ ID NO:46; from amino acids 8 to 321 of SEQ ID NO:48; from amino acids 6 to 318 of SEQ ID NO:50; from amino acids 56 to 382 of SEQ ID NO:52; and from amino acids 23 to 333 of SEQ ID NO:54.

In another embodiment, the invention provides a transgenic plant transformed with an expression cassette comprising an polynucleotide encoding a histone deacetylase protein. The transgenic plant of this embodiment may comprise any polynucleotide encoding a histone deacetylase protein comprising a domain having a sequence selected from the group consisting of amino acids 6 to 318 of SEQ ID NO:36; amino acids 6 to 318 of SEQ ID NO:38; amino acids 20 to 332 of SEQ ID NO:40; amino acids 8 to 322 of SEQ ID NO:42; amino acids 6 to 318 of SEQ ID NO:44; amino acids 23 to 333 of SEQ ID NO:46; amino acids 8 to 321 of SEQ ID NO:48; amino acids 6 to 318 of SEQ ID NO:50; amino acids 56 to 382 of SEQ ID NO:52; and amino acids 23 to 333 of SEQ ID NO:54. More preferably, the transgenic plant of this embodiment comprises a polynucleotide encoding a histone deacteylase protein selected from the group consisting of a protein having a sequence comprising amino acids 1 to 431 of SEQ ID NO:36; a protein having a sequence comprising amino acids 1 to 426 of SEQ ID NO:38; a protein having a sequence comprising amino acids 1 to 470 of SEQ ID NO:40; a protein having a sequence comprising amino acids 1 to 363 of SEQ ID NO:42; a protein having a sequence comprising amino acids 1 to 429 of SEQ ID NO:44; a protein having a sequence comprising amino acids 1 to 518 of SEQ ID NO:46; a protein having a sequence comprising amino acids 1 to 334 of SEQ ID NO:48; a protein having a sequence comprising amino acids 1 to 429 of SEQ ID NO:50; a protein having a sequence comprising amino acids 1 to 417 of SEQ ID NO:52; and a protein having a sequence comprising amino acids 1 to 519 of SEQ ID NO:54.

In another embodiment, the invention provides a transgenic plant transformed with an expression cassette comprising an isolated polynucleotide encoding a leucine-rich repeat (LRR) protein. LRRs are typically found in proteins as 20 to 29 amino acids repeats, each containing an 11 amino acid conserved region with the consensus sequence of LXXLX-LXXN/CXL with X as any amino acid and L as valine, leucine, or phenylalanine. The LRR protein of the present invention contains an LRR represented by amino acids 422 to 441 of SEQ ID NO:56. The generally accepted major function of LLRs is to provide a structural scaffold for the formation of protein-protein interactions. LLR-containing proteins are known to be involved in hormone-receptor interactions, enzyme inhibition, cell adhesion, celluar trafficking, plant disease resistance, and bacterial virulence.

The transgenic plant of this embodiment may comprise any polynucleotide encoding an LRR protein having a sequence comprising amino acids 422 to 441 of SEQ ID NO:56. More preferably, the transgenic plant of this embodiment comprises a polynucleotide encoding a LRR protein having a sequence comprising amino acids 1 to 698 of SEQ ID NO:56.

In another embodiment, the invention provides a transgenic plant transformed with an expression cassette comprising an isolated polynucleotide encoding a leucine-rich repeat (LRR) protein. LRRs are typically found in proteins as 20 to 29 amino acids repeats, each containing an 11 amino acid conserved region with the consensus sequence of LXXLX-LXXN/CXL with X as any amino acid and L as valine, leucine, or phenylalanine. The LRR protein of the present invention contains an LRR represented by amino acids 422 to 441 of SEQ ID NO:58. The generally accepted major function of LLRs is to provide a structural scaffold for the formation of protein-protein interactions. LLR-containing proteins are known to be involved in hormone-receptor interactions, enzyme inhibition, cell adhesion, celluar trafficking, plant disease resistance, and bacterial virulence.

The transgenic plant of this embodiment may comprise any polynucleotide encoding an LRR protein having a sequence comprising amino acids 422 to 441 of SEQ ID NO:58. More preferably, the transgenic plant of this embodiment comprises a polynucleotide encoding a LRR protein having a sequence comprising amino acids 1 to 665 of SEQ ID NO:58.

The invention further provides a seed produced by a transgenic plant expressing polynucleotide listed in Table 1, wherein the seed contains the polynucleotide, and wherein the plant is true breeding for increased growth and/or yield under normal and/or stress conditions and/or increased tolerance to an environmental stress as compared to a wild type variety of the plant. The invention also provides a product produced by or from the transgenic plants expressing the polynucleotide, their plant parts, or their seeds. The product can be obtained using various methods well known in the art. As used herein, the word "product" includes, but not limited to, a foodstuff, feedstuff, a food supplement, feed supplement, cosmetic or pharmaceutical. Foodstuffs are regarded as compositions used for nutrition or for supplementing nutrition. Animal feedstuffs and animal feed supplements, in particular, are regarded as foodstuffs. The invention further provides an agricultural product produced by any of the transgenic plants, plant parts, and plant seeds. Agricultural products include, but are not limited to, plant extracts, proteins, amino acids, carbohydrates, fats, oils, polymers, vitamins, and the like.

In a preferred embodiment, an isolated polynucleotide of the invention comprises a polynucleotide having a sequence selected from the group consisting of the polynucleotide sequences listed in Table 1. These polynucleotides may comprise sequences of the coding region, as well as 5' untranslated sequences and 3' untranslated sequences. Table 2 describes potential start and end positions of the coding regions of the P. patens polynucleotides of the invention, and alternative open reading frames that may be present in the sense or antisense strands of these polynucleotides. Alternatively, the polynucleotides of the invention can comprise only the coding region of the nucleotide sequences listed in Table 1, as indicated in Table 2, or the polynucleotides can contain whole genomic fragments isolated from genomic DNA. Thus the invention is also embodied as an isolated polynucleotide having a sequence selected from the group consisting of the sequences listed in Table 1 or Table 2.

TABLE 2

| Gene Name | GENE ID | SEQ ID NO | ORFs | Orf Number | Strand | Start Position | End Position |
|---|---|---|---|---|---|---|---|
| PpTPT-1 | EST 214 | 1 | 1 | 1 | sense | 113 | 1104 |
| PpCDC2-1 | EST 280 | 3 | 2 | 1 | sense | 37 | 921 |
| PpCDC2-1 | EST 280 | 3 | 2 | 2 | antisense | 380 | 42 |
| PpLRP-1 | EST 298a | 5 | 1 | 1 | sense | 144 | 2084 |
| | EST 298b | 55 | 1 | 1 | sense | 143 | 2236 |
| | EST 298c | 57 | 1 | 1 | sense | 1 | 1998 |
| PpRBP-1 | EST 300 | 7 | 1 | 1 | sense | 55 | 696 |
| PpPD-1 | EST 362 | 9 | 2 | 1 | sense | 47 | 1519 |
| PpPD-1 | EST 362 | 9 | 2 | 2 | antisense | 1197 | 604 |
| PpMSC-1 | EST 378 | 11 | 2 | 1 | sense | 453 | 1346 |
| PpMSC-1 | EST 378 | 11 | 2 | 2 | antisense | 1314 | 1027 |
| PpMBP-1 | EST 398 | 13 | 1 | 1 | sense | 33 | 878 |
| PpAK-1 | EST 407 | 15 | 3 | 1 | sense | 25 | 1056 |
| PpAK-1 | EST 407 | 15 | 3 | 2 | sense | 381 | 632 |
| PpAK-1 | EST 407 | 15 | 3 | 3 | antisense | 506 | 270 |
| PpZF-6 | EST 458 | 17 | 1 | 1 | sense | 126 | 1910 |
| PpCDK-1 | EST 479 | 19 | 2 | 1 | sense | 248 | 523 |
| PpCDK-1 | EST 479 | 19 | 2 | 2 | antisense | 304 | 104 |
| PpZF-7 | EST 520 | 21 | 2 | 1 | sense | 276 | 1319 |
| PpZF-7 | EST 520 | 21 | 2 | 2 | sense | 583 | 813 |
| PpMFP-1 | EST 544 | 23 | 1 | 1 | sense | 127 | 2571 |
| PpLRP-2 | EST 545 | 25 | 3 | 1 | sense | 225 | 980 |
| PpLRP-2 | EST 545 | 25 | 3 | 2 | sense | 416 | 694 |
| PpLRP-2 | EST 545 | 25 | 3 | 3 | antisense | 469 | 167 |
| PpPPK-1 | EST 549 | 27 | 1 | 1 | sense | 145 | 2214 |
| PpSRP-1 | EST 554 | 29 | 1 | 1 | sense | 20 | 688 |
| PpCBL-1 | EST 321 | 31 | 2 | 1 | sense | 43 | 591 |
| PpCBL-1 | EST 321 | 31 | 2 | 2 | sense | 803 | 1171 |
| PpCBL-2 | EST 416 | 33 | 1 | 1 | sense | 16 | 735 |
| PpHD-1 | EST 468 | 35 | 2 | 1 | sense | 166 | 1461 |
| PpHD-1 | EST 468 | 35 | 2 | 2 | antisense | 420 | 175 |

A polynucleotide of the invention can be isolated using standard molecular biology techniques and the sequence information provided herein. For example, P. patens cDNAs of the invention were isolated from a P. patens library using a portion of the sequence disclosed herein. Synthetic oligonucleotide primers for polymerase chain reaction amplification can be designed based upon the nucleotide sequence shown in Table 1. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to the nucleotide sequences listed in Table 1 can be prepared by standard synthetic techniques, e.g., using an automated DNA synthesizer.

"Homologs" are defined herein as two nucleic acids or polypeptides that have similar, or substantially identical, nucleotide or amino acid sequences, respectively. Homologs include allelic variants, analogs, and orthologs, as defined below. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. The term homolog further encompasses nucleic acid molecules that differ from one of the nucleotide sequences shown in Table 1 due to degeneracy of the genetic code and thus encode the same polypeptide. As used herein, a "naturally occurring" nucleic acid molecule refers to an RNA or DNA molecule having a nucleotide sequence that occurs in nature (e.g., encodes a natural polypeptide).

To determine the percent sequence identity of two amino acid sequences (e.g., one of the polypeptide sequences of Table 1 and a homolog thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence is occupied by the same amino acid residue as the corresponding position in the other sequence then the molecules are identical at that position. The same type of comparison can be made between two nucleic acid sequences.

Preferably, the isolated amino acid homologs, analogs, and orthologs of the polypeptides of the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence identified in Table 1. In another preferred embodiment, an isolated nucleic acid homolog of the invention comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence shown in Table 1 or Table 2.

For the purposes of the invention, the percent sequence identity between two nucleic acid or polypeptide sequences is determined using the Vector NTI 9.0 (PC) software package (Invitrogen, 1600 Faraday Ave., Carlsbad, Calif. 92008). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

Nucleic acid molecules corresponding to homologs, analogs, and orthologs of the polypeptides listed in Table 1 can be isolated based on their identity to said polypeptides, using the polynucleotides encoding the respective polypeptides or primers based thereon, as hybridization probes according to standard hybridization techniques under stringent hybridization conditions. As used herein with regard to hybridization for DNA to a DNA blot, the term "stringent conditions" refers to hybridization overnight at 60° C. in 10× Denhart's solution, 6×SSC, 0.5% SDS, and 100 µg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. As also used herein, in a preferred embodiment, the phrase "stringent conditions" refers to hybridization in a 6×SSC solution at 65° C. In another embodiment, "highly stringent conditions" refers to hybridization overnight at 65° C. in 10× Denhart's solution, 6×SSC, 0.5% SDS and 100 µg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for nucleic acid hybridizations are described in Meinkoth and Wahl, 1984, Anal. Biochem. 138:267-284; well known in the art (see, for example, Current Protocols in Molecular Biology, Chapter 2, Ausubel et al., eds., Greene Publishing and Wiley-Interscience, New York, 1995; and Tijssen, 1993, Laboratory Techniques in Biochemistry and Molecular Biology: Hybridization with Nucleic Acid Probes, Part I, Chapter 2, Elsevier, New York, 1993). Preferably, an isolated nucleic acid molecule of the invention that hybridizes under stringent or highly stringent conditions to a nucleotide sequence listed in Table 1 corresponds to a naturally occurring nucleic acid molecule.

There are a variety of methods that can be used to produce libraries of potential homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential sequences. Methods for synthesizing degenerate oligonucleotides are known in the art (See, e.g., Narang, 1983, Tetrahedron 39:3; Itakura et al., 1984, Annu. Rev. Biochem. 53:323; Itakura et al., 1984, Science 198:1056; Ike et al., 1983, Nucleic Acid Res. 11:477).

Additionally, optimized nucleic acids can be created. Preferably, an optimized nucleic acid encodes a polypeptide that has a function similar to those of the polypeptides listed in Table 1 and/or modulates a plant's growth and/or yield under normal and/or water-limited conditions and/or tolerance to an environmental stress, and more preferably increases a plant's growth and/or yield under normal and/or water-limited conditions and/or tolerance to an environmental stress upon its overexpression in the plant. As used herein, "optimized" refers to a nucleic acid that is genetically engineered to increase its expression in a given plant or animal. To provide plant optimized nucleic acids, the DNA sequence of the gene can be modified to: 1) comprise codons preferred by highly expressed plant genes; 2) comprise an A+T content in nucleotide base composition to that substantially found in plants; 3) form a plant initiation sequence; 4) to eliminate sequences that cause destabilization, inappropriate polyadenylation, degradation and termination of RNA, or that form secondary structure hairpins or RNA splice sites; or 5) elimination of antisense open reading frames. Increased expression of nucleic acids in plants can be achieved by utilizing the distribution frequency of codon usage in plants in general or in a particular plant. Methods for optimizing nucleic acid expression in plants can be found in EPA 0359472; EPA 0385962; PCT Application No. WO 91/16432; U.S. Pat. No. 5,380,831; U.S. Pat. No. 5,436,391; Perlack et al., 1991, Proc. Natl. Acad. Sci. USA 88:3324-3328; and Murray et al., 1989, Nucleic Acids Res. 17:477-498.

An isolated polynucleotide of the invention can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots, whereas the XTA codon is avoided in both monocots and dicots. Optimized nucleic acids of this invention also preferably have CG and TA doublet avoidance indices closely approximating those of the chosen host plant. More preferably, these indices deviate from that of the host by no more than about 10-15%.

The invention further provides an isolated recombinant expression vector comprising a polynucleotide as described above, wherein expression of the vector in a host cell results in the plant's increased growth and/or yield under normal or water-limited conditions and/or increased tolerance to environmental stress as compared to a wild type variety of the host cell. The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequence(s) in a manner which allows for expression of the nucleotide sequence (e.g., in a bacterial or plant host cell when the vector is introduced into the host cell). The term "regulatory sequence" is intended to include promoters, enhancers, and other expression control elements (e.g., polyadenylation signals). Such regulatory sequences are well known in the art. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides encoded by nucleic acids as described herein.

Plant gene expression should be operatively linked to an appropriate promoter conferring gene expression in a timely, cell specific, or tissue specific manner. Promoters useful in the expression cassettes of the invention include any promoter that is capable of initiating transcription in a plant cell. Such promoters include, but are not limited to, those that can be obtained from plants, plant viruses, and bacteria that contain genes that are expressed in plants, such as Agrobacterium and Rhizobium.

The promoter may be constitutive, inducible, developmental stage-preferred, cell type-preferred, tissue-preferred, or organ-preferred. Constitutive promoters are active under most conditions. Examples of constitutive promoters include the CaMV 19S and 35S promoters (Odell et al., 1985, Nature 313:810-812), the sX CaMV 35S promoter (Kay et al., 1987, Science 236:1299-1302) the Sep1 promoter, the rice actin promoter (McElroy et al., 1990, Plant Cell 2:163-171), the Arabidopsis actin promoter, the ubiquitan promoter (Christensen et al., 1989, Plant Molec. Biol. 18:675-689), pEmu (Last et al., 1991, Theor. Appl. Genet. 81:581-588), the figwort mosaic virus 35S promoter, the Smas promoter (Velten et al., 1984, EMBO J 3:2723-2730), the super promoter (U.S. Pat. No. 5,955,646), the GRP1-8 promoter, the cinnamyl alcohol dehydrogenase promoter (U.S. Pat. No. 5,683,439), promoters from the T-DNA of Agrobacterium, such as mannopine synthase, nopaline synthase, and octopine synthase, the small subunit of ribulose biphosphate carboxylase (ssu-RUBISCO) promoter, and the like.

Inducible promoters are preferentially active under certain environmental conditions, such as the presence or absence of a nutrient or metabolite, heat or cold, light, pathogen attack, anaerobic conditions, and the like. For example, the hsp80 promoter from Brassica is induced by heat shock; the PPDK promoter is induced by light; the PR-1 promoters from tobacco, Arabi-dopsis, and maize are inducible by infection with a pathogen; and the Adh1 promoter is induced by hypoxia and cold stress. Plant gene expression can also be facilitated via an inducible pro-moter (For a review, see Gatz, 1997, Annu. Rev. Plant Physiol. Plant Mol. Biol. 48:89-108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992, Plant J. 2: 397-404), and an ethanol inducible promoter (PCT Application No. WO 93/21334).

In one preferred embodiment of the present invention, the inducible promoter is a stress-inducible promoter. For the purposes of the invention, stress-inducible promoters are preferentially active under one or more of the following stresses: sub-optimal conditions associated with salinity, drought, nitrogen, temperature, metal, chemical, pathogenic, and oxidative stresses. Stress inducible promoters include, but are not limited to, Cor78 (Chak et al., 2000, Planta 210: 875-883; Hovath et al., 1993, Plant Physiol. 103:1047-1053), Cor15a (Artus et al., 1996, PNAS 93(23):13404-09), Rci2A (Medina et al., 2001, Plant Physiol. 125:1655-66; Nylander et al., 2001, Plant Mol. Biol. 45:341-52; Navarre and Goffeau, 2000, EMBO J. 19:2515-24; Capel et al., 1997, Plant Physiol. 115:569-76), Rd22 (Xiong et al., 2001, Plant Cell 13:2063-83; Abe et al., 1997, Plant Cell 9:1859-68; Iwasaki et al., 1995, Mol. Gen. Genet. 247:391-8), cDet6 (Lang and Palve, 1992, Plant Mol. Biol. 20:951-62), ADH1 (Hoeren et al., 1998, Genetics 149:479-90), KAT1 (Nakamura et al., 1995, Plant Physiol. 109:371-4), KST1 (Müller-Röber et al., 1995, EMBO 14:2409-16), Rha1 (Terryn et al., 1993, Plant Cell 5:1761-9; Terryn et al., 1992, FEBS Lett. 299(3):287-90), ARSK1 (Atkinson et al., 1997, GenBank Accession #L22302, and PCT Application No. WO 97/20057), PtxA (Plesch et al., GenBank Accession #X67427), SbHRGP3 (Ahn et al., 1996, Plant Cell 8:1477-90), GH3 (Liu et al., 1994, Plant Cell 6:645-57), the pathogen inducible PRP1-gene promoter (Ward et al., 1993, Plant. Mol. Biol. 22:361-366), the heat inducible hsp80-promoter from tomato (U.S. Pat. No. 5,187,267), cold inducible alpha-amylase promoter from potato (PCT Application No. WO 96/12814), or the wound-inducible pinII-promoter (European Patent No. 375091). For other examples of drought, cold, and salt-inducible promoters, such as the RD29A promoter, see Yamaguchi-Shinozalei et al., 1993, Mol. Gen. Genet. 236:331-340.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue-preferred and organ-preferred promoters include, but are not limited to fruit-preferred, ovule-preferred, male tissue-preferred, seed-preferred, integument-preferred, tuber-preferred, stalk-preferred, pericarp-preferred, leaf-preferred, stigma-preferred, pollen-preferred, anther-preferred, petal-preferred, sepal-preferred, pedicel-preferred, silique-preferred, stem-preferred, root-preferred promoters, and the like. Seed-preferred promoters are preferentially expressed during seed development and/or germination. For example, seed-preferred promoters can be embryo-preferred, endosperm-preferred, and seed coat-preferred (See Thompson et al., 1989, BioEssays 10:108). Examples of seed-preferred promoters include, but are not limited to, cellulose synthase (celA), Cim1, gamma-zein, globulin-1, maize 19 kD zein (cZ19B1), and the like.

Other suitable tissue-preferred or organ-preferred promoters include the napin-gene promoter from rapeseed (U.S. Pat. No. 5,608,152), the USP-promoter from Vicia faba (Baeumlein et al., 1991, Mol. Gen. Genet. 225(3): 459-67), the oleosin-promoter from Arabidopsis (PCT Application No. WO 98/45461), the phaseolin-promoter from Phaseolus vulgaris (U.S. Pat. No. 5,504,200), the Bce4-promoter from Brassica (PCT Application No. WO 91/13980), or the legumin B4 promoter (LeB4; Baeumlein et al., 1992, Plant Journal, 2(2): 233-9), as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, and bronze promoters, the Zm13 promoter (U.S. Pat. No. 5,086,169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, 1985, Cell 43:729-736).

In a preferred embodiment of the present invention, the polynucleotides listed in Table 1 are expressed in plant cells from higher plants (e.g., the spermatophytes, such as crop plants). A polynucleotide may be "introduced" into a plant cell by any means, including transfection, transformation or transduction, electroporation, particle bombardment, agroinfection, and the like. Suitable methods for transforming or transfecting plant cells are disclosed, for example, using particle bombardment as set forth in U.S. Pat. Nos. 4,945,050; 5,036,006; 5,100,792; 5,302,523; 5,464,765; 5,120,657; 6,084,154; and the like. More preferably, the transgenic corn seed of the invention may be made using Agrobacterium transformation, as described in U.S. Pat. Nos. 5,591,616; 5,731,179; 5,981,840; 5,990,387; 6,162,965; 6,420,630, U.S. patent application publication number 2002/0104132, and the like. Transformation of soybean can be performed using for example a technique described in European Patent No. EP 0424047, U.S. Pat. No. 5,322,783, European Patent No. EP 0397 687, U.S. Pat. No. 5,376,543, or U.S. Pat. No. 5,169,770. A specific example of wheat transformation can be found in PCT Application No. WO 93/07256. Cotton may be transformed using methods disclosed in U.S. Pat. Nos. 5,004,863; 5,159,135; 5,846,797, and the like. Rice may be transformed using methods disclosed in U.S. Pat. Nos. 4,666,844; 5,350,688; 6,153,813; 6,333,449; 6,288,312; 6,365,807; 6,329,571, and the like. Other plant transformation methods are disclosed, for example, in U.S. Pat. Nos. 5,932,782; 6,153,811; 6,140,553; 5,969,213; 6,020,539, and the like. Any plant transformation method suitable for inserting a transgene into a particular plant may be used in accordance with the invention.

According to the present invention, the introduced polynucleotide may be maintained in the plant cell stably if it is incorporated into a non-chromosomal autonomous replicon or integrated into the plant chromosomes. Alternatively, the introduced polynucleotide may be present on an extra-chromosomal non-replicating vector and may be transiently expressed or transiently active.

Another aspect of the invention pertains to an isolated polypeptide having a sequence selected from the group consisting of the polypeptide sequences listed in Table 1. An "isolated" or "purified" polypeptide is free of some of the cellular material when produced by recombinant DNA techniques, or chemical precursors or other chemicals when chemically synthesized. The language "substantially free of cellular material" includes preparations of a polypeptide in which the polypeptide is separated from some of the cellular components of the cells in which it is naturally or recombinantly produced. In one embodiment, the language "substantially free of cellular material" includes preparations of a polypeptide of the invention having less than about 30% (by dry weight) of contaminating polypeptides, more preferably less than about 20% of contaminating polypeptides, still more preferably less than about 10% of contaminating polypeptides, and most preferably less than about 5% contaminating polypeptides.

The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities are abundant and well known to one skilled in the art.

The invention is also embodied in a method of producing a transgenic plant comprising at least one polynucleotide listed in Table 1 or Table 2, wherein expression of the polynucleotide in the plant results in the plant's increased growth and/or yield under normal and/or water-limited conditions and/or increased tolerance to an environmental stress as compared to a wild type variety of the plant comprising the steps of: (a) introducing into a plant cell an expression vector comprising at least one polynucleotide listed in Table 1 or Table 2, and (b) generating from the plant cell a transgenic plant that expresses the polynucleotide, wherein expression of the polynucleotide in the transgenic plant results in the plant's increased growth and/or yield under normal or water-limited conditions and/or increased tolerance to environmental stress as compared to a wild type variety of the plant. The plant cell may be, but is not limited to, a protoplast, gamete producing cell, and a cell that regenerates into a whole plant. As used herein, the term "transgenic" refers to any plant, plant cell, callus, plant tissue, or plant part, that contains at least one recombinant polynucleotide listed in Table 1 or Table 2. In many cases, the recombinant polynucleotide is stably integrated into a chromosome or stable extra-chromosomal element, so that it is passed on to successive generations.

The present invention also provides a method of increasing a plant's growth and/or yield under normal and/or water-limited conditions and/or increasing a plant's tolerance to an environmental stress comprising the steps of increasing the expression of at least one polynucleotide listed in Table 1 or Table 2 in the plant. Expression of a polynucleotide listed in Table 1 or Table 2 can be increased by any method known to those of skill in the art.

The effect of the genetic modification on plant growth and/or yield and/or stress tolerance can be assessed by growing the modified plant under normal and/or less than suitable conditions and then analyzing the growth characteristics and/or metabolism of the plant. Such analysis techniques are well known to one skilled in the art, and include dry weight, wet weight, polypeptide synthesis, carbohydrate synthesis, lipid synthesis, evapotranspiration rates, general plant and/or crop yield, flowering, reproduction, seed setting, root growth, respiration rates, photosynthesis rates, metabolite composition, etc., using methods known to those of skill in bio-technology.

The invention is further illustrated by the following examples, which are not to be construed in any way as imposing limitations upon the scope thereof.

EXAMPLE 1

Identification of *P. patens* Open Reading Frames cDNA libraries made from plants of the species *P. patens* (Hedw.) B.S.G. from the collection of the genetic studies section of the University of Hamburg were sequences using standard methods. The plants originated from the strain 16/14 collected by H. L. K. Whitehouse in Gransden Wood, Huntingdonshire (England), which was subcultured from a spore by Engel (1968, Am. J. Bot. 55:438-446).

Sequences were processed and annotated using the software package EST-MAX commercially provided by Bio-Max (Munich, Germany). The program incorporates practically all bioinformatics methods important for functional and structural characterization of protein sequences. For reference, see the website at pedant.mips.biochem.mpg.de. The most important algorithms incorporated in EST-MAX are: FASTA (Very sensitive sequence database searches with estimates of statistical significance; Pearson, 1990, Methods Enzymol. 183:63-98); BLAST (Very sensitive sequence database searches with estimates of statistical significance; Altschul et al., 1990, Journal of Molecular Biology 215:403-10); PREDATOR (High-accuracy secondary structure prediction from single and multiple sequences; Frishman and Argos, 1997, Proteins 27:329-335); CLUSTALW (Multiple sequence alignment; Thompson et al., 1994, Nucleic Acids Research 22:4673-4680); TMAP (Transmembrane region prediction from multiply aligned sequences; Persson and Argos, 1994, J. Mol. Biol. 237:182-192); ALOM2 (Transmembrane region prediction from single sequences; Klein et al., 1984, Biochim. Biophys. Acta 787:221-226. Version 2 by Dr. K. Nakai); PROSEARCH (Detection of PROSITE protein sequence patterns; Kolakowski et al., 1992, Biotechniques 13, 919-921); BLIMPS (Similarity searches against a database of ungapped blocks, Wallace and Henikoff, 1992, Comput Appl Biosci. 8(3):249-54); PATMAT (a searching and extraction program for sequence, pattern and block queries and databases, CABIOS 8:249-254. Written by Bill Alford).

*P. patens* partial cDNAs (ESTs) were identified in the *P. patens* EST sequencing program using the program EST-MAX through BLAST analysis. The full-length nucleotide cDNA sequences were determined using known methods. The identity and similarity of the amino acid sequences of the disclosed polypeptide sequences to known protein sequences are shown in Tables 2-19 (Pairwise Comparison was used: gap penalty: 10; gap extension penalty: 0.1; score matrix: blosum 62).

TABLE 3

Comparison of PpTPT-1 (SEQ ID NO: 2) to known RNA 2' phosphotransferases

| Public Database Accession # | Species | Sequence Identity (%) | Sequence Similarity (%) |
|---|---|---|---|
| XP_550615 | O. sativa | 45.4 | 56.2 |
| NP_197750 | A. thaliana | 34.1 | 43.0 |
| NP_182058 | A. thaliana | 39.6 | 48.9 |
| NP_594515 | Schizosaccharomyces pombe | 21.3 | 29.1 |
| NP_788477 | Drosophila melanogaster | 25.5 | 34.7 |

TABLE 4

Comparison of PpCDC2-1 (SEQ ID NO: 4) to known Cell Division Control Protein 2

| Public Database Accession # | Species | Sequence Identity (%) | Sequence Similarity (%) |
|---|---|---|---|
| S42049 | Picea abies | 92.9 | 96.3 |
| Q40790 | Pinus contorta | 92.5 | 96.3 |
| CDC2_CHERU | Chenopodium rubrum | 91.5 | 95.9 |
| Q9AUH4 | Populus tremula x P. tremuloides | 90.5 | 95.9 |
| Q8W2D3 | Helianthus annuus | 89.5 | 95.2 |

TABLE 5

Comparison of PpLRP-1 (SEQ ID NO: 6) to known Leucine Rich Repeat Family Proteins

| Public Database Accession # | Species | Sequence Identity (%) | Sequence Similarity (%) |
|---|---|---|---|
| NP_912570 | O. sativa | 27.6 | 42.1 |
| NP_921136 | O. sativa | 27.2 | 40.3 |
| AAF71805 | A. thaliana | 24.4 | 33.6 |
| NP_177947 | A. thaliana | 28.1 | 38.5 |
| G96811 | A. thaliana | 28.8 | 40.3 |

TABLE 6

Comparison of PpRBP-1 (SEQ ID NO: 8) to known Ran binding protein 1

| Public Database Accession # | Species | Sequence Identity (%) | Sequence Similarity (%) |
|---|---|---|---|
| Q94K24 | Lycopersicon esculentum | 50.7 | 63.3 |
| Q9LUZ8 | A. thaliana | 39.4 | 51.9 |
| NP_200667 | A. thaliana | 44.3 | 58.3 |
| O04149 | A. thaliana | 44.1 | 55.1 |
| NP_172194 | A thaliana | 44.4 | 55.1 |

TABLE 7

Comparison of PpPD-1 (SEQ ID NO: 10) to known Plastid division ftsZ proteins

| Public Database Accession # | Species | Sequence Identity (%) | Sequence Similarity (%) |
|---|---|---|---|
| Q70ZZ6 | P. patens | 100 | 100 |
| Q75ZR3 | Nannochloris bacillaris | 42.6 | 53.0 |
| ZP_00177632 | Crocosphaera watsonii | 41.3 | 51.8 |
| NP_440816 | Synechocystis sp. | 41.0 | 52.1 |
| T51092 | Synechocystis sp. | 40.0 | 51.5 |

TABLE 8

Comparison of PpMSC-1 (SEQ ID NO: 12) to known Mitochondiral substrate carrier proteins

| Public Database Accession # | Species | Sequence Identity (%) | Sequence Similarity (%) |
|---|---|---|---|
| NP_194188 | A. thaliana | 56.6 | 70.0 |
| T05577 | A. thaliana | 56.7 | 69.8 |
| Q66PX4 | Saccharum officinarum | 55.4 | 69.9 |
| NP_179836 | A. thaliana | 54.3 | 71.4 |
| D84613 | A. thaliana | 54.5 | 71.2 |

TABLE 9

Comparison of PpMBP-1 (SEQ ID NO: 14) to known MADS-box proteins

| Public Database Accession # | Species | Sequence Identity (%) | Sequence Similarity (%) |
|---|---|---|---|
| Q8LPA5 | P. patens | 63.0 | 63.0 |
| Q6QAF0 | P. patens | 62.6 | 62.6 |
| Q9FE71 | P. patens | 53.4 | 55.8 |
| Q9FE89 | P. patens | 49.1 | 53.7 |
| Q8LLC8 | Lycopodium annotinum | 46.1 | 59.5 |

TABLE 10

Comparison of PpAK-1 (SEQ ID NO: 16) to known Adenosine kinase proteins

| Public Database Accession # | Species | Sequence Identity (%) | Sequence Similarity (%) |
|---|---|---|---|
| ADK_PHYPA | P. patens | 100 | 100 |
| NP_195950 | A. thaliana | 66.3 | 77.8 |
| XP_466836 | O. sativa | 68.2 | 77.6 |
| Q84P58 | O. sativa | 62.9 | 71.5 |
| NP_187593 | A. thaliana | 64.7 | 76.6 |

TABLE 11

Comparison of PpZF-6 (SEQ ID NO: 18) to known zinc finger proteins

| Public Database Accession # | Species | Sequence Identity (%) | Sequence Similarity (%) |
|---|---|---|---|
| NP_180709 | A. thaliana | 61.1 | 71.0 |
| XP_472997 | O. sativa | 63.4 | 72.1 |
| NP_176722 | A. thaliana | 61.8 | 72.4 |
| T02366 | A. thaliana | 54.7 | 64.1 |
| NP_172080 | A. thaliana | 58.9 | 69.0 |

TABLE 12

Comparison of PpCDK-1 (SEQ ID NO: 20) to known Cyclin-dependent kinase regulatory subunits

| Public Database Accession # | Species | Sequence Identity (%) | Sequence Similarity (%) |
|---|---|---|---|
| Q6JJ57 | Ipomoea trifida | 76.9 | 83.5 |
| Q6T300 | G. max | 79.1 | 82.4 |
| NP_180364 | A. thaliana | 74.7 | 82.4 |
| XP_470214 | O. sativa | 80.2 | 84.6 |
| Q8GZU5 | Populus tremula × P. tremuloides | 75.8 | 80.2 |

TABLE 13

Comparison of PpZF-7 (SEQ ID NO: 22) to known RING zinc finger proteins

| Public Database Accession # | Species | Sequence Identity (%) | Sequence Similarity (%) |
|---|---|---|---|
| Q6F3A0 | O. sativa | 34.7 | 47.3 |
| Q852N7 | O. sativa | 35.5 | 48.5 |
| Q7XJB5 | O. sativa | 33.1 | 45.9 |
| NP_851050 | A. thaliana | 35.3 | 46.2 |
| NP_851051 | A. thaliana | 35.3 | 46.2 |

TABLE 14

Comparison of PpMFP-1 (SEQ ID NO: 24) to known MAR binding filament-like protein 1

| Public Database Accession # | Species | Sequence Identity (%) | Sequence Similarity (%) |
|---|---|---|---|
| MFP1_TOBAC | Nicotiana tabacum | 18.0 | 30.5 |
| NP_914440 | O. sativa | 16.8 | 30.1 |
| MFP1_ARATH | A. thaliana | 19.2 | 30.3 |
| NP_188221 | A. thaliana | 20.1 | 31.1 |
| T07111 | Lycopersicon esculentum | 19.6 | 31.6 |

TABLE 15

Comparison of PpLRP-2 (SEQ ID NO: 26) to known Leucine rich repeat receptor-like protein kinases

| Public Database Accession # | Species | Sequence Identity (%) | Sequence Similarity (%) |
|---|---|---|---|
| Q9XGG1 | Sorghum bicolor | 9.3 | 16.1 |
| NP_189183 | A. thaliana | 9.2 | 14.6 |
| Q708X5 | Cicer arietinum | 18.0 | 28.6 |
| XP_474976 | O. sativa | 5.9 | 10.3 |
| Q9LSU7 | A. thaliana | 9.2 | 14.0 |

TABLE 16

Comparison of PpPPK-1 (SEQ ID NO: 28) to known light-sensor protein kinases

| Public Database Accession # | Species | Sequence Identity (%) | Sequence Similarity (%) |
|---|---|---|---|
| S27396 | Ceratodon purpureus | 5.7 | 11.4 |
| P93098 | Ceratodon purpureus | 5.8 | 11.5 |
| PHY1_CERPU | Ceratodon purpureus | 5.7 | 11.4 |
| NP_564829 | A. thaliana | 19.0 | 32.1 |
| H96666 | A. thaliana | 19.5 | 31.6 |

TABLE 17

Comparison of PpSRP-1 (SEQ ID NO: 30) to Synaptobrevin-related proteins

| Public Database Accession # | Species | Sequence Identity (%) | Sequence Similarity (%) |
|---|---|---|---|
| NP_180871 | A. thaliana | 73.0 | 84.2 |
| Q7X9C5 | Pyrus pyrifolia | 64.9 | 75.2 |
| NP_180826 | A. thaliana | 55.4 | 63.8 |
| Q681H0 | A. thaliana | 71.2 | 83.8 |

TABLE 18

Comparison of PpCBL-1 (SEQ ID NO: 32) to known Calcineurin B proteins

| Public Database Accession # | Species | Sequence Identity (%) | Sequence Similarity (%) |
|---|---|---|---|
| XP_3133573 | Anopheles gambiae | 19.1 | 36.7 |
| NP_505885 | Caenorhabditis elegans | 16.6 | 34.8 |
| Q95P81 | Bombyx mori | 18.7 | 36.4 |
| NP_524874 | D. melanogaster | 17.1 | 35.3 |

TABLE 19

Comparison of PpCBL-2 (SEQ ID NO: 34) to known caleosin-related proteins

| Public Database Accession # | Species | Sequence Identity (%) | Sequence Similarity (%) |
|---|---|---|---|
| Q9SQ57 | Sesamum indicum | 64.9 | 78.4 |
| T07092 | G. max | 67.5 | 74.6 |
| NP_194404 | A. thaliana | 61.2 | 74.7 |
| NP_200335 | A. thaliana | 62.1 | 72.8 |
| XP_473140 | O. sativa | 60.2 | 73.0 |

TABLE 20

Comparison of PpHD-1 (SEQ ID NO: 36) to known histone deacetylase proteins

| Public Database Accession # | Species | Sequence Identity (%) | Sequence Similarity (%) |
|---|---|---|---|
| Q8W508 | Zea mays | 81.9 | 88.6 |
| NP_190054 | A. thaliana | 78.7 | 88.2 |
| T47443 | A. thaliana | 76.1 | 85.8 |
| Q6JJ24 | Ipomoea trifida | 68.2 | 75.6 |
| Q7XLX3 | Oryza sativa | 70.1 | 77.5 |

EXAMPLE 2

Cloning of Full-Length cDNAs from Other Plants

Canola, soybean, rice, maize, linseed, and wheat plants were grown under a variety of conditions and treatments, and different tissues were harvested at various developmental stages. Plant growth and harvesting were done in a strategic manner such that the probability of harvesting all expressable genes in at least one or more of the resulting libraries is maximized. The mRNA was isolated from each of the collected samples, and cDNA libraries were constructed. No amplification steps were used in the library production process in order to minimize redundancy of genes within the sample and to retain expression information. All libraries were 3' generated from mRNA purified on oligo dT columns. Colonies from the transformation of the cDNA library into *E. coli* were randomly picked and placed into microtiter plates.

Plasmid DNA was isolated from the *E. coli* colonies and then spotted on membranes. A battery of 288 $^{33}$P radiolabeled 7-mer oligonucleotides were sequentially hybridized to these membranes. To increase throughput, duplicate membranes were processed. After each hybridization, a blot image was captured during a phosphorimage scan to generate a hybridization profile for each oligonucleotide. This raw data image was automatically transferred to a computer. Absolute identity was maintained by barcoding for the image cassette, filter, and orientation within the cassette. The filters were then treated using relatively mild conditions to strip the bound probes and returned to the hybridization chambers for another round of hybridization. The hybridization and imaging cycle was repeated until the set of 288 oligomers was completed.

After completion of the hybridizations, a profile was generated for each spot (representing a cDNA insert), as to which of the 288 $^{33}$P radiolabeled 7-mer oligonucleotides bound to that particular spot (cDNA insert), and to what degree. This profile is defined as the signature generated from that clone. Each clone's signature was compared with all other signatures generated from the same organism to identify clusters of related signatures. This process "sorts" all of the clones from an organism into clusters before sequencing.

The clones were sorted into various clusters based on their having identical or similar hybridization signatures. A cluster should be indicative of the expression of an individual gene or gene family. A by-product of this analysis is an expression profile for the abundance of each gene in a particular library. One-path sequencing from the 5' end was used to predict the function of the particular clones by similarity and motif searches in sequence databases.

The full-length DNA sequence of the *P. patens* PpHD-1 (SEQ ID NO:35) was blasted against proprietary databases of canola, soybean, rice, maize, linseed, and wheat cDNAS at an e value of $e^{-10}$ (Altschul et al., 1997, Nucleic Acids Res. 25: 3389-3402). All the contig hits were analyzed for the putative full length sequences, and the longest clones representing the putative full length contigs were fully sequenced. Two homologs from canola (BnHD-1, SEQ ID NO:38 and BnHD-2, SEQ ID NO:40), one homolog from maize (ZmHD-1, SEQ ID NO:42), one homolog from linseed (LuHD-1, SEQ ID NO:44), one sequence from rice (OsHD-1, SEQ ID NO:46) three sequences from soybean (GmHD-1, SEQ ID NO:48, GmHD-2, SEQ ID NO:50, and GmHD-3, SEQ ID NO:52) and one sequence from wheat (TaHD-1, SEQ ID NO:54) were identified. The degree of amino acid identity and similarity of these sequences to the closest known public sequence is indicated in Table 21 (Pairwise Comparison was used: gap penalty: 10; gap extension penalty: 0.1; score matrix: blosum62).

TABLE 21

Degree of Amino Acid Identity and Similarity of Histone Deacetylases

| Gene Name (SEQ ID NO) | Public Database Accession # | Species | Sequence Identity (%) | Sequence Similarity (%) |
|---|---|---|---|---|
| BnHD-1 (SEQ ID NO: 38) | NP_190054 | A. thaliana | 96% | 98.1% |
| BnHD-2 (SEQ ID NO: 40) | NP_201116 | A. thaliana | 92.6% | 95.3% |
| ZmHD-1 (SEQ ID NO: 42) | NP_563817 | A. thaliana | 66.4% | 77.2% |
| LuHD-1 (SEQ ID NO: 44) | NP_190054 | A. thaliana | 87.4% | 94.4% |
| OsHD-1 (SEQ ID NO: 46) | Q7Y0Y8 | O. sativa | 100% | 100% |
| GmHD-1 (SEQ ID NO: 48) | NP_563817 | A. thaliana | 63.1% | 74% |
| GmHD-2 (SEQ ID NO: 50) | NP_190054 | A. thaliana | 85.6% | 92.1% |
| GmHD-2 (SEQ ID NO: 52) | NP_567921 | A. thaliana | 67.2% | 77.4% |
| TaHD-1 (SEQ ID NO: 54) | Q7Y0Y8 | O. sativa | 89.4% | 93.8% |

EXAMPLE 3

Stress-Tolerant Arabidopsis Plants

A fragment containing the *P. patens* polynucleotide was ligated into a binary vector containing a selectable marker gene. The resulting recombinant vector contained the corresponding polynucleotide listed in Table 1 in the sense orientation under the constitutive super promoter. The recombinant vectors were transformed into *Agrobacterium tumefaciens* C58C1 and PMP90 plants according to standard conditions. *A. thaliana* ecotype C24 plants were grown and transformed according to standard conditions. T1 plants were screened for resistance to the selection agent conferred by the selectable marker gene, and T1 seeds were collected.

The *P. patens* polynucleotides were overexpressed in *A. thaliana* under the control of a constitutive promoter. T2 and/or T3 seeds were screened for resistance to the selection agent conferred by the selectable marker gene on plates, and positive plants were transplanted into soil and grown in a growth chamber for 3 weeks. Soil moisture was maintained throughout this time at approximately 50% of the maximum water-holding capacity of soil.

The total water lost (transpiration) by the plant during this time was measured. After 3 weeks, the entire above-ground plant material was collected, dried at 65° C. for 2 days and weighed. The ratio of above-ground plant dry weight (DW) to plant water use is water use efficiency (WUE). Tables 22-41 present WUE and DW for independent transformation events (lines) of transgenic plants overexpressing the *P. patens* polynucleotides. Least square means (LSM), standard errors, and significant value (P) of a line compared to wild-type controls from an Analysis of Variance are presented. The percent improvement of each *P. patens* polynucleotides line as compared to wild-type control plants for WUE and DW is also presented.

TABLE 22

*A. thaliana* lines overexpressing PpTPT-1 (SEQ ID NO: 2)

| Measurement | Genotype | Line | LSM | Standard Error | % Improvement | P |
|---|---|---|---|---|---|---|
| DW | Wild-type | | 0.136 | 0.011 | — | — |
| | PpTPT-1 | 8 | 0.217 | 0.025 | 60 | 0.0033 |
| | (SEQ ID | 6 | 0.222 | 0.028 | 64 | 0.0047 |
| | NO: 2) | 5 | 0.226 | 0.032 | 67 | 0.0085 |
| | | 10 | 0.228 | 0.025 | 68 | 0.0009 |
| | | 2 | 0.230 | 0.032 | 70 | 0.0063 |
| WUE | Wild-type | | 2.270 | 0.085 | — | — |
| | PpTPT-1 | 8 | 2.274 | 0.190 | 0 | 0.9822 |
| | (SEQ ID | 6 | 2.308 | 0.212 | 2 | 0.8656 |
| | NO: 2) | 2 | 2.426 | 0.245 | 7 | 0.5465 |
| | | 5 | 2.675 | 0.245 | 18 | 0.1207 |

TABLE 23

*A. thaliana* lines overexpressing PpCDC2-1 (SEQ ID NO: 4)

| Measurement | Genotype | Line | LSM | Standard Error | % Improvement | P |
|---|---|---|---|---|---|---|
| DW | Wild-type | | 0.088 | 0.009 | — | — |
| | PpCDC2-1 | 4 | 0.117 | 0.016 | 33 | 0.1147 |
| | (SEQ ID NO: 4) | 1 | 0.125 | 0.016 | 42 | 0.0473 |
| WUE | Wild-type | | 1.446 | 0.097 | — | — |
| | PpCDC2-1 | 4 | 1.890 | 0.186 | 31 | 0.036 |
| | (SEQ ID NO: 4) | 1 | 1.947 | 0.186 | 35 | 0.0183 |

TABLE 24

*A. thaliana* lines overexpressing PpLRP-1 (SEQ ID NO: 6)

| Measurement | Genotype | Line | LSM | Standard Error | % Improvement | P |
|---|---|---|---|---|---|---|
| DW | Wild-type | | 0.109 | 0.033 | — | — |
| | PpLRP-1 | 10 | 0.161 | 0.034 | 48 | 0.2835 |
| | (SEQ ID NO: 6) | | | | | |
| WUE | Wild-type | | 1.782 | 0.119 | — | — |
| | PpLRP-1 | 10 | 2.205 | 0.169 | 24 | 0.0529 |
| | (SEQ ID NO: 6) | | | | | |

TABLE 25

*A. thaliana* lines overexpressing PpRBP-1 (SEQ ID NO: 8)

| Measurement | Genotype | Line | LSM | Standard Error | % Improvement | P |
|---|---|---|---|---|---|---|
| DW | Wild-type | | 0.088 | 0.008 | — | — |
| | PpRBP-1 | 2 | 0.130 | 0.017 | 48 | 0.0276 |
| | (SEQ ID NO: 8) | | | | | |
| WUE | Wild-type | | 1.446 | 0.102 | — | — |
| | PpRBP-1 | 2 | 2.301 | 0.214 | 59 | 0.0004 |
| | (SEQ ID NO: 8) | | | | | |

TABLE 26

*A. thaliana* lines overexpressing PpPD-1 (SEQ ID NO: 10)

| Measurement | Genotype | Line | LSM | Standard Error | % Improvement | P |
|---|---|---|---|---|---|---|
| DW | Wild-type | | 0.114 | 0.006 | — | — |
| | PpPD-1 | 3 | 0.171 | 0.019 | 50 | 0.0045 |
| | (SEQ ID | 1 | 0.171 | 0.017 | 50 | 0.0019 |
| | NO: 10) | 8 | 0.174 | 0.019 | 53 | 0.0026 |
| | | 2 | 0.182 | 0.019 | 60 | 0.0007 |
| | | 11 | 0.191 | 0.017 | 67 | <.0001 |
| | | 5 | 0.201 | 0.019 | 76 | <.0001 |
| | | 9 | 0.204 | 0.017 | 79 | <.0001 |
| WUE | Wild-type | | 1.958 | 0.058 | — | — |
| | PpPD-1 | 11 | 2.328 | 0.165 | 19 | 0.0353 |
| | (SEQ ID | 1 | 2.343 | 0.165 | 20 | 0.0286 |
| | NO: 10) | 8 | 2.354 | 0.180 | 20 | 0.0383 |
| | | 2 | 2.450 | 0.180 | 25 | 0.0102 |
| | | 3 | 2.517 | 0.180 | 29 | 0.0036 |
| | | 5 | 2.552 | 0.180 | 30 | 0.002 |
| | | 9 | 2.572 | 0.165 | 31 | 0.0006 |

TABLE 27

*A. thaliana* lines overexpressing PpMSC-1 (SEQ ID NO: 12)

| Measurement | Genotype | Line | LSM | Standard Error | % Improvement | P |
|---|---|---|---|---|---|---|
| DW | Wild-type | | 0.136 | 0.011 | — | — |
| | PpMSC-1 | 3 | 0.227 | 0.027 | 68 | 0.0026 |
| | (SEQ ID | 2 | 0.240 | 0.025 | 77 | 0.0002 |
| | NO: 12) | 1 | 0.247 | 0.025 | 82 | <.0001 |
| | | 4 | 0.271 | 0.022 | 100 | <.0001 |
| WUE | Wild-type | | 2.270 | 0.085 | — | — |
| | PpMSC-1 | 2 | 2.343 | 0.191 | 3 | 0.7268 |
| | (SEQ ID | 4 | 2.631 | 0.174 | 16 | 0.0654 |
| | NO: 12) | 1 | 2.820 | 0.191 | 24 | 0.0097 |

TABLE 28

*A. thaliana* lines overexpressing PpMBP-1 (SEQ ID NO: 14)

| Measurement | Genotype | Line | LSM | Standard Error | % Improvement | P |
|---|---|---|---|---|---|---|
| DW | Wild-type | | 0.110 | 0.005 | — | — |
| | PpMBP-1 | 1 | 0.154 | 0.017 | 39 | 0.0146 |
| | (SEQ ID NO: 14) | | | | | |
| WUE | Wild-type | | 1.620 | 0.066 | — | — |
| | PpMBP-1 | 1 | 2.144 | 0.209 | 32 | 0.0182 |
| | (SEQ ID NO: 14) | | | | | |

TABLE 29

*A. thaliana* lines overexpressing PpAK-1 (SEQ ID NO: 16)

| Measurement | Genotype | Line | LSM | Standard Error | % Improvement | P |
|---|---|---|---|---|---|---|
| DW | Wild-type | | 0.136 | 0.011 | — | — |
| | PpAK-1 (SEQ ID NO: 16) | 1 | 0.185 | 0.022 | 36 | 0.049 |
| | | 5 | 0.216 | 0.022 | 59 | 0.0014 |
| | | 3 | 0.217 | 0.027 | 60 | 0.0063 |
| | | 7 | 0.217 | 0.024 | 60 | 0.0026 |
| | | 8 | 0.227 | 0.024 | 68 | 0.0008 |
| | | 4 | 0.230 | 0.024 | 69 | 0.0006 |
| WUE | Wild-type | | 2.270 | 0.084 | — | — |
| | PpAK-1 (SEQ ID NO: 16) | 8 | 2.285 | 0.188 | 1 | 0.9394 |
| | | 7 | 2.358 | 0.188 | 4 | 0.6683 |
| | | 5 | 2.374 | 0.172 | 5 | 0.5851 |
| | | 3 | 2.377 | 0.211 | 5 | 0.6369 |
| | | 4 | 2.403 | 0.188 | 6 | 0.5191 |

TABLE 30

*A. thaliana* lines overexpressing PpZF-6 (SEQ ID NO: 18)

| Measurement | Genotype | Line | LSM | Standard Error | % Improvement | P |
|---|---|---|---|---|---|---|
| DW | Wild-type | | 0.107 | 0.015 | — | — |
| | PpZF-6 (SEQ ID NO: 18) | 4 | 0.131 | 0.018 | 22 | 0.3091 |
| WUE | Wild-type | | 1.897 | 0.316 | — | — |
| | PpZF-6 (SEQ ID NO: 18) | 4 | 2.026 | 0.371 | 7 | 0.7946 |

TABLE 31

*A. thaliana* lines overexpressing PpCDK-1 (SEQ ID NO: 20)

| Measurement | Genotype | Line | LSM | Standard Error | % Improvement | P |
|---|---|---|---|---|---|---|
| DW | Wild-type | | 0.088 | 0.009 | — | — |
| | PpCDK-1 (SEQ ID NO: 20) | 7 | 0.148 | 0.017 | 69 | 0.0029 |
| WUE | Wild-type | | 1.446 | 0.102 | — | — |
| | PpCDK-1 (SEQ ID NO: 20) | 7 | 1.963 | 0.195 | 36 | 0.0207 |

TABLE 32

*A. thaliana* lines overexpressing PpZF-7 (SEQ ID NO: 22)

| Measurement | Genotype | Line | LSM | Standard Error | % Improvement | P |
|---|---|---|---|---|---|---|
| DW | Wild-type | | 0.114 | 0.006 | — | — |
| | PpZF-7 (SEQ ID NO: 22) | 1 | 0.151 | 0.019 | 32 | 0.0617 |
| | | 10 | 0.153 | 0.019 | 35 | 0.0456 |
| | | 2 | 0.159 | 0.019 | 39 | 0.0226 |
| | | 7 | 0.160 | 0.019 | 40 | 0.0198 |
| | | 3 | 0.163 | 0.019 | 43 | 0.0139 |
| | | 6 | 0.175 | 0.019 | 54 | 0.0021 |
| | | 9 | 0.176 | 0.019 | 55 | 0.0018 |
| | | 5 | 0.177 | 0.019 | 56 | 0.0014 |
| | | 8 | 0.196 | 0.019 | 72 | <.0001 |
| | | 4 | 0.217 | 0.019 | 90 | <.0001 |
| WUE | Wild-type | | 1.958 | 0.057 | — | — |
| | PpZF-7 (SEQ ID NO: 22) | 2 | 2.185 | 0.176 | 12 | 0.2224 |
| | | 10 | 2.237 | 0.176 | 14 | 0.1331 |
| | | 7 | 2.242 | 0.176 | 15 | 0.1262 |
| | | 9 | 2.327 | 0.176 | 19 | 0.0479 |
| | | 3 | 2.359 | 0.176 | 20 | 0.0318 |
| | | 6 | 2.378 | 0.176 | 21 | 0.0245 |
| | | 1 | 2.435 | 0.176 | 24 | 0.0108 |
| | | 5 | 2.490 | 0.176 | 27 | 0.0045 |
| | | 8 | 2.537 | 0.176 | 30 | 0.002 |
| | | 4 | 2.707 | 0.176 | 38 | <.0001 |

TABLE 33

*A. thaliana* lines overexpressing PpMFP-1 (SEQ ID NO: 24)

| Measurement | Genotype | Line | LSM | Standard Error | % Improvement | P |
|---|---|---|---|---|---|---|
| DW | Wild-type | | 0.110 | 0.005 | — | — |
| | PpMFP-1 (SEQ ID NO: 24) | 4 | 0.128 | 0.016 | 16 | 0.3008 |
| | | 2 | 0.130 | 0.016 | 18 | 0.25 |
| | | 10 | 0.145 | 0.016 | 31 | 0.0465 |
| | | 3 | 0.146 | 0.016 | 32 | 0.0417 |
| | | 6 | 0.159 | 0.016 | 44 | 0.0048 |
| | | 7 | 0.164 | 0.016 | 48 | 0.0022 |
| | | 5 | 0.166 | 0.016 | 50 | 0.0015 |
| | | 1 | 0.168 | 0.016 | 52 | 0.0011 |
| | | 8 | 0.172 | 0.016 | 56 | 0.0004 |
| WUE | Wild-type | | 1.620 | 0.064 | — | — |
| | PpMFP-1 (SEQ ID NO: 24) | 3 | 1.979 | 0.203 | 22 | 0.0929 |
| | | 8 | 2.049 | 0.203 | 26 | 0.0451 |
| | | 7 | 2.049 | 0.203 | 26 | 0.0449 |
| | | 4 | 2.095 | 0.203 | 29 | 0.0267 |
| | | 1 | 2.113 | 0.203 | 30 | 0.0215 |
| | | 6 | 2.178 | 0.203 | 34 | 0.0094 |
| | | 5 | 2.217 | 0.203 | 37 | 0.0055 |
| | | 10 | 2.324 | 0.203 | 43 | 0.0011 |
| | | 2 | 2.345 | 0.203 | 45 | 0.0008 |

TABLE 34

*A. thaliana* lines overexpressing PpLRP-2 (SEQ ID NO: 26)

| Measurement | Genotype | Line | LSM | Standard Error | % Improvement | P |
|---|---|---|---|---|---|---|
| DW | Wild-type | | 0.136 | 0.011 | — | — |
| | PpLRP-2 (SEQ ID NO: 26) | 4 | 0.199 | 0.029 | 47 | 0.042 |
| | | 2 | 0.206 | 0.023 | 52 | 0.0078 |
| | | 3 | 0.224 | 0.029 | 65 | 0.0049 |
| | | 1 | 0.227 | 0.023 | 67 | 0.0007 |
| | | 5 | 0.235 | 0.026 | 74 | 0.0006 |
| | | 8 | 0.266 | 0.040 | 96 | 0.0026 |
| WUE | Wild-type | | 2.270 | 0.090 | — | — |
| | PpLRP-2 (SEQ ID NO: 26) | 4 | 2.360 | 0.224 | 4 | 0.7073 |
| | | 5 | 2.402 | 0.200 | 6 | 0.5481 |
| | | 1 | 2.404 | 0.183 | 6 | 0.5095 |
| | | 8 | 2.471 | 0.317 | 9 | 0.5426 |

TABLE 35

*A. thaliana* lines overexpressing PpPPK-1 (SEQ ID NO: 28)

| Measurement | Genotype | Line | LSM | Standard Error | % Improvement | P |
|---|---|---|---|---|---|---|
| DW | Wild-type | | 0.108 | 0.007 | — | — |
| | PpPPK-1 (SEQ ID NO: 28) | 4 | 0.157 | 0.020 | 45 | 0.023 |
| | | 2 | 0.159 | 0.018 | 47 | 0.0097 |
| | | 10 | 0.175 | 0.020 | 62 | 0.0018 |
| | | 9 | 0.177 | 0.022 | 64 | 0.0037 |

TABLE 35-continued

A. thaliana lines overexpressing PpPPK-1 (SEQ ID NO: 28)

| Measurement | Genotype | Line | LSM | Standard Error | % Improvement | P |
|---|---|---|---|---|---|---|
| WUE | Wild-type | | 1.951 | 0.078 | — | — |
| | PpPPK-1 | 4 | 2.043 | 0.219 | 5 | 0.6913 |
| | (SEQ ID | 9 | 2.158 | 0.245 | 11 | 0.4225 |
| | NO: 28) | 2 | 2.177 | 0.200 | 12 | 0.2948 |
| | | 10 | 2.523 | 0.219 | 29 | 0.0149 |

TABLE 36

A. thaliana lines overexpressing PpSRP-1 (SEQ ID NO: 30)

| Measurement | Genotype | Line | LSM | Standard Error | % Improvement | P |
|---|---|---|---|---|---|---|
| DW | Wild-type | | 0.114 | 0.006 | — | — |
| | PpSRP-1 | 7 | 0.152 | 0.018 | 33 | 0.0495 |
| | (SEQ ID | 6 | 0.159 | 0.018 | 39 | 0.0196 |
| | NO: 30) | 1 | 0.162 | 0.020 | 42 | 0.026 |
| | | 10 | 0.164 | 0.017 | 44 | 0.0054 |
| | | 9 | 0.167 | 0.015 | 46 | 0.0015 |
| | | 8 | 0.174 | 0.018 | 53 | 0.0019 |
| | | 2 | 0.179 | 0.018 | 57 | 0.0008 |
| WUE | Wild-type | | 1.958 | 0.057 | — | — |
| | PpSRP-1 | 10 | 2.109 | 0.161 | 8 | 0.3776 |
| | (SEQ ID | 8 | 2.197 | 0.177 | 12 | 0.1991 |
| | NO: 30) | 9 | 2.239 | 0.149 | 14 | 0.0802 |
| | | 2 | 2.302 | 0.177 | 18 | 0.0659 |
| | | 6 | 2.405 | 0.177 | 23 | 0.017 |
| | | 1 | 2.450 | 0.197 | 25 | 0.0178 |

TABLE 37

A. thaliana lines overexpressing PpCBL-1 (SEQ ID NO: 32)

| Measurement | Genotype | Line | LSM | Standard Error | % Improvement | P |
|---|---|---|---|---|---|---|
| DW | Wild-type | | 0.114 | 0.006 | — | — |
| | PpCBL-1 | 5 | 0.156 | 0.019 | 37 | 0.034 |
| | (SEQ ID | 8 | 0.163 | 0.019 | 43 | 0.0153 |
| | NO: 32) | 4 | 0.179 | 0.019 | 57 | 0.0012 |
| | | 3 | 0.180 | 0.019 | 58 | 0.0011 |
| | | 6 | 0.181 | 0.017 | 59 | 0.0003 |
| | | 1 | 0.182 | 0.017 | 59 | 0.0003 |
| | | 9 | 0.214 | 0.017 | 87 | <.0001 |
| WUE | Wild-type | | 1.958 | 0.057 | — | — |
| | PpCBL-1 | 3 | 2.109 | 0.177 | 8 | 0.4181 |
| | (SEQ ID | 5 | 2.152 | 0.177 | 10 | 0.2991 |
| | NO: 32) | 8 | 2.158 | 0.177 | 10 | 0.2836 |
| | | 1 | 2.298 | 0.162 | 17 | 0.0489 |
| | | 6 | 2.306 | 0.162 | 18 | 0.0438 |
| | | 9 | 2.319 | 0.162 | 18 | 0.0367 |
| | | 4 | 2.440 | 0.177 | 25 | 0.0105 |

TABLE 38

A. thaliana lines overexpressing PpCBL-2 (SEQ ID NO: 34)

| Measurement | Genotype | Line | LSM | Standard Error | % Improvement | P |
|---|---|---|---|---|---|---|
| DW | Wild-type | | 0.114 | 0.006 | — | — |
| | PpCBL-2 | 9 | 0.156 | 0.017 | 37 | 0.0226 |
| | (SEQ ID | 10 | 0.170 | 0.017 | 49 | 0.0027 |
| | NO: 34) | 1 | 0.179 | 0.017 | 57 | 0.0005 |
| | | 4 | 0.188 | 0.017 | 65 | <.0001 |
| | | 7 | 0.188 | 0.017 | 65 | <.0001 |
| | | 3 | 0.192 | 0.017 | 68 | <.0001 |
| | | 8 | 0.194 | 0.017 | 70 | <.0001 |
| | | 2 | 0.203 | 0.017 | 78 | <.0001 |

TABLE 38-continued

A. thaliana lines overexpressing PpCBL-2 (SEQ ID NO: 34)

| Measurement | Genotype | Line | LSM | Standard Error | % Improvement | P |
|---|---|---|---|---|---|---|
| WUE | Wild-type | | 1.958 | 0.054 | — | — |
| | PpCBL-2 | 9 | 1.944 | 0.168 | −1 | 0.9357 |
| | (SEQ ID | 2 | 2.314 | 0.168 | 18 | 0.0451 |
| | NO: 34) | 10 | 2.322 | 0.168 | 19 | 0.0405 |
| | | 8 | 2.448 | 0.168 | 25 | 0.0061 |
| | | 3 | 2.545 | 0.168 | 30 | 0.0011 |
| | | 4 | 2.569 | 0.168 | 31 | 0.0007 |
| | | 1 | 2.617 | 0.168 | 34 | 0.0003 |
| | | 7 | 2.771 | 0.168 | 42 | <.0001 |

TABLE 39

A. thaliana lines overexpressing PpHD-1 (SEQ ID NO: 36)

| Measurement | Genotype | Line | LSM | Standard Error | % Improvement | P |
|---|---|---|---|---|---|---|
| DW | Wild-type | | 1.620 | 0.065 | — | — |
| | PpHD-1 | 7 | 1.976 | 0.207 | 22 | 0.1027 |
| | (SEQ ID | 3 | 1.985 | 0.207 | 23 | 0.0944 |
| | NO: 36) | 6 | 2.144 | 0.207 | 32 | 0.0169 |
| | | 2 | 2.374 | 0.207 | 47 | 0.0007 |
| | | 8 | 2.444 | 0.207 | 51 | 0.0002 |
| WUE | Wild-type | | 0.110 | 0.005 | — | — |
| | PpHD-1 | 2 | 0.126 | 0.016 | 14 | 0.3655 |
| | (SEQ ID | 8 | 0.143 | 0.016 | 30 | 0.0566 |
| | NO: 36) | 6 | 0.149 | 0.016 | 35 | 0.0246 |
| | | 3 | 0.152 | 0.016 | 37 | 0.0177 |
| | | 7 | 0.191 | 0.016 | 73 | <.0001 |

TABLE 40

A. thaliana lines overexpressing PpLRP-1 (SEQ ID NO: 56)

| Measurement | Genotype | Line | LSM | Standard Error | % Improvement | P |
|---|---|---|---|---|---|---|
| DW | Wild-type | | 0.109 | 0.033 | — | — |
| | PpLRP-1 | 10 | 0.161 | 0.034 | 48 | 0.2835 |
| | (SEQ ID | | | | | |
| | NO: 56) | | | | | |
| WUE | Wild-type | | 1.782 | 0.119 | — | — |
| | PpLRP-1 | 10 | 2.205 | 0.169 | 24 | 0.0529 |
| | (SEQ ID | | | | | |
| | NO: 56) | | | | | |

TABLE 41

A. thaliana lines overexpressing PpLRP-1 (SEQ ID NO: 58)

| Measurement | Genotype | Line | LSM | Standard Error | % Improvement | P |
|---|---|---|---|---|---|---|
| DW | Wild-type | | 0.109 | 0.033 | — | — |
| | PpLRP-1 | 10 | 0.161 | 0.034 | 48 | 0.2835 |
| | (SEQ ID | | | | | |
| | NO: 58) | | | | | |
| WUE | Wild-type | | 1.782 | 0.119 | — | — |
| | PpLRP-1 | 10 | 2.205 | 0.169 | 24 | 0.0529 |
| | (SEQ ID | | | | | |
| | NO: 58) | | | | | |

EXAMPLE 4

Stress-Tolerant Rapeseed/Canola Plants

Canola cotyledonary petioles of 4 day-old young seedlings are used as explants for tissue culture and transformed according to EP1566443. The commercial cultivar Westar (Agriculture Canada) is the standard variety used for transformation, but other varieties can be used. *A. tumefaciens* GV3101:pMP90RK containing a binary vector is used for canola transformation. The standard binary vector used for transformation is pSUN (WO 02/00900), but many different binary vector systems have been described for plant transformation (e.g. An, G. in Agrobacterium Protocols, Methods in Molecular Biology vol 44, pp 47-62, Gartland KMA and MR Davey eds. Humana Press, Totowa, N.J.). A plant gene expression cassette comprising a selection marker gene and a plant promoter regulating the transcription of the cDNA encoding the polynucleotide is employed. Various selection marker genes can be used including the mutated acetohydroxy acid synthase (AHAS) gene disclosed in U.S. Pat. Nos. 5,767,366 and 6,225,105. A suitable promoter is used to regulate the trait gene to provide constitutive, developmental, tissue or environmental regulation of gene transcription.

Canola seeds are surface-sterilized in 70% ethanol for 2 min, incubated for 15 min in 55° C. warm tap water and then in 1.5% sodium hypochlorite for 10 minutes, followed by three rinses with sterilized distilled water. Seeds are then placed on MS medium without hormones, containing Gamborg B5 vitamins, 3% sucrose, and 0.8% Oxoidagar. Seeds are germinated at 24° C. for 4 days in low light (<50 µMol/$m^2$s, 16 hours light). The cotyledon petiole explants with the cotyledon attached are excised from the in vitro seedlings, and inoculated with Agrobacterium by dipping the cut end of the petiole explant into the bacterial suspension. The explants are then cultured for 3 days on MS medium including vitamins containing 3.75 mg/l BAP, 3% sucrose, 0.5 g/l MES, pH 5.2, 0.5 mg/l GA3, 0.8% Oxoidagar at 24° C., 16 hours of light. After three days of co-cultivation with Agrobacterium, the petiole explants are transferred to regeneration medium containing 3.75 mg/l BAP, 0.5 mg/l GA3, 0.5 g/l MES, pH 5.2, 300 mg/l timentin and selection agent until shoot regeneration. As soon as explants start to develop shoots, they are transferred to shoot elongation medium (A6, containing full strength MS medium including vitamins, 2% sucrose, 0.5% Oxoidagar, 100 mg/l myo-inositol, 40 mg/l adenine sulfate, 0.5 g/l MES, pH 5.8, 0.0025 mg/l BAP, 0.1 mg/l IBA, 300 mg/l timentin and selection agent).

Samples from both in vitro and greenhouse material of the primary transgenic plants (T0) are analyzed by qPCR using TaqMan probes to confirm the presence of T-DNA and to determine the number of T-DNA integrations.

Seed is produced from the primary transgenic plants by self-pollination. The second-generation plants are grown in greenhouse conditions and self-pollinated. The plants are analyzed by qPCR using TaqMan probes to confirm the presence of T-DNA and to determine the number of T-DNA integrations. Homozygous transgenic, heterozygous transgenic and azygous (null transgenic) plants are compared for their stress tolerance, for example, in the assays described in Example 3, and for yield, both in the greenhouse and in field studies.

EXAMPLE 5

Screening for Stress-Tolerant Rice Plants

Transgenic rice plants comprising a polynucleotide of the invention are generated using known methods. Approximately 15 to 20 independent transformants (T0) are generated. The primary transformants are transferred from tissue culture chambers to a greenhouse for growing and harvest of T1 seeds. Five events of the T1 progeny segregated 3:1 for presence/absence of the transgene are retained. For each of these events, 10 T1 seedlings containing the transgene (hetero- and homozygotes), and 10 T1 seedlings lacking the transgene (nullizygotes) are selected by visual marker screening. The selected T1 plants are transferred to a greenhouse. Each plant receives a unique barcode label to link unambiguously the phenotyping data to the corresponding plant. The selected T1 plants are grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes are grown side-by-side at random positions. From the stage of sowing until the stage of maturity, the plants are passed several times through a digital imaging cabinet. At each time point digital, images (2048× 1536 pixels, 16 million colours) of each plant are taken from at least 6 different angles.

The data obtained in the first experiment with T1 plants are confirmed in a second experiment with T2 plants. Lines that have the correct expression pattern are selected for further analysis. Seed batches from the positive plants (both hetero- and homozygotes) in T1 are screened by monitoring marker expression. For each chosen event, the heterozygote seed batches are then retained for T2 evaluation. Within each seed batch, an equal number of positive and negative plants are grown in the greenhouse for evaluation.

Transgenic plants are screened for their improved growth and/or yield and/or stress tolerance, for example, using the assays described in Example 3, and for yield, both in the greenhouse and in field studies.

EXAMPLE 6

Stress-Tolerant Soybean Plants

The polynucleotides of Tables 1 and 2 are transformed into soybean using the methods described in commonly owned copending international application number WO 2005/121345, the contents of which are incorporated herein by reference. The transgenic plants are then screened for their improved growth under water-limited conditions and/or drought, salt, and/or cold tolerance, for example, using the assays described in Example 3, and for yield, both in the greenhouse and in field studies.

EXAMPLE 7

Stress-Tolerant Wheat Plants

Transformation of wheat is performed with the method described by Ishida et al., 1996, Nature Biotech. 14745-50. Immature embryos are co-cultivated with Agrobacterium tumefaciens that carry "super binary" vectors, and transgenic plants are recovered through organogenesis. This procedure provides a transformation efficiency between 2.5% and 20%. The transgenic plants are then screened for their improved growth and/or yield under water-limited conditions and/or stress tolerance, for example, is the assays described in Example 3, and for yield, both in the greenhouse and in field studies.

EXAMPLE 8

Stress-Tolerant Corn Plants

Agrobacterium cells harboring the genes and the maize ahas gene on the same plasmid are grown in YP medium supplemented with appropriate antibiotics for 1-3 days. A loop of Agrobacterium cells is collected and suspended in 1.5 ml M-LS-002 medium (LS-inf) and the tube containing Agrobacterium cells is kept on a shaker for 1-4 hours at 1,000 rpm.

Corncobs [genotype J553×(HIIIAxA188)] are harvested at 7-12 days after pollination. The cobs are sterilized in 20% Clorox solution for 15 minutes followed by thorough rinse with sterile water. Immature embryos with size 0.8-2.0 mm are dissected into the tube containing Agrobacterium cells in LS-inf solution.

Agro-infection is carried out by keeping the tube horizontally in the laminar hood at room temperature for 30 minutes. Mixture of the agro infection is poured on to a plate containing the co-cultivation medium (M-LS-011). After the liquid agro-solution is piped out, the embryos transferred to the surface of a filter paper that is placed on the agar co-cultivation medium. The excess bacterial solution is removed with a pipette. The embryos are placed on the co-cultivation medium with scutellum side up and cultured in the dark at 22° C. for 2-4 days.

Embryos are transferred to M-MS-101 medium without selection. Seven to ten days later, embryos are transferred to M-LS-401 medium containing 0.50 μM imazethapyr and grown for 4 weeks (two 2-week transfers) to select for transformed callus cells. Plant regeneration is initiated by transferring resistant calli to M-LS-504 medium supplemented with 0.75 μM imazethapyr and grown under light at 25-27° C. for two to three weeks. Regenerated shoots are then transferred to rooting box with M-MS-618 medium (0.5 μM imazethapyr). Plantlets with roots are transferred to potting mixture in small pots in the greenhouse and after acclimatization are then transplanted to larger pots and maintained in greenhouse till maturity.

The copy number of the transgene in each plantlet is assayed using Taqman analysis of genomic DNA, and transgene expression is assayed using qRT-PCR of total RNA isolated from leaf samples.

Using assays such as the assay described in Example 3, each of these plants is uniquely labeled, sampled and analyzed for transgene copy number. Transgene positive and negative plants are marked and paired with similar sizes for transplanting together to large pots. This provides a uniform and competitive environment for the transgene positive and negative plants. The large pots are watered to a certain percentage of the field water capacity of the soil depending the severity of water-stress desired. The soil water level is maintained by watering every other day. Plant growth and physiology traits such as height, stem diameter, leaf rolling, plant wilting, leaf extension rate, leaf water status, chlorophyll content and photosynthesis rate are measured during the growth period. After a period of growth, the above ground portion of the plants is harvested, and the fresh weight and dry weight of each plant are taken. A comparison of the drought tolerance phenotype between the transgene positive and negative plants is then made.

Using assays such as the assay described in Example 3, the pots are covered with caps that permit the seedlings to grow through but minimize water loss. Each pot is weighed periodically and water added to maintain the initial water content. At the end of the experiment, the fresh and dry weight of each plant is measured, the water consumed by each plant is calculated and WUE of each plant is computed. Plant growth and physiology traits such as WUE, height, stem diameter, leaf rolling, plant wilting, leaf extension rate, leaf water status, chlorophyll content and photosynthesis rate are measured during the experiment. A comparison of WUE phenotype between the transgene positive and negative plants is then made.

Using assays such as the assay described in Example 3, these pots are kept in an area in the greenhouse that has uniform environmental conditions, and cultivated optimally. Each of these plants is uniquely labeled, sampled and analyzed for transgene copy number.

The plants are allowed to grow under theses conditions until they reach a predefined growth stage. Water is then withheld. Plant growth and physiology traits such as height, stem diameter, leaf rolling, plant wilting, leaf extension rate, leaf water status, chlorophyll content and photosynthesis rate are measured as stress intensity increases. A comparison of the dessication tolerance phenotype between transgene positive and negative plants is then made.

Segregating transgenic corn seeds for a transformation event are planted in small pots for testing in a cycling drought assay. These pots are kept in an area in the greenhouse that has uniform environmental conditions, and cultivated optimally. Each of these plants is uniquely labeled, sampled and analyzed for transgene copy number. The plants are allowed to grow under theses conditions until they reach a predefined growth stage. Plants are then repeatedly watered to saturation at a fixed interval of time. This water/drought cycle is repeated for the duration of the experiment. Plant growth and physiology traits such as height, stem diameter, leaf rolling, leaf extension rate, leaf water status, chlorophyll content and photosynthesis rate are measured during the growth period. At the end of the experiment, the plants are harvested for above-ground fresh and dry weight. A comparison of the cycling drought tolerance phenotype between transgene positive and negative plants is then made.

In order to test segregating transgenic corn for drought tolerance under rain-free conditions, managed-drought stress at a single location or multiple locations is used. Crop water availability is controlled by drip tape or overhead irrigation at a location which has less than 10 cm rainfall and minimum temperatures greater than 5° C. expected during an average 5 month season, or a location with expected in-season precipitation intercepted by an automated "rain-out shelter" which retracts to provide open field conditions when not required. Standard agronomic nomic practices in the area are followed for soil preparation, planting, fertilization and pest con-trol. Each plot is sown with seed segregating for the presence of a single transgenic insertion event. A Taqman transgene copy number assay is used on leaf samples to differentiate the transgenics from null-segregant control plants. Plants that have been genotyped in this manner are also scored for a range of phenotypes related to drought-tolerance, growth and yield. These phenotypes include plant height, grain weight per plant, grain number per plant, ear number per plant, above ground dry-weight, leaf conductance to water vapor, leaf $CO_2$ uptake, leaf chlorophyll content, photosynthesis-related chlorophyll fluorescence parameters, water use efficiency, leaf water potential, leaf relative water content, stem sap flow rate, stem hydraulic conductivity, leaf temperature, leaf reflectance, leaf light absorptance, leaf area, days to flowering, anthesis-silking interval, duration of grain fill, osmotic potential, osmotic adjustment, root size, leaf extension rate, leaf angle, leaf rolling and survival. All measurements are made with commercially available instrumentation for field physiology, using the standard protocols provided by the manufacturers. Individual plants are used as the replicate unit per event.

In order to test non-segregating transgenic corn for drought tolerance under rain-free conditions, managed-drought stress at a single location or multiple locations is used. Crop water availability is controlled by drip tape or overhead irrigation at a location which has less than 10 cm rainfall and minimum temperatures greater than 5° C. expected during an average 5 month season, or a location with expected in-season precipitation intercepted by an automated "rain-out shelter" which retracts to provide open field conditions when not required. Standard agronomic practices in the area are followed for soil preparation, planting, fertilization and pest control. Trial layout is designed to pair a plot containing a non-segregating transgenic event with an adjacent plot of null-segregant controls. A null segregant is progeny (or lines derived from the progeny) of a transgenic plant that does not contain the transgene due to Mendelian segregation. Additional replicated paired plots for a particular event are distributed around the trial. A range of phenotypes related to drought-tolerance, growth and yield are scored in the paired plots and estimated at the plot level. When the measurement technique could only be applied to individual plants, these are selected at random each time from within the plot. These pheno-types include plant height, grain weight per plant, grain number per plant, ear number per plant, above ground dry-weight, leaf conductance to water vapor, leaf $CO_2$ uptake, leaf chlorophyll content, photosynthesis-related chlorophyll fluorescence parameters, water use efficiency, leaf water potential, leaf relative water content, stem sap flow rate, stem hydraulic conductivity, leaf temperature, leaf reflectance, leaf light absorptance, leaf area, days to flowering, anthesis-silking interval, duration of grain fill, osmotic potential, osmotic adjustment, root size, leaf extension rate, leaf angle, leaf rolling and survival. All measurements are made with commercially available instrumentation for field physiology, using the standard protocols provided by the manufacturers. Individual plots are used as the replicate unit per event.

To perform multi-location testing of transgenic corn for drought tolerance and yield, five to twenty locations encompassing major corn growing regions are selected. These are widely distributed to provide a range of expected crop water availabilities based on average temperature, humidity, precipitation and soil type. Crop water availability is not modified beyond standard agronomic practices. Trial layout is designed to pair a plot containing a non-segregating transgenic event with an adjacent plot of null-segregant controls. A range of pheno-types related to drought-tolerance, growth and yield are scored in the paired plots and estimated at the plot level. When the measurement technique could only be applied to individual plants, these are selected at random each time from within the plot. These phenotypes included plant height, grain weight per plant, grain number per plant, ear number per plant, above ground dry-weight, leaf conductance to water vapor, leaf $CO_2$ uptake, leaf chlorophyll content, photo-synthesis-related chlorophyll fluorescence parameters, water use efficiency, leaf water potential, leaf relative water content, stem sap flow rate, stem hydraulic conductivity, leaf temperature, leaf reflectance, leaf light absorptance, leaf area, days to flowering, anthesis-silking interval, duration of grain fill, osmotic potential, osmotic adjustment, root size, leaf extension rate, leaf angle, leaf rolling and survival. All measurements are made with commercially available instru-mentation for field physiology, using the standard protocols provided by the manufacturers. Individual plots are used as the replicate unit per event.

The invention claimed is:

1. A transgenic plant cell or a transgenic plant transformed with an expression cassette comprising an isolated polynucleotide encoding a polypeptide having a sequence comprising amino acids 1 to 91 of SEQ ID NO:20.

2. An isolated polynucleotide having a sequence selected from the group consisting of
(a) a polynucleotide having a sequence comprising nucleotides 248 to 520 of SEQ ID NO:19; and
(b) a polynucleotide which encodes a polypeptide having a sequence comprising amino acids 1 to 91 of SEQ ID NO:20.

3. An isolated polypeptide having a sequence comprising amino acids 1 to 91 of SEQ ID NO:20.

4. A method of producing a transgenic plant comprising the steps of:
(a) introducing into a plant cell an expression vector comprising at least one polynucleotide having a sequence selected from the group consisting of (i) a polynucleotide having a sequence comprising nucleotides 248 to 520 of SEQ ID NO:19 and (ii) a polynucleotide which encodes a polypeptide having a sequence comprising amino acids 1 to 91 of SEQ ID NO:20; and
(b) generating from the plant cell a transgenic plant that expresses the polynucleotide.

5. A method of increasing a plant's growth or yield under normal or water-limited conditions or increasing a plant's tolerance to an environmental stress comprising the steps of: (a) inserting into an expression vector a polynucleotide having a sequence selected from the group consisting of (i) a polynucleotide having a sequence comprising nucleotides 248 to 520 of SEQ ID NO:19 and (ii) a polynucleotide which encodes a polypeptide having a sequence comprising amino acids 1 to 91 of SEQ ID NO:20; and (b) introducing the expression vector into the plant.

* * * * *

SEQUENCE LISTING

```
<160> NUMBER OF SEQ ID NOS: 54

<210> SEQ ID NO 1
<211> LENGTH: 1350
<212> TYPE: DNA
<213> ORGANISM: Physcomitrella patens
<220> FEATURE:
<221> NAME/KEY: CDS
<222> LOCATION: (133)..(1101)

<400> SEQUENCE: 1
atcccgggtg tctctcagtt gccatcgtgg agtcagcgag cacgcttttg tgtatctctg      60
cgcggagttt tcttttggaa gcggctaaag tatatcagcg tggtcgatag ggctgactcg     120
ttttctgtag tc atg gct ggc aga gga gga aag aga ttc tcc ttt gga gga    171
              Met Ala Gly Arg Gly Gly Lys Arg Phe Ser Phe Gly Gly
                1               5                   10 atg ggt agt gca gct gct ttc gga ggt gga gag ggt agc agg gtt gtg      219
Met Gly Ser Ala Ala Ala Phe Gly Gly Gly Glu Gly Ser Arg Val Val
     15                  20                  25 gga gat ggt tct act gct cca gag tca tcg tcc aga cag cat gaa tac      267
Gly Asp Gly Ser Thr Ala Pro Glu Ser Ser Ser Arg Gln His Glu Tyr
 30                  35                  40                  45 cga caa cca gcg gct act aga gag cgt ttt ggg gag gta gaa cac gaa      315
Arg Gln Pro Ala Ala Thr Arg Glu Arg Phe Gly Glu Val Glu His Glu
                 50                  55                  60 gat gaa gat gta tca ggt tca ggt gct ggt ggt agt caa gtg agg cca      363
Asp Glu Asp Val Ser Gly Ser Gly Ala Gly Gly Ser Gln Val Arg Pro
```

|   |   |   | 65 |   |   | 70 |   |   |   | 75 |   |   |   |   |
|---|---|---|---|---|---|---|---|---|---|---|---|---|---|---|
| tca | ggg | ggt | gga | ggt | cga | ggt | cga | ggc | cga | ggc | cga | ggt | cga | ggg | aga | 411 |
| Ser | Gly | Gly | Gly | Gly | Arg | Gly | Arg | Gly | Arg | Gly | Arg | Gly | Arg | Gly | Arg |
|   |   | 80 |   |   |   | 85 |   |   |   | 90 |   |   |   |   |

```
tca ggg ggt gga ggt cga ggt cga ggc cga ggc cga ggt cga ggg aga      411
Ser Gly Gly Gly Gly Arg Gly Arg Gly Arg Gly Arg Gly Arg Gly Arg
        80                  85                  90 agg gat gct atg gat tca acg gaa gct ctg ggg aga tgc atg act gcg      459
Arg Asp Ala Met Asp Ser Thr Glu Ala Leu Gly Arg Cys Met Thr Ala
        95                  100                 105 att cta gga cat cga gcc tcg gac tat gga cta gaa atg cag aac gat      507
Ile Leu Gly His Arg Ala Ser Asp Tyr Gly Leu Glu Met Gln Asn Asp
110                 115                 120                 125 ggt ttc gtc tta gta gct gat ctt tta aaa cta agc aag aat act gca      555
Gly Phe Val Leu Val Ala Asp Leu Leu Lys Leu Ser Lys Asn Thr Ala
                130                 135                 140 gct ggt att cca tta agt tct cac agc gtg gaa gat gtg cgc aag gct      603
Ala Gly Ile Pro Leu Ser Ser His Ser Val Glu Asp Val Arg Lys Ala
                145                 150                 155 gtt gca agg gat ggg aaa cga cgt ttt gga cta aaa gaa gag gat ggg      651
Val Ala Arg Asp Gly Lys Arg Arg Phe Gly Leu Lys Glu Glu Asp Gly
        160                 165                 170 cat ctt tac atc agg gca aat caa ggt cat agt atc agg acc gtg gaa      699
His Leu Tyr Ile Arg Ala Asn Gln Gly His Ser Ile Arg Thr Val Glu
        175                 180                 185 tct gga caa ctt ttg tcg ttg gtt aca tct cct tca caa att cca gtc      747
Ser Gly Gln Leu Leu Ser Leu Val Thr Ser Pro Ser Gln Ile Pro Val
190                 195                 200                 205 tgt gtt cat ggc acg tac gag aga ttt atg gac agt atc tgg caa gaa      795
Cys Val His Gly Thr Tyr Glu Arg Phe Met Asp Ser Ile Trp Gln Glu
                210                 215                 220 ggg tta aaa cgc atg aat cga aat cat gtt cat ttt gct act ggc ttg      843
Gly Leu Lys Arg Met Asn Arg Asn His Val His Phe Ala Thr Gly Leu
        225                 230                 235 cct gaa cag gac ggt gtc atc agt ggg atg cgt gga tct gct cag gtt      891
Pro Glu Gln Asp Gly Val Ile Ser Gly Met Arg Gly Ser Ala Gln Val
        240                 245                 250 ctc ata tac ctg gat gtg gag aag gct atg gag gat gga atg aag ctc      939
Leu Ile Tyr Leu Asp Val Glu Lys Ala Met Glu Asp Gly Met Lys Leu
        255                 260                 265 tac gtt tca gat aac aaa gtc gtt ctc acc gaa ggc ttt gat ggg gtg      987
Tyr Val Ser Asp Asn Lys Val Val Leu Thr Glu Gly Phe Asp Gly Val
270                 275                 280                 285 gtt ccg act aaa tat ttt aag aat gtc gtc aag aag ttg cct cgt ggc     1035
Val Pro Thr Lys Tyr Phe Lys Asn Val Val Lys Lys Leu Pro Arg Gly
                290                 295                 300 aga gag atg cca ctc cat cca tca agt aat cag cct aag cct cat gag     1083
Arg Glu Met Pro Leu His Pro Ser Ser Asn Gln Pro Lys Pro His Glu
        305                 310                 315 aat act gca gca gat gtc tagaaaacag agaacccaga attggtgatc             1131
Asn Thr Ala Ala Asp Val
        320 aaagaggatg cctatcagaa tgccagcagc tcccttgctt aatgtctgat tatttctagt    1191 ggttttgtg gaatcaattg caccaaatgc cctgaactta ttggaagaat acaccaactt     1251 tctggattta gttatgtaaa tgggagcaga tcgttgaaac tcatgttaca ttatcgacct    1311 gatttattag gagagacagc tatcaaccat agagctcgc                           1350

<210> SEQ ID NO 2
<211> LENGTH: 323
<212> TYPE: PRT
<213> ORGANISM: Physcomitrella patens
```

-continued

<400> SEQUENCE: 2

| | | | | | | | | | | | | | | |
|---|---|---|---|---|---|---|---|---|---|---|---|---|---|---|
| Met | Ala | Gly | Arg | Gly | Gly | Lys | Arg | Phe | Ser | Phe | Gly | Gly | Met | Gly | Ser |
| 1 | | | | 5 | | | | | 10 | | | | | 15 | |
| Ala | Ala | Ala | Phe | Gly | Gly | Gly | Glu | Gly | Ser | Arg | Val | Val | Gly | Asp | Gly |
| | | | 20 | | | | | 25 | | | | | 30 | | |
| Ser | Thr | Ala | Pro | Glu | Ser | Ser | Ser | Arg | Gln | His | Glu | Tyr | Arg | Gln | Pro |
| | | 35 | | | | | 40 | | | | | 45 | | | |
| Ala | Ala | Thr | Arg | Glu | Arg | Phe | Gly | Glu | Val | Glu | His | Glu | Asp | Glu | Asp |
| | 50 | | | | | 55 | | | | | 60 | | | | |
| Val | Ser | Gly | Ser | Gly | Ala | Gly | Gly | Ser | Gln | Val | Arg | Pro | Ser | Gly | Gly |
| 65 | | | | | 70 | | | | | 75 | | | | | 80 |
| Gly | Gly | Arg | Gly | Arg | Gly | Arg | Gly | Arg | Gly | Arg | Arg | Asp | Ala |
| | | | | 85 | | | | | 90 | | | | | 95 |
| Met | Asp | Ser | Thr | Glu | Ala | Leu | Gly | Arg | Cys | Met | Thr | Ala | Ile | Leu | Gly |
| | | | 100 | | | | | 105 | | | | | 110 | | |
| His | Arg | Ala | Ser | Asp | Tyr | Gly | Leu | Glu | Met | Gln | Asn | Asp | Gly | Phe | Val |
| | | | 115 | | | | | 120 | | | | | 125 | | |
| Leu | Val | Ala | Asp | Leu | Leu | Lys | Leu | Ser | Lys | Asn | Thr | Ala | Ala | Gly | Ile |
| | 130 | | | | | 135 | | | | | 140 | | | | |
| Pro | Leu | Ser | Ser | His | Ser | Val | Glu | Asp | Val | Arg | Lys | Ala | Val | Ala | Arg |
| 145 | | | | | 150 | | | | | 155 | | | | | 160 |
| Asp | Gly | Lys | Arg | Arg | Phe | Gly | Leu | Lys | Glu | Glu | Asp | Gly | His | Leu | Tyr |
| | | | | 165 | | | | | 170 | | | | | 175 | |
| Ile | Arg | Ala | Asn | Gln | Gly | His | Ser | Ile | Arg | Thr | Val | Glu | Ser | Gly | Gln |
| | | | 180 | | | | | 185 | | | | | 190 | | |
| Leu | Leu | Ser | Leu | Val | Thr | Ser | Pro | Ser | Gln | Ile | Pro | Val | Cys | Val | His |
| | | 195 | | | | | 200 | | | | | 205 | | | |
| Gly | Thr | Tyr | Glu | Arg | Phe | Met | Asp | Ser | Ile | Trp | Gln | Glu | Gly | Leu | Lys |
| | 210 | | | | | 215 | | | | | 220 | | | | |
| Arg | Met | Asn | Arg | Asn | His | Val | His | Phe | Ala | Thr | Gly | Leu | Pro | Glu | Gln |
| 225 | | | | | 230 | | | | | 235 | | | | | 240 |
| Asp | Gly | Val | Ile | Ser | Gly | Met | Arg | Gly | Ser | Ala | Gln | Val | Leu | Ile | Tyr |
| | | | | 245 | | | | | 250 | | | | | 255 | |
| Leu | Asp | Val | Glu | Lys | Ala | Met | Glu | Asp | Gly | Met | Lys | Leu | Tyr | Val | Ser |
| | | | 260 | | | | | 265 | | | | | 270 | | |
| Asp | Asn | Lys | Val | Val | Leu | Thr | Glu | Gly | Phe | Asp | Gly | Val | Val | Pro | Thr |
| | | 275 | | | | | 280 | | | | | 285 | | | |
| Lys | Tyr | Phe | Lys | Asn | Val | Val | Lys | Lys | Leu | Pro | Arg | Gly | Arg | Glu | Met |
| | 290 | | | | | 295 | | | | | 300 | | | | |
| Pro | Leu | His | Pro | Ser | Ser | Asn | Gln | Pro | Lys | Pro | His | Glu | Asn | Thr | Ala |
| 305 | | | | | 310 | | | | | 315 | | | | | 320 |
| Ala | Asp | Val | | | | | | | | | | | | | |

<210> SEQ ID NO 3
<211> LENGTH: 980
<212> TYPE: DNA
<213> ORGANISM: Physcomitrella patens
<220> FEATURE:
<221> NAME/KEY: CDS
<222> LOCATION: (37)..(918)

<400> SEQUENCE: 3

```
gcgttaacgg tctgatctcg ttacctcaag tttcaa atg gat cag tat gag aaa      54
                                      Met Asp Gln Tyr Glu Lys
                                       1               5 gtg gag aag att gga gag ggc aca tac ggt gtc gta tac aag gcc cgg    102
```

```
                Val Glu Lys Ile Gly Glu Gly Thr Tyr Gly Val Val Tyr Lys Ala Arg
                             10                  15                  20 gat cgc ctc act aat gaa act att gct ctg aaa aaa ata cgg ctg gag         150
Asp Arg Leu Thr Asn Glu Thr Ile Ala Leu Lys Lys Ile Arg Leu Glu
             25                  30                  35 caa gaa gat gaa ggt gtt cca agc acc gcc att cga gaa att tca ctc         198
Gln Glu Asp Glu Gly Val Pro Ser Thr Ala Ile Arg Glu Ile Ser Leu
 40                  45                  50 ctg aaa gaa atg cac cat ggc aac atc gtt cgg cta caa gat gtg gtg         246
Leu Lys Glu Met His His Gly Asn Ile Val Arg Leu Gln Asp Val Val
 55                  60                  65                  70 cat agt gag aaa cga ttg tac ttg gtt ttt gaa tac ctg gac ctc gac         294
His Ser Glu Lys Arg Leu Tyr Leu Val Phe Glu Tyr Leu Asp Leu Asp
                 75                  80                  85 cta aag aag cat atg gac acc tgc ccg gac ctt gcc aaa gac cca cgc         342
Leu Lys Lys His Met Asp Thr Cys Pro Asp Leu Ala Lys Asp Pro Arg
                 90                  95                 100 ttg atc aag acc ttt cta tac cag atc ttg cgg ggc att gct tat tgc         390
Leu Ile Lys Thr Phe Leu Tyr Gln Ile Leu Arg Gly Ile Ala Tyr Cys
                105                 110                 115 cat gcc cac agg gtc ctt cac aga gac ttg aaa cct cag aat ctt ttg         438
His Ala His Arg Val Leu His Arg Asp Leu Lys Pro Gln Asn Leu Leu
120                 125                 130 att gat cga cgt acc aat gct ttg aag cta gct gac ttt ggc ctt gca         486
Ile Asp Arg Arg Thr Asn Ala Leu Lys Leu Ala Asp Phe Gly Leu Ala
135                 140                 145                 150 cga gct ttt ggt att cct gtc agg aca ttc act cat gag gtg gta aca         534
Arg Ala Phe Gly Ile Pro Val Arg Thr Phe Thr His Glu Val Val Thr
                155                 160                 165 ttg tgg tac aga gca cca gaa att ctc tta ggt tct cgc cac tac tct         582
Leu Trp Tyr Arg Ala Pro Glu Ile Leu Leu Gly Ser Arg His Tyr Ser
                170                 175                 180 aca cct gta gat gtg tgg tct gta gga tgc att ttc gct gag atg gtc         630
Thr Pro Val Asp Val Trp Ser Val Gly Cys Ile Phe Ala Glu Met Val
                185                 190                 195 aat caa cgg ccc ttg ttt cca gga gat tct gag ata gat gag ctg ttc         678
Asn Gln Arg Pro Leu Phe Pro Gly Asp Ser Glu Ile Asp Glu Leu Phe
200                 205                 210 aaa atc ttc agg aca ctt ggc act cca aat gaa gaa gtt tgg cca ggt         726
Lys Ile Phe Arg Thr Leu Gly Thr Pro Asn Glu Glu Val Trp Pro Gly
215                 220                 225                 230 gta act tca ttg cca gat ttc aag act gct ttt cca aag tgg cct ccg         774
Val Thr Ser Leu Pro Asp Phe Lys Thr Ala Phe Pro Lys Trp Pro Pro
                235                 240                 245 aag cct ttg tca tca gtc gta cct agc ctt gag cca gca ggc atc gac         822
Lys Pro Leu Ser Ser Val Val Pro Ser Leu Glu Pro Ala Gly Ile Asp
                250                 255                 260 ttg cta gag aaa atg ctg aca ctt gag cca agt cga cgg gta aca gca         870
Leu Leu Glu Lys Met Leu Thr Leu Glu Pro Ser Arg Arg Val Thr Ala
                265                 270                 275 cga aat gca ttg gaa cac gag tat ttc aag gat atc ggt ctt gta ccc         918
Arg Asn Ala Leu Glu His Glu Tyr Phe Lys Asp Ile Gly Leu Val Pro
280                 285                 290 tgattcttgt atgcaacttg tatgatactg tctagggtat ccctgcaagg cagcgagctc       978
gc                                                                      980

<210> SEQ ID NO 4
<211> LENGTH: 294
<212> TYPE: PRT
<213> ORGANISM: Physcomitrella patens
```

<400> SEQUENCE: 4

```
Met Asp Gln Tyr Glu Lys Val Glu Lys Ile Gly Glu Gly Thr Tyr Gly
1               5                   10                  15

Val Val Tyr Lys Ala Arg Asp Arg Leu Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met His His Gly Asn Ile Val
50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Thr Cys Pro Asp
                85                  90                  95

Leu Ala Lys Asp Pro Arg Leu Ile Lys Thr Phe Leu Tyr Gln Ile Leu
            100                 105                 110

Arg Gly Ile Ala Tyr Cys His Ala His Arg Val Leu His Arg Asp Leu
        115                 120                 125

Lys Pro Gln Asn Leu Leu Ile Asp Arg Thr Asn Ala Leu Lys Leu
130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Gln Arg Pro Leu Phe Pro Gly Asp Ser
        195                 200                 205

Glu Ile Asp Glu Leu Phe Lys Ile Phe Arg Thr Leu Gly Thr Pro Asn
210                 215                 220

Glu Glu Val Trp Pro Gly Val Thr Ser Leu Pro Asp Phe Lys Thr Ala
225                 230                 235                 240

Phe Pro Lys Trp Pro Pro Lys Pro Leu Ser Ser Val Val Pro Ser Leu
                245                 250                 255

Glu Pro Ala Gly Ile Asp Leu Leu Glu Lys Met Leu Thr Leu Glu Pro
            260                 265                 270

Ser Arg Arg Val Thr Ala Arg Asn Ala Leu Glu His Glu Tyr Phe Lys
        275                 280                 285

Asp Ile Gly Leu Val Pro
    290
```

<210> SEQ ID NO 5
<211> LENGTH: 2497
<212> TYPE: DNA
<213> ORGANISM: Physcomitrella patens
<220> FEATURE:
<221> NAME/KEY: CDS
<222> LOCATION: (144)..(2081)

<400> SEQUENCE: 5

```
gcgttaacga gctagtatct gttcctccat aacagaatgg gtaaaacaag gtgacgtgtc      60 atgcaggggac tctccttgcg tcgaagtctc acaagcaagt ccacgctgaa ttatttgaat    120
ttgatacaac aggcgtaaat aag atg aaa aac gat gag gcc cat agc cac gat    173
                          Met Lys Asn Asp Glu Ala His Ser His Asp
                          1               5                   10 aac cac ata tcc ggc ggt atg aag gct gcc gaa gca ttt gtg gaa ggt      221
```

```
Asn His Ile Ser Gly Gly Met Lys Ala Ala Glu Ala Phe Val Glu Gly
            15                  20                  25 gca tac gag ggt gac gag gag gaa gag ttt gag aaa gac cga aat tct        269
Ala Tyr Glu Gly Asp Glu Glu Glu Glu Phe Glu Lys Asp Arg Asn Ser
            30                  35                  40 cgc agt atc cgg act ggg cgt cat tcc gag gga tca cgt agt ggt cag        317
Arg Ser Ile Arg Thr Gly Arg His Ser Glu Gly Ser Arg Ser Gly Gln
            45                  50                  55 ctt ttt cca gat gaa cgg cac tca ggg tct agt gcg ggc gat gca tct        365
Leu Phe Pro Asp Glu Arg His Ser Gly Ser Ser Ala Gly Asp Ala Ser
        60                  65                  70 gct aca tat tat gag ctc cac tcc aac atg gct tgc aag tct ggc aca        413
Ala Thr Tyr Tyr Glu Leu His Ser Asn Met Ala Cys Lys Ser Gly Thr
75                  80                  85                  90 gca gca ggg cat atc ttt gat gag gaa ggt gtt gga gat tac gcc agt        461
Ala Ala Gly His Ile Phe Asp Glu Glu Gly Val Gly Asp Tyr Ala Ser
                95                  100                 105 gat cca ggt gtt tac cat gat gac tcc tgt ctg aac cca ttg gaa aaa        509
Asp Pro Gly Val Tyr His Asp Asp Ser Cys Leu Asn Pro Leu Glu Lys
            110                 115                 120 gac ttg gag gat gat caa ctc tgc cat ggt gaa gat gca gat cac ttc        557
Asp Leu Glu Asp Asp Gln Leu Cys His Gly Glu Asp Ala Asp His Phe
        125                 130                 135 ctc aag aag gcc cgt agt gaa gga ggt ctg tac gaa ctg ggg ctt ata        605
Leu Lys Lys Ala Arg Ser Glu Gly Gly Leu Tyr Glu Leu Gly Leu Ile
        140                 145                 150 tct cag caa ctt aca ggt caa tca act gaa caa gat ttg gca cat cat        653
Ser Gln Gln Leu Thr Gly Gln Ser Thr Glu Gln Asp Leu Ala His His
155                 160                 165                 170 tct caa gga agc cca tca tat caa ggt atc agc aga cag gac tcc tcc        701
Ser Gln Gly Ser Pro Ser Tyr Gln Gly Ile Ser Arg Gln Asp Ser Ser
                175                 180                 185 att cac ttg cca aaa ggt cta gtt gaa ggt ccc cac tca gaa att gat        749
Ile His Leu Pro Lys Gly Leu Val Glu Gly Pro His Ser Glu Ile Asp
            190                 195                 200 caa aga gat gcc aaa gat ctt ttc ttg aat gag agg tct tct gac aaa        797
Gln Arg Asp Ala Lys Asp Leu Phe Leu Asn Glu Arg Ser Ser Asp Lys
        205                 210                 215 gat gtc gat tac tgc aat ggt tcc tca agg ttg gaa ttt gac gca tat        845
Asp Val Asp Tyr Cys Asn Gly Ser Ser Arg Leu Glu Phe Asp Ala Tyr
        220                 225                 230 tat ccc agg agt gat gtt cat aac ccc gag agc ata cgt agt gga tct        893
Tyr Pro Arg Ser Asp Val His Asn Pro Glu Ser Ile Arg Ser Gly Ser
235                 240                 245                 250 ttc tta caa aaa gat gac att gcg gaa ttt gat gct gac aat gtt aag        941
Phe Leu Gln Lys Asp Asp Ile Ala Glu Phe Asp Ala Asp Asn Val Lys
                255                 260                 265 tca cat aat tcg gct gga gtt gat gga gtc cct gat ggt tgc ata tct        989
Ser His Asn Ser Ala Gly Val Asp Gly Val Pro Asp Gly Cys Ile Ser
            270                 275                 280 ggt cac ttt caa gat ttg aac ttg gat tta gtt gct ggg cac gat gag       1037
Gly His Phe Gln Asp Leu Asn Leu Asp Leu Val Ala Gly His Asp Glu
        285                 290                 295 aat gac cac act aag caa gac gcg aga gcg tct gag cta gac cgg cct       1085
Asn Asp His Thr Lys Gln Asp Ala Arg Ala Ser Glu Leu Asp Arg Pro
        300                 305                 310 aat ttg tca agg gtt gag gag tgg att agg agt ata gaa cca act ccc       1133
Asn Leu Ser Arg Val Glu Glu Trp Ile Arg Ser Ile Glu Pro Thr Pro
315                 320                 325                 330 ttc tta gca gat gaa gaa gtt gag ccc aca gct tac tca gat aca gag       1181
```

```
                Phe Leu Ala Asp Glu Val Glu Pro Thr Ala Tyr Ser Asp Thr Glu
                            335                 340                 345 cct tca gca ccg gcc gct tcc ttt ttc cgg gct aga gct cga cct gat          1229
Pro Ser Ala Pro Ala Ala Ser Phe Phe Arg Ala Arg Ala Arg Pro Asp
            350                 355                 360 cag atg cat cta gat gga atc gct ctt gtg gac cgt aga aac cat cag          1277
Gln Met His Leu Asp Gly Ile Ala Leu Val Asp Arg Arg Asn His Gln
            365                 370                 375 gga gag caa ctg ata gat gct gac agt gaa atg gca agc ttt att gct          1325
Gly Glu Gln Leu Ile Asp Ala Asp Ser Glu Met Ala Ser Phe Ile Ala
380                 385                 390 cgg tct gtg aat cca ctt tgt aca gtg gct cat ttc tcg gga gtg gga          1373
Arg Ser Val Asn Pro Leu Cys Thr Val Ala His Phe Ser Gly Val Gly
395                 400                 405                 410 tta aag tta cct cca ccc ctt ggc gcg cac aat aat ttg aaa act ctc          1421
Leu Lys Leu Pro Pro Pro Leu Gly Ala His Asn Asn Leu Lys Thr Leu
                415                 420                 425 aac ctc tct gcc aac gct atc gta cgc atg tta ccc ggg tgt ctt cca          1469
Asn Leu Ser Ala Asn Ala Ile Val Arg Met Leu Pro Gly Cys Leu Pro
            430                 435                 440 aag agc tta cat aca ttg gat ttg tca cga aat aag ata gtt gtg ata          1517
Lys Ser Leu His Thr Leu Asp Leu Ser Arg Asn Lys Ile Val Val Ile
            445                 450                 455 gaa ggg ctc cgt gaa ctc tct cga ctc cgt gtg ctg aac cta tca cat          1565
Glu Gly Leu Arg Glu Leu Ser Arg Leu Arg Val Leu Asn Leu Ser His
            460                 465                 470 aat cga att att cga att gga cat ggt ttg gcg aac tgt act tct ttg          1613
Asn Arg Ile Ile Arg Ile Gly His Gly Leu Ala Asn Cys Thr Ser Leu
475                 480                 485                 490 agg gaa atc tat ttg gct ggt aac aag att agc gag att gag gga cta          1661
Arg Glu Ile Tyr Leu Ala Gly Asn Lys Ile Ser Glu Ile Glu Gly Leu
                495                 500                 505 cat cga cta ctg aaa ctt agc ttc att gat ttg agt ttc aac aaa atc          1709
His Arg Leu Leu Lys Leu Ser Phe Ile Asp Leu Ser Phe Asn Lys Ile
            510                 515                 520 gcc tca gct aaa tct att ggg cag cta gcc gcc aac tac aat tcc ctc          1757
Ala Ser Ala Lys Ser Ile Gly Gln Leu Ala Ala Asn Tyr Asn Ser Leu
            525                 530                 535 cag gca atc aac ctt ttg gga aat cca tta cac agc aac ctt ggt gag          1805
Gln Ala Ile Asn Leu Leu Gly Asn Pro Leu His Ser Asn Leu Gly Glu
            540                 545                 550 gag cca tta cgg aaa ttg atc gtt gga ctt act ccg cat gta gtg tac          1853
Glu Pro Leu Arg Lys Leu Ile Val Gly Leu Thr Pro His Val Val Tyr
555                 560                 565                 570 ctt aac aaa caa gct acg aag gcc gta tct gca cga gat gct tca gtg          1901
Leu Asn Lys Gln Ala Thr Lys Ala Val Ser Ala Arg Asp Ala Ser Val
            575                 580                 585 gat agc gtg gcc aga gct gct ttg gca aat cct agt cac cac act cac          1949
Asp Ser Val Ala Arg Ala Ala Leu Ala Asn Pro Ser His His Thr His
            590                 595                 600 caa cga gga aag acc tct tca caa agc aaa tcc ttc ggc gaa gcg gtg          1997
Gln Arg Gly Lys Thr Ser Ser Gln Ser Lys Ser Phe Gly Glu Ala Val
            605                 610                 615 cgc ctg ccc cat cca ctg ctt cca gcc ccc gtc acc ggg aca aac gga          2045
Arg Leu Pro His Pro Leu Leu Pro Ala Pro Val Thr Gly Thr Asn Gly
            620                 625                 630 ctg gcg aga agt ctg cag cag gtc gta cca atg cac tgaagagtag               2091
Leu Ala Arg Ser Leu Gln Gln Val Val Pro Met His
635                 640                 645 aacgccctct gagctgcctc ctcgacatcg atattctcac agccggcttg ttcatggctc       2151
```

-continued

```
tggggtcact aaggatcacc ctcgtttagc ccatcttcca atgcctccac cagtccagaa    2211
ttttatcaga gccgaggaaa aggtttaatt gacctgacgt ttgcaatatt gttgcagtcg    2271
gagacaagac tagagggagg aagtttggca agtttgtccg tttggtttgg tgttcacaat    2331
atctgcagag ttgtgttagc aacctggtca tttctgtttc agtgtacggt atgctagtgc    2391
tctaaaagtt tgatatgttc atgccataat gaataccctg tgggcatttt cattttaata    2451
ttgctgcctc aattaattga tgagattctc tggcatgagt taacgc                  2497
```

<210> SEQ ID NO 6
<211> LENGTH: 646
<212> TYPE: PRT
<213> ORGANISM: Physcomitrella patens

<400> SEQUENCE: 6

```
Met Lys Asn Asp Glu Ala His Ser His Asp Asn His Ile Ser Gly Gly
1               5                   10                  15

Met Lys Ala Ala Glu Ala Phe Val Glu Gly Ala Tyr Glu Gly Asp Glu
            20                  25                  30

Glu Glu Glu Phe Glu Lys Asp Arg Asn Ser Arg Ser Ile Arg Thr Gly
        35                  40                  45

Arg His Ser Glu Gly Ser Arg Ser Gly Gln Leu Phe Pro Asp Glu Arg
    50                  55                  60

His Ser Gly Ser Ser Ala Gly Asp Ala Ser Ala Thr Tyr Tyr Glu Leu
65                  70                  75                  80

His Ser Asn Met Ala Cys Lys Ser Gly Thr Ala Ala Gly His Ile Phe
                85                  90                  95

Asp Glu Glu Gly Val Gly Asp Tyr Ala Ser Asp Pro Gly Val Tyr His
            100                 105                 110

Asp Asp Ser Cys Leu Asn Pro Leu Glu Lys Asp Leu Glu Asp Asp Gln
        115                 120                 125

Leu Cys His Gly Glu Asp Ala Asp His Phe Leu Lys Lys Ala Arg Ser
    130                 135                 140

Glu Gly Gly Leu Tyr Glu Leu Gly Leu Ile Ser Gln Gln Leu Thr Gly
145                 150                 155                 160

Gln Ser Thr Glu Gln Asp Leu Ala His Ser Gln Gly Ser Pro Ser
                165                 170                 175

Tyr Gln Gly Ile Ser Arg Gln Asp Ser Ser Ile His Leu Pro Lys Gly
            180                 185                 190

Leu Val Glu Gly Pro His Ser Glu Ile Asp Gln Arg Asp Ala Lys Asp
        195                 200                 205

Leu Phe Leu Asn Glu Arg Ser Ser Asp Lys Asp Val Asp Tyr Cys Asn
    210                 215                 220

Gly Ser Ser Arg Leu Glu Phe Asp Ala Tyr Tyr Pro Arg Ser Asp Val
225                 230                 235                 240

His Asn Pro Glu Ser Ile Arg Ser Gly Ser Phe Leu Gln Lys Asp
                245                 250                 255

Ile Ala Glu Phe Asp Ala Asp Asn Val Lys Ser His Asn Ser Ala Gly
            260                 265                 270

Val Asp Gly Val Pro Asp Gly Cys Ile Ser Gly His Phe Gln Asp Leu
        275                 280                 285

Asn Leu Asp Leu Val Ala Gly His Asp Glu Asn Asp His Thr Lys Gln
    290                 295                 300

Asp Ala Arg Ala Ser Glu Leu Asp Arg Pro Asn Leu Ser Arg Val Glu
305                 310                 315                 320
```

Glu Trp Ile Arg Ser Ile Glu Pro Thr Pro Phe Leu Ala Asp Glu Glu
            325                 330                 335

Val Glu Pro Thr Ala Tyr Ser Asp Thr Glu Pro Ser Ala Pro Ala Ala
        340                 345                 350

Ser Phe Phe Arg Ala Arg Ala Arg Pro Asp Gln Met His Leu Asp Gly
            355                 360                 365

Ile Ala Leu Val Asp Arg Arg Asn His Gln Gly Glu Gln Leu Ile Asp
        370                 375                 380

Ala Asp Ser Glu Met Ala Ser Phe Ile Ala Arg Ser Val Asn Pro Leu
385                 390                 395                 400

Cys Thr Val Ala His Phe Ser Gly Val Gly Leu Lys Leu Pro Pro Pro
                405                 410                 415

Leu Gly Ala His Asn Asn Leu Lys Thr Leu Asn Leu Ser Ala Asn Ala
            420                 425                 430

Ile Val Arg Met Leu Pro Gly Cys Leu Pro Lys Ser Leu His Thr Leu
            435                 440                 445

Asp Leu Ser Arg Asn Lys Ile Val Ile Glu Gly Leu Arg Glu Leu
        450                 455                 460

Ser Arg Leu Arg Val Leu Asn Leu Ser His Asn Arg Ile Ile Arg Ile
465                 470                 475                 480

Gly His Gly Leu Ala Asn Cys Thr Ser Leu Arg Glu Ile Tyr Leu Ala
                485                 490                 495

Gly Asn Lys Ile Ser Glu Ile Glu Gly Leu His Arg Leu Leu Lys Leu
            500                 505                 510

Ser Phe Ile Asp Leu Ser Phe Asn Lys Ile Ala Ser Ala Lys Ser Ile
        515                 520                 525

Gly Gln Leu Ala Ala Asn Tyr Asn Ser Leu Gln Ala Ile Asn Leu Leu
        530                 535                 540

Gly Asn Pro Leu His Ser Asn Leu Gly Glu Glu Pro Leu Arg Lys Leu
545                 550                 555                 560

Ile Val Gly Leu Thr Pro His Val Val Tyr Leu Asn Lys Gln Ala Thr
                565                 570                 575

Lys Ala Val Ser Ala Arg Asp Ala Ser Val Asp Ser Val Ala Arg Ala
            580                 585                 590

Ala Leu Ala Asn Pro Ser His His Thr His Gln Arg Gly Lys Thr Ser
            595                 600                 605

Ser Gln Ser Lys Ser Phe Gly Glu Ala Val Arg Leu Pro His Pro Leu
        610                 615                 620

Leu Pro Ala Pro Val Thr Gly Thr Asn Gly Leu Ala Arg Ser Leu Gln
625                 630                 635                 640

Gln Val Val Pro Met His
                645

<210> SEQ ID NO 7
<211> LENGTH: 944
<212> TYPE: DNA
<213> ORGANISM: Physcomitrella patens
<220> FEATURE:
<221> NAME/KEY: CDS
<222> LOCATION: (55)..(693)

<400> SEQUENCE: 7
gcgatatcct cccttgcact gatccttact caccctcagt cgggtcagtg cgca atg    57
                                                              Met
                                                              1 gcc ggt gac gat gag aag gat gtg cgc gag gta gag gag gcc act tcc   105

```
                Ala Gly Asp Asp Glu Lys Asp Val Arg Glu Val Glu Glu Ala Thr Ser
                                  5                   10                  15 tcg gga gcc act gcg gag gga tcc gac gaa gtc tcg aag gct ggt gag         153
Ser Gly Ala Thr Ala Glu Gly Ser Asp Glu Val Ser Lys Ala Gly Glu
            20                  25                  30 gaa gag gat act ggt gct cag atc gct cct atc gtg acg ctg cag gaa         201
Glu Glu Asp Thr Gly Ala Gln Ile Ala Pro Ile Val Thr Leu Gln Glu
 35                  40                  45 gtt gcc gtt atc acc ggc gag gag aat gag gac gtg cta att gat atg         249
Val Ala Val Ile Thr Gly Glu Glu Asn Glu Asp Val Leu Ile Asp Met
 50                  55                  60                  65 aag gct aag ctg tat cga ttt gat aag gag gga aca cag tgg aaa gag         297
Lys Ala Lys Leu Tyr Arg Phe Asp Lys Glu Gly Thr Gln Trp Lys Glu
                 70                  75                  80 aga ggt gtt ggt cag gtg aag atc ctg gag cac aag aca act gga aag         345
Arg Gly Val Gly Gln Val Lys Ile Leu Glu His Lys Thr Thr Gly Lys
             85                  90                  95 gtt cga ttg cta atg cga cag aac agg acc ctt aag atc tgt gcc aac         393
Val Arg Leu Leu Met Arg Gln Asn Arg Thr Leu Lys Ile Cys Ala Asn
         100                 105                 110 cac atg gtc tcg tca tct acg caa ctg caa gag cac gct ggt agc gat         441
His Met Val Ser Ser Ser Thr Gln Leu Gln Glu His Ala Gly Ser Asp
    115                 120                 125 aag act tgg gtc tgg cat gct cgg gat tac tca gat ggt gaa tta aaa         489
Lys Thr Trp Val Trp His Ala Arg Asp Tyr Ser Asp Gly Glu Leu Lys
130                 135                 140                 145 gag gag ctt ttc tgc atg cga ttt ggc agc gtt gaa agc gct caa aaa         537
Glu Glu Leu Phe Cys Met Arg Phe Gly Ser Val Glu Ser Ala Gln Lys
                150                 155                 160 ttc aag gat gtg tac gag gcc gcc caa gaa aag gca tcc agc aag aca         585
Phe Lys Asp Val Tyr Glu Ala Ala Gln Glu Lys Ala Ser Ser Lys Thr
            165                 170                 175 gag gag aag gac gaa gag gct gat gag gct gca gat ctt ttg gat aag         633
Glu Glu Lys Asp Glu Glu Ala Asp Glu Ala Ala Asp Leu Leu Asp Lys
        180                 185                 190 ttg aag gtg ggc tca aaa gcc gag aag gct gat gca cct gaa gag gcc         681
Leu Lys Val Gly Ser Lys Ala Glu Lys Ala Asp Ala Pro Glu Glu Ala
    195                 200                 205 aag act gaa aac tagggtgtg attaacatgt gcttgagttg atgttaggta              733
Lys Thr Glu Asn
210 gtcgatcgtg ggttacccgg gctacatgat acagtgtttt gctaacccttt tagcagggtc      793 ttagtgtggg atgtttccct ccaagttcaa tagctcaatc gtctcgacct gttgtttaga       853 gttaattagt atgacatcag ttgcttttaa atgcctgttc tactacttct agcagcatgt       913 attggatcac ttgctaggtg ctcgagctcg c                                      944

<210> SEQ ID NO 8
<211> LENGTH: 213
<212> TYPE: PRT
<213> ORGANISM: Physcomitrella patens

<400> SEQUENCE: 8

Met Ala Gly Asp Asp Glu Lys Asp Val Arg Glu Val Glu Glu Ala Thr
 1               5                  10                  15

Ser Ser Gly Ala Thr Ala Glu Gly Ser Asp Glu Val Ser Lys Ala Gly
             20                  25                  30

Glu Glu Glu Asp Thr Gly Ala Gln Ile Ala Pro Ile Val Thr Leu Gln
         35                  40                  45
```

```
Glu Val Ala Val Ile Thr Gly Glu Glu Asn Glu Asp Val Leu Ile Asp
     50                  55                  60
Met Lys Ala Lys Leu Tyr Arg Phe Asp Lys Glu Gly Thr Gln Trp Lys
 65                  70                  75                  80
Glu Arg Gly Val Gly Gln Val Lys Ile Leu Glu His Lys Thr Thr Gly
                 85                  90                  95
Lys Val Arg Leu Leu Met Arg Gln Asn Arg Thr Leu Lys Ile Cys Ala
            100                 105                 110
Asn His Met Val Ser Ser Thr Gln Leu Gln Glu His Ala Gly Ser
        115                 120                 125
Asp Lys Thr Trp Val Trp His Ala Arg Asp Tyr Ser Asp Gly Glu Leu
    130                 135                 140
Lys Glu Glu Leu Phe Cys Met Arg Phe Gly Ser Val Glu Ser Ala Gln
145                 150                 155                 160
Lys Phe Lys Asp Val Tyr Glu Ala Ala Gln Glu Lys Ala Ser Ser Lys
                165                 170                 175
Thr Glu Glu Lys Asp Glu Ala Asp Glu Ala Ala Asp Leu Leu Asp
            180                 185                 190
Lys Leu Lys Val Gly Ser Lys Ala Glu Lys Ala Asp Ala Pro Glu Glu
        195                 200                 205
Ala Lys Thr Glu Asn
    210

<210> SEQ ID NO 9
<211> LENGTH: 1772
<212> TYPE: DNA
<213> ORGANISM: Physcomitrella patens
<220> FEATURE:
<221> NAME/KEY: CDS
<222> LOCATION: (47)..(1516)

<400> SEQUENCE: 9
atggcgcgcc ttgtggacga ctgtgaatga gtcgaatcgc accatc atg atc acg          55
                                                  Met Ile Thr
                                                    1 tgt agg gtt tgg gtt ggt ttg ggg ccg gtg agc cct tct ttg att ctt        103
Cys Arg Val Trp Val Gly Leu Gly Pro Val Ser Pro Ser Leu Ile Leu
      5                  10                  15 ctg ccc tcg aag agt aac gga gaa tgc gtc cta agt gca aga aaa gct        151
Leu Pro Ser Lys Ser Asn Gly Glu Cys Val Leu Ser Ala Arg Lys Ala
 20                  25                  30                  35 gat tgg gga tta ctg agc caa gtg caa tgc caa cgc ttt cga tgt cta        199
Asp Trp Gly Leu Leu Ser Gln Val Gln Cys Gln Arg Phe Arg Cys Leu
             40                  45                  50 tct tca gaa tat aag ggt cat aat ctt aaa ctt aga aga cgt agc cgt        247
Ser Ser Glu Tyr Lys Gly His Asn Leu Lys Leu Arg Arg Arg Ser Arg
         55                  60                  65 gtc tca gct tcc aac aga gaa aac ggt agt tta aat ggg cgt ttc cag        295
Val Ser Ala Ser Asn Arg Glu Asn Gly Ser Leu Asn Gly Arg Phe Gln
     70                  75                  80 gaa tca ctg agt caa gag aat ggg tat ccg gca cca act gaa ggg act        343
Glu Ser Leu Ser Gln Glu Asn Gly Tyr Pro Ala Pro Thr Glu Gly Thr
 85                  90                  95 gat cct cac act ttc tcc acg gcg atg gac tcc tta gct att aaa gca        391
Asp Pro His Thr Phe Ser Thr Ala Met Asp Ser Leu Ala Ile Lys Ala
100                 105                 110                 115 gag gaa gct tac aat gac gta cag gat tct ttt gcc aag agt agt aaa        439
Glu Glu Ala Tyr Asn Asp Val Gln Asp Ser Phe Ala Lys Ser Ser Lys
                120                 125                 130
```

```
                                                -continued caa cgg agc tta tct ggc tgc gct tct atc aaa gtg ttc ggt gtc ggg     487
Gln Arg Ser Leu Ser Gly Cys Ala Ser Ile Lys Val Phe Gly Val Gly
        135                 140                 145 ggt ggt gga tgc aat gcg gta gac gaa atg gtg agg tca gaa cta ttg     535
Gly Gly Gly Cys Asn Ala Val Asp Glu Met Val Arg Ser Glu Leu Leu
        150                 155                 160 aat gtt gag ttc tgg gcc gtc aat act gac aaa caa gca ttg aac aag     583
Asn Val Glu Phe Trp Ala Val Asn Thr Asp Lys Gln Ala Leu Asn Lys
        165                 170                 175 tcg ctg gct ccc aat aaa att caa att gga cag gac acg aca gcc ggc     631
Ser Leu Ala Pro Asn Lys Ile Gln Ile Gly Gln Asp Thr Thr Ala Gly
180                 185                 190                 195 cgc ggt gca ggt gga aga agt gca acc ggt gag gaa gca gct aca gag     679
Arg Gly Ala Gly Gly Arg Ser Ala Thr Gly Glu Glu Ala Ala Thr Glu
                200                 205                 210 tca ttg gcg gag ctt tcg atg gca ctt gaa ggt gcc gat tta gtc ttc     727
Ser Leu Ala Glu Leu Ser Met Ala Leu Glu Gly Ala Asp Leu Val Phe
            215                 220                 225 atc gcc tcc ggt atg ggt ggc ggt act ggt tca gga gca gct cct gtg     775
Ile Ala Ser Gly Met Gly Gly Gly Thr Gly Ser Gly Ala Ala Pro Val
            230                 235                 240 gtg gct cgg ttg gcg aag gct atg gga gcg tta acg att ggc ata gta     823
Val Ala Arg Leu Ala Lys Ala Met Gly Ala Leu Thr Ile Gly Ile Val
            245                 250                 255 act gaa cct ttc aca ttt gaa ggg ttc acc cga gct cga caa gct agg     871
Thr Glu Pro Phe Thr Phe Glu Gly Phe Thr Arg Ala Arg Gln Ala Arg
260                 265                 270                 275 aaa gcc att gag gac atg cgc cat gcg gct gac act gtg gtt gta gtt     919
Lys Ala Ile Glu Asp Met Arg His Ala Ala Asp Thr Val Val Val Val
                280                 285                 290 cca aat gat cgg ttg ctc cag act gta gca cct gac aca tct atg ctg     967
Pro Asn Asp Arg Leu Leu Gln Thr Val Ala Pro Asp Thr Ser Met Leu
            295                 300                 305 gag gct ttc cat ctt gca gat gac gtc ttg cgg cag gga gtg caa gga     1015
Glu Ala Phe His Leu Ala Asp Asp Val Leu Arg Gln Gly Val Gln Gly
            310                 315                 320 att tca gac atc atc acg ata ccc ggg cta gtc aac gtc gac ttt gcg     1063
Ile Ser Asp Ile Ile Thr Ile Pro Gly Leu Val Asn Val Asp Phe Ala
            325                 330                 335 gat gtg aaa gct atc atg tca aat gca ggg agt gca atg ttg gga atc     1111
Asp Val Lys Ala Ile Met Ser Asn Ala Gly Ser Ala Met Leu Gly Ile
340                 345                 350                 355 ggc gct ggt ttt ggg aag aac cgt gct gag gag gtg gca cgg tca gcc     1159
Gly Ala Gly Phe Gly Lys Asn Arg Ala Glu Glu Val Ala Arg Ser Ala
                360                 365                 370 atc atg tct cct cta ctc cgc tcc gtc tcg aga ccc atg ggt att gtg     1207
Ile Met Ser Pro Leu Leu Arg Ser Val Ser Arg Pro Met Gly Ile Val
            375                 380                 385 tac aat gtg aca ggt ggg agc gac cta act ctt cac gag gtc aac atc     1255
Tyr Asn Val Thr Gly Gly Ser Asp Leu Thr Leu His Glu Val Asn Ile
            390                 395                 400 gct gcc gaa att gtt cat gac atg gct gat cca aac gca aat gtt atc     1303
Ala Ala Glu Ile Val His Asp Met Ala Asp Pro Asn Ala Asn Val Ile
405                 410                 415 ttt ggg gcg gtc att gat gag agc ttt aag ggg atg ata cgt atg act     1351
Phe Gly Ala Val Ile Asp Glu Ser Phe Lys Gly Met Ile Arg Met Thr
420                 425                 430                 435 gtc att gca act gga ttt aga gag cct gga gag gag aag gtc gtt ggt     1399
Val Ile Ala Thr Gly Phe Arg Glu Pro Gly Glu Glu Lys Val Val Gly
                440                 445                 450
```

```
agt gtt cga act gta gac gat gat ata ttc tac tgg gaa cag aat aag     1447
Ser Val Arg Thr Val Asp Asp Asp Ile Phe Tyr Trp Glu Gln Asn Lys
            455                 460                 465 aat agg tcc gac ctt ggc aaa gtg ccg gac gtt ttg cga aga aaa gat     1495
Asn Arg Ser Asp Leu Gly Lys Val Pro Asp Val Leu Arg Arg Lys Asp
    470                 475                 480 cga agg cgt ggc agt ggc agg taactgccgg gtttactctt tatgcgtatg        1546
Arg Arg Arg Gly Ser Gly Arg
    485                 490 ggatttaaag agaagccgct gagcctgaga ttctacagga ggtttgtgga gttgttgtga   1606
tcaagcacca tctttcaata gaatgaagat catggtttta aaaacagtga gcatttctca   1666
atcgatactc tgaaagcctg tactcaaagc tggagctgcg aaaacagtgt acgaagggca   1726
ctgatttgat gacacagcat ctttgtgaat agaaccagga tatcgc                  1772

<210> SEQ ID NO 10
<211> LENGTH: 490
<212> TYPE: PRT
<213> ORGANISM: Physcomitrella patens

<400> SEQUENCE: 10

Met Ile Thr Cys Arg Val Trp Val Gly Leu Gly Pro Val Ser Pro Ser
1               5                   10                  15

Leu Ile Leu Leu Pro Ser Lys Ser Asn Gly Glu Cys Val Leu Ser Ala
            20                  25                  30

Arg Lys Ala Asp Trp Gly Leu Leu Ser Gln Val Gln Cys Gln Arg Phe
        35                  40                  45

Arg Cys Leu Ser Ser Glu Tyr Lys Gly His Asn Leu Lys Leu Arg Arg
    50                  55                  60

Arg Ser Arg Val Ser Ala Ser Asn Arg Glu Asn Gly Ser Leu Asn Gly
65                  70                  75                  80

Arg Phe Gln Glu Ser Leu Ser Gln Glu Asn Gly Tyr Pro Ala Pro Thr
                85                  90                  95

Glu Gly Thr Asp Pro His Thr Phe Ser Thr Ala Met Asp Ser Leu Ala
            100                 105                 110

Ile Lys Ala Glu Glu Ala Tyr Asn Asp Val Gln Asp Ser Phe Ala Lys
        115                 120                 125

Ser Ser Lys Gln Arg Ser Leu Ser Gly Cys Ala Ser Ile Lys Val Phe
    130                 135                 140

Gly Val Gly Gly Gly Cys Asn Ala Val Asp Glu Met Val Arg Ser
145                 150                 155                 160

Glu Leu Leu Asn Val Glu Phe Trp Ala Val Asn Thr Asp Lys Gln Ala
                165                 170                 175

Leu Asn Lys Ser Leu Ala Pro Asn Lys Ile Gln Ile Gly Gln Asp Thr
            180                 185                 190

Thr Ala Gly Arg Gly Ala Gly Gly Arg Ser Ala Thr Gly Glu Glu Ala
        195                 200                 205

Ala Thr Glu Ser Leu Ala Glu Leu Ser Met Ala Leu Glu Gly Ala Asp
    210                 215                 220

Leu Val Phe Ile Ala Ser Gly Met Gly Gly Thr Gly Ser Gly Ala
225                 230                 235                 240

Ala Pro Val Val Ala Arg Leu Ala Lys Ala Met Gly Ala Leu Thr Ile
                245                 250                 255

Gly Ile Val Thr Glu Pro Phe Thr Phe Glu Gly Phe Thr Arg Ala Arg
            260                 265                 270

Gln Ala Arg Lys Ala Ile Glu Asp Met Arg His Ala Ala Asp Thr Val
```

```
                275                 280                 285
Val Val Val Pro Asn Asp Arg Leu Leu Gln Thr Val Ala Pro Asp Thr
        290                 295                 300

Ser Met Leu Glu Ala Phe His Leu Ala Asp Asp Val Leu Arg Gln Gly
305                 310                 315                 320

Val Gln Gly Ile Ser Asp Ile Ile Thr Ile Pro Gly Leu Val Asn Val
                325                 330                 335

Asp Phe Ala Asp Val Lys Ala Ile Met Ser Asn Ala Gly Ser Ala Met
            340                 345                 350

Leu Gly Ile Gly Ala Gly Phe Gly Lys Asn Arg Ala Glu Glu Val Ala
        355                 360                 365

Arg Ser Ala Ile Met Ser Pro Leu Leu Arg Ser Val Ser Arg Pro Met
    370                 375                 380

Gly Ile Val Tyr Asn Val Thr Gly Gly Ser Asp Leu Thr Leu His Glu
385                 390                 395                 400

Val Asn Ile Ala Ala Glu Ile Val His Asp Met Ala Asp Pro Asn Ala
                405                 410                 415

Asn Val Ile Phe Gly Ala Val Ile Asp Glu Ser Phe Lys Gly Met Ile
            420                 425                 430

Arg Met Thr Val Ile Ala Thr Gly Phe Arg Glu Pro Gly Glu Glu Lys
        435                 440                 445

Val Val Gly Ser Val Arg Thr Val Asp Asp Asp Ile Phe Tyr Trp Glu
    450                 455                 460

Gln Asn Lys Asn Arg Ser Asp Leu Gly Lys Val Pro Asp Val Leu Arg
465                 470                 475                 480

Arg Lys Asp Arg Arg Gly Ser Gly Arg
                485                 490

<210> SEQ ID NO 11
<211> LENGTH: 1446
<212> TYPE: DNA
<213> ORGANISM: Physcomitrella patens
<220> FEATURE:
<221> NAME/KEY: CDS
<222> LOCATION: (453)..(1343)

<400> SEQUENCE: 11
atcccgggca gtgaagtccg ggtttgggtg cttcttaact tttcttctct tttggagttg      60
ggaagatttt tttttgcgga ggatgttttg ggagggttgg ggttgaagtt gtcttggtga     120
ttgaggctgt ggcggaggag tattgatcga agtttggtgt caaggaggt gttgcctttc      180 atggtcagaa acgatcttcg tcgccgctct gcgtgcagtc ttgcagcagt tgctggtttt     240
cacgatcggg aggttcgtgt ggagcgcggg gtggacttgc tgctcgtttc tggtgtgcgt     300
ttgctgcacg actgttgttc cctttcctgg gaattcaaca ttgattgatt gacgagcgac     360
ttcgcgatcg gcattggtat ttgccgcgtc gtgagctttg cgacgttttc agatatggag     420
tggaaggggt ttgctgaggt ggtttggcgt cg atg atc gcc ggg ttc gct acg      473
                                    Met Ile Ala Gly Phe Ala Thr
                                    1               5 cac cct ctg gac ctt atc aag gtc cgc atg cag tta caa ggg gag gtt      521
His Pro Leu Asp Leu Ile Lys Val Arg Met Gln Leu Gln Gly Glu Val
            10                  15                  20 gct acg tcg ggt ttc gcc ctc gcg ctc gaa ggt agt cat gtt gct cct      569
Ala Thr Ser Gly Phe Ala Leu Ala Leu Glu Gly Ser His Val Ala Pro
        25                  30                  35 gct gta ctc ggt gtc ccg aaa ccg ggt ccc ttg gga gtc ggt ttg aat      617
Ala Val Leu Gly Val Pro Lys Pro Gly Pro Leu Gly Val Gly Leu Asn
```

```
                40                  45                  50                  55
gtg gct cgt gca gaa gga gtg tat gcc ctc tac tcc ggt gtc tcc gcc        665
Val Ala Arg Ala Glu Gly Val Tyr Ala Leu Tyr Ser Gly Val Ser Ala
                    60                  65                  70 act ttg tta aga caa gcc atg tat tcg tct aca cgg atg ggt ctt tac        713
Thr Leu Leu Arg Gln Ala Met Tyr Ser Ser Thr Arg Met Gly Leu Tyr
            75                  80                  85 gag ttc ttg aag cat cag tgg aga gac gag aaa caa gaa ggc tct ggg        761
Glu Phe Leu Lys His Gln Trp Arg Asp Glu Lys Gln Glu Gly Ser Gly
        90                  95                  100 ctt cct ctg tac aaa aaa gtg acc gct gca ttg att gcc ggg gct tcc        809
Leu Pro Leu Tyr Lys Lys Val Thr Ala Ala Leu Ile Ala Gly Ala Ser
    105                 110                 115 ggc gcc gtt gtt gga aac cct gca gac ttg gcc atg gtc agg atg caa        857
Gly Ala Val Val Gly Asn Pro Ala Asp Leu Ala Met Val Arg Met Gln
120                 125                 130                 135 gcc gac ggt agg ctg cct atg cat gag agg agg aac tac acc ggg gtc        905
Ala Asp Gly Arg Leu Pro Met His Glu Arg Arg Asn Tyr Thr Gly Val
                140                 145                 150 ggc aat gct ctg tta cgg atg gtg aaa caa gac ggc gtg atg tca ttg        953
Gly Asn Ala Leu Leu Arg Met Val Lys Gln Asp Gly Val Met Ser Leu
            155                 160                 165 tgg acg gga tcg gct ccg act gtg act cga gcc atg ctg gtg acc gcc        1001
Trp Thr Gly Ser Ala Pro Thr Val Thr Arg Ala Met Leu Val Thr Ala
        170                 175                 180 gct cag ttg gcc acc tac gac cag atc aag gac tcc att gct gag acc        1049
Ala Gln Leu Ala Thr Tyr Asp Gln Ile Lys Asp Ser Ile Ala Glu Thr
    185                 190                 195 cac atg gtg ccg gaa ggg ctg gcc acg cag gtg gtg gca agc tgc gga        1097
His Met Val Pro Glu Gly Leu Ala Thr Gln Val Val Ala Ser Cys Gly
200                 205                 210                 215 gcg ggg gtg ctg gca tcc gtc gct tca aac ccc atc gac gtc gtg aag        1145
Ala Gly Val Leu Ala Ser Val Ala Ser Asn Pro Ile Asp Val Val Lys
                220                 225                 230 acg aga gtg atg aac atg aaa gtg acg cct gga gaa gga gct cct tat        1193
Thr Arg Val Met Asn Met Lys Val Thr Pro Gly Glu Gly Ala Pro Tyr
            235                 240                 245 cga ggt gct ttg gat tgt gct gtg aag acg gtg cga gcg gaa ggt ccc        1241
Arg Gly Ala Leu Asp Cys Ala Val Lys Thr Val Arg Ala Glu Gly Pro
        250                 255                 260 atg gct ctg tac aag gga ttt gtc ccg acg gtg act cgt caa ggc ccc        1289
Met Ala Leu Tyr Lys Gly Phe Val Pro Thr Val Thr Arg Gln Gly Pro
    265                 270                 275 ttc gcc ata gtt ctg ttc ctg tca ttg gag cag atc aag aag ctg atc        1337
Phe Ala Ile Val Leu Phe Leu Ser Leu Glu Gln Ile Lys Lys Leu Ile
280                 285                 290                 295 gag ggc tgaatcagat aatgacgaaa gatgtgtagt taagcaatag ttgaagtgga        1393
Glu Gly tataataagg tccatatctg aagaggttgt ctcggagaat tgggcgttaa cgc            1446

<210> SEQ ID NO 12
<211> LENGTH: 297
<212> TYPE: PRT
<213> ORGANISM: Physcomitrella patens

<400> SEQUENCE: 12

Met Ile Ala Gly Phe Ala Thr His Pro Leu Asp Leu Ile Lys Val Arg
1               5                   10                  15

Met Gln Leu Gln Gly Glu Val Ala Thr Ser Gly Phe Ala Leu Ala Leu
            20                  25                  30
```

```
Glu Gly Ser His Val Ala Pro Ala Val Leu Gly Val Pro Lys Pro Gly
         35                  40                  45

Pro Leu Gly Val Gly Leu Asn Val Ala Arg Ala Glu Gly Val Tyr Ala
 50                  55                  60

Leu Tyr Ser Gly Val Ser Ala Thr Leu Leu Arg Gln Ala Met Tyr Ser
 65                  70                  75                  80

Ser Thr Arg Met Gly Leu Tyr Glu Phe Leu Lys His Gln Trp Arg Asp
                 85                  90                  95

Glu Lys Gln Glu Gly Ser Gly Leu Pro Leu Tyr Lys Lys Val Thr Ala
            100                 105                 110

Ala Leu Ile Ala Gly Ala Ser Gly Ala Val Val Gly Asn Pro Ala Asp
            115                 120                 125

Leu Ala Met Val Arg Met Gln Ala Asp Gly Arg Leu Pro Met His Glu
            130                 135                 140

Arg Arg Asn Tyr Thr Gly Val Gly Asn Ala Leu Leu Arg Met Val Lys
145                 150                 155                 160

Gln Asp Gly Val Met Ser Leu Trp Thr Gly Ser Ala Pro Thr Val Thr
                165                 170                 175

Arg Ala Met Leu Val Thr Ala Ala Gln Leu Ala Thr Tyr Asp Gln Ile
            180                 185                 190

Lys Asp Ser Ile Ala Glu Thr His Met Val Pro Glu Gly Leu Ala Thr
            195                 200                 205

Gln Val Val Ala Ser Cys Gly Ala Gly Val Leu Ala Ser Val Ala Ser
            210                 215                 220

Asn Pro Ile Asp Val Val Lys Thr Arg Val Met Asn Met Lys Val Thr
225                 230                 235                 240

Pro Gly Glu Gly Ala Pro Tyr Arg Gly Ala Leu Asp Cys Ala Val Lys
                245                 250                 255

Thr Val Arg Ala Glu Gly Pro Met Ala Leu Tyr Lys Gly Phe Val Pro
            260                 265                 270

Thr Val Thr Arg Gln Gly Pro Phe Ala Ile Val Leu Phe Leu Ser Leu
            275                 280                 285

Glu Gln Ile Lys Lys Leu Ile Glu Gly
            290                 295

<210> SEQ ID NO 13
<211> LENGTH: 937
<212> TYPE: DNA
<213> ORGANISM: Physcomitrella patens
<220> FEATURE:
<221> NAME/KEY: CDS
<222> LOCATION: (33)..(593)

<400> SEQUENCE: 13
atcccgggtc gacacggcgg aagggtgggg tt atg ggt cgc ggc aaa att gag         53
                                    Met Gly Arg Gly Lys Ile Glu
                                     1               5 atc aag aag att gag aat aca acc agc agg cag gtg aca ttc tcc aag        101
Ile Lys Lys Ile Glu Asn Thr Thr Ser Arg Gln Val Thr Phe Ser Lys
         10                  15                  20 agg cgc ggt ggt ctt ttg aag aag gcg cac gag ctt gcg gtt ctg tgt        149
Arg Arg Gly Gly Leu Leu Lys Lys Ala His Glu Leu Ala Val Leu Cys
 25                  30                  35 gat gcc gag gtg gcg ctg gtt att ttc tcc agc act gga aag cac ttt        197
Asp Ala Glu Val Ala Leu Val Ile Phe Ser Ser Thr Gly Lys His Phe
 40                  45                  50                  55 gag ttt gcc agt tca ggc agc atg cgg gac atc att gag cgg tac agg        245
```

```
            Glu Phe Ala Ser Ser Gly Ser Met Arg Asp Ile Ile Glu Arg Tyr Arg
                            60                  65                  70 aag agc tcg gat ggt gca gtg aag cgt ggc acc aat act gat tta ctt        293
Lys Ser Ser Asp Gly Ala Val Lys Arg Gly Thr Asn Thr Asp Leu Leu
                75                  80                  85 ggt cgg gag gtg att aag tta aaa cag caa gta gaa cga ttg gaa agc        341
Gly Arg Glu Val Ile Lys Leu Lys Gln Gln Val Glu Arg Leu Glu Ser
        90                  95                  100 tct caa agg cat atg ctt ggt gag gat ctt tca gct ttg aag gta tct        389
Ser Gln Arg His Met Leu Gly Glu Asp Leu Ser Ala Leu Lys Val Ser
        105                 110                 115 gac ctt ttg gag ctg gag cag cag ctt gat cag ggt gct tca cga gtg        437
Asp Leu Leu Glu Leu Glu Gln Gln Leu Asp Gln Gly Ala Ser Arg Val
120                 125                 130                 135 aga gca agg aag aat caa ctc att tta gaa gag atc gaa gac ttg cgg        485
Arg Ala Arg Lys Asn Gln Leu Ile Leu Glu Glu Ile Glu Asp Leu Arg
                140                 145                 150 aga aag gag cat gaa ctg atg att gca aac gag gct ctt cgc aag aag        533
Arg Lys Glu His Glu Leu Met Ile Ala Asn Glu Ala Leu Arg Lys Lys
                155                 160                 165 att gca gac gct gaa ggt gct gcg gaa gca gag ctc gag cta att tcc        581
Ile Ala Asp Ala Glu Gly Ala Ala Glu Ala Glu Leu Glu Leu Ile Ser
                170                 175                 180 cgg atg ctc ggc tagaaagccc caaaccgttc gccagcgatt tctcacgaga            633
Arg Met Leu Gly
        185 tatgagtgtg agttcgcagc tggcagcatc agtctaccct catcccaacc ttctacaggc      693 gcaaagatca cagacgtcat tacagcttgg atggctatct gagcaacaga tccccagcac      753 ggaagaaggt tgtgcaggtg aatctagctt gaaatgggat catccgcact ttcacattca      813 gaatagactc catgcaaaca tatcaccaag tgtgagaatt tataagttac atgtcgatcg      873 ataagccact tcgaacgaca gaaggctctt tgggagccca ggctatgggt cctagcgtta      933 acgc                                                                  937

<210> SEQ ID NO 14
<211> LENGTH: 187
<212> TYPE: PRT
<213> ORGANISM: Physcomitrella patens

<400> SEQUENCE: 14

Met Gly Arg Gly Lys Ile Glu Ile Lys Lys Ile Glu Asn Thr Thr Ser
1               5                   10                  15

Arg Gln Val Thr Phe Ser Lys Arg Arg Gly Gly Leu Leu Lys Lys Ala
                20                  25                  30

His Glu Leu Ala Val Leu Cys Asp Ala Glu Val Ala Leu Val Ile Phe
            35                  40                  45

Ser Ser Thr Gly Lys His Phe Glu Phe Ala Ser Gly Ser Met Arg
        50                  55                  60

Asp Ile Ile Glu Arg Tyr Arg Lys Ser Ser Asp Gly Ala Val Lys Arg
65                  70                  75                  80

Gly Thr Asn Thr Asp Leu Leu Gly Arg Glu Val Ile Lys Leu Lys Gln
                85                  90                  95

Gln Val Glu Arg Leu Glu Ser Ser Gln Arg His Met Leu Gly Glu Asp
            100                 105                 110

Leu Ser Ala Leu Lys Val Ser Asp Leu Leu Glu Leu Glu Gln Gln Leu
        115                 120                 125

Asp Gln Gly Ala Ser Arg Val Arg Ala Arg Lys Asn Gln Leu Ile Leu
```

```
                130                 135                 140
Glu Glu Ile Glu Asp Leu Arg Arg Lys Glu His Glu Leu Met Ile Ala
145                 150                 155                 160

Asn Glu Ala Leu Arg Lys Lys Ile Ala Asp Ala Glu Gly Ala Ala Glu
                165                 170                 175

Ala Glu Leu Glu Leu Ile Ser Arg Met Leu Gly
            180                 185

<210> SEQ ID NO 15
<211> LENGTH: 1082
<212> TYPE: DNA
<213> ORGANISM: Physcomitrella patens
<220> FEATURE:
<221> NAME/KEY: CDS
<222> LOCATION: (25)..(1053)

<400> SEQUENCE: 15
atcccgggca ttctctctct cgca atg gcg tcc gag ggt gtg ctt ttg ggc        51
                          Met Ala Ser Glu Gly Val Leu Leu Gly
                           1               5 atg gga aac ccc ctg ctc gac atc tcc tgc gtg gtc gac gac gca ttc       99
Met Gly Asn Pro Leu Leu Asp Ile Ser Cys Val Val Asp Asp Ala Phe
 10                  15                  20                  25 ctc gag aag tac ggg ctg acg cta aac aac gct att ctt gct gag gac      147
Leu Glu Lys Tyr Gly Leu Thr Leu Asn Asn Ala Ile Leu Ala Glu Asp
                 30                  35                  40 aag cac ctt ccc atg tac aag gaa ctg gct gcc aat ccc gat gta gag      195
Lys His Leu Pro Met Tyr Lys Glu Leu Ala Ala Asn Pro Asp Val Glu
             45                  50                  55 tac att gca gga ggt gct act cag aac acc atc agg att gcc cag tgg      243
Tyr Ile Ala Gly Gly Ala Thr Gln Asn Thr Ile Arg Ile Ala Gln Trp
         60                  65                  70 atg cta ggt gaa tcg aac gca act agc tac ttt ggc tgt gtt ggc aag      291
Met Leu Gly Glu Ser Asn Ala Thr Ser Tyr Phe Gly Cys Val Gly Lys
     75                  80                  85 gat gag tat ggc gac cgt atg ttc aag ctc gcc tct gag gga ggt gtc      339
Asp Glu Tyr Gly Asp Arg Met Phe Lys Leu Ala Ser Glu Gly Gly Val
 90                  95                 100                 105 aat atc cga tac gat gtg gac gag gat ctt ccc act gga aca tgc ggc      387
Asn Ile Arg Tyr Asp Val Asp Glu Asp Leu Pro Thr Gly Thr Cys Gly
                110                 115                 120 gtg ctc gtg gtg aag gga gag agg tcc ttg gta gcc aat ctt tca gcc      435
Val Leu Val Val Lys Gly Glu Arg Ser Leu Val Ala Asn Leu Ser Ala
            125                 130                 135 gcc aac aaa tac aag atc gac cac ttg aag aag cca gaa aac tgg gct      483
Ala Asn Lys Tyr Lys Ile Asp His Leu Lys Lys Pro Glu Asn Trp Ala
        140                 145                 150 ttc gtg gag aag gca aag tac atc tac agc gcc ggt ttc ttc ctg act      531
Phe Val Glu Lys Ala Lys Tyr Ile Tyr Ser Ala Gly Phe Phe Leu Thr
    155                 160                 165 gtt tca ccg gaa tct atg atg acc gtg gcc aaa cat gct gcc gag acc      579
Val Ser Pro Glu Ser Met Met Thr Val Ala Lys His Ala Ala Glu Thr
170                 175                 180                 185 gga aaa tac tac atg atc aac tta gcc gct ccg ttc atc tgc cag ttc      627
Gly Lys Tyr Tyr Met Ile Asn Leu Ala Ala Pro Phe Ile Cys Gln Phe
                190                 195                 200 ttt aag gac cct ctt atg gag ctt ttc cct tac gtg gat ttc att ttc      675
Phe Lys Asp Pro Leu Met Glu Leu Phe Pro Tyr Val Asp Phe Ile Phe
            205                 210                 215 ggc aac gag agc gag gcc aga gca ttt gcg caa gtt caa ggc tgg gag      723
Gly Asn Glu Ser Glu Ala Arg Ala Phe Ala Gln Val Gln Gly Trp Glu
```

```
                      220                 225                 230
aca gag gac acc aag gtg ata gcc gta aag ttg gct gcg tta ccg aaa         771
Thr Glu Asp Thr Lys Val Ile Ala Val Lys Leu Ala Ala Leu Pro Lys
            235                 240                 245 gct ggc ggc acc cac aag cgt gtc gct gtc atc acc cag gga act gac         819
Ala Gly Gly Thr His Lys Arg Val Ala Val Ile Thr Gln Gly Thr Asp
250                 255                 260                 265 ccc aca att gtt gct gaa gat gga aag gtg act gaa ttc ccc gtc acc         867
Pro Thr Ile Val Ala Glu Asp Gly Lys Val Thr Glu Phe Pro Val Thr
                270                 275                 280 cct att cct aag gag aag ttg gtc gac act aat gca gct ggt gac tct         915
Pro Ile Pro Lys Glu Lys Leu Val Asp Thr Asn Ala Ala Gly Asp Ser
            285                 290                 295 ttt gtc gga ggg ttc ttg tct cag ctg gtg ttg ggt aaa gac atc gca         963
Phe Val Gly Gly Phe Leu Ser Gln Leu Val Leu Gly Lys Asp Ile Ala
300                 305                 310 cag tgc gtc aga gca gga aac tac gca gcc agc gtc atc atc cag cgc        1011
Gln Cys Val Arg Ala Gly Asn Tyr Ala Ala Ser Val Ile Ile Gln Arg
            315                 320                 325 tct gga tgc act ttc cct tcc aaa cca tcc ttc gaa agt cag               1053
Ser Gly Cys Thr Phe Pro Ser Lys Pro Ser Phe Glu Ser Gln
330                 335                 340 tagaaaattg ttagggtagg ggagctcgc                                        1082
```

<210> SEQ ID NO 16
<211> LENGTH: 343
<212> TYPE: PRT
<213> ORGANISM: Physcomitrella patens

<400> SEQUENCE: 16

```
Met Ala Ser Glu Gly Val Leu Leu Gly Met Gly Asn Pro Leu Leu Asp
1               5                   10                  15

Ile Ser Cys Val Val Asp Asp Ala Phe Leu Glu Lys Tyr Gly Leu Thr
                20                  25                  30

Leu Asn Asn Ala Ile Leu Ala Glu Asp Lys His Leu Pro Met Tyr Lys
            35                  40                  45

Glu Leu Ala Ala Asn Pro Asp Val Glu Tyr Ile Ala Gly Gly Ala Thr
        50                  55                  60

Gln Asn Thr Ile Arg Ile Ala Gln Trp Met Leu Gly Glu Ser Asn Ala
65                  70                  75                  80

Thr Ser Tyr Phe Gly Cys Val Gly Lys Asp Glu Tyr Gly Asp Arg Met
                85                  90                  95

Phe Lys Leu Ala Ser Glu Gly Gly Val Asn Ile Arg Tyr Asp Val Asp
            100                 105                 110

Glu Asp Leu Pro Thr Gly Thr Cys Gly Val Leu Val Lys Gly Glu
        115                 120                 125

Arg Ser Leu Val Ala Asn Leu Ser Ala Ala Asn Lys Tyr Lys Ile Asp
130                 135                 140

His Leu Lys Lys Pro Glu Asn Trp Ala Phe Val Glu Lys Ala Lys Tyr
145                 150                 155                 160

Ile Tyr Ser Ala Gly Phe Phe Leu Thr Val Ser Pro Glu Ser Met Met
                165                 170                 175

Thr Val Ala Lys His Ala Ala Glu Thr Gly Lys Tyr Tyr Met Ile Asn
            180                 185                 190

Leu Ala Ala Pro Phe Ile Cys Gln Phe Phe Lys Asp Pro Leu Met Glu
        195                 200                 205

Leu Phe Pro Tyr Val Asp Phe Ile Phe Gly Asn Glu Ser Glu Ala Arg
```

```
              210                 215                 220
Ala Phe Ala Gln Val Gln Gly Trp Glu Thr Glu Asp Thr Lys Val Ile
225                 230                 235                 240

Ala Val Lys Leu Ala Ala Leu Pro Lys Ala Gly Gly Thr His Lys Arg
                245                 250                 255

Val Ala Val Ile Thr Gln Gly Thr Asp Pro Thr Ile Val Ala Glu Asp
                260                 265                 270

Gly Lys Val Thr Glu Phe Pro Val Thr Pro Ile Pro Lys Glu Lys Leu
                275                 280                 285

Val Asp Thr Asn Ala Ala Gly Asp Ser Phe Val Gly Gly Phe Leu Ser
                290                 295                 300

Gln Leu Val Leu Gly Lys Asp Ile Ala Gln Cys Val Arg Ala Gly Asn
305                 310                 315                 320

Tyr Ala Ala Ser Val Ile Ile Gln Arg Ser Gly Cys Thr Phe Pro Ser
                325                 330                 335

Lys Pro Ser Phe Glu Ser Gln
            340

<210> SEQ ID NO 17
<211> LENGTH: 2357
<212> TYPE: DNA
<213> ORGANISM: Physcomitrella patens
<220> FEATURE:
<221> NAME/KEY: CDS
<222> LOCATION: (126)..(1907)

<400> SEQUENCE: 17
atcccgggag tggtggtgat ggtattggtc atcgtggtcg cgtaaaagaa gaagacaagg      60
tgacaatttt ggtcctcctc ccttccttgc tactcctcga agagtatttc ctactgagtt     120 gagac atg gag tct gag gac gaa atg caa gat gca tgg gct ggt aca tca    170
      Met Glu Ser Glu Asp Glu Met Gln Asp Ala Trp Ala Gly Thr Ser
        1               5                  10                  15 gat ggt gag ttt gta aac gaa gag gaa gat gag gaa tca gat gct tta    218
Asp Gly Glu Phe Val Asn Glu Glu Glu Asp Glu Glu Ser Asp Ala Leu
                 20                  25                  30 gct agt gat gac gac aat gat gaa tcg gat tat ggt ttt gat tac tcg    266
Ala Ser Asp Asp Asp Asn Asp Glu Ser Asp Tyr Gly Phe Asp Tyr Ser
             35                  40                  45 aac gtg gac gac ctt cac cct agt tct cgg cta ccc cag act aac ttc    314
Asn Val Asp Asp Leu His Pro Ser Ser Arg Leu Pro Gln Thr Asn Phe
         50                  55                  60 aca atc ctt agt gag aaa gat ata cgg caa cga caa gac gaa gcc gta    362
Thr Ile Leu Ser Glu Lys Asp Ile Arg Gln Arg Gln Asp Glu Ala Val
 65                  70                  75 tca act atc act aat ttc ttg tct ata tct cca gcg gat gcc ggg gtt    410
Ser Thr Ile Thr Asn Phe Leu Ser Ile Ser Pro Ala Asp Ala Gly Val
 80                  85                  90                  95 ctg ctt cgg cac ttt aag tgg agt gtg agt aaa gtg aat gac gag tgg    458
Leu Leu Arg His Phe Lys Trp Ser Val Ser Lys Val Asn Asp Glu Trp
                100                 105                 110 ttt gcg gat gag gaa cga gtg cgc gca agc gtc ggt tta ctg gag aaa    506
Phe Ala Asp Glu Glu Arg Val Arg Ala Ser Val Gly Leu Leu Glu Lys
            115                 120                 125 ccc gct acc agc aaa aga caa act caa aca gag atg act tgc gag ata    554
Pro Ala Thr Ser Lys Arg Gln Thr Gln Thr Glu Met Thr Cys Glu Ile
        130                 135                 140 tgt ttt gag gtg cat ccg ttt gaa aaa atg agg gca cct aga tgc ggt    602
Cys Phe Glu Val His Pro Phe Glu Lys Met Arg Ala Pro Arg Cys Gly
    145                 150                 155
```

```
cac tat ttc tgt gag acc tgt tgg aca ggt tac ata cac aca gct att    650
His Tyr Phe Cys Glu Thr Cys Trp Thr Gly Tyr Ile His Thr Ala Ile
160             165                 170                 175 aat gat ggg cct gga tgt ttg act ctt cga tgt gcg gat cca tcc tgt    698
Asn Asp Gly Pro Gly Cys Leu Thr Leu Arg Cys Ala Asp Pro Ser Cys
            180                 185                 190 ggc tca gcc att gga gaa gat atg gta cta agt tta gtc tcg acg gat    746
Gly Ser Ala Ile Gly Glu Asp Met Val Leu Ser Leu Val Ser Thr Asp
                195                 200                 205 gat caa cag aag tac atg cgt tat cta tta aga tct tac gtg gag gac    794
Asp Gln Gln Lys Tyr Met Arg Tyr Leu Leu Arg Ser Tyr Val Glu Asp
                    210                 215                 220 aac cga aag gtc aag tgg tgc cca gca cct ggc tgt gaa tat gct gtg    842
Asn Arg Lys Val Lys Trp Cys Pro Ala Pro Gly Cys Glu Tyr Ala Val
225                 230                 235 gaa ttt caa cct ggc gtt ggt tcc tat gac ctt gtc tgc aag tgt gga    890
Glu Phe Gln Pro Gly Val Gly Ser Tyr Asp Leu Val Cys Lys Cys Gly
240                 245                 250                 255 ttt aac ttc tgc tgg aat tgt cga gaa gag gca cac cgg ccc gtg gat    938
Phe Asn Phe Cys Trp Asn Cys Arg Glu Glu Ala His Arg Pro Val Asp
                260                 265                 270 tgt gag aca gtc aat aaa tgg ata ttg aaa aat tgt gca gag tcg gag    986
Cys Glu Thr Val Asn Lys Trp Ile Leu Lys Asn Cys Ala Glu Ser Glu
                275                 280                 285 aac atg aac tgg att ctt gcg aac agc aaa ccc tgt ccc aaa tgt aaa   1034
Asn Met Asn Trp Ile Leu Ala Asn Ser Lys Pro Cys Pro Lys Cys Lys
                290                 295                 300 agg cca atc gaa aag aat caa ggc tgc atg cac att act tgc aca cca   1082
Arg Pro Ile Glu Lys Asn Gln Gly Cys Met His Ile Thr Cys Thr Pro
305                 310                 315 cct tgc aaa ttt gag ttt tgc tgg ctt tgc ctt gga gca tgg act gat   1130
Pro Cys Lys Phe Glu Phe Cys Trp Leu Cys Leu Gly Ala Trp Thr Asp
320                 325                 330                 335 cat ggg gaa agg acg ggt ggt ttc tat gca tgc aat cgg tat gaa acc   1178
His Gly Glu Arg Thr Gly Gly Phe Tyr Ala Cys Asn Arg Tyr Glu Thr
                340                 345                 350 gcg aag caa gaa ggc gtg tat gat gaa gca gag cgg aga agg gaa atg   1226
Ala Lys Gln Glu Gly Val Tyr Asp Glu Ala Glu Arg Arg Arg Glu Met
                    355                 360                 365 gcg aag aac tcc ctt gaa cgt tac aca cac tat tat gag cgt tgg gct   1274
Ala Lys Asn Ser Leu Glu Arg Tyr Thr His Tyr Tyr Glu Arg Trp Ala
                370                 375                 380 aca aac gaa tct tcc agg gca aag gcg ctt gca gat ctt caa gat atg   1322
Thr Asn Glu Ser Ser Arg Ala Lys Ala Leu Ala Asp Leu Gln Asp Met
385                 390                 395 cag aac gtg cag att gaa aag ctg agc gtc act caa tgc caa cca gtg   1370
Gln Asn Val Gln Ile Glu Lys Leu Ser Val Thr Gln Cys Gln Pro Val
400                 405                 410                 415 tcg cag ctg aaa ttt gta aca gat gca tgg ctc cag att gta gaa tgc   1418
Ser Gln Leu Lys Phe Val Thr Asp Ala Trp Leu Gln Ile Val Glu Cys
                420                 425                 430 cgg cgt gta ttg aag tgg aca tat gct tat gga tat tac tta cct gag   1466
Arg Arg Val Leu Lys Trp Thr Tyr Ala Tyr Gly Tyr Tyr Leu Pro Glu
                435                 440                 445 aat gag cac acg aaa aga caa ttc ttt gaa tac tcg caa ggt gag gcc   1514
Asn Glu His Thr Lys Arg Gln Phe Phe Glu Tyr Ser Gln Gly Glu Ala
                450                 455                 460 gaa gct ggt tta gag cgc ctc cac cag tgt gcg gag aag gat ttg cta   1562
Glu Ala Gly Leu Glu Arg Leu His Gln Cys Ala Glu Lys Asp Leu Leu
465                 470                 475
```

| | | | | | | | | | | | | | | |
|---|---|---|---|---|---|---|---|---|---|---|---|---|---|---|
| acc | ttt | ctt | gga | ggc | act | cca | acc | agc | tca | ttc | aat | gac | ttc | cgc | acc | 1610 |
| Thr | Phe | Leu | Gly | Gly | Thr | Pro | Thr | Ser | Ser | Phe | Asn | Asp | Phe | Arg | Thr |
| 480 | | | | | 485 | | | | | 490 | | | | | 495 |

| aag | ctt | gct | ggc | ctg | acc | agt | gtg | aca | aag | aca | tac | ttc | gag | aac | ctg | 1658 |
| Lys | Leu | Ala | Gly | Leu | Thr | Ser | Val | Thr | Lys | Thr | Tyr | Phe | Glu | Asn | Leu |
| | | | | 500 | | | | | 505 | | | | | 510 | |

| gtt | cgc | gcc | cta | gag | aac | aat | ctt | tcg | gac | gtg | gat | att | cca | aaa | gca | 1706 |
| Val | Arg | Ala | Leu | Glu | Asn | Asn | Leu | Ser | Asp | Val | Asp | Ile | Pro | Lys | Ala |
| | | | 515 | | | | | 520 | | | | | 525 | | |

| gct | gct | aag | tcc | agc | agc | agc | tcg | aag | gct | tca | gga | agt | tcc | aaa | ggg | 1754 |
| Ala | Ala | Lys | Ser | Ser | Ser | Ser | Ser | Lys | Ala | Ser | Gly | Ser | Ser | Lys | Gly |
| | | 530 | | | | | 535 | | | | | 540 | | | |

| cga | ggg | ggc | agg | cct | aaa | gtg | gga | agt | tcc | aaa | agt | ggg | ggt | tct | agt | 1802 |
| Arg | Gly | Gly | Arg | Pro | Lys | Val | Gly | Ser | Ser | Lys | Ser | Gly | Gly | Ser | Ser |
| 545 | | | | | 550 | | | | | 555 | | | | | |

| cgg | agc | gga | gag | gag | tca | act | cac | tgg | tct | tgt | gag | cat | tgc | acg | tac | 1850 |
| Arg | Ser | Gly | Glu | Glu | Ser | Thr | His | Trp | Ser | Cys | Glu | His | Cys | Thr | Tyr |
| 560 | | | | | 565 | | | | | 570 | | | | | 575 |

| gcc | aat | acc | aca | gcc | gcg | tct | tcc | att | gtg | tgc | gtc | ata | tgc | aat | cac | 1898 |
| Ala | Asn | Thr | Thr | Ala | Ala | Ser | Ser | Ile | Val | Cys | Val | Ile | Cys | Asn | His |
| | | | | 580 | | | | | 585 | | | | | 590 | |

| gct | cga | tcg | tgatgtaaat | tctcgcttca | gtatctcttt | cccgactgag | | | | | | | | | | 1947 |
| Ala | Arg | Ser | | | | | | | | | | | | | |

| cttgtcagtt | ctcctaacac | tccagatcct | tcaaatttgc | tatgtcattg | ttgatccagt | 2007 |
| ccaggatcaa | agaccactgt | attcagatat | ggtggttgaa | ggcatttctg | ctttgtttaa | 2067 |
| ggctattcat | agaagttaat | cacaatgttg | acagttaaat | ccttgcgtca | ggcatctggg | 2127 |
| tattgttgat | atcagttgtc | catcccctaa | attttttgtt | gtatacaatc | tagccaacaa | 2187 |
| agtgggtgaa | aatgaagaac | ggagggattt | tatgtatcga | gaccttgtgg | tgcacaattt | 2247 |
| gcaacggcag | tctatctagt | tgcgatgtac | cacatctgtc | tctatctact | gtaaatgtgg | 2307 |
| tagttgtaaa | agcgtactcc | aaaacagaat | tcccccctcgt | gcgagctcgc | | 2357 |

<210> SEQ ID NO 18
<211> LENGTH: 594
<212> TYPE: PRT
<213> ORGANISM: Physcomitrella patens

<400> SEQUENCE: 18

Met Glu Ser Glu Asp Glu Met Gln Asp Ala Trp Ala Gly Thr Ser Asp
1               5                   10                  15

Gly Glu Phe Val Asn Glu Glu Asp Glu Ser Asp Ala Leu Ala
            20                  25                  30

Ser Asp Asp Asp Asn Asp Glu Ser Asp Tyr Gly Phe Asp Tyr Ser Asn
                35                  40                  45

Val Asp Asp Leu His Pro Ser Ser Arg Leu Pro Gln Thr Asn Phe Thr
    50                  55                  60

Ile Leu Ser Glu Lys Asp Ile Arg Gln Arg Gln Asp Glu Ala Val Ser
65                  70                  75                  80

Thr Ile Thr Asn Phe Leu Ser Ile Ser Pro Ala Asp Ala Gly Val Leu
                85                  90                  95

Leu Arg His Phe Lys Trp Ser Val Ser Lys Val Asn Asp Glu Trp Phe
            100                 105                 110

Ala Asp Glu Glu Arg Val Arg Ala Ser Val Gly Leu Leu Glu Lys Pro
        115                 120                 125

Ala Thr Ser Lys Arg Gln Thr Gln Thr Glu Met Thr Cys Glu Ile Cys
    130                 135                 140

```
Phe Glu Val His Pro Phe Glu Lys Met Arg Ala Pro Arg Cys Gly His
145                 150                 155                 160

Tyr Phe Cys Glu Thr Cys Trp Thr Gly Tyr Ile His Thr Ala Ile Asn
                165                 170                 175

Asp Gly Pro Gly Cys Leu Thr Leu Arg Cys Ala Asp Pro Ser Cys Gly
            180                 185                 190

Ser Ala Ile Gly Glu Asp Met Val Leu Ser Leu Val Ser Thr Asp Asp
        195                 200                 205

Gln Gln Lys Tyr Met Arg Tyr Leu Leu Arg Ser Tyr Val Glu Asp Asn
    210                 215                 220

Arg Lys Val Lys Trp Cys Pro Ala Pro Gly Cys Glu Tyr Ala Val Glu
225                 230                 235                 240

Phe Gln Pro Gly Val Gly Ser Tyr Asp Leu Val Cys Lys Cys Gly Phe
                245                 250                 255

Asn Phe Cys Trp Asn Cys Arg Glu Glu Ala His Arg Pro Val Asp Cys
            260                 265                 270

Glu Thr Val Asn Lys Trp Ile Leu Lys Asn Cys Ala Glu Ser Glu Asn
        275                 280                 285

Met Asn Trp Ile Leu Ala Asn Ser Lys Pro Cys Pro Lys Cys Lys Arg
    290                 295                 300

Pro Ile Glu Lys Asn Gln Gly Cys Met His Ile Thr Cys Thr Pro Pro
305                 310                 315                 320

Cys Lys Phe Glu Phe Cys Trp Leu Cys Leu Gly Ala Trp Thr Asp His
                325                 330                 335

Gly Glu Arg Thr Gly Gly Phe Tyr Ala Cys Asn Arg Tyr Glu Thr Ala
            340                 345                 350

Lys Gln Glu Gly Val Tyr Asp Glu Ala Glu Arg Arg Glu Met Ala
        355                 360                 365

Lys Asn Ser Leu Glu Arg Tyr Thr His Tyr Tyr Glu Arg Trp Ala Thr
    370                 375                 380

Asn Glu Ser Ser Arg Ala Lys Ala Leu Ala Asp Leu Gln Asp Met Gln
385                 390                 395                 400

Asn Val Gln Ile Glu Lys Leu Ser Val Thr Gln Cys Gln Pro Val Ser
                405                 410                 415

Gln Leu Lys Phe Val Thr Asp Ala Trp Leu Gln Ile Val Glu Cys Arg
            420                 425                 430

Arg Val Leu Lys Trp Thr Tyr Ala Tyr Gly Tyr Tyr Leu Pro Glu Asn
        435                 440                 445

Glu His Thr Lys Arg Gln Phe Phe Glu Tyr Ser Gln Gly Glu Ala Glu
    450                 455                 460

Ala Gly Leu Glu Arg Leu His Gln Cys Ala Glu Lys Asp Leu Leu Thr
465                 470                 475                 480

Phe Leu Gly Gly Thr Pro Thr Ser Ser Phe Asn Asp Phe Arg Thr Lys
                485                 490                 495

Leu Ala Gly Leu Thr Ser Val Thr Lys Thr Tyr Phe Glu Asn Leu Val
            500                 505                 510

Arg Ala Leu Glu Asn Asn Leu Ser Asp Val Asp Ile Pro Lys Ala Ala
        515                 520                 525

Ala Lys Ser Ser Ser Ser Lys Ala Ser Gly Ser Lys Gly Arg
530                 535                 540

Gly Gly Arg Pro Lys Val Gly Ser Ser Lys Ser Gly Ser Ser Arg
545                 550                 555                 560

Ser Gly Glu Glu Ser Thr His Trp Ser Cys Glu His Cys Thr Tyr Ala
```

```
                565                 570                 575
Asn Thr Thr Ala Ala Ser Ser Ile Val Cys Val Ile Cys Asn His Ala
        580                 585                 590
Arg Ser

<210> SEQ ID NO 19
<211> LENGTH: 884
<212> TYPE: DNA
<213> ORGANISM: Physcomitrella patens
<220> FEATURE:
<221> NAME/KEY: CDS
<222> LOCATION: (248)..(520)

<400> SEQUENCE: 19
atcccgggcc tgcgctcagc ctcgtcttcc tcgcattccg tcacctccgc ctgccctgca       60
tcgaaacatc gatcccactc ctcgcatcct gctcttgcct tcgtcacctt gtgctctcga      120
atctcgtacc ccgttttttg gttcgaaatt gcagttgaag atcgcgtgta tattggtatc      180
tgcttgtggg agtgggagtg gaagtgtgct cacacccttg agccagaagt gagagaaact      240 cggtaca atg ccc cag atc cag tac tcg gag aag tac ttc gac gat acc        289
        Met Pro Gln Ile Gln Tyr Ser Glu Lys Tyr Phe Asp Asp Thr
        1               5                   10 tac gag tat cgg cat gtc gtg ctt ccc ccc gac att gcc aaa ttg ctg        337
Tyr Glu Tyr Arg His Val Val Leu Pro Pro Asp Ile Ala Lys Leu Leu
15                  20                  25                  30 ccc aaa aac cga ctc ctg tct gag gcc gaa tgg cgt ggt atc gga gtg        385
Pro Lys Asn Arg Leu Leu Ser Glu Ala Glu Trp Arg Gly Ile Gly Val
                35                  40                  45 cag cag tca cgt ggg tgg gtt cac tac gca att cac cgc cct gag cca        433
Gln Gln Ser Arg Gly Trp Val His Tyr Ala Ile His Arg Pro Glu Pro
            50                  55                  60 cac att atg ctc ttc cgt aga ccc ctg aat tac ggt caa cct cag caa        481
His Ile Met Leu Phe Arg Arg Pro Leu Asn Tyr Gly Gln Pro Gln Gln
        65                  70                  75 gct gcc gct gtg cag caa caa ccc aca ggc atg aaa gct taatcatcct        530
Ala Ala Ala Val Gln Gln Gln Pro Thr Gly Met Lys Ala
    80                  85                  90 atcaattgat tccaggaatt gaacatcatg tgctcatgat gttgtatggc cagtgctctc      590
agttttttgg tcactatgtg atgttggata gttggtcctt aagtagtgac agctcttcgt      650
actgtacaag atttgtcggg aagtagccat gttaattagt gaatgagcat cactgaggag      710
tctctcgtga gctgattggt attctctgaa ggtggaagcg agcgggtgat agaaaactct      770
tatgacttgc tttcctacaa atattgtgat acaattcttt tgatgcgctc ctcgtcaatc      830
ttaagcacgt aggagacttc accatctgct actgcaacgc tcgtgcgagc tcgc           884

<210> SEQ ID NO 20
<211> LENGTH: 91
<212> TYPE: PRT
<213> ORGANISM: Physcomitrella patens

<400> SEQUENCE: 20

Met Pro Gln Ile Gln Tyr Ser Glu Lys Tyr Phe Asp Asp Thr Tyr Glu
1               5                   10                  15

Tyr Arg His Val Val Leu Pro Pro Asp Ile Ala Lys Leu Leu Pro Lys
            20                  25                  30

Asn Arg Leu Leu Ser Glu Ala Glu Trp Arg Gly Ile Gly Val Gln Gln
        35                  40                  45

Ser Arg Gly Trp Val His Tyr Ala Ile His Arg Pro Glu Pro His Ile
```

```
                    50                  55                  60
Met Leu Phe Arg Arg Pro Leu Asn Tyr Gly Gln Pro Gln Gln Ala Ala
 65                  70                  75                  80

Ala Val Gln Gln Gln Pro Thr Gly Met Lys Ala
                 85                  90

<210> SEQ ID NO 21
<211> LENGTH: 1389
<212> TYPE: DNA
<213> ORGANISM: Physcomitrella patens
<220> FEATURE:
<221> NAME/KEY: CDS
<222> LOCATION: (276)..(1316)

<400> SEQUENCE: 21
atcccgggag tagcttggag tggcgttgca aggtgggatt aggatcgatt agttgttgat      60
tgagtgcggc cctcggtgtt ggttatttgt ttaggtagat tgtagtctcg ctgggagtgg     120
agaggaggta ttcgtttttt tggttttat tgtttgacgt aggcttgtgg ttaggttttg     180
acttatactt tctgttgagg aattgggaag aaagaacag ggtgttctag catttagggg     240
aattgaccag ggtaggaggt gaagccgaag cttcg atg tca tct gct gtg gac        293
                                         Met Ser Ser Ala Val Asp
                                           1               5 ttt gta gag ggc ggt acc caa gac ccg tgc gaa gat gcg tgc agc atc       341
Phe Val Glu Gly Gly Thr Gln Asp Pro Cys Glu Asp Ala Cys Ser Ile
         10                  15                  20 tgc ctt gaa act ttt tgt gaa gat gat cct gcc acc gtc act agc tgc       389
Cys Leu Glu Thr Phe Cys Glu Asp Asp Pro Ala Thr Val Thr Ser Cys
     25                  30                  35 aag cac gac tat cat ctg caa tgc att ctt gaa tgg tcg cag cgg agt       437
Lys His Asp Tyr His Leu Gln Cys Ile Leu Glu Trp Ser Gln Arg Ser
 40                  45                  50 acg gag tgt cca atg tgc ttg caa cca ctt agt ttg aaa gat cct gac       485
Thr Glu Cys Pro Met Cys Leu Gln Pro Leu Ser Leu Lys Asp Pro Asp
 55                  60                  65                  70 agc caa gag ctg ctg aaa gca gtt ggg caa gaa cgg aca tta cgc cgg       533
Ser Gln Glu Leu Leu Lys Ala Val Gly Gln Glu Arg Thr Leu Arg Arg
             75                  80                  85 aat aag atg cag gcc tct cac att tac cgt cga tcc cca gct gag gag       581
Asn Lys Met Gln Ala Ser His Ile Tyr Arg Arg Ser Pro Ala Glu Glu
         90                  95                 100 tat gag ttc gaa cga ttt gca ccc tac ggg gac gaa ggt tgc att atg       629
Tyr Glu Phe Glu Arg Phe Ala Pro Tyr Gly Asp Glu Gly Cys Ile Met
    105                 110                 115 cag cat ttg gcg gcg gca gca atg ggc cgg aga gaa cat att cgc ttt       677
Gln His Leu Ala Ala Ala Ala Met Gly Arg Arg Glu His Ile Arg Phe
120                 125                 130 cgg cca tcc act act gcc caa ggt cat ccg cat ttt gtt gtt gtg tct       725
Arg Pro Ser Thr Thr Ala Gln Gly His Pro His Phe Val Val Val Ser
135                 140                 145                 150 ggt gca cct gca gga gca tcg tct tcc cct gca tcc agt tcg cca gtt       773
Gly Ala Pro Ala Gly Ala Ser Ser Ser Pro Ala Ser Ser Ser Pro Val
             155                 160                 165 gta tcc cct cct caa agt aca aat ggc gag gca tct cta gga gcc gtc       821
Val Ser Pro Pro Gln Ser Thr Asn Gly Glu Ala Ser Leu Gly Ala Val
        170                 175                 180 ttc tca ttt cct cat tat tct gct ccc aat agg gac ggt agc tca gct       869
Phe Ser Phe Pro His Tyr Ser Ala Pro Asn Arg Asp Gly Ser Ser Ala
    185                 190                 195 aac tct cca acc att aga tca cgg agc ctt gag tcg gag gag cat gca       917
```

```
                Asn Ser Pro Thr Ile Arg Ser Arg Ser Leu Glu Ser Glu His Ala
                    200                 205                 210 act tct tca tca gag tct cta gat acc ttt gca tct cgt ttg gtc gca           965
Thr Ser Ser Ser Glu Ser Leu Asp Thr Phe Ala Ser Arg Leu Val Ala
215                 220                 225                 230 gca tct tca agg tac aag gag tcc ctg agt aag agt acg aag gga ttc          1013
Ala Ser Ser Arg Tyr Lys Glu Ser Leu Ser Lys Ser Thr Lys Gly Phe
                235                 240                 245 cgt gaa agg ttg cga act cgt ggt ggt atc atg caa gac ctt ggt gca          1061
Arg Glu Arg Leu Arg Thr Arg Gly Gly Ile Met Gln Asp Leu Gly Ala
            250                 255                 260 cgg gca cga gag atg agt gca ggg atg gca cgg gcg tta gaa agg atg          1109
Arg Ala Arg Glu Met Ser Ala Gly Met Ala Arg Ala Leu Glu Arg Met
265                 270                 275 tct gta gag aca gga act gat cgg tca gat gcg gcc agc tct ctt cct          1157
Ser Val Glu Thr Gly Thr Asp Arg Ser Asp Ala Ala Ser Ser Leu Pro
        280                 285                 290 ggg cag cct tct ggc act acc cat cac cca ccc gat cat cct cct gat          1205
Gly Gln Pro Ser Gly Thr Thr His His Pro Pro Asp His Pro Pro Asp
295                 300                 305                 310 cgc cct gat tct ggc cat tct tca gga ggg tcg ccg agt agc cac tct          1253
Arg Pro Asp Ser Gly His Ser Ser Gly Gly Ser Pro Ser Ser His Ser
                315                 320                 325 gcc gtc act cgc aca act cca agc ccc act tca gca cct gaa cta agt          1301
Ala Val Thr Arg Thr Thr Pro Ser Pro Thr Ser Ala Pro Glu Leu Ser
            330                 335                 340 aca ggg aca gaa cac taggtttaaa actacttagt tcaaacatat cactttcgaa         1356
Thr Gly Thr Glu His
            345 taagagcgga tgctggcatc cgtccgagct cgc                                    1389

<210> SEQ ID NO 22
<211> LENGTH: 347
<212> TYPE: PRT
<213> ORGANISM: Physcomitrella patens

<400> SEQUENCE: 22

Met Ser Ser Ala Val Asp Phe Val Glu Gly Gly Thr Gln Asp Pro Cys
1               5                   10                  15

Glu Asp Ala Cys Ser Ile Cys Leu Glu Thr Phe Cys Gly Asp Asp Pro
                20                  25                  30

Ala Thr Val Thr Ser Cys Lys His Asp Tyr His Leu Gln Cys Ile Leu
            35                  40                  45

Glu Trp Ser Gln Arg Ser Thr Glu Cys Pro Met Cys Leu Gln Pro Leu
50                  55                  60

Ser Leu Lys Asp Pro Asp Ser Gln Glu Leu Leu Lys Ala Val Gly Gln
65                  70                  75                  80

Glu Arg Thr Leu Arg Arg Asn Lys Met Gln Ala Ser His Ile Tyr Arg
                85                  90                  95

Arg Ser Pro Ala Glu Glu Tyr Glu Phe Glu Arg Phe Ala Pro Tyr Gly
                100                 105                 110

Asp Glu Gly Cys Ile Met Gln His Leu Ala Ala Ala Met Gly Arg
            115                 120                 125

Arg Glu His Ile Arg Phe Arg Pro Ser Thr Thr Ala Gln Gly His Pro
        130                 135                 140

His Phe Val Val Ser Gly Ala Pro Ala Gly Ala Ser Ser Ser Pro
145                 150                 155                 160

Ala Ser Ser Ser Pro Val Val Ser Pro Pro Gln Ser Thr Asn Gly Glu
```

```
                        165                 170                 175
Ala Ser Leu Gly Ala Val Phe Ser Phe Pro His Tyr Ser Ala Pro Asn
            180                 185                 190

Arg Asp Gly Ser Ser Ala Asn Ser Pro Thr Ile Arg Ser Arg Ser Leu
            195                 200                 205

Glu Ser Glu Glu His Ala Thr Ser Ser Ser Glu Ser Leu Asp Thr Phe
            210                 215                 220

Ala Ser Arg Leu Val Ala Ala Ser Ser Arg Tyr Lys Glu Ser Leu Ser
225                 230                 235                 240

Lys Ser Thr Lys Gly Phe Arg Glu Arg Leu Arg Thr Arg Gly Gly Ile
                245                 250                 255

Met Gln Asp Leu Gly Ala Arg Ala Arg Glu Met Ser Ala Gly Met Ala
                260                 265                 270

Arg Ala Leu Glu Arg Met Ser Val Glu Thr Gly Thr Asp Arg Ser Asp
            275                 280                 285

Ala Ala Ser Ser Leu Pro Gly Gln Pro Ser Gly Thr Thr His His Pro
            290                 295                 300

Pro Asp His Pro Pro Asp Arg Pro Asp Ser Gly His Ser Ser Gly Gly
305                 310                 315                 320

Ser Pro Ser Ser His Ser Ala Val Thr Arg Thr Thr Pro Ser Pro Thr
                325                 330                 335

Ser Ala Pro Glu Leu Ser Thr Gly Thr Glu His
            340                 345

<210> SEQ ID NO 23
<211> LENGTH: 2776
<212> TYPE: DNA
<213> ORGANISM: Physcomitrella patens
<220> FEATURE:
<221> NAME/KEY: CDS
<222> LOCATION: (127)..(2568)

<400> SEQUENCE: 23
cgttgtaaaa cgacggccag tgaattgtaa tacgactcac tatagggcga attgggccct      60
ctagatgcat gctcgagcgg ccgccagtgt gatggatatc tgcagaattc gcccttatcc     120 cgggcc atg gct gtg tcc cgt ctt ggt ccc gct cca agt cca tcg gcc        168
       Met Ala Val Ser Arg Leu Gly Pro Ala Pro Ser Pro Ser Ala
       1               5                   10 gtt caa tgg agt ctc tcc agc agg cct ctc cct ctc gca acg agt agg        216
Val Gln Trp Ser Leu Ser Ser Arg Pro Leu Pro Leu Ala Thr Ser Arg
15              20                  25                  30 ttc agt gtg gtt cca gtt cgc gct tcg aaa aat gta gaa gat gga gat        264
Phe Ser Val Val Pro Val Arg Ala Ser Lys Asn Val Glu Asp Gly Asp
                35                  40                  45 act agt ggt ggg tgc gcg gct cta tca cgt cga gct ttg att gct ttg        312
Thr Ser Gly Gly Cys Ala Ala Leu Ser Arg Arg Ala Leu Ile Ala Leu
            50                  55                  60 ata gct ctg tct act caa ttg ggt ggt gtt gcg tcg gcc cga gac att        360
Ile Ala Leu Ser Thr Gln Leu Gly Gly Val Ala Ser Ala Arg Asp Ile
            65                  70                  75 agt ggt ctc ata gag tct tca gtg ggc gag gag gtg tcc tca tta tcc        408
Ser Gly Leu Ile Glu Ser Ser Val Gly Glu Glu Val Ser Ser Leu Ser
        80                  85                  90 ctg agt gca gtt gaa gta ccg aac acg cct aaa atc tct cca ata agc        456
Leu Ser Ala Val Glu Val Pro Asn Thr Pro Lys Ile Ser Pro Ile Ser
95                  100                 105                 110 act gac cta ggg att ata aat gaa gtg cca aga gct ctt gcg gac agt        504
Thr Asp Leu Gly Ile Ile Asn Glu Val Pro Arg Ala Leu Ala Asp Ser
```

```
                        115                 120                 125
gga gtt ggt gca gtt gag gaa aag ata aac cag tca gca tct gag gtt      552
Gly Val Gly Ala Val Glu Glu Lys Ile Asn Gln Ser Ala Ser Glu Val
                130                 135                 140 tca tct ggt ggg agt aat ggg ttt gga cct tta agt ctt ggg ggt atc      600
Ser Ser Gly Gly Ser Asn Gly Phe Gly Pro Leu Ser Leu Gly Gly Ile
            145                 150                 155 tta gga acc ggt gtg gcg ggg gcg ttg ttt tat agc gag cga caa tct      648
Leu Gly Thr Gly Val Ala Gly Ala Leu Phe Tyr Ser Glu Arg Gln Ser
        160                 165                 170 aaa gct cag gct gaa tct gca ctt gat gct gcg aaa aag cag ctc cag      696
Lys Ala Gln Ala Glu Ser Ala Leu Asp Ala Ala Lys Lys Gln Leu Gln
175                 180                 185                 190 gag ctt aga gag acc tca gaa ggg caa tta ctt gca gaa aag cag cta      744
Glu Leu Arg Glu Thr Ser Glu Gly Gln Leu Leu Ala Glu Lys Gln Leu
                195                 200                 205 gca caa aag gag gcg agc aag gcc cag gag caa cgc aca acg ctt act      792
Ala Gln Lys Glu Ala Ser Lys Ala Gln Glu Gln Arg Thr Thr Leu Thr
            210                 215                 220 aat gag ctc atg gct tca aga tcc tcg gtt act gat ctg gaa ggt aag      840
Asn Glu Leu Met Ala Ser Arg Ser Ser Val Thr Asp Leu Glu Gly Lys
        225                 230                 235 ctt caa atg gca aaa gct tca gtg gtc gat ctt cag gaa agg gtt tca      888
Leu Gln Met Ala Lys Ala Ser Val Val Asp Leu Gln Glu Arg Val Ser
240                 245                 250 agt ctg caa gtc act ctc gcg gac caa gag aag aat tac agt tca ctg      936
Ser Leu Gln Val Thr Leu Ala Asp Gln Glu Lys Asn Tyr Ser Ser Leu
255                 260                 265                 270 aat gga aga ttt gta gag gaa aaa gaa gta agt gaa aag cta cgg aat      984
Asn Gly Arg Phe Val Glu Glu Lys Glu Val Ser Glu Lys Leu Arg Asn
                275                 280                 285 gaa att aca acg tta aaa tat acg ctt tcg gac aaa gaa aag gat tac     1032
Glu Ile Thr Thr Leu Lys Tyr Thr Leu Ser Asp Lys Glu Lys Asp Tyr
            290                 295                 300 aca tca ctc aat gag aga ttt gtg gag gag aaa gca act gct gaa gag     1080
Thr Ser Leu Asn Glu Arg Phe Val Glu Glu Lys Ala Thr Ala Glu Glu
        305                 310                 315 ctg cag gag aag att aaa gta ttg aag atg gac atc gag gct aag gaa     1128
Leu Gln Glu Lys Ile Lys Val Leu Lys Met Asp Ile Glu Ala Lys Glu
320                 325                 330 aat gaa att aat gtt caa act gca agg atc aaa gaa gaa cag gac tct     1176
Asn Glu Ile Asn Val Gln Thr Ala Arg Ile Lys Glu Glu Gln Asp Ser
335                 340                 345                 350 gtt gca tcg ttg caa aat gag ctt caa att gca gga aca caa ctt tct     1224
Val Ala Ser Leu Gln Asn Glu Leu Gln Ile Ala Gly Thr Gln Leu Ser
                355                 360                 365 gaa gag cgc agt aga ctg act gaa gtg agc agt aaa ctt gca act ctt     1272
Glu Glu Arg Ser Arg Leu Thr Glu Val Ser Ser Lys Leu Ala Thr Leu
            370                 375                 380 gag ggt agt tat gct gct tca cag gat tta aat aca cag ctg gat ctt     1320
Glu Gly Ser Tyr Ala Ala Ser Gln Asp Leu Asn Thr Gln Leu Asp Leu
        385                 390                 395 tcg atc agt gat ttg aaa caa aaa cta cag act aca aac agt aga aag     1368
Ser Ile Ser Asp Leu Lys Gln Lys Leu Gln Thr Thr Asn Ser Arg Lys
400                 405                 410 gag gcg ctc gag aaa gag gtg aca agc ttg aat gaa gtg ata aac tcg     1416
Glu Ala Leu Glu Lys Glu Val Thr Ser Leu Asn Glu Val Ile Asn Ser
415                 420                 425                 430 ctg aaa gga acc ttg gca gaa gag aat gac aag aag gac acc ctg tat     1464
Leu Lys Gly Thr Leu Ala Glu Glu Asn Asp Lys Lys Asp Thr Leu Tyr
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 435 |     |     |     |     | 440 |     |     |     |     | 445 |     |     |      |
| ggc | cag | ctc | aag | gta | act | tca | ggg | gct | tta | gag | aag | gca | aca | tcg | gag | 1512 |
| Gly | Gln | Leu | Lys | Val | Thr | Ser | Gly | Ala | Leu | Glu | Lys | Ala | Thr | Ser | Glu |      |
|     |     |     | 450 |     |     |     |     | 455 |     |     |     |     | 460 |     |     |      |
| gtg | cag | ttg | ctg | gag | caa | cgg | gtt | acg | aat | atg | tct | gca | gct | gta | aaa | 1560 |
| Val | Gln | Leu | Leu | Glu | Gln | Arg | Val | Thr | Asn | Met | Ser | Ala | Ala | Val | Lys |      |
|     |     |     |     | 465 |     |     |     |     | 470 |     |     |     |     | 475 |     |      |
| gca | ctt | gaa | aaa | gag | aaa | aat | ggt | gag | atc | aat | caa | ctt | acc | aag | gaa | 1608 |
| Ala | Leu | Glu | Lys | Glu | Lys | Asn | Gly | Glu | Ile | Asn | Gln | Leu | Thr | Lys | Glu |      |
|     |     | 480 |     |     |     |     | 485 |     |     |     |     | 490 |     |     |     |      |
| ctc | caa | gag | aga | att | aag | tca | ctt | gat | gtg | gcc | cag | caa | aaa | tgt | caa | 1656 |
| Leu | Gln | Glu | Arg | Ile | Lys | Ser | Leu | Asp | Val | Ala | Gln | Gln | Lys | Cys | Gln |      |
| 495 |     |     |     |     | 500 |     |     |     |     | 505 |     |     |     |     | 510 |      |
| gca | ttt | tct | aac | gaa | ata | tcc | act | ctc | aag | agg | cag | cag | gca | gct | cta | 1704 |
| Ala | Phe | Ser | Asn | Glu | Ile | Ser | Thr | Leu | Lys | Arg | Gln | Gln | Ala | Ala | Leu |      |
|     |     |     |     | 515 |     |     |     |     | 520 |     |     |     |     | 525 |     |      |
| aat | gaa | gag | ttg | gac | aac | aca | aac | aaa | gaa | ttg | gag | gca | tca | acc | gat | 1752 |
| Asn | Glu | Glu | Leu | Asp | Asn | Thr | Asn | Lys | Glu | Leu | Glu | Ala | Ser | Thr | Asp |      |
|     |     |     | 530 |     |     |     |     | 535 |     |     |     |     | 540 |     |     |      |
| gaa | ttt | aaa | acc | ata | agt | gag | cag | cta | aca | gtc | gct | gtt | aac | tta | agt | 1800 |
| Glu | Phe | Lys | Thr | Ile | Ser | Glu | Gln | Leu | Thr | Val | Ala | Val | Asn | Leu | Ser |      |
|     |     |     |     | 545 |     |     |     |     | 550 |     |     |     |     | 555 |     |      |
| ttg | aag | ctg | gaa | acc | caa | tta | aac | gag | acg | aga | gca | gca | tat | caa | agc | 1848 |
| Leu | Lys | Leu | Glu | Thr | Gln | Leu | Asn | Glu | Thr | Arg | Ala | Ala | Tyr | Gln | Ser |      |
|     |     |     | 560 |     |     |     |     | 565 |     |     |     |     | 570 |     |     |      |
| gca | aat | gtt | gca | ctt | gca | gag | gag | cga | aag | gta | aca | gct | gct | gct | aag | 1896 |
| Ala | Asn | Val | Ala | Leu | Ala | Glu | Glu | Arg | Lys | Val | Thr | Ala | Ala | Ala | Lys |      |
| 575 |     |     |     |     | 580 |     |     |     |     | 585 |     |     |     |     | 590 |      |
| aat | cag | tta | gct | aca | aca | caa | agg | tct | ctc | ata | gcg | gaa | aag | aac | agt | 1944 |
| Asn | Gln | Leu | Ala | Thr | Thr | Gln | Arg | Ser | Leu | Ile | Ala | Glu | Lys | Asn | Ser |      |
|     |     |     |     | 595 |     |     |     |     | 600 |     |     |     |     | 605 |     |      |
| gta | aaa | gct | ctg | cga | gga | agt | gtg | gac | caa | gct | ctc | cag | gca | ctt | cag | 1992 |
| Val | Lys | Ala | Leu | Arg | Gly | Ser | Val | Asp | Gln | Ala | Leu | Gln | Ala | Leu | Gln |      |
|     |     |     | 610 |     |     |     |     | 615 |     |     |     |     | 620 |     |     |      |
| gag | ctc | aac | caa | gat | tca | gtc | gcc | tta | gca | gat | gag | ctc | gac | aaa | gca | 2040 |
| Glu | Leu | Asn | Gln | Asp | Ser | Val | Ala | Leu | Ala | Asp | Glu | Leu | Asp | Lys | Ala |      |
|     |     |     |     | 625 |     |     |     |     | 630 |     |     |     |     | 635 |     |      |
| aaa | aag | aaa | atc | gcc | aac | ttg | gag | gca | gag | agt | gca | tca | gta | cgt | caa | 2088 |
| Lys | Lys | Lys | Ile | Ala | Asn | Leu | Glu | Ala | Glu | Ser | Ala | Ser | Val | Arg | Gln |      |
|     |     | 640 |     |     |     |     | 645 |     |     |     |     | 650 |     |     |     |      |
| aag | ctt | ggt | aag | gag | aaa | gaa | atg | tct | gct | aat | tta | aga | tca | ggg | gct | 2136 |
| Lys | Leu | Gly | Lys | Glu | Lys | Glu | Met | Ser | Ala | Asn | Leu | Arg | Ser | Gly | Ala |      |
| 655 |     |     |     |     | 660 |     |     |     |     | 665 |     |     |     |     | 670 |      |
| gca | gaa | gct | gaa | ggt | act | ata | gct | agg | ctc | ctt | aag | gag | aat | gac | gcc | 2184 |
| Ala | Glu | Ala | Glu | Gly | Thr | Ile | Ala | Arg | Leu | Leu | Lys | Glu | Asn | Asp | Ala |      |
|     |     |     |     | 675 |     |     |     |     | 680 |     |     |     |     | 685 |     |      |
| ggc | aat | aaa | aag | gtg | aag | cag | ttg | gaa | ggt | gag | gta | ctg | aag | agc | aaa | 2232 |
| Gly | Asn | Lys | Lys | Val | Lys | Gln | Leu | Glu | Gly | Glu | Val | Leu | Lys | Ser | Lys |      |
|     |     |     | 690 |     |     |     |     | 695 |     |     |     |     | 700 |     |     |      |
| ggg | gag | acg | gcc | aaa | cag | aag | gga | aag | ctt | ttg | gaa | caa | aaa | cgt | gca | 2280 |
| Gly | Glu | Thr | Ala | Lys | Gln | Lys | Gly | Lys | Leu | Leu | Glu | Gln | Lys | Arg | Ala |      |
|     |     | 705 |     |     |     |     | 710 |     |     |     |     | 715 |     |     |     |      |
| ttg | caa | caa | gct | gag | aca | cgt | ctg | aaa | atg | atc | cct | cag | gtt | cgt | gcg | 2328 |
| Leu | Gln | Gln | Ala | Glu | Thr | Arg | Leu | Lys | Met | Ile | Pro | Gln | Val | Arg | Ala |      |
|     |     | 720 |     |     |     |     | 725 |     |     |     |     | 730 |     |     |     |      |
| gag | gct | gca | tta | ttg | gtt | gag | aag | tac | gag | gat | cta | gct | tat | caa | gaa | 2376 |
| Glu | Ala | Ala | Leu | Leu | Val | Glu | Lys | Tyr | Glu | Asp | Leu | Ala | Tyr | Gln | Glu |      |
| 735 |     |     |     |     | 740 |     |     |     |     | 745 |     |     |     |     | 750 |      |
| aaa | gag | caa | aag | gaa | gct | ata | atg | cgt | gag | aat | gaa | cag | ctg | aat | aag | 2424 |
| Lys | Glu | Gln | Lys | Glu | Ala | Ile | Met | Arg | Glu | Asn | Glu | Gln | Leu | Asn | Lys |      |

```
                755                 760                 765
tct ggc aag acg gtc ggt gca gac ctc agt gag gtt aaa cag agc tta    2472
Ser Gly Lys Thr Val Gly Ala Asp Leu Ser Glu Val Lys Gln Ser Leu
        770                 775                 780 gag gac ggt caa ggc agc acg atc gat atc gaa ggg cga att cca gca    2520
Glu Asp Gly Gln Gly Ser Thr Ile Asp Ile Glu Gly Arg Ile Pro Ala
            785                 790                 795 cac tgg cgg ccg tta cta gtg gat ccg agc tcg gta cca agc ttg gcg    2568
His Trp Arg Pro Leu Leu Val Asp Pro Ser Ser Val Pro Ser Leu Ala
    800                 805                 810 taatcatggt catagctgtt tcctgtgtga aattgttatc cgctcacaat tccacacaac    2628
atacgagccg aagcataaa gtgtaaagcc tggggtgcct aatgagtgag ctaactcaca    2688
ttaattgcgt tgcgctcact gcccgctttc cagtcgggaa acctgtcgtg ccagctgcat    2748
taatgaatcg gccaacgcgc ggggagaa                                      2776

<210> SEQ ID NO 24
<211> LENGTH: 814
<212> TYPE: PRT
<213> ORGANISM: Physcomitrella patens

<400> SEQUENCE: 24

Met Ala Val Ser Arg Leu Gly Pro Ala Pro Ser Pro Ser Ala Val Gln
1               5                   10                  15

Trp Ser Leu Ser Ser Arg Pro Leu Pro Leu Ala Thr Ser Arg Phe Ser
            20                  25                  30

Val Val Pro Val Arg Ala Ser Lys Asn Val Glu Asp Gly Asp Thr Ser
        35                  40                  45

Gly Gly Cys Ala Ala Leu Ser Arg Arg Ala Leu Ile Ala Leu Ile Ala
    50                  55                  60

Leu Ser Thr Gln Leu Gly Gly Val Ala Ser Ala Arg Asp Ile Ser Gly
65                  70                  75                  80

Leu Ile Glu Ser Ser Val Gly Glu Glu Val Ser Ser Leu Ser Leu Ser
                85                  90                  95

Ala Val Glu Val Pro Asn Thr Pro Lys Ile Ser Pro Ser Thr Asp
            100                 105                 110

Leu Gly Ile Ile Asn Glu Val Pro Arg Ala Leu Ala Asp Ser Gly Val
        115                 120                 125

Gly Ala Val Glu Glu Lys Ile Asn Gln Ser Ala Ser Glu Val Ser Ser
    130                 135                 140

Gly Gly Ser Asn Gly Phe Gly Pro Leu Ser Leu Gly Gly Ile Leu Gly
145                 150                 155                 160

Thr Gly Val Ala Gly Ala Leu Phe Tyr Ser Glu Arg Gln Ser Lys Ala
                165                 170                 175

Gln Ala Glu Ser Ala Leu Asp Ala Ala Lys Lys Gln Leu Gln Glu Leu
            180                 185                 190

Arg Glu Thr Ser Glu Gly Gln Leu Leu Ala Glu Lys Gln Leu Ala Gln
        195                 200                 205

Lys Glu Ala Ser Lys Ala Gln Glu Gln Arg Thr Thr Leu Thr Asn Glu
    210                 215                 220

Leu Met Ala Ser Arg Ser Ser Val Thr Asp Leu Glu Gly Lys Leu Gln
225                 230                 235                 240

Met Ala Lys Ala Ser Val Val Asp Leu Gln Glu Arg Val Ser Ser Leu
                245                 250                 255

Gln Val Thr Leu Ala Asp Gln Glu Lys Asn Tyr Ser Ser Leu Asn Gly
            260                 265                 270
```

```
Arg Phe Val Glu Glu Lys Glu Val Ser Glu Lys Leu Arg Asn Glu Ile
        275                 280                 285

Thr Thr Leu Lys Tyr Thr Leu Ser Asp Lys Glu Lys Asp Tyr Thr Ser
        290                 295                 300

Leu Asn Glu Arg Phe Val Glu Glu Lys Ala Thr Ala Glu Glu Leu Gln
305                 310                 315                 320

Glu Lys Ile Lys Val Leu Lys Met Asp Ile Glu Ala Lys Glu Asn Glu
                325                 330                 335

Ile Asn Val Gln Thr Ala Arg Ile Lys Glu Glu Gln Asp Ser Val Ala
                340                 345                 350

Ser Leu Gln Asn Glu Leu Gln Ile Ala Gly Thr Gln Leu Ser Glu Glu
        355                 360                 365

Arg Ser Arg Leu Thr Glu Val Ser Ser Lys Leu Ala Thr Leu Glu Gly
        370                 375                 380

Ser Tyr Ala Ala Ser Gln Asp Leu Asn Thr Gln Leu Asp Leu Ser Ile
385                 390                 395                 400

Ser Asp Leu Lys Gln Lys Leu Gln Thr Thr Asn Ser Arg Lys Glu Ala
                405                 410                 415

Leu Glu Lys Glu Val Thr Ser Leu Asn Glu Val Ile Asn Ser Leu Lys
                420                 425                 430

Gly Thr Leu Ala Glu Glu Asn Asp Lys Lys Asp Thr Leu Tyr Gly Gln
        435                 440                 445

Leu Lys Val Thr Ser Gly Ala Leu Glu Lys Ala Thr Ser Glu Val Gln
        450                 455                 460

Leu Leu Glu Gln Arg Val Thr Asn Met Ser Ala Ala Val Lys Ala Leu
465                 470                 475                 480

Glu Lys Glu Lys Asn Gly Glu Ile Asn Gln Leu Thr Lys Glu Leu Gln
                485                 490                 495

Glu Arg Ile Lys Ser Leu Asp Val Ala Gln Gln Lys Cys Gln Ala Phe
                500                 505                 510

Ser Asn Glu Ile Ser Thr Leu Lys Arg Gln Gln Ala Ala Leu Asn Glu
        515                 520                 525

Glu Leu Asp Asn Thr Asn Lys Glu Leu Glu Ala Ser Thr Asp Glu Phe
        530                 535                 540

Lys Thr Ile Ser Glu Gln Leu Thr Val Ala Val Asn Leu Ser Leu Lys
545                 550                 555                 560

Leu Glu Thr Gln Leu Asn Glu Thr Arg Ala Ala Tyr Gln Ser Ala Asn
                565                 570                 575

Val Ala Leu Ala Glu Glu Arg Lys Val Thr Ala Ala Lys Asn Gln
                580                 585                 590

Leu Ala Thr Thr Gln Arg Ser Leu Ile Ala Glu Lys Asn Ser Val Lys
        595                 600                 605

Ala Leu Arg Gly Ser Val Asp Gln Ala Leu Gln Ala Leu Gln Glu Leu
        610                 615                 620

Asn Gln Asp Ser Val Ala Leu Ala Asp Glu Leu Asp Lys Ala Lys Lys
625                 630                 635                 640

Lys Ile Ala Asn Leu Glu Ala Glu Ser Ala Ser Val Arg Gln Lys Leu
                645                 650                 655

Gly Lys Glu Lys Glu Met Ser Ala Asn Leu Arg Ser Gly Ala Ala Glu
                660                 665                 670

Ala Glu Gly Thr Ile Ala Arg Leu Leu Lys Glu Asn Asp Ala Gly Asn
        675                 680                 685

Lys Lys Val Lys Gln Leu Glu Gly Glu Val Leu Lys Ser Lys Gly Glu
```

```
                690                 695                 700
Thr Ala Lys Gln Lys Gly Lys Leu Leu Glu Gln Lys Arg Ala Leu Gln
705                 710                 715                 720

Gln Ala Glu Thr Arg Leu Lys Met Ile Pro Gln Val Arg Ala Glu Ala
                725                 730                 735

Ala Leu Leu Val Glu Lys Tyr Glu Asp Leu Ala Tyr Gln Glu Lys Glu
                740                 745                 750

Gln Lys Glu Ala Ile Met Arg Glu Asn Glu Gln Leu Asn Lys Ser Gly
                755                 760                 765

Lys Thr Val Gly Ala Asp Leu Ser Glu Val Lys Gln Ser Leu Glu Asp
770                 775                 780

Gly Gln Gly Ser Thr Ile Asp Ile Glu Gly Arg Ile Pro Ala His Trp
785                 790                 795                 800

Arg Pro Leu Leu Val Asp Pro Ser Ser Val Pro Ser Leu Ala
                805                 810

<210> SEQ ID NO 25
<211> LENGTH: 1461
<212> TYPE: DNA
<213> ORGANISM: Physcomitrella patens
<220> FEATURE:
<221> NAME/KEY: CDS
<222> LOCATION: (225)..(977)

<400> SEQUENCE: 25
atcccgggag agcctccact acgtctgtcg aatgctcaca gcgcatgacg ttgaatcccc      60
aagccgacag tttcttgaga agagaaaaat acagtcggag tgttctgttc tccatcacca    120
ttatcgctga tgaagaagtg aggagcttct gagaggcaga gttgcatcag gttgtaacaa    180
aacgcgattc cttcagtgtc gaatcaccag caggaggctt aaaa atg gta ggg aat    236
                                                  Met Val Gly Asn
                                                  1 ggc aga aga atg aac cgc ttg gtg gcg ttc tta gtg gtg gtc tgt tca    284
Gly Arg Arg Met Asn Arg Leu Val Ala Phe Leu Val Val Val Cys Ser
5               10                  15                  20 gcc gtc tca gga tgc aga gca tgg gac tgc tcg gca gcg gat aaa cag    332
Ala Val Ser Gly Cys Arg Ala Trp Asp Cys Ser Ala Ala Asp Lys Gln
                25                  30                  35 aca ctg cta gac ttc aag aat ggg ttc gtg gac acg aac gga gtg ttc    380
Thr Leu Leu Asp Phe Lys Asn Gly Phe Val Asp Thr Asn Gly Val Phe
            40                  45                  50 aac acc tgg agt gat agc act gtg aac tgc tgc gca tgg aag ggc atc    428
Asn Thr Trp Ser Asp Ser Thr Val Asn Cys Cys Ala Trp Lys Gly Ile
        55                  60                  65 aca tgt cgc gag tca gat ggc gca att ttg gag atc aac atc gtg gga    476
Thr Cys Arg Glu Ser Asp Gly Ala Ile Leu Glu Ile Asn Ile Val Gly
    70                  75                  80 tcc tct ggc aca aac cag cag cca tac cgc agc ccg agc tac caa ggc    524
Ser Ser Gly Thr Asn Gln Gln Pro Tyr Arg Ser Pro Ser Tyr Gln Gly
85                  90                  95                  100 aca gtt ggc gca ggg ctg gtg gcg ctc acc caa ttg cag aaa ctc aag    572
Thr Val Gly Ala Gly Leu Val Ala Leu Thr Gln Leu Gln Lys Leu Lys
                105                 110                 115 atc gag tgg gtg ctc ttc aac ggc ccc atc cct cag cag tgg gga gat    620
Ile Glu Trp Val Leu Phe Asn Gly Pro Ile Pro Gln Gln Trp Gly Asp
            120                 125                 130 ttc tcc acc act ctc gtg ttg atc acc atc aac aac gcc aac ctc cgc    668
Phe Ser Thr Thr Leu Val Leu Ile Thr Ile Asn Asn Ala Asn Leu Arg
        135                 140                 145
```

-continued

```
aac gac ata ccc tcc acc ctg gtt aac atc cag aac cta cgg cac ctg    716
Asn Asp Ile Pro Ser Thr Leu Val Asn Ile Gln Asn Leu Arg His Leu
        150                 155                 160 gac ctc aag aac aac cac ctt acg ggc tcc atc ccc tcc acc ttc tgc    764
Asp Leu Lys Asn Asn His Leu Thr Gly Ser Ile Pro Ser Thr Phe Cys
165                 170                 175                 180 acg cac aag aag atc aac tac atc gat gtc tcc tac aac gac atg acc    812
Thr His Lys Lys Ile Asn Tyr Ile Asp Val Ser Tyr Asn Asp Met Thr
                    185                 190                 195 tac ctt ctt gtc cct ccg tgc tta gta aac caa aat aac ctc acc gtc    860
Tyr Leu Leu Val Pro Pro Cys Leu Val Asn Gln Asn Asn Leu Thr Val
                200                 205                 210 atc ttt gat cac cag ggt aac agt act agc ccc ggc tat cct gcg gca    908
Ile Phe Asp His Gln Gly Asn Ser Thr Ser Pro Gly Tyr Pro Ala Ala
            215                 220                 225 ggc tcc acc ctc aca gtc tcg tcg ttg ctc ctc gca atc gga gct ctc    956
Gly Ser Thr Leu Thr Val Ser Ser Leu Leu Leu Ala Ile Gly Ala Leu
230                 235                 240 acc act gct ctc ctc ttc ctc tgaggaaatc cacccccttt cctcgtggtc      1007
Thr Thr Ala Leu Leu Phe Leu
245                 250 aggcaaaccc taactcatta ctgcaatacc cagaacacag ttcttgagaa gggaattttg 1067 atgccgtctc catccctaac tctctcgctc tcactcgtgc gcgcgcacgc gggatctctt 1127 cgttatgaaa aaattaataa gtgccccgga gagattttgt ctgtgatgtc ggaatttgca 1187 gaggaatgaa gcagtcaggt gcacgtaatg tccaaaaggt aacaatcgaa tcacaaggat 1247 attgtagagt tgtcaatgga accgtggcta cacgccagga aaaagtgag tacatattgt  1307 ttgatccttg ggatgtatgc tgtattagtg aaaacctttg tcaaggacag cgctactctg 1367 ttgaatgttt aagcttaagc tgggctgtaa catccagtta aggaataaag ccttaactat 1427 tagttgtctc ggctgtgcga ttatccgata tccg                            1461
```

<210> SEQ ID NO 26
<211> LENGTH: 251
<212> TYPE: PRT
<213> ORGANISM: Physcomitrella patens

<400> SEQUENCE: 26

```
Met Val Gly Asn Gly Arg Arg Met Asn Arg Leu Val Ala Phe Leu Val
1               5                   10                  15

Val Val Cys Ser Ala Val Ser Gly Cys Arg Ala Trp Asp Cys Ser Ala
            20                  25                  30

Ala Asp Lys Gln Thr Leu Leu Asp Phe Lys Asn Gly Phe Val Asp Thr
        35                  40                  45

Asn Gly Val Phe Asn Thr Trp Ser Asp Ser Thr Val Asn Cys Cys Ala
    50                  55                  60

Trp Lys Gly Ile Thr Cys Arg Glu Ser Asp Gly Ala Ile Leu Glu Ile
65                  70                  75                  80

Asn Ile Val Gly Ser Ser Gly Thr Asn Gln Gln Pro Tyr Arg Ser Pro
                85                  90                  95

Ser Tyr Gln Gly Thr Val Gly Ala Gly Leu Val Ala Leu Thr Gln Leu
            100                 105                 110

Gln Lys Leu Lys Ile Glu Trp Val Leu Phe Asn Gly Pro Ile Pro Gln
        115                 120                 125

Gln Trp Gly Asp Phe Ser Thr Thr Leu Val Leu Ile Thr Ile Asn Asn
    130                 135                 140

Ala Asn Leu Arg Asn Asp Ile Pro Ser Thr Leu Val Asn Ile Gln Asn
```

```
                145                 150                 155                 160
Leu Arg His Leu Asp Leu Lys Asn Asn His Leu Thr Gly Ser Ile Pro
                165                 170                 175

Ser Thr Phe Cys Thr His Lys Lys Ile Asn Tyr Ile Asp Val Ser Tyr
                180                 185                 190

Asn Asp Met Thr Tyr Leu Leu Val Pro Pro Cys Leu Val Asn Gln Asn
                195                 200                 205

Asn Leu Thr Val Ile Phe Asp His Gln Gly Asn Ser Thr Ser Pro Gly
                210                 215                 220

Tyr Pro Ala Ala Gly Ser Thr Leu Thr Val Ser Ser Leu Leu Leu Ala
225                 230                 235                 240

Ile Gly Ala Leu Thr Thr Ala Leu Leu Phe Leu
                245                 250

<210> SEQ ID NO 27
<211> LENGTH: 2489
<212> TYPE: DNA
<213> ORGANISM: Physcomitrella patens
<220> FEATURE:
<221> NAME/KEY: CDS
<222> LOCATION: (145)..(2211)

<400> SEQUENCE: 27
atcccgggag gaaccatgtg tgtagagagg ccttgtcaat tctctgtggg catgaggcct    60
tgtagacatg gctccattgt gaggtagcaa ttatgtttgt agacagacct tgtctatcct   120
ctgtggggtt gtgtccttgt agac atg gca ggc att tcg agg gat atc cgc      171
                           Met Ala Gly Ile Ser Arg Asp Ile Arg
                             1               5 gga aca gta gag aat ttg gtc cgt ctg acc tcc gat agc aac agc acc     219
Gly Thr Val Glu Asn Leu Val Arg Leu Thr Ser Asp Ser Asn Ser Thr
 10              15                  20                  25 gat cca ctc aaa ctc aac gtt cta caa tgt cag ttg gtt gct aag aaa     267
Asp Pro Leu Lys Leu Asn Val Leu Gln Cys Gln Leu Val Ala Lys Lys
                 30                  35                  40 gcg gcc gac agt tcg tac acc ttg aac gac ctt gag gct tat cag cgc     315
Ala Ala Asp Ser Ser Tyr Thr Leu Asn Asp Leu Glu Ala Tyr Gln Arg
             45                  50                  55 agg cat gag aaa agc tcc gat gga cgc atc gct ggt acc gga ttt cga     363
Arg His Glu Lys Ser Ser Asp Gly Arg Ile Ala Gly Thr Gly Phe Arg
         60                  65                  70 gcc gct aag gaa ctt ctc cga gtg ctg aag gac gcc gag att ctt atc     411
Ala Ala Lys Glu Leu Leu Arg Val Leu Lys Asp Ala Glu Ile Leu Ile
 75                  80                  85 aga gag tgc tgc tct gaa aag tgg aag aaa gtg gtg ttc aaa cgc gga     459
Arg Glu Cys Cys Ser Glu Lys Trp Lys Lys Val Val Phe Lys Arg Gly
 90                  95                 100                 105 aaa ttg caa gag act ttt gcg aag ata gcg tat gag att gag tgg cac     507
Lys Leu Gln Glu Thr Phe Ala Lys Ile Ala Tyr Glu Ile Glu Trp His
                110                 115                 120 tcg ttg gtg ttg tac agc gtc ttg gtg gca cag agc gac atc tat gac     555
Ser Leu Val Leu Tyr Ser Val Leu Val Ala Gln Ser Asp Ile Tyr Asp
            125                 130                 135 aag agg acg tgc gat ggt aag ctg agg tcc atc gac cat gcc agg ttg     603
Lys Arg Thr Cys Asp Gly Lys Leu Arg Ser Ile Asp His Ala Arg Leu
        140                 145                 150 ata ctt gcg gca agg caa gac cta gat tct ttg agg gcc ctt ctc caa     651
Ile Leu Ala Ala Arg Gln Asp Leu Asp Ser Leu Arg Ala Leu Leu Gln
    155                 160                 165 ggc cca cac gtt tgt gat gaa ata tgt aaa cca gac ttt tgt tcc gaa     699
```

```
Gly Pro His Val Cys Asp Glu Ile Cys Lys Pro Asp Phe Cys Ser Glu
170             175                 180             185 tgc ctc aag gat aaa gta ctt cag cag tgg gat aca gaa gaa aaa gaa    747
Cys Leu Lys Asp Lys Val Leu Gln Gln Trp Asp Thr Glu Glu Lys Glu
            190             195                 200 ttg gag gac agg agc tct ctg tcg caa att atg tca tct atc ttc tca    795
Leu Glu Asp Arg Ser Ser Leu Ser Gln Ile Met Ser Ser Ile Phe Ser
            205             210                 215 tgg gtt caa ccg cag ttt gat tct aaa aga caa cag aat gga aaa gta    843
Trp Val Gln Pro Gln Phe Asp Ser Lys Arg Gln Gln Asn Gly Lys Val
            220             225                 230 ggc gtt gct gaa gtg aaa gag ata aaa tgg ctt ggg caa atg tat gca    891
Gly Val Ala Glu Val Lys Glu Ile Lys Trp Leu Gly Gln Met Tyr Ala
        235             240                 245 atg aag act ttc aac aaa gat gcg act cac gag gca cac ttc agg gag    939
Met Lys Thr Phe Asn Lys Asp Ala Thr His Glu Ala His Phe Arg Glu
250             255                 260             265 gag gtt tct gat atg gct gcc ctt gac cat ccg aat gta gtc cgt atc    987
Glu Val Ser Asp Met Ala Ala Leu Asp His Pro Asn Val Val Arg Ile
            270             275                 280 atc tgt tgt tgg gaa gac aaa aac tac gta agt atc ttg atg gaa ccg   1035
Ile Cys Cys Trp Glu Asp Lys Asn Tyr Val Ser Ile Leu Met Glu Pro
            285             290                 295 ctg cgc aaa agc ttg cac aat ctg cta ctg aat tac aaa gat gga act   1083
Leu Arg Lys Ser Leu His Asn Leu Leu Leu Asn Tyr Lys Asp Gly Thr
        300             305                 310 cat gct ccg tct gca cct acc cca ttt aca atc tta aat tca gtc gat   1131
His Ala Pro Ser Ala Pro Thr Pro Phe Thr Ile Leu Asn Ser Val Asp
        315             320                 325 att atg ctg caa att gcc gaa ggc gtc aga tat gtc cac agc aaa aac   1179
Ile Met Leu Gln Ile Ala Glu Gly Val Arg Tyr Val His Ser Lys Asn
330             335                 340             345 ttt act cac ctt gac atc atg tcg ctc aat gtt cta gta caa ttt gcc   1227
Phe Thr His Leu Asp Ile Met Ser Leu Asn Val Leu Val Gln Phe Ala
            350             355                 360 gat cct atc acc tca aca gat gtg aag gat tct gat aca gtg acc att   1275
Asp Pro Ile Thr Ser Thr Asp Val Lys Asp Ser Asp Thr Val Thr Ile
            365             370                 375 tcc agc aga tct aca tct ttc acg gtc aaa ctt gca gac ttc ggt ttg   1323
Ser Ser Arg Ser Thr Ser Phe Thr Val Lys Leu Ala Asp Phe Gly Leu
            380             385                 390 aag agg ata atc aat gaa aaa ggt cgt cgg aca tca aac tct gtc aag   1371
Lys Arg Ile Ile Asn Glu Lys Gly Arg Arg Thr Ser Asn Ser Val Lys
        395             400                 405 aca gca tgg aca gct cca gag gct tac aag ctc aga aaa ggc gaa gat   1419
Thr Ala Trp Thr Ala Pro Glu Ala Tyr Lys Leu Arg Lys Gly Glu Asp
410             415                 420             425 tca gcc tgg ttc cac ccc agg aaa gca gac gtt tat agc ttt gcg ata   1467
Ser Ala Trp Phe His Pro Arg Lys Ala Asp Val Tyr Ser Phe Ala Ile
            430             435                 440 acg tgc tcc gag ata ctt aca gga gat cac cct ttc gca cat ttc aat   1515
Thr Cys Ser Glu Ile Leu Thr Gly Asp His Pro Phe Ala His Phe Asn
            445             450                 455 gcg gac tac aat ttc gat gct gta aag gat ggg gac cgg ccg agg ttg   1563
Ala Asp Tyr Asn Phe Asp Ala Val Lys Asp Gly Asp Arg Pro Arg Leu
            460             465                 470 cca ggg gaa act ccc agg cga ttg gct gct ttg att cat cga tgc tgg   1611
Pro Gly Glu Thr Pro Arg Arg Leu Ala Ala Leu Ile His Arg Cys Trp
        475             480                 485 cac cga aac cct caa cta cgc cct gat ttt acc gca att tgc acg gag   1659
```

```
His Arg Asn Pro Gln Leu Arg Pro Asp Phe Thr Ala Ile Cys Thr Glu
490                 495                 500                 505 ctt cga ttc atc aag ggg ctt gcc ttg cga ggt gat atc aaa tca ctg        1707
Leu Arg Phe Ile Lys Gly Leu Ala Leu Arg Gly Asp Ile Lys Ser Leu
                510                 515                 520 cac caa aca gat gtt ggc aat gaa gcc aat ttt cat atg gag aca gga        1755
His Gln Thr Asp Val Gly Asn Glu Ala Asn Phe His Met Glu Thr Gly
            525                 530                 535 gtt aag gta caa ggg cca tgg gga ggc aat ggg gga ggt caa ttc ttt        1803
Val Lys Val Gln Gly Pro Trp Gly Gly Asn Gly Gly Gly Gln Phe Phe
        540                 545                 550 gat gga ata gtc aca tcc ata aag cag ata acc atg aag tat agc aca        1851
Asp Gly Ile Val Thr Ser Ile Lys Gln Ile Thr Met Lys Tyr Ser Thr
555                 560                 565 gac cca tcc cct tgc ata ttc tac atg gag atg gag tac aac atg aat        1899
Asp Pro Ser Pro Cys Ile Phe Tyr Met Glu Met Glu Tyr Asn Met Asn
570                 575                 580                 585 gga aca tca ttt ttt att ggt cat gga gat gcc aat cat ggt tcg aac        1947
Gly Thr Ser Phe Phe Ile Gly His Gly Asp Ala Asn His Gly Ser Asn
                590                 595                 600 tct tca act atc aag ata gac gag cct agt gaa tac atc aca aaa gtt        1995
Ser Ser Thr Ile Lys Ile Asp Glu Pro Ser Glu Tyr Ile Thr Lys Val
            605                 610                 615 gaa ggg tca tat ggc agc acc cca atg tgg tgt gga ggc aag caa gtg        2043
Glu Gly Ser Tyr Gly Ser Thr Pro Met Trp Cys Gly Gly Lys Gln Val
        620                 625                 630 gag agt tta aca tcc tta acc ata cac acc aat gtg aaa gca cat gga        2091
Glu Ser Leu Thr Ser Leu Thr Ile His Thr Asn Val Lys Ala His Gly
635                 640                 645 ccc ttt gga ggg aag tgc aca tcc aag ttc aaa agt gaa tat ggc aga        2139
Pro Phe Gly Gly Lys Cys Thr Ser Lys Phe Lys Ser Glu Tyr Gly Arg
650                 655                 660                 665 gtt gtg ggt ttc cat gga aga agt ggt ttg ggg ctt gat tct att ggt        2187
Val Val Gly Phe His Gly Arg Ser Gly Leu Gly Leu Asp Ser Ile Gly
                670                 675                 680 tgt ttt aca gta ccc att gaa gtt tgatgtatcc aaaatgaata ccttgggaga       2241
Cys Phe Thr Val Pro Ile Glu Val
                685 tgattgtcat gtgcatcaat ctttacagta actgtgtaat aatattgtca taggcttgta     2301 gaaagttact taccaaaagt aggtatacag tagaaatgga tgtgattcta ttggctaagt     2361 agcaatgtag taaattggtg aggtgtagca cttcaatatt tcatcatgaa tactcgtggc     2421 agaagaaaac attaaaaaaa actaaaagca ttatcttaca ggaatgttat gagtgcaagg     2481 cgttaacc                                                              2489

<210> SEQ ID NO 28
<211> LENGTH: 689
<212> TYPE: PRT
<213> ORGANISM: Physcomitrella patens

<400> SEQUENCE: 28

Met Ala Gly Ile Ser Arg Asp Ile Arg Gly Thr Val Glu Asn Leu Val
1               5                   10                  15

Arg Leu Thr Ser Asp Ser Asn Ser Thr Asp Pro Leu Lys Leu Asn Val
            20                  25                  30

Leu Gln Cys Gln Leu Val Ala Lys Lys Ala Asp Ser Ser Tyr Thr
        35                  40                  45

Leu Asn Asp Leu Glu Ala Tyr Gln Arg Arg His Glu Lys Ser Ser Asp
    50                  55                  60
```

```
Gly Arg Ile Ala Gly Thr Gly Phe Arg Ala Ala Lys Glu Leu Leu Arg
 65                  70                  75                  80

Val Leu Lys Asp Ala Glu Ile Leu Ile Arg Glu Cys Cys Ser Glu Lys
                 85                  90                  95

Trp Lys Lys Val Val Phe Lys Arg Gly Lys Leu Gln Glu Thr Phe Ala
                100                 105                 110

Lys Ile Ala Tyr Glu Ile Glu Trp His Ser Leu Val Leu Tyr Ser Val
                115                 120                 125

Leu Val Ala Gln Ser Asp Ile Tyr Asp Lys Arg Thr Cys Asp Gly Lys
130                 135                 140

Leu Arg Ser Ile Asp His Ala Arg Leu Ile Leu Ala Ala Arg Gln Asp
145                 150                 155                 160

Leu Asp Ser Leu Arg Ala Leu Leu Gln Gly Pro His Val Cys Asp Glu
                165                 170                 175

Ile Cys Lys Pro Asp Phe Cys Ser Glu Cys Leu Lys Asp Lys Val Leu
                180                 185                 190

Gln Gln Trp Asp Thr Glu Glu Lys Glu Leu Glu Asp Arg Ser Ser Leu
                195                 200                 205

Ser Gln Ile Met Ser Ser Ile Phe Ser Trp Val Gln Pro Gln Phe Asp
210                 215                 220

Ser Lys Arg Gln Gln Asn Gly Lys Val Gly Val Ala Glu Val Lys Glu
225                 230                 235                 240

Ile Lys Trp Leu Gly Gln Met Tyr Ala Met Lys Thr Phe Asn Lys Asp
                245                 250                 255

Ala Thr His Glu Ala His Phe Arg Glu Val Ser Asp Met Ala Ala
                260                 265                 270

Leu Asp His Pro Asn Val Val Arg Ile Ile Cys Cys Trp Glu Asp Lys
                275                 280                 285

Asn Tyr Val Ser Ile Leu Met Glu Pro Leu Arg Lys Ser Leu His Asn
                290                 295                 300

Leu Leu Leu Asn Tyr Lys Asp Gly Thr His Ala Pro Ser Ala Pro Thr
305                 310                 315                 320

Pro Phe Thr Ile Leu Asn Ser Val Asp Ile Met Leu Gln Ile Ala Glu
                325                 330                 335

Gly Val Arg Tyr Val His Ser Lys Asn Phe Thr His Leu Asp Ile Met
                340                 345                 350

Ser Leu Asn Val Leu Val Gln Phe Ala Asp Pro Ile Thr Ser Thr Asp
                355                 360                 365

Val Lys Asp Ser Asp Thr Val Thr Ile Ser Ser Arg Ser Thr Ser Phe
370                 375                 380

Thr Val Lys Leu Ala Asp Phe Gly Leu Lys Arg Ile Ile Asn Glu Lys
385                 390                 395                 400

Gly Arg Arg Thr Ser Asn Ser Val Lys Thr Ala Trp Thr Ala Pro Glu
                405                 410                 415

Ala Tyr Lys Leu Arg Lys Gly Glu Asp Ser Ala Trp Phe His Pro Arg
                420                 425                 430

Lys Ala Asp Val Tyr Ser Phe Ala Ile Thr Cys Ser Glu Ile Leu Thr
                435                 440                 445

Gly Asp His Pro Phe Ala His Phe Asn Ala Asp Tyr Asn Phe Asp Ala
                450                 455                 460

Val Lys Asp Gly Asp Arg Pro Arg Leu Pro Gly Glu Thr Pro Arg Arg
465                 470                 475                 480

Leu Ala Ala Leu Ile His Arg Cys Trp His Arg Asn Pro Gln Leu Arg
```

| | | 485 | | | | 490 | | | | 495 | | |
|---|---|---|---|---|---|---|---|---|---|---|---|---|
| Pro | Asp | Phe | Thr | Ala | Ile | Cys | Thr | Glu | Leu | Arg | Phe | Ile | Lys | Gly | Leu |
| | | | | 500 | | | | | 505 | | | | | 510 | |

Ala Leu Arg Gly Asp Ile Lys Ser Leu His Gln Thr Asp Val Gly Asn
            515                 520                 525

Glu Ala Asn Phe His Met Glu Thr Gly Val Lys Val Gln Gly Pro Trp
530                 535                 540

Gly Gly Asn Gly Gly Gln Phe Phe Asp Gly Ile Val Thr Ser Ile
545                 550                 555                 560

Lys Gln Ile Thr Met Lys Tyr Ser Thr Asp Pro Ser Pro Cys Ile Phe
                565                 570                 575

Tyr Met Glu Met Glu Tyr Asn Met Asn Gly Thr Ser Phe Phe Ile Gly
            580                 585                 590

His Gly Asp Ala Asn His Gly Ser Asn Ser Ser Thr Ile Lys Ile Asp
        595                 600                 605

Glu Pro Ser Glu Tyr Ile Thr Lys Val Glu Gly Ser Tyr Gly Ser Thr
    610                 615                 620

Pro Met Trp Cys Gly Gly Lys Gln Val Glu Ser Leu Thr Ser Leu Thr
625                 630                 635                 640

Ile His Thr Asn Val Lys Ala His Gly Pro Phe Gly Gly Lys Cys Thr
                645                 650                 655

Ser Lys Phe Lys Ser Glu Tyr Gly Arg Val Val Gly Phe His Gly Arg
            660                 665                 670

Ser Gly Leu Gly Leu Asp Ser Ile Gly Cys Phe Thr Val Pro Ile Glu
        675                 680                 685

Val

```
<210> SEQ ID NO 29
<211> LENGTH: 831
<212> TYPE: DNA
<213> ORGANISM: Physcomitrella patens
<220> FEATURE:
<221> NAME/KEY: CDS
<222> LOCATION: (20)..(685)

<400> SEQUENCE: 29
```

| atcccgggcc gttgtaaag atg ggt act cag tcg ctg att tac agc ttt gtt | | | | | | | | | | | 52 |
|---|---|---|---|---|---|---|---|---|---|---|---|
| | | Met | Gly | Thr | Gln | Ser | Leu | Ile | Tyr | Ser | Phe | Val |
| | | 1 | | | | 5 | | | | | 10 | |

| gcc | aga | ggc | tca | acg | gtg | ctg | gcc | gag | tac | act | gcc | ttt | tct | ggc | aac | 100 |
|---|---|---|---|---|---|---|---|---|---|---|---|---|---|---|---|---|
| Ala | Arg | Gly | Ser | Thr | Val | Leu | Ala | Glu | Tyr | Thr | Ala | Phe | Ser | Gly | Asn | |
| | | | 15 | | | | | 20 | | | | | 25 | | | |

| ttc | agc | acc | att | gca | gtg | caa | tgt | ctt | cag | aag | ctt | cca | cca | aac | aac | 148 |
|---|---|---|---|---|---|---|---|---|---|---|---|---|---|---|---|---|
| Phe | Ser | Thr | Ile | Ala | Val | Gln | Cys | Leu | Gln | Lys | Leu | Pro | Pro | Asn | Asn | |
| | | 30 | | | | | 35 | | | | | 40 | | | | |

| aat | aaa | ttc | act | tac | acc | tgt | gat | cga | cac | acc | ttc | aac | tac | ctt | gtt | 196 |
|---|---|---|---|---|---|---|---|---|---|---|---|---|---|---|---|---|
| Asn | Lys | Phe | Thr | Tyr | Thr | Cys | Asp | Arg | His | Thr | Phe | Asn | Tyr | Leu | Val | |
| | 45 | | | | | 50 | | | | | 55 | | | | | |

| gag | gaa | ggc | tac | aca | tat | ttg | gtt | gtg | gct | gat | gag | gaa | ttt | ggg | agg | 244 |
|---|---|---|---|---|---|---|---|---|---|---|---|---|---|---|---|---|
| Glu | Glu | Gly | Tyr | Thr | Tyr | Leu | Val | Val | Ala | Asp | Glu | Glu | Phe | Gly | Arg | |
| 60 | | | | | 65 | | | | | 70 | | | | | 75 | |

| caa | att | ccg | ttt | gct | ttc | ctt | gag | cga | gtg | aag | gag | gac | ttt | aag | cgg | 292 |
|---|---|---|---|---|---|---|---|---|---|---|---|---|---|---|---|---|
| Gln | Ile | Pro | Phe | Ala | Phe | Leu | Glu | Arg | Val | Lys | Glu | Asp | Phe | Lys | Arg | |
| | | | 80 | | | | | 85 | | | | | 90 | | | |

| cgt | tat | gca | gga | gga | aag | gcc | gac | tcg | gcc | atc | gcc | aac | agt | tta | gat | 340 |
|---|---|---|---|---|---|---|---|---|---|---|---|---|---|---|---|---|
| Arg | Tyr | Ala | Gly | Gly | Lys | Ala | Asp | Ser | Ala | Ile | Ala | Asn | Ser | Leu | Asp | |
| | | 95 | | | | | 100 | | | | | 105 | | | | |

| aaa | gaa | ttc | ggt | ccg | aaa | ctg | aag | gac | cac | atg | cag | tac | tgc | gtc | gat | 388 |

-continued

```
                Lys Glu Phe Gly Pro Lys Leu Lys Asp His Met Gln Tyr Cys Val Asp
                        110                 115                 120 cac cct gat gaa atg aac aaa att tcg aag att aag tcc caa gtt gcg        436
His Pro Asp Glu Met Asn Lys Ile Ser Lys Ile Lys Ser Gln Val Ala
125                 130                 135 gaa gtc aag gga atc atg atg gac aat atc gag aag gtg ctt gat cgt        484
Glu Val Lys Gly Ile Met Met Asp Asn Ile Glu Lys Val Leu Asp Arg
140                 145                 150                 155 gga gag aag att gag ctt ctt gtt gat aag aca gag aac ttg cgt ttc        532
Gly Glu Lys Ile Glu Leu Leu Val Asp Lys Thr Glu Asn Leu Arg Phe
            160                 165                 170 cag gct gac aac ttt cag cga caa ggc aag caa ctg cgt cgc aag atg        580
Gln Ala Asp Asn Phe Gln Arg Gln Gly Lys Gln Leu Arg Arg Lys Met
            175                 180                 185 tgg ttc cag aac atg aaa gtg aag ctt ata gtt ctt gcc atc att atc        628
Trp Phe Gln Asn Met Lys Val Lys Leu Ile Val Leu Ala Ile Ile Ile
        190                 195                 200 gtc atc atc atc atc att tgg ctt tcc att tgc cgt gga ttc act tgc        676
Val Ile Ile Ile Ile Ile Trp Leu Ser Ile Cys Arg Gly Phe Thr Cys
205                 210                 215 agc aat cgc taagtgtata tactgactgg aggtggaaag cagaagcctg                725
Ser Asn Arg
220 cactaattt tcattgtttt tgttttttcgc tttctgccca aatcttcagg tagtgaatca      785
tgaaatttga gtctgtggcc tctgtcaggg agttgtgtga gctcgc                     831

<210> SEQ ID NO 30
<211> LENGTH: 222
<212> TYPE: PRT
<213> ORGANISM: Physcomitrella patens

<400> SEQUENCE: 30

Met Gly Thr Gln Ser Leu Ile Tyr Ser Phe Val Ala Arg Gly Ser Thr
1               5                   10                  15

Val Leu Ala Glu Tyr Thr Ala Phe Ser Gly Asn Phe Ser Thr Ile Ala
            20                  25                  30

Val Gln Cys Leu Gln Lys Leu Pro Asn Asn Asn Lys Phe Thr Tyr
        35                  40                  45

Thr Cys Asp Arg His Thr Phe Asn Tyr Leu Val Glu Glu Gly Tyr Thr
    50                  55                  60

Tyr Leu Val Val Ala Asp Glu Glu Phe Gly Arg Gln Ile Pro Phe Ala
65                  70                  75                  80

Phe Leu Glu Arg Val Lys Glu Asp Phe Lys Arg Arg Tyr Ala Gly Gly
                85                  90                  95

Lys Ala Asp Ser Ala Ile Ala Asn Ser Leu Asp Lys Glu Phe Gly Pro
            100                 105                 110

Lys Leu Lys Asp His Met Gln Tyr Cys Val Asp His Pro Asp Glu Met
        115                 120                 125

Asn Lys Ile Ser Lys Ile Lys Ser Gln Val Ala Glu Val Lys Gly Ile
    130                 135                 140

Met Met Asp Asn Ile Glu Lys Val Leu Asp Arg Gly Glu Lys Ile Glu
145                 150                 155                 160

Leu Leu Val Asp Lys Thr Glu Asn Leu Arg Phe Gln Ala Asp Asn Phe
                165                 170                 175

Gln Arg Gln Gly Lys Gln Leu Arg Arg Lys Met Trp Phe Gln Asn Met
            180                 185                 190

Lys Val Lys Leu Ile Val Leu Ala Ile Ile Ile Val Ile Ile Ile Ile
```

```
                    195                 200                 205
Ile Trp Leu Ser Ile Cys Arg Gly Phe Thr Cys Ser Asn Arg
    210                 215                 220

<210> SEQ ID NO 31
<211> LENGTH: 1342
<212> TYPE: DNA
<213> ORGANISM: Physcomitrella patens
<220> FEATURE:
<221> NAME/KEY: CDS
<222> LOCATION: (43)..(588)

<400> SEQUENCE: 31
atcccgggtg tgccagtgac cgagcatacg cacggtgatc tt atg tta tct ttg        54
                                               Met Leu Ser Leu
                                                 1 cat gcc cgg cgg ctt tgc ttg aat tca ccg tcg aat tac atg gtt gaa      102
His Ala Arg Arg Leu Cys Leu Asn Ser Pro Ser Asn Tyr Met Val Glu
  5              10                  15                  20 ttg ggg aga gtg gag aag gta ctt ggc ctg agg gca ggt gcc gtg aag      150
Leu Gly Arg Val Glu Lys Val Leu Gly Leu Arg Ala Gly Ala Val Lys
                 25                  30                  35 atc ttt cta gag aag ttt gcc gct atg aat cca act tct tgc ggt acc      198
Ile Phe Leu Glu Lys Phe Ala Ala Met Asn Pro Thr Ser Cys Gly Thr
             40                  45                  50 gtc agc ttg aac caa ttt gtc aaa tgg cat cat atg ccg aaa tgc tgg      246
Val Ser Leu Asn Gln Phe Val Lys Trp His His Met Pro Lys Cys Trp
         55                  60                  65 atg tcg aag aag ata ttt gat ctt ttc gac aaa tcg gga cag ggc ttc      294
Met Ser Lys Lys Ile Phe Asp Leu Phe Asp Lys Ser Gly Gln Gly Phe
 70                  75                  80 acg act ttt aga gag ttc gtg gcg gta atg gga tca atc act aaa agc      342
Thr Thr Phe Arg Glu Phe Val Ala Val Met Gly Ser Ile Thr Lys Ser
 85                  90                  95                 100 aag gag ttt aag agt caa atg aaa gca gct tac gat gca tgt aac ctt      390
Lys Glu Phe Lys Ser Gln Met Lys Ala Ala Tyr Asp Ala Cys Asn Leu
                105                 110                 115 caa aac agt gac tgc atc tca caa ctg gag ctg gaa aaa tgc ctg aag      438
Gln Asn Ser Asp Cys Ile Ser Gln Leu Glu Leu Glu Lys Cys Leu Lys
            120                 125                 130 tta agt atg cca aca att agc tct gca tac gtg agg gcg tgg ttc agt      486
Leu Ser Met Pro Thr Ile Ser Ser Ala Tyr Val Arg Ala Trp Phe Ser
        135                 140                 145 aag att tct cag cac gat gat ggg gcc ata agc tgg gag gat ttc caa      534
Lys Ile Ser Gln His Asp Asp Gly Ala Ile Ser Trp Glu Asp Phe Gln
    150                 155                 160 gtc ttc tta gag acg aac cca gag cta ttg ccc att ttc atg gtg gga      582
Val Phe Leu Glu Thr Asn Pro Glu Leu Leu Pro Ile Phe Met Val Gly
165                 170                 175                 180 act ttt taacttcgag ccagcctgtg agatgggtta tctcaaagtg gactttctct       638
Thr Phe ctgtcttggc ttgaactcta ctttgacata gcccacttca aggtaactt gaatacactc     698 aaaacgacgt caagttcgct gtgtaccggc cctatcaaca cccaggcagc ccagattgta    758
ctggtaatca gggcctaatt cttgatgtca tcgctgcctg tagaatgcaa agacgtgaac    818
agggttcacc agtgagggtg tttgattcct accgaattat cgggaccttg attgtgaggt    878
tcgtgacaaa tccggaactt gacgttgatg gtatatttcg agattcgctt gagagtcgac    938
tgtcaagttt gctagtgta ctgaagaaca ttgtttatca ttttggaatt ctactgagca     998
gaccgcagtg tctggtgagt tgcaatgctt gggaaacgga aagctccgtt gaattcaacg   1058
```

```
tcctacactc gaagaatcaa gctgcagctt tgcgagttga acacatcgtg acagtctatt    1118
acggtgcttc attatgtgca gtatcggtgt tcaacaaatt agcaccaatc tagaacagca    1178
ttccgttgca aaagcagaga acaaagccta tgtggtcatt cttcacagag gactttggtg    1238
tgcacctctt gtaaacccat tacatttctc cttgatgtag attgaaccat gttttatga    1298 atttaaaatg ccacggtgac tggtgttgtg tagcccgagc tcgc                     1342
```

```
<210> SEQ ID NO 32
<211> LENGTH: 182
<212> TYPE: PRT
<213> ORGANISM: Physcomitrella patens

<400> SEQUENCE: 32
```

```
Met Leu Ser Leu His Ala Arg Arg Leu Cys Leu Asn Ser Pro Ser Asn
1               5                   10                  15

Tyr Met Val Glu Leu Gly Arg Val Glu Lys Val Leu Gly Leu Arg Ala
            20                  25                  30

Gly Ala Val Lys Ile Phe Leu Glu Lys Phe Ala Ala Met Asn Pro Thr
        35                  40                  45

Ser Cys Gly Thr Val Ser Leu Asn Gln Phe Val Lys Trp His His Met
    50                  55                  60

Pro Lys Cys Trp Met Ser Lys Lys Ile Phe Asp Leu Phe Asp Lys Ser
65                  70                  75                  80

Gly Gln Gly Phe Thr Thr Phe Arg Glu Phe Val Ala Val Met Gly Ser
                85                  90                  95

Ile Thr Lys Ser Lys Glu Phe Lys Ser Gln Met Lys Ala Ala Tyr Asp
            100                 105                 110

Ala Cys Asn Leu Gln Asn Ser Asp Cys Ile Ser Gln Leu Glu Leu Glu
        115                 120                 125

Lys Cys Leu Lys Leu Ser Met Pro Thr Ile Ser Ser Ala Tyr Val Arg
    130                 135                 140

Ala Trp Phe Ser Lys Ile Ser Gln His Asp Asp Gly Ala Ile Ser Trp
145                 150                 155                 160

Glu Asp Phe Gln Val Phe Leu Glu Thr Asn Pro Glu Leu Leu Pro Ile
                165                 170                 175

Phe Met Val Gly Thr Phe
            180
```

```
<210> SEQ ID NO 33
<211> LENGTH: 804
<212> TYPE: DNA
<213> ORGANISM: Physcomitrella patens
<220> FEATURE:
<221> NAME/KEY: CDS
<222> LOCATION: (16)..(732)

<400> SEQUENCE: 33
```

```
atcccgggcg gaaag atg acc gaa acg acg ggc agc ggt gca ttg tca cag     51
              Met Thr Glu Thr Thr Gly Ser Gly Ala Leu Ser Gln
              1               5                   10 gcg gcg gat tgt tta ccg ttg act tat caa agg cca gta cgg gat gac      99
Ala Ala Asp Cys Leu Pro Leu Thr Tyr Gln Arg Pro Val Arg Asp Asp
        15                  20                  25 ttg gaa act cat ctt cca aaa cct tac cta gcg aga gca ttg gta gct     147
Leu Glu Thr His Leu Pro Lys Pro Tyr Leu Ala Arg Ala Leu Val Ala
    30                  35                  40 cca gat aca gaa cat cca aac ggg acg tta ggg cac agg cat aat ggc     195
Pro Asp Thr Glu His Pro Asn Gly Thr Leu Gly His Arg His Asn Gly
```

```
                45                  50                  55                  60
atg act gtt ctt cag cag cat att gct ttc ttt gat caa aat ggt gac         243
Met Thr Val Leu Gln Gln His Ile Ala Phe Phe Asp Gln Asn Gly Asp
                65                  70                  75 gga atc att tac cca tgg gag acc tat gct gga ctg cgt gaa ata gga         291
Gly Ile Ile Tyr Pro Trp Glu Thr Tyr Ala Gly Leu Arg Glu Ile Gly
                80                  85                  90 ttc aat gtc ata tgg tcc gca atg gtt gcc ttt ata atc aat gtg gtg         339
Phe Asn Val Ile Trp Ser Ala Met Val Ala Phe Ile Ile Asn Val Val
                95                 100                 105 atg agc tat gca tcc ctc cct ggg tgg ttg cct tcg ccc ttt ttg ccc         387
Met Ser Tyr Ala Ser Leu Pro Gly Trp Leu Pro Ser Pro Phe Leu Pro
        110                 115                 120 ata tat atc tac aat ata cac aag gca aaa cat gga agc gac tcg ggg         435
Ile Tyr Ile Tyr Asn Ile His Lys Ala Lys His Gly Ser Asp Ser Gly
125                 130                 135                 140 gct tat gat acc gag gga aga tat gtg ccg gtg tac ttt gag aac gtg         483
Ala Tyr Asp Thr Glu Gly Arg Tyr Val Pro Val Tyr Phe Glu Asn Val
                145                 150                 155 ttt agc aag tat gct aga aca gtg cct gat aag ctc aca ctc gga gag         531
Phe Ser Lys Tyr Ala Arg Thr Val Pro Asp Lys Leu Thr Leu Gly Glu
                160                 165                 170 att tgg agc atg acc gaa ggg aat cga gta gct tat gat ttc ttt gga         579
Ile Trp Ser Met Thr Glu Gly Asn Arg Val Ala Tyr Asp Phe Phe Gly
                175                 180                 185 tgg gct gcg gct aag gga gaa tgg ata ctt ttg tat atg ctt gct aag         627
Trp Ala Ala Ala Lys Gly Glu Trp Ile Leu Leu Tyr Met Leu Ala Lys
        190                 195                 200 gac gag gaa ggc atg ctg tca aag gag gcg tgt agg cgt tgt ttt gac         675
Asp Glu Glu Gly Met Leu Ser Lys Glu Ala Cys Arg Arg Cys Phe Asp
205                 210                 215                 220 ggt agc ttg ttt gag tat tgc gcc aag atg aac agg atg caa cac gag         723
Gly Ser Leu Phe Glu Tyr Cys Ala Lys Met Asn Arg Met Gln His Glu
                225                 230                 235 aag gcg tat tgagcattat tagattttta gaaaccgttt gtgttgataa                 772
Lys Ala Tyr tgtagagtat gttgtttaga tcgggagctc gc                                     804

<210> SEQ ID NO 34
<211> LENGTH: 239
<212> TYPE: PRT
<213> ORGANISM: Physcomitrella patens

<400> SEQUENCE: 34

Met Thr Glu Thr Thr Gly Ser Gly Ala Leu Ser Gln Ala Ala Asp Cys
1               5                   10                  15

Leu Pro Leu Thr Tyr Gln Arg Pro Val Arg Asp Asp Leu Glu Thr His
                20                  25                  30

Leu Pro Lys Pro Tyr Leu Ala Arg Ala Leu Val Ala Pro Asp Thr Glu
        35                  40                  45

His Pro Asn Gly Thr Leu Gly His Arg His Asn Gly Met Thr Val Leu
    50                  55                  60

Gln Gln His Ile Ala Phe Phe Asp Gln Asn Gly Asp Gly Ile Ile Tyr
65              70                  75                  80

Pro Trp Glu Thr Tyr Ala Gly Leu Arg Glu Ile Gly Phe Asn Val Ile
                85                  90                  95

Trp Ser Ala Met Val Ala Phe Ile Ile Asn Val Val Met Ser Tyr Ala
            100                 105                 110
```

```
Ser Leu Pro Gly Trp Leu Pro Ser Pro Phe Leu Pro Ile Tyr Ile Tyr
        115                 120                 125

Asn Ile His Lys Ala Lys His Gly Ser Asp Ser Gly Ala Tyr Asp Thr
130                 135                 140

Glu Gly Arg Tyr Val Pro Val Tyr Phe Glu Asn Val Phe Ser Lys Tyr
145                 150                 155                 160

Ala Arg Thr Val Pro Asp Lys Leu Thr Leu Gly Glu Ile Trp Ser Met
                165                 170                 175

Thr Glu Gly Asn Arg Val Ala Tyr Asp Phe Phe Gly Trp Ala Ala Ala
            180                 185                 190

Lys Gly Glu Trp Ile Leu Leu Tyr Met Leu Ala Lys Asp Glu Gly
        195                 200                 205

Met Leu Ser Lys Glu Ala Cys Arg Arg Cys Phe Asp Gly Ser Leu Phe
210                 215                 220

Glu Tyr Cys Ala Lys Met Asn Arg Met Gln His Glu Lys Ala Tyr
225                 230                 235

<210> SEQ ID NO 35
<211> LENGTH: 1562
<212> TYPE: DNA
<213> ORGANISM: Physcomitrella patens
<220> FEATURE:
<221> NAME/KEY: CDS
<222> LOCATION: (166)..(1458)

<400> SEQUENCE: 35
gcgttaacgg gtgtgagcga cgagcttcat gagtagcact tcctgagatg aattgatcct      60
cccgctgggt cgcacccgga tgttcgcagt gctggagaat gtatacgtaa cgaggatcat     120
tgcccacttt cgtccggagc gctttgctga gcctcgtcgt ccact atg cct gtt aag     177
                                                Met Pro Val Lys
                                                  1 gat cgc att tcg tac ttt tac gat ggg gac gtg ggt agt gtg tac tat     225
Asp Arg Ile Ser Tyr Phe Tyr Asp Gly Asp Val Gly Ser Val Tyr Tyr
  5                  10                  15                  20 ggg cca aac cat cca atg aag ccc cat cgg ttg tgt atg aca aac agt     273
Gly Pro Asn His Pro Met Lys Pro His Arg Leu Cys Met Thr Asn Ser
                 25                  30                  35 ctc gtc ctt gct tat gga ctt cac aac aag atg gag att tat cga ccc     321
Leu Val Leu Ala Tyr Gly Leu His Asn Lys Met Glu Ile Tyr Arg Pro
         40                  45                  50 cac aaa gcc tac ccg gtg gaa ctc gcg cag ttt cac tct gtt gac tat     369
His Lys Ala Tyr Pro Val Glu Leu Ala Gln Phe His Ser Val Asp Tyr
     55                  60                  65 gtt gag ttt ctc ggc cga att act cct gaa tct cag gaa aag tat gca     417
Val Glu Phe Leu Gly Arg Ile Thr Pro Glu Ser Gln Glu Lys Tyr Ala
 70                  75                  80 gcg gag ttg ata aga tat aac atg ggg gag gat tgc cct gtt ttt gac     465
Ala Glu Leu Ile Arg Tyr Asn Met Gly Glu Asp Cys Pro Val Phe Asp
85                  90                  95                 100 aac ctt ttt gaa ttt tgt caa att tat gct ggg ggt act att gat gcc     513
Asn Leu Phe Glu Phe Cys Gln Ile Tyr Ala Gly Gly Thr Ile Asp Ala
                105                 110                 115 gcg cat cgt ctg aac cat ggc tta tgt gac ata gcc atc aac tgg gct     561
Ala His Arg Leu Asn His Gly Leu Cys Asp Ile Ala Ile Asn Trp Ala
            120                 125                 130 gga ggt tta cat cat gca aag aag tgt gaa gcc tct gga ttt tgt tac     609
Gly Gly Leu His His Ala Lys Lys Cys Glu Ala Ser Gly Phe Cys Tyr
        135                 140                 145 gtg aat gac cta gtt ttg ggc att tta gaa ctt ttg aag tat cac gct     657
```

```
Val Asn Asp Leu Val Leu Gly Ile Leu Glu Leu Leu Lys Tyr His Ala
    150                 155                 160 cgc gtg cta tat att gac ata gat att cac cat gga gac gga gta gaa      705
Arg Val Leu Tyr Ile Asp Ile Asp Ile His His Gly Asp Gly Val Glu
165                 170                 175                 180 gaa gcg ttt tat ctt act gac aga gta atg acc gtt agt ttt cat aaa      753
Glu Ala Phe Tyr Leu Thr Asp Arg Val Met Thr Val Ser Phe His Lys
                185                 190                 195 ttt gga gac tac ttc ttc cca ggc act ggg gat gta aag gac gtt gga      801
Phe Gly Asp Tyr Phe Phe Pro Gly Thr Gly Asp Val Lys Asp Val Gly
                200                 205                 210 gag aga gaa gga aaa tat tat gca atc aac gtg ccg cta aaa gat ggc      849
Glu Arg Glu Gly Lys Tyr Tyr Ala Ile Asn Val Pro Leu Lys Asp Gly
                215                 220                 225 att gat gac gca aat ttc ata cgg atg ttt cgc gtg gta atc caa aag      897
Ile Asp Asp Ala Asn Phe Ile Arg Met Phe Arg Val Val Ile Gln Lys
230                 235                 240 gtt gtg gaa gtt tat caa cct ggt gcc att gtt ctg caa tgt gga gct      945
Val Val Glu Val Tyr Gln Pro Gly Ala Ile Val Leu Gln Cys Gly Ala
245                 250                 255                 260 gac tca ctt gca ggg gat cgt tta ggc tgc ttc aat ctt tcc att gat      993
Asp Ser Leu Ala Gly Asp Arg Leu Gly Cys Phe Asn Leu Ser Ile Asp
                265                 270                 275 gga cac tcg gaa tgt gtg aag ttt gtg aag aag ttc aac ata ccc ctt     1041
Gly His Ser Glu Cys Val Lys Phe Val Lys Lys Phe Asn Ile Pro Leu
                280                 285                 290 ctg gtg aca ggt ggg gga gga tac acc aag gag aat gtc gca cgc tgt     1089
Leu Val Thr Gly Gly Gly Gly Tyr Thr Lys Glu Asn Val Ala Arg Cys
                295                 300                 305 tgg aca gtg gag act ggt gtt ctt gtg gat act gag ctg ccg aat gaa     1137
Trp Thr Val Glu Thr Gly Val Leu Val Asp Thr Glu Leu Pro Asn Glu
310                 315                 320 att cct gac aat gac tac ctg aag tat ttc aaa cca gat tgc act ttg     1185
Ile Pro Asp Asn Asp Tyr Leu Lys Tyr Phe Lys Pro Asp Cys Thr Leu
325                 330                 335                 340 aag acc aca tca gga aat cac atg gaa aac ttg aac ggt aag acc tac     1233
Lys Thr Thr Ser Gly Asn His Met Glu Asn Leu Asn Gly Lys Thr Tyr
                345                 350                 355 ctg agc act atc aag cag cag gtt atg gag aac tta cgg aga att gct     1281
Leu Ser Thr Ile Lys Gln Gln Val Met Glu Asn Leu Arg Arg Ile Ala
                360                 365                 370 cat gca cct agt gtt caa atg cac gag gta cct ccg gac act tat ata     1329
His Ala Pro Ser Val Gln Met His Glu Val Pro Pro Asp Thr Tyr Ile
                375                 380                 385 cca gag ttt gat gag gat gaa ttg aat cct gac gag cgc atg gac caa     1377
Pro Glu Phe Asp Glu Asp Glu Leu Asn Pro Asp Glu Arg Met Asp Gln
390                 395                 400 cac aca cag gac aag cac atc caa agg gag gag gag tat tat gaa gat     1425
His Thr Gln Asp Lys His Ile Gln Arg Glu Glu Glu Tyr Tyr Glu Asp
405                 410                 415                 420 gac aac gac aac gac cat gac atg gat gac tca tgactgttta ttagatgttt   1478
Asp Asn Asp Asn Asp His Asp Met Asp Asp Ser
                425                 430 ttagaagata actgaaaaca tgtcctcatt tgtacactag attttacccc tactaacaca   1538
ttgaatgaaa gagttggagc tcgc                                          1562

<210> SEQ ID NO 36
<211> LENGTH: 431
<212> TYPE: PRT
<213> ORGANISM: Physcomitrella patens
```

<400> SEQUENCE: 36

```
Met Pro Val Lys Asp Arg Ile Ser Tyr Phe Tyr Asp Gly Asp Val Gly
1               5                   10                  15

Ser Val Tyr Tyr Gly Pro Asn His Pro Met Lys Pro His Arg Leu Cys
            20                  25                  30

Met Thr Asn Ser Leu Val Leu Ala Tyr Gly Leu His Asn Lys Met Glu
        35                  40                  45

Ile Tyr Arg Pro His Lys Ala Tyr Pro Val Glu Leu Ala Gln Phe His
    50                  55                  60

Ser Val Asp Tyr Val Glu Phe Leu Gly Arg Ile Thr Pro Glu Ser Gln
65                  70                  75                  80

Glu Lys Tyr Ala Ala Glu Leu Ile Arg Tyr Asn Met Gly Glu Asp Cys
                85                  90                  95

Pro Val Phe Asp Asn Leu Phe Glu Phe Cys Gln Ile Tyr Ala Gly Gly
            100                 105                 110

Thr Ile Asp Ala Ala His Arg Leu Asn His Gly Leu Cys Asp Ile Ala
        115                 120                 125

Ile Asn Trp Ala Gly Gly Leu His His Ala Lys Cys Glu Ala Ser
    130                 135                 140

Gly Phe Cys Tyr Val Asn Asp Leu Val Leu Gly Ile Leu Glu Leu Leu
145                 150                 155                 160

Lys Tyr His Ala Arg Val Leu Tyr Ile Asp Ile Asp Ile His His Gly
                165                 170                 175

Asp Gly Val Glu Glu Ala Phe Tyr Leu Thr Asp Arg Val Met Thr Val
            180                 185                 190

Ser Phe His Lys Phe Gly Asp Tyr Phe Phe Pro Gly Thr Gly Asp Val
        195                 200                 205

Lys Asp Val Gly Glu Arg Glu Gly Lys Tyr Tyr Ala Ile Asn Val Pro
    210                 215                 220

Leu Lys Asp Gly Ile Asp Asp Ala Asn Phe Ile Arg Met Phe Arg Val
225                 230                 235                 240

Val Ile Gln Lys Val Val Glu Val Tyr Gln Pro Gly Ala Ile Val Leu
                245                 250                 255

Gln Cys Gly Ala Asp Ser Leu Ala Gly Asp Arg Leu Gly Cys Phe Asn
            260                 265                 270

Leu Ser Ile Asp Gly His Ser Glu Cys Val Lys Phe Val Lys Lys Phe
        275                 280                 285

Asn Ile Pro Leu Leu Val Thr Gly Gly Gly Gly Tyr Thr Lys Glu Asn
    290                 295                 300

Val Ala Arg Cys Trp Thr Val Glu Thr Gly Val Leu Val Asp Thr Glu
305                 310                 315                 320

Leu Pro Asn Glu Ile Pro Asp Asn Asp Tyr Leu Lys Tyr Phe Lys Pro
                325                 330                 335

Asp Cys Thr Leu Lys Thr Thr Ser Gly Asn His Met Glu Asn Leu Asn
            340                 345                 350

Gly Lys Thr Tyr Leu Ser Thr Ile Lys Gln Gln Val Met Glu Asn Leu
        355                 360                 365

Arg Arg Ile Ala His Ala Pro Ser Val Gln Met His Glu Val Pro Pro
    370                 375                 380

Asp Thr Tyr Ile Pro Glu Phe Asp Glu Asp Glu Leu Asn Pro Asp Glu
385                 390                 395                 400

Arg Met Asp Gln His Thr Gln Asp Lys His Ile Gln Arg Glu Glu Glu
                405                 410                 415
```

```
Tyr Tyr Glu Asp Asp Asn Asp Asn Asp His Asp Met Asp Asp Ser
            420                 425                 430

<210> SEQ ID NO 37
<211> LENGTH: 1544
<212> TYPE: DNA
<213> ORGANISM: Brassica napus
<220> FEATURE:
<221> NAME/KEY: CDS
<222> LOCATION: (84)..(1361)

<400> SEQUENCE: 37
aggaatcgtc tcacatctat tgaagccata attgttgtta acaggtcgat ctcggttgta        60
gttttttttt tttcttagaa gag atg cgg tcc aag gac aaa atc tcc tac ttt      113
                         Met Arg Ser Lys Asp Lys Ile Ser Tyr Phe
                           1               5                  10 tac gat gga gat gta ggg agc gtt tat ttt ggt ccg aat cac cca atg        161
Tyr Asp Gly Asp Val Gly Ser Val Tyr Phe Gly Pro Asn His Pro Met
                 15                  20                  25 aaa cct cac agg ctt tgt atg acc cat cat ctt atc ctt gca tat ggc        209
Lys Pro His Arg Leu Cys Met Thr His His Leu Ile Leu Ala Tyr Gly
         30                  35                  40 ctc cat agc aag atg gaa gtt tat cgt cca cac aag gca tac cct atc        257
Leu His Ser Lys Met Glu Val Tyr Arg Pro His Lys Ala Tyr Pro Ile
     45                  50                  55 gag atg gcc cag ttc cat tct cca gac tat gtc gag ttc ctg caa cga        305
Glu Met Ala Gln Phe His Ser Pro Asp Tyr Val Glu Phe Leu Gln Arg
 60                  65                  70 atc aac cca gaa aat aag gat ttg ttt ccc aac gaa atg gct aga tat        353
Ile Asn Pro Glu Asn Lys Asp Leu Phe Pro Asn Glu Met Ala Arg Tyr
 75                  80                  85                  90 aat tta gga gag gat tgt cct gtc ttt gag gat atg ttc gag ttt tgt        401
Asn Leu Gly Glu Asp Cys Pro Val Phe Glu Asp Met Phe Glu Phe Cys
                 95                 100                 105 caa att tat gcg ggt gca acc ata gat gct gca cgc aga tta aac aac        449
Gln Ile Tyr Ala Gly Ala Thr Ile Asp Ala Ala Arg Arg Leu Asn Asn
            110                 115                 120 aaa ctc tgt gac att gcg ata aac tgg gcg ggc ggg ttg cac cat gct        497
Lys Leu Cys Asp Ile Ala Ile Asn Trp Ala Gly Gly Leu His His Ala
        125                 130                 135 aaa aaa tgc gat gca tct ggt ttt tgt tac atc aac gat ctc gta cta        545
Lys Lys Cys Asp Ala Ser Gly Phe Cys Tyr Ile Asn Asp Leu Val Leu
    140                 145                 150 gga atc ctc gag ctg ttg aaa cac cat cct cgt gtg ctc tac att gat        593
Gly Ile Leu Glu Leu Leu Lys His His Pro Arg Val Leu Tyr Ile Asp
155                 160                 165                 170 ata gac gtt cac cac ggt gat gga gtt gaa gag gct ttt tac ttt act        641
Ile Asp Val His His Gly Asp Gly Val Glu Glu Ala Phe Tyr Phe Thr
                175                 180                 185 gac aga gtg atg act gtt agt ttt cac aag ttt ggg gat aag ttc ttt        689
Asp Arg Val Met Thr Val Ser Phe His Lys Phe Gly Asp Lys Phe Phe
            190                 195                 200 cca ggg acc ggc gat gtt aag gaa ata gga gaa agg gaa ggg aag ttt        737
Pro Gly Thr Gly Asp Val Lys Glu Ile Gly Glu Arg Glu Gly Lys Phe
        205                 210                 215 tac gcc ata aat gtt ccg ctc agg gat ggg att gat gac agt agt ttc        785
Tyr Ala Ile Asn Val Pro Leu Arg Asp Gly Ile Asp Asp Ser Ser Phe
    220                 225                 230 aac cgt ctg ttc agg gca ata att tca aag gtg gtt gag ata tat cag        833
Asn Arg Leu Phe Arg Ala Ile Ile Ser Lys Val Val Glu Ile Tyr Gln
235                 240                 245                 250
```

| | | |
|---|---|---|
| cca ggt gca ata gta ctt cag tgt gga gca gat tca cta gca agg gat<br>Pro Gly Ala Ile Val Leu Gln Cys Gly Ala Asp Ser Leu Ala Arg Asp<br>                      255                      260                   265 | 881 |
| cga cta gga tgc ttt aat ctc tct att gat gga cat gct gaa tgt gtt<br>Arg Leu Gly Cys Phe Asn Leu Ser Ile Asp Gly His Ala Glu Cys Val<br>                   270                      275                   280 | 929 |
| aaa ttc gtc aag aaa ttc aat att cct ttg ctg gtg act gga ggt gga<br>Lys Phe Val Lys Lys Phe Asn Ile Pro Leu Leu Val Thr Gly Gly Gly<br>               285                      290                   295 | 977 |
| ggg tac aca aag gag aac gta gct cgg tgt tgg acc gtt gag act ggc<br>Gly Tyr Thr Lys Glu Asn Val Ala Arg Cys Trp Thr Val Glu Thr Gly<br>300                      305                      310 | 1025 |
| att ctt ttg gac aca gaa ctt cct aat gag att cct gat aat gat tat<br>Ile Leu Leu Asp Thr Glu Leu Pro Asn Glu Ile Pro Asp Asn Asp Tyr<br>315                      320                      325                   330 | 1073 |
| ata aag tat ttt ggg ccg gat tat tca ttg aag att cct ggt ggt cac<br>Ile Lys Tyr Phe Gly Pro Asp Tyr Ser Leu Lys Ile Pro Gly Gly His<br>                   335                      340                   345 | 1121 |
| att gag aat cta aat acg aaa tcg tat atc agt acg ata aaa gca cag<br>Ile Glu Asn Leu Asn Thr Lys Ser Tyr Ile Ser Thr Ile Lys Ala Gln<br>                   350                      355                   360 | 1169 |
| att ttg gat aat ttg aga tac atc cag cac gct cca agc gtg cag atg<br>Ile Leu Asp Asn Leu Arg Tyr Ile Gln His Ala Pro Ser Val Gln Met<br>               365                      370                   375 | 1217 |
| cag gag gtt cca ccg gat ttc tac ata ccg gat ttt gat gaa gac gaa<br>Gln Glu Val Pro Pro Asp Phe Tyr Ile Pro Asp Phe Asp Glu Asp Glu<br>380                      385                      390 | 1265 |
| cga aat cca gat gtg cgt gtg gac cag cgt tcg cgg gat aag cag att<br>Arg Asn Pro Asp Val Arg Val Asp Gln Arg Ser Arg Asp Lys Gln Ile<br>395                      400                      405                  410 | 1313 |
| cag agg gac gat gaa tat ttc gat ggt gac aag gat aac gat gcg tcg<br>Gln Arg Asp Asp Glu Tyr Phe Asp Gly Asp Lys Asp Asn Asp Ala Ser<br>                   415                      420                   425 | 1361 |
| tagcatagat tattattagc gcagaagact taagacaaaa ccaaagttgt gtttgggaga | 1421 |
| tttgttataa acttataatg ataacatttt aacggcttgt agaaaattct atttatctgg | 1481 |
| gcaccaaaac ccactcatga ttcttaaatc gttcgtcttt tctccaaaaa aaaaaaaaaa | 1541 |
| aaa | 1544 |

<210> SEQ ID NO 38
<211> LENGTH: 426
<212> TYPE: PRT
<213> ORGANISM: Brassica napus

<400> SEQUENCE: 38

Met Arg Ser Lys Asp Lys Ile Ser Tyr Phe Tyr Asp Gly Asp Val Gly
1               5                   10                  15

Ser Val Tyr Phe Gly Pro Asn His Pro Met Lys Pro His Arg Leu Cys
            20                  25                  30

Met Thr His His Leu Ile Leu Ala Tyr Gly Leu His Ser Lys Met Glu
        35                  40                  45

Val Tyr Arg Pro His Lys Ala Tyr Pro Ile Glu Met Ala Gln Phe His
    50                  55                  60

Ser Pro Asp Tyr Val Glu Phe Leu Gln Arg Ile Asn Pro Glu Asn Lys
65                  70                  75                  80

Asp Leu Phe Pro Asn Glu Met Ala Arg Tyr Asn Leu Gly Glu Asp Cys
                85                  90                  95

Pro Val Phe Glu Asp Met Phe Glu Phe Cys Gln Ile Tyr Ala Gly Ala

-continued

```
                    100                 105                 110
Thr Ile Asp Ala Ala Arg Arg Leu Asn Asn Lys Leu Cys Asp Ile Ala
        115                 120                 125

Ile Asn Trp Ala Gly Gly Leu His His Ala Lys Lys Cys Asp Ala Ser
130                 135                 140

Gly Phe Cys Tyr Ile Asn Asp Leu Val Leu Gly Ile Leu Glu Leu Leu
145                 150                 155                 160

Lys His His Pro Arg Val Leu Tyr Ile Asp Ile Asp Val His His Gly
                165                 170                 175

Asp Gly Val Glu Glu Ala Phe Tyr Phe Thr Asp Arg Val Met Thr Val
            180                 185                 190

Ser Phe His Lys Phe Gly Asp Lys Phe Phe Pro Gly Thr Gly Asp Val
        195                 200                 205

Lys Glu Ile Gly Glu Arg Glu Gly Lys Phe Tyr Ala Ile Asn Val Pro
    210                 215                 220

Leu Arg Asp Gly Ile Asp Asp Ser Ser Phe Asn Arg Leu Phe Arg Ala
225                 230                 235                 240

Ile Ile Ser Lys Val Val Glu Ile Tyr Gln Pro Gly Ala Ile Val Leu
                245                 250                 255

Gln Cys Gly Ala Asp Ser Leu Ala Arg Asp Arg Leu Gly Cys Phe Asn
            260                 265                 270

Leu Ser Ile Asp Gly His Ala Glu Cys Val Lys Phe Val Lys Lys Phe
        275                 280                 285

Asn Ile Pro Leu Leu Val Thr Gly Gly Gly Tyr Thr Lys Glu Asn
    290                 295                 300

Val Ala Arg Cys Trp Thr Val Glu Thr Gly Ile Leu Leu Asp Thr Glu
305                 310                 315                 320

Leu Pro Asn Glu Ile Pro Asp Asn Asp Tyr Ile Lys Tyr Phe Gly Pro
                325                 330                 335

Asp Tyr Ser Leu Lys Ile Pro Gly Gly His Ile Glu Asn Leu Asn Thr
            340                 345                 350

Lys Ser Tyr Ile Ser Thr Ile Lys Ala Gln Ile Leu Asp Asn Leu Arg
        355                 360                 365

Tyr Ile Gln His Ala Pro Ser Val Gln Met Gln Glu Val Pro Pro Asp
    370                 375                 380

Phe Tyr Ile Pro Asp Phe Asp Glu Asp Glu Arg Asn Pro Asp Val Arg
385                 390                 395                 400

Val Asp Gln Arg Ser Arg Asp Lys Gln Ile Gln Arg Asp Asp Glu Tyr
                405                 410                 415

Phe Asp Gly Asp Lys Asp Asn Asp Ala Ser
            420                 425
```

<210> SEQ ID NO 39
<211> LENGTH: 1594
<212> TYPE: DNA
<213> ORGANISM: Brassica napus
<220> FEATURE:
<221> NAME/KEY: CDS
<222> LOCATION: (18)..(1427)

<400> SEQUENCE: 39

```
gagaaaggaa gggcgac atg gag aca gac gag agc ggc gtc tct tta gcg        50
                   Met Glu Thr Asp Glu Ser Gly Val Ser Leu Ala
                    1               5                   10 tca ggg ccc gac ggt cgt aag cga cga gtc agc tac ttc tac gag cca        98
Ser Gly Pro Asp Gly Arg Lys Arg Arg Val Ser Tyr Phe Tyr Glu Pro
        15                  20                  25
```

| | | |
|---|---|---|
| acg atc ggt aac tac tac tac ggt caa ggc cac ccc atg aag cct cac<br>Thr Ile Gly Asn Tyr Tyr Tyr Gly Gln Gly His Pro Met Lys Pro His<br>       30                         35                        40 | 146 | |
| cgg atc cgt atg gct cat agt cta atc gtc cac tac aac ctc cac cgc<br>Arg Ile Arg Met Ala His Ser Leu Ile Val His Tyr Asn Leu His Arg<br> 45                        50                        55 | 194 | |
| cgc ctc gag atc agc cgc cct tac ctc gcc gac gct gcc gac atc ggt<br>Arg Leu Glu Ile Ser Arg Pro Tyr Leu Ala Asp Ala Ala Asp Ile Gly<br>60                     65                      70                   75 | 242 | |
| cgc ttc cac tct ccc gag tac gtc gat ttc ctc cgc tcc gtt tcg ccg<br>Arg Phe His Ser Pro Glu Tyr Val Asp Phe Leu Arg Ser Val Ser Pro<br>                   80                        85                   90 | 290 | |
| gag tcc gtc ggc gat tcg tcc gcg cgt aac cta agg cga ttc aat gtc<br>Glu Ser Val Gly Asp Ser Ser Ala Arg Asn Leu Arg Arg Phe Asn Val<br>               95                      100                  105 | 338 | |
| ggc gag gat tgt ccc gtc ttc gac ggt ctt ttc gag ttt tgc cgc gct<br>Gly Glu Asp Cys Pro Val Phe Asp Gly Leu Phe Glu Phe Cys Arg Ala<br>          110                      115                  120 | 386 | |
| tcc gcc gga ggt tcg atc ggc gcc gcc gtt aaa ttg aac cgg cag gac<br>Ser Ala Gly Gly Ser Ile Gly Ala Ala Val Lys Leu Asn Arg Gln Asp<br>     125                      130                      135 | 434 | |
| gcg gat atc gcc atc aat tgg ggc ggt ggg ctt cac cac gct aag aag<br>Ala Asp Ile Ala Ile Asn Trp Gly Gly Gly Leu His His Ala Lys Lys<br>140                     145                      150                  155 | 482 | |
| agc gag gcg tct ggg ttt tgc tac gta aac gac atc gtt ttg ggg att<br>Ser Glu Ala Ser Gly Phe Cys Tyr Val Asn Asp Ile Val Leu Gly Ile<br>                   160                      165                  170 | 530 | |
| ctc gag ttg ctt aag atg ttt agg cgg gtt ctc tac att gat atc gat<br>Leu Glu Leu Leu Lys Met Phe Arg Arg Val Leu Tyr Ile Asp Ile Asp<br>             175                      180                  185 | 578 | |
| gtt cac cat gga gat gga gta gag gaa gcg ttt tac acc act gat aga<br>Val His His Gly Asp Gly Val Glu Glu Ala Phe Tyr Thr Thr Asp Arg<br>          190                      195                  200 | 626 | |
| gtt atg acc gtt tct ttt cac aag ttt ggg gac ttc ttc cct gga act<br>Val Met Thr Val Ser Phe His Lys Phe Gly Asp Phe Phe Pro Gly Thr<br>     205                      210                      215 | 674 | |
| ggt cac atc aga gac gtt ggc gct gag aaa ggg aag tac tat gct ctc<br>Gly His Ile Arg Asp Val Gly Ala Glu Lys Gly Lys Tyr Tyr Ala Leu<br>220                     225                      230                  235 | 722 | |
| aat gtc ccg ttg aac gat ggt atg gac gat gag agt ttc cgc agc ttg<br>Asn Val Pro Leu Asn Asp Gly Met Asp Asp Glu Ser Phe Arg Ser Leu<br>                   240                      245                  250 | 770 | |
| ttt aga cct ctt atc cag aag gtt atg gag gtt tat cgg cca gaa gca<br>Phe Arg Pro Leu Ile Gln Lys Val Met Glu Val Tyr Arg Pro Glu Ala<br>             255                      260                  265 | 818 | |
| gtt gtt ctt cag tgc ggg gct gac tcc ttg agc ggt gat cgg ctg ggt<br>Val Val Leu Gln Cys Gly Ala Asp Ser Leu Ser Gly Asp Arg Leu Gly<br>          270                      275                  280 | 866 | |
| tgc ttc aac ttg tca gtc aag ggc cat gct gat tgc ctc cgg ttc ttg<br>Cys Phe Asn Leu Ser Val Lys Gly His Ala Asp Cys Leu Arg Phe Leu<br>     285                      290                      295 | 914 | |
| aga tct tat aat gtt cct ctc atg gtc ttg ggt ggt gga ggg tat act<br>Arg Ser Tyr Asn Val Pro Leu Met Val Leu Gly Gly Gly Gly Tyr Thr<br>300                     305                      310                  315 | 962 | |
| att cgg aat gtt gct cgt tgc tgg tgt tat gag act gca gtt gcg gtt<br>Ile Arg Asn Val Ala Arg Cys Trp Cys Tyr Glu Thr Ala Val Ala Val<br>                   320                      325                  330 | 1010 | |
| gga gta gag ccg gac aac aag cta ccg tac aat gag tac ttt gag tat<br>Gly Val Glu Pro Asp Asn Lys Leu Pro Tyr Asn Glu Tyr Phe Glu Tyr<br>             335                      340                  345 | 1058 | |

```
ttc ggt cca gac tat acg ctt cat gtc gag cca ggc cca atg gag aat      1106
Phe Gly Pro Asp Tyr Thr Leu His Val Glu Pro Gly Pro Met Glu Asn
350                 355                 360 ttg aac aca cca aaa gat atg gag agg ata agg aac aca ttg cta gaa      1154
Leu Asn Thr Pro Lys Asp Met Glu Arg Ile Arg Asn Thr Leu Leu Glu
365                 370                 375 caa ctt tct gga cta ata cac gca cct agt gtg ccg ttt cag cac aca      1202
Gln Leu Ser Gly Leu Ile His Ala Pro Ser Val Pro Phe Gln His Thr
380                 385                 390                 395 cct cca gtt aat cga gtc tta gat gag ccg gaa gaa gac ttg gag aag      1250
Pro Pro Val Asn Arg Val Leu Asp Glu Pro Glu Glu Asp Leu Glu Lys
                400                 405                 410 aga cca aag cct cga att tgg agt gga act gcg aat tat gaa tca gac      1298
Arg Pro Lys Pro Arg Ile Trp Ser Gly Thr Ala Asn Tyr Glu Ser Asp
        415                 420                 425 agt gac gat gat gag aaa cct ctt ggt ggt ttc tca ggt att aat ggc      1346
Ser Asp Asp Asp Glu Lys Pro Leu Gly Gly Phe Ser Gly Ile Asn Gly
            430                 435                 440 cca act atg gac agg gac tct aca ggg gaa gat gaa atg gaa gat gat      1394
Pro Thr Met Asp Arg Asp Ser Thr Gly Glu Asp Glu Met Glu Asp Asp
445                 450                 455 agc gca gag ccg gag gtg gat cca cca tcg tct tgaaaccagc ttgatgtagt    1447
Ser Ala Glu Pro Glu Val Asp Pro Pro Ser Ser
460                 465                 470 gtcaaaagtt aaggaattga ttcttggtga tgcttttctt cagtatgtga ttttttttt    1507 gtttgcaaag aaaccttttt gttttggcct cagacgtatt taataggaat gtatttccat    1567
taccattcga aaaaaaaaaa aaaaaaa                                        1594

<210> SEQ ID NO 40
<211> LENGTH: 470
<212> TYPE: PRT
<213> ORGANISM: Brassica napus

<400> SEQUENCE: 40

Met Glu Thr Asp Glu Ser Gly Val Ser Leu Ala Ser Gly Pro Asp Gly
1               5                   10                  15

Arg Lys Arg Arg Val Ser Tyr Phe Tyr Glu Pro Thr Ile Gly Asn Tyr
                20                  25                  30

Tyr Tyr Gly Gln Gly His Pro Met Lys Pro His Arg Ile Arg Met Ala
            35                  40                  45

His Ser Leu Ile Val His Tyr Asn Leu His Arg Leu Glu Ile Ser
        50                  55                  60

Arg Pro Tyr Leu Ala Asp Ala Ala Asp Ile Gly Arg Phe His Ser Pro
65                  70                  75                  80

Glu Tyr Val Asp Phe Leu Arg Ser Val Ser Pro Glu Ser Val Gly Asp
                85                  90                  95

Ser Ser Ala Arg Asn Leu Arg Arg Phe Asn Val Gly Glu Asp Cys Pro
            100                 105                 110

Val Phe Asp Gly Leu Phe Glu Phe Cys Arg Ala Ser Ala Gly Gly Ser
        115                 120                 125

Ile Gly Ala Ala Val Lys Leu Asn Arg Gln Asp Ala Asp Ile Ala Ile
    130                 135                 140

Asn Trp Gly Gly Gly Leu His His Ala Lys Lys Ser Glu Ala Ser Gly
145                 150                 155                 160

Phe Cys Tyr Val Asn Asp Ile Val Leu Gly Ile Leu Glu Leu Leu Lys
                165                 170                 175
```

```
Met Phe Arg Arg Val Leu Tyr Ile Asp Ile Asp Val His His Gly Asp
            180                 185                 190

Gly Val Glu Glu Ala Phe Tyr Thr Thr Asp Arg Val Met Thr Val Ser
        195                 200                 205

Phe His Lys Phe Gly Asp Phe Phe Pro Gly Thr Gly His Ile Arg Asp
210                 215                 220

Val Gly Ala Glu Lys Gly Lys Tyr Tyr Ala Leu Asn Val Pro Leu Asn
225                 230                 235                 240

Asp Gly Met Asp Asp Glu Ser Phe Arg Ser Leu Phe Arg Pro Leu Ile
                245                 250                 255

Gln Lys Val Met Glu Val Tyr Arg Pro Glu Ala Val Val Leu Gln Cys
            260                 265                 270

Gly Ala Asp Ser Leu Ser Gly Asp Arg Leu Gly Cys Phe Asn Leu Ser
        275                 280                 285

Val Lys Gly His Ala Asp Cys Leu Arg Phe Leu Arg Ser Tyr Asn Val
290                 295                 300

Pro Leu Met Val Leu Gly Gly Gly Gly Tyr Thr Ile Arg Asn Val Ala
305                 310                 315                 320

Arg Cys Trp Cys Tyr Glu Thr Ala Val Ala Val Gly Val Glu Pro Asp
                325                 330                 335

Asn Lys Leu Pro Tyr Asn Glu Tyr Phe Glu Tyr Phe Gly Pro Asp Tyr
            340                 345                 350

Thr Leu His Val Glu Pro Gly Pro Met Glu Asn Leu Asn Thr Pro Lys
        355                 360                 365

Asp Met Glu Arg Ile Arg Asn Thr Leu Leu Glu Gln Leu Ser Gly Leu
370                 375                 380

Ile His Ala Pro Ser Val Pro Phe Gln His Thr Pro Val Asn Arg
385                 390                 395                 400

Val Leu Asp Glu Pro Glu Glu Asp Leu Glu Lys Arg Pro Lys Pro Arg
                405                 410                 415

Ile Trp Ser Gly Thr Ala Asn Tyr Glu Ser Asp Ser Asp Asp Glu
            420                 425                 430

Lys Pro Leu Gly Gly Phe Ser Gly Ile Asn Gly Pro Thr Met Asp Arg
        435                 440                 445

Asp Ser Thr Gly Glu Asp Glu Met Glu Asp Ser Ala Glu Pro Glu
450                 455                 460

Val Asp Pro Pro Ser Ser
465                 470

<210> SEQ ID NO 41
<211> LENGTH: 1367
<212> TYPE: DNA
<213> ORGANISM: Zea mays
<220> FEATURE:
<221> NAME/KEY: CDS
<222> LOCATION: (12)..(1100)

<400> SEQUENCE: 41
gatttcgtgg c atg ctg gcc cac gac gcc ggc cgc ggc gtg ttc gac tcg      50
           Met Leu Ala His Asp Ala Gly Arg Gly Val Phe Asp Ser
           1               5                   10 ggc cgc gac ccc gga ttc ctg gat gtg ctc gac caa cac ccg gag aac      98
Gly Arg Asp Pro Gly Phe Leu Asp Val Leu Asp Gln His Pro Glu Asn
 15                  20                  25 gcc gac cgc gtc cgc aac atg gtc tcc atc ctc cgc cgc ggg ccc atc     146
Ala Asp Arg Val Arg Asn Met Val Ser Ile Leu Arg Arg Gly Pro Ile
 30                  35                  40                  45
```

```
gcg cac ttc ctc tcc tgg cac tcg ggc cgc cct gcc cac gcc tcc gag      194
Ala His Phe Leu Ser Trp His Ser Gly Arg Pro Ala His Ala Ser Glu
         50                  55                  60 ctc ctc tcc ttc cac tcc tca gaa tac ata gag gag ctc gtc cag acg      242
Leu Leu Ser Phe His Ser Ser Glu Tyr Ile Glu Glu Leu Val Gln Thr
             65                  70                  75 aac gcc acc gga gcc aag aag aag ctc tgt gag ggc acg ttc ttg aac      290
Asn Ala Thr Gly Ala Lys Lys Lys Leu Cys Glu Gly Thr Phe Leu Asn
         80                  85                  90 ccg ggc tcc tgg ggt gcg gcg ctt cta gcg gcc ggg acc acg ctc tcc      338
Pro Gly Ser Trp Gly Ala Ala Leu Leu Ala Ala Gly Thr Thr Leu Ser
     95                 100                 105 tcc gcg aag cac ata cta gac ggg cag ggg aac ctg gcc tac gcg ttg      386
Ser Ala Lys His Ile Leu Asp Gly Gln Gly Asn Leu Ala Tyr Ala Leu
110                 115                 120                 125 gtt cgc ccc cct ggc cac cac gcg cag ccc gac cac gcc gat ggc tac      434
Val Arg Pro Pro Gly His His Ala Gln Pro Asp His Ala Asp Gly Tyr
                130                 135                 140 tgc ttt ctg aac aat gcc gga ctt gct gtg caa ctg gct ctg gat tcc      482
Cys Phe Leu Asn Asn Ala Gly Leu Ala Val Gln Leu Ala Leu Asp Ser
             145                 150                 155 ggg cgc gca aag gtc gcc gtt gtg gat att gat gtg cac tac ggg aat      530
Gly Arg Ala Lys Val Ala Val Val Asp Ile Asp Val His Tyr Gly Asn
         160                 165                 170 ggc acc gcg gag ggc ttc tat cgg aca gac acc gtg ttg acg atg tct      578
Gly Thr Ala Glu Gly Phe Tyr Arg Thr Asp Thr Val Leu Thr Met Ser
     175                 180                 185 ctt cac atg atg cat ggt tct tgg ggg cca tcg cat ccg cag agt ggc      626
Leu His Met Met His Gly Ser Trp Gly Pro Ser His Pro Gln Ser Gly
190                 195                 200                 205 tcc gtc gat gag att ggt gag ggc aag ggg ctt ggg tac aat ctc aat      674
Ser Val Asp Glu Ile Gly Glu Gly Lys Gly Leu Gly Tyr Asn Leu Asn
                210                 215                 220 ata cct ttg cct aat gga agt gga gat gct ggg tat gaa tat gcg atg      722
Ile Pro Leu Pro Asn Gly Ser Gly Asp Ala Gly Tyr Glu Tyr Ala Met
             225                 230                 235 aac gag ttg gtt gtt cca tcg att gat aag ttt cag cct caa ctg ttg      770
Asn Glu Leu Val Val Pro Ser Ile Asp Lys Phe Gln Pro Gln Leu Leu
         240                 245                 250 ttt ctt gtg gtc ggc caa gat tcc agt gcg ttt gat ccc aat gga aga      818
Phe Leu Val Val Gly Gln Asp Ser Ser Ala Phe Asp Pro Asn Gly Arg
     255                 260                 265 cag tgc ttg acc atg gaa ggc tac agg aaa att gga caa ata atg agg      866
Gln Cys Leu Thr Met Glu Gly Tyr Arg Lys Ile Gly Gln Ile Met Arg
270                 275                 280                 285 cgc ctg gct gat cgc cat tgc aat ggg caa ata ctg gtt gtc cag gaa      914
Arg Leu Ala Asp Arg His Cys Asn Gly Gln Ile Leu Val Val Gln Glu
                290                 295                 300 ggg ggt tac cac atc act tat tcg gca tat tgt ctg cat gct aca ctg      962
Gly Gly Tyr His Ile Thr Tyr Ser Ala Tyr Cys Leu His Ala Thr Leu
             305                 310                 315 gaa gga gtt ttg gat ctg gaa gcc ccg ctt ctt gat gac cca atc gct     1010
Glu Gly Val Leu Asp Leu Glu Ala Pro Leu Leu Asp Asp Pro Ile Ala
         320                 325                 330 tat tat ccg gag gat gat aaa tac act atg aaa gtc gtt gac atg ata     1058
Tyr Tyr Pro Glu Asp Asp Lys Tyr Thr Met Lys Val Val Asp Met Ile
     335                 340                 345 aag agc tac tgg aag gaa tcg gtt cct ttc cta aag gaa att              1100
Lys Ser Tyr Trp Lys Glu Ser Val Pro Phe Leu Lys Glu Ile
350                 355                 360
```

```
tagaggaaat aatgttcgcg ccctcaatgt tcaaattgca ggaaactcca cattcctgga    1160
catcttcaat tgaattggga agaacattgc acgtctacgt tttcaggccg tttaagatta    1220
tctgattgac agtttcacgc ctaacattgt acaggataga ttaagaacat tgtttgctgc    1280
tgctcttgaa tttctgcaat caggatctcg tcagcctatt tttgataaac agtcgatctt    1340
ttttttttca aaaaaaaaaa aaaaaaa                                        1367
```

<210> SEQ ID NO 42
<211> LENGTH: 363
<212> TYPE: PRT
<213> ORGANISM: Zea mays

<400> SEQUENCE: 42

```
Met Leu Ala His Asp Ala Gly Arg Gly Val Phe Asp Ser Gly Arg Asp
1               5                   10                  15

Pro Gly Phe Leu Asp Val Leu Asp Gln His Pro Glu Asn Ala Asp Arg
            20                  25                  30

Val Arg Asn Met Val Ser Ile Leu Arg Arg Gly Pro Ile Ala His Phe
        35                  40                  45

Leu Ser Trp His Ser Gly Arg Pro Ala His Ala Ser Glu Leu Leu Ser
50                  55                  60

Phe His Ser Ser Glu Tyr Ile Glu Leu Val Gln Thr Asn Ala Thr
65                  70                  75                  80

Gly Ala Lys Lys Lys Leu Cys Glu Gly Thr Phe Leu Asn Pro Gly Ser
                85                  90                  95

Trp Gly Ala Ala Leu Leu Ala Ala Gly Thr Thr Leu Ser Ser Ala Lys
            100                 105                 110

His Ile Leu Asp Gly Gln Gly Asn Leu Ala Tyr Ala Leu Val Arg Pro
        115                 120                 125

Pro Gly His His Ala Gln Pro Asp His Ala Asp Gly Tyr Cys Phe Leu
    130                 135                 140

Asn Asn Ala Gly Leu Ala Val Gln Leu Ala Leu Asp Ser Gly Arg Ala
145                 150                 155                 160

Lys Val Ala Val Val Asp Ile Asp Val His Tyr Gly Asn Gly Thr Ala
                165                 170                 175

Glu Gly Phe Tyr Arg Thr Asp Thr Val Leu Thr Met Ser Leu His Met
            180                 185                 190

Met His Gly Ser Trp Gly Pro Ser His Pro Gln Ser Gly Ser Val Asp
        195                 200                 205

Glu Ile Gly Glu Gly Lys Gly Leu Gly Tyr Asn Leu Asn Ile Pro Leu
    210                 215                 220

Pro Asn Gly Ser Gly Asp Ala Gly Tyr Glu Tyr Ala Met Asn Glu Leu
225                 230                 235                 240

Val Val Pro Ser Ile Asp Lys Phe Gln Pro Gln Leu Leu Phe Leu Val
                245                 250                 255

Val Gly Gln Asp Ser Ser Ala Phe Asp Pro Asn Gly Arg Gln Cys Leu
            260                 265                 270

Thr Met Glu Gly Tyr Arg Lys Ile Gly Gln Ile Met Arg Arg Leu Ala
        275                 280                 285

Asp Arg His Cys Asn Gly Gln Ile Leu Val Val Gln Glu Gly Gly Tyr
    290                 295                 300

His Ile Thr Tyr Ser Ala Tyr Cys Leu His Ala Thr Leu Glu Gly Val
305                 310                 315                 320

Leu Asp Leu Glu Ala Pro Leu Leu Asp Asp Pro Ile Ala Tyr Tyr Pro
                325                 330                 335
```

```
Glu Asp Asp Lys Tyr Thr Met Lys Val Val Asp Met Ile Lys Ser Tyr
            340                 345                 350
Trp Lys Glu Ser Val Pro Phe Leu Lys Glu Ile
            355                 360

<210> SEQ ID NO 43
<211> LENGTH: 1598
<212> TYPE: DNA
<213> ORGANISM: Linum usitatissimum
<220> FEATURE:
<221> NAME/KEY: CDS
<222> LOCATION: (101)..(1387)

<400> SEQUENCE: 43
gctctgacaa tggcggagtc gtctttgtaa gctcagctca actttcttcg ccctctctgc      60
tcaaccctcg tccttctcgt cgctgaattc ggtctgagaa atg aag tcg aag gac     115
                                             Met Lys Ser Lys Asp
                                              1               5 aaa atc tcc tac ttt tac gat ggg gat gtt ggc agt gtt tac ttc ggt     163
Lys Ile Ser Tyr Phe Tyr Asp Gly Asp Val Gly Ser Val Tyr Phe Gly
         10                  15                  20 ccg aat cac ccg atg aaa cca cac agg ctc tgt atg acc cac cat ctt     211
Pro Asn His Pro Met Lys Pro His Arg Leu Cys Met Thr His His Leu
             25                  30                  35 gtt ctt tct tat gac ctt cac aag aag atg gag att tat cgg cca cac     259
Val Leu Ser Tyr Asp Leu His Lys Lys Met Glu Ile Tyr Arg Pro His
         40                  45                  50 aag gca tac cct gtt gag cta gct cag ttc cat tct gct gat tac gtt     307
Lys Ala Tyr Pro Val Glu Leu Ala Gln Phe His Ser Ala Asp Tyr Val
     55                  60                  65 gag ttc ttg cac cgg att aca cct gat act cag cac ttg tac aga act     355
Glu Phe Leu His Arg Ile Thr Pro Asp Thr Gln His Leu Tyr Arg Thr
 70                  75                  80                  85 gat tta gca aga tat aat ctt gga gaa gat tgc ccc gtg ttc gag aat     403
Asp Leu Ala Arg Tyr Asn Leu Gly Glu Asp Cys Pro Val Phe Glu Asn
                 90                  95                 100 ctg ttt gaa ttt tgt caa atc tat gct ggg ggg aca ata gac gcc gct     451
Leu Phe Glu Phe Cys Gln Ile Tyr Ala Gly Gly Thr Ile Asp Ala Ala
            105                 110                 115 cga aga ttg aac aat caa ctg tgt gat att gct ata aat tgg gct ggt     499
Arg Arg Leu Asn Asn Gln Leu Cys Asp Ile Ala Ile Asn Trp Ala Gly
        120                 125                 130 gga tta cat cat gcc aaa aag tgc gag gct tct gga ttt tgt tac atc     547
Gly Leu His His Ala Lys Lys Cys Glu Ala Ser Gly Phe Cys Tyr Ile
    135                 140                 145 aac gac ttg gtt ctc ggg atc ttg gag ctt cta aaa tac cat gct cgt     595
Asn Asp Leu Val Leu Gly Ile Leu Glu Leu Leu Lys Tyr His Ala Arg
150                 155                 160                 165 gtt ctg tac ata gac ata gat gtc cat cat ggt gat ggc gta gag gag     643
Val Leu Tyr Ile Asp Ile Asp Val His His Gly Asp Gly Val Glu Glu
                170                 175                 180 gcc ttc tat ttt act gac agg gtg atg act gta agt ttt cac aag ttt     691
Ala Phe Tyr Phe Thr Asp Arg Val Met Thr Val Ser Phe His Lys Phe
            185                 190                 195 gga gat ttg ttc ttc ccg gga acc ggt gat gtt aag gaa ata gga gaa     739
Gly Asp Leu Phe Phe Pro Gly Thr Gly Asp Val Lys Glu Ile Gly Glu
        200                 205                 210 aga gaa ggg aag ttc tac gcc ata aat gtt cct ctt agg gac ggg ata     787
Arg Glu Gly Lys Phe Tyr Ala Ile Asn Val Pro Leu Arg Asp Gly Ile
    215                 220                 225
```

```
gat gac tcg agc ttc aac cgt ctc ttt aaa acc atc ata tct aag gtt      835
Asp Asp Ser Ser Phe Asn Arg Leu Phe Lys Thr Ile Ile Ser Lys Val
230                 235                 240                 245 gta gaa atc tac caa cct ggc gct ata gtt ctc caa tgc gga gca gat      883
Val Glu Ile Tyr Gln Pro Gly Ala Ile Val Leu Gln Cys Gly Ala Asp
            250                 255                 260 tcg ctg gct ggg gac cgt ttg ggc tgt ttc aat ctc tcg att gat gga      931
Ser Leu Ala Gly Asp Arg Leu Gly Cys Phe Asn Leu Ser Ile Asp Gly
        265                 270                 275 cat gcg gaa tgt gtt aag ttt gtg aag aag ttc aac att cct tta ctg      979
His Ala Glu Cys Val Lys Phe Val Lys Lys Phe Asn Ile Pro Leu Leu
    280                 285                 290 gtt act gga ggt gga gga tat acg aag gag aat gta gct cga tgc tgg     1027
Val Thr Gly Gly Gly Gly Tyr Thr Lys Glu Asn Val Ala Arg Cys Trp
295                 300                 305 aca gtt gaa aca gga gta ctg ctg gat act gaa ctg ccc aat gag atc     1075
Thr Val Glu Thr Gly Val Leu Leu Asp Thr Glu Leu Pro Asn Glu Ile
310                 315                 320                 325 ccc gaa aac gag tac ata aag tat ttc gga cct gac tat act ttg aag     1123
Pro Glu Asn Glu Tyr Ile Lys Tyr Phe Gly Pro Asp Tyr Thr Leu Lys
            330                 335                 340 att ccg agc aga tac att gag aat ttg aac agt aaa tct tat ctc agc     1171
Ile Pro Ser Arg Tyr Ile Glu Asn Leu Asn Ser Lys Ser Tyr Leu Ser
        345                 350                 355 tcc ctc aaa gtt caa gta atg gag aat ttg cgg tac att cag cac gct     1219
Ser Leu Lys Val Gln Val Met Glu Asn Leu Arg Tyr Ile Gln His Ala
    360                 365                 370 cca agt gtg cag atg caa gag gtt cca ccg gat ttt tac atc cca gac     1267
Pro Ser Val Gln Met Gln Glu Val Pro Pro Asp Phe Tyr Ile Pro Asp
375                 380                 385 ttc gac gaa gat gag cag aac cca gat gaa cga atg gat cag cat act     1315
Phe Asp Glu Asp Glu Gln Asn Pro Asp Glu Arg Met Asp Gln His Thr
390                 395                 400                 405 cga gac aag caa gtc cag cgg gac gat gaa tac tac gat ggg gac aat     1363
Arg Asp Lys Gln Val Gln Arg Asp Asp Glu Tyr Tyr Asp Gly Asp Asn
            410                 415                 420 gac aac gac ccc aca gat cga tca tgatggtgcg gtagtggagc tttagtgttc    1417
Asp Asn Asp Pro Thr Asp Arg Ser
        425 atgctagttc agatgttttg tacatgctat actgatataa gcttgactct gtgatatcag   1477 gatttcaatt ggtcaaaatc ccttgtgtaa accattccat tccatgggga tatatcgctt   1537 ttgtaactct taaaagcaca atgctttagt tggaaatggg aactcgggag accgacacgc   1597 a                                                                    1598

<210> SEQ ID NO 44
<211> LENGTH: 429
<212> TYPE: PRT
<213> ORGANISM: Linum usitatissimum

<400> SEQUENCE: 44

Met Lys Ser Lys Asp Lys Ile Ser Tyr Phe Tyr Asp Gly Asp Val Gly
1               5                   10                  15

Ser Val Tyr Phe Gly Pro Asn His Pro Met Lys Pro His Arg Leu Cys
            20                  25                  30

Met Thr His His Leu Val Leu Ser Tyr Asp Leu His Lys Lys Met Glu
        35                  40                  45

Ile Tyr Arg Pro His Lys Ala Tyr Pro Val Glu Leu Ala Gln Phe His
    50                  55                  60
```

```
Ser Ala Asp Tyr Val Glu Phe Leu His Arg Ile Thr Pro Asp Thr Gln
 65                  70                  75                  80

His Leu Tyr Arg Thr Asp Leu Ala Arg Tyr Asn Leu Gly Glu Asp Cys
                 85                  90                  95

Pro Val Phe Glu Asn Leu Phe Glu Phe Cys Gln Ile Tyr Ala Gly Gly
            100                 105                 110

Thr Ile Asp Ala Ala Arg Arg Leu Asn Asn Gln Leu Cys Asp Ile Ala
        115                 120                 125

Ile Asn Trp Ala Gly Gly Leu His Ala Lys Lys Cys Glu Ala Ser
    130                 135                 140

Gly Phe Cys Tyr Ile Asn Asp Leu Val Leu Gly Ile Leu Glu Leu Leu
145                 150                 155                 160

Lys Tyr His Ala Arg Val Leu Tyr Ile Asp Ile Asp Val His His Gly
                165                 170                 175

Asp Gly Val Glu Glu Ala Phe Tyr Phe Thr Asp Arg Val Met Thr Val
            180                 185                 190

Ser Phe His Lys Phe Gly Asp Leu Phe Phe Pro Gly Thr Gly Asp Val
        195                 200                 205

Lys Glu Ile Gly Glu Arg Glu Gly Lys Phe Tyr Ala Ile Asn Val Pro
210                 215                 220

Leu Arg Asp Gly Ile Asp Asp Ser Ser Phe Asn Arg Leu Phe Lys Thr
225                 230                 235                 240

Ile Ile Ser Lys Val Val Glu Ile Tyr Gln Pro Gly Ala Ile Val Leu
                245                 250                 255

Gln Cys Gly Ala Asp Ser Leu Ala Gly Asp Arg Leu Gly Cys Phe Asn
            260                 265                 270

Leu Ser Ile Asp Gly His Ala Glu Cys Val Lys Phe Val Lys Lys Phe
        275                 280                 285

Asn Ile Pro Leu Leu Val Thr Gly Gly Gly Tyr Thr Lys Glu Asn
    290                 295                 300

Val Ala Arg Cys Trp Thr Val Glu Thr Gly Val Leu Leu Asp Thr Glu
305                 310                 315                 320

Leu Pro Asn Glu Ile Pro Glu Asn Glu Tyr Ile Lys Tyr Phe Gly Pro
                325                 330                 335

Asp Tyr Thr Leu Lys Ile Pro Ser Arg Tyr Ile Glu Asn Leu Asn Ser
            340                 345                 350

Lys Ser Tyr Leu Ser Ser Leu Lys Val Gln Val Met Glu Asn Leu Arg
        355                 360                 365

Tyr Ile Gln His Ala Pro Ser Val Gln Met Gln Glu Val Pro Pro Asp
    370                 375                 380

Phe Tyr Ile Pro Asp Phe Asp Glu Asp Glu Gln Asn Pro Asp Glu Arg
385                 390                 395                 400

Met Asp Gln His Thr Arg Asp Lys Gln Val Gln Arg Asp Asp Glu Tyr
                405                 410                 415

Tyr Asp Gly Asp Asn Asp Asn Asp Pro Thr Asp Arg Ser
            420                 425

<210> SEQ ID NO 45
<211> LENGTH: 1854
<212> TYPE: DNA
<213> ORGANISM: Oryza sativa
<220> FEATURE:
<221> NAME/KEY: CDS
<222> LOCATION: (64)..(1617)

<400> SEQUENCE: 45
```

```
aaagaaaaaa aaaagagata aaaaaaaaat ctcctcctcc tcgccgccgc cgccgccgcc      60 gcc atg gac gcc tcc gcc gga ggc ggg ggg aac tcg ctg ccg acg gcg     108
    Met Asp Ala Ser Ala Gly Gly Gly Gly Asn Ser Leu Pro Thr Ala
    1               5                   10                  15 ggg gcc gac ggg gcc aag cgg cgg gtg tgc tac ttc tac gac gcg gag     156
Gly Ala Asp Gly Ala Lys Arg Arg Val Cys Tyr Phe Tyr Asp Ala Glu
                20                  25                  30 gtg ggg aac tac tac tac ggg cag ggg cac ccg atg aag ccg cac cgc     204
Val Gly Asn Tyr Tyr Tyr Gly Gln Gly His Pro Met Lys Pro His Arg
            35                  40                  45 atc cgg atg acc cac gcg ctg ctc gcc cac tac ggc ctc ctc gac cag     252
Ile Arg Met Thr His Ala Leu Leu Ala His Tyr Gly Leu Leu Asp Gln
        50                  55                  60 atg cag gtg ctc aag ccc cac ccg gcg cgc gac cgc gac ctc tgc cgc     300
Met Gln Val Leu Lys Pro His Pro Ala Arg Asp Arg Asp Leu Cys Arg
65                  70                  75 ttc cac gcc gac gac tac gtc gcc ttc ctc cgc tcc gtc acg ccg gag     348
Phe His Ala Asp Asp Tyr Val Ala Phe Leu Arg Ser Val Thr Pro Glu
80                  85                  90                  95 acc cag cag gac cag atc cgg gcg ctc aag cgc ttc aac gtc ggc gag     396
Thr Gln Gln Asp Gln Ile Arg Ala Leu Lys Arg Phe Asn Val Gly Glu
                100                 105                 110 gac tgc ccc gtc ttc gac ggc ctc tac agc ttc tgc cag acc tac gcc     444
Asp Cys Pro Val Phe Asp Gly Leu Tyr Ser Phe Cys Gln Thr Tyr Ala
            115                 120                 125 ggg gga tcc gtc ggc ggc gcc gtc aag ctc aac cac ggc cac gac atc     492
Gly Gly Ser Val Gly Gly Ala Val Lys Leu Asn His Gly His Asp Ile
        130                 135                 140 gcc atc aac tgg gcc ggc ggc ctc cac cac gcc aag aag tgc gag gcc     540
Ala Ile Asn Trp Ala Gly Gly Leu His His Ala Lys Lys Cys Glu Ala
145                 150                 155 tcg gga ttc tgc tac gtc aac gac atc gtc ctc gcc atc ctc gag ctc     588
Ser Gly Phe Cys Tyr Val Asn Asp Ile Val Leu Ala Ile Leu Glu Leu
160                 165                 170                 175 ctc aaa tac cac cag cgt gtt ctc tat gtg gat atc gat atc cac cat     636
Leu Lys Tyr His Gln Arg Val Leu Tyr Val Asp Ile Asp Ile His His
                180                 185                 190 ggg gat ggt gtg gag gag gcg ttc tac acg acg gac agg gtg atg acg     684
Gly Asp Gly Val Glu Glu Ala Phe Tyr Thr Thr Asp Arg Val Met Thr
            195                 200                 205 gtc tcg ttc cac aag ttt ggg gat tat ttc ccg ggg acc ggg gac att     732
Val Ser Phe His Lys Phe Gly Asp Tyr Phe Pro Gly Thr Gly Asp Ile
        210                 215                 220 cgc gat att ggg cac tca aag ggg aag tat tac tct ctg aat gtc ccg     780
Arg Asp Ile Gly His Ser Lys Gly Lys Tyr Tyr Ser Leu Asn Val Pro
225                 230                 235 ttg gac gac ggt atc gac gac gag agc tac cag tcg ttg ttc aag ccg     828
Leu Asp Asp Gly Ile Asp Asp Glu Ser Tyr Gln Ser Leu Phe Lys Pro
240                 245                 250                 255 atc atg ggg aag gtg atg gag gtt ttt cgc cct ggc gcg gtg gtg ctc     876
Ile Met Gly Lys Val Met Glu Val Phe Arg Pro Gly Ala Val Val Leu
                260                 265                 270 cag tgc ggt gcg gac tct ctg tcg ggt gat agg ttg ggt tgc ttc aac     924
Gln Cys Gly Ala Asp Ser Leu Ser Gly Asp Arg Leu Gly Cys Phe Asn
            275                 280                 285 ctg tca atc agg ggc cac gcg gaa tgc gtg aga ttc atg agg tcc ttc     972
Leu Ser Ile Arg Gly His Ala Glu Cys Val Arg Phe Met Arg Ser Phe
        290                 295                 300 aat gtc ccg ctg ttg ctg ctt ggt ggt ggt ggg tat acc ata aga aat    1020
Asn Val Pro Leu Leu Leu Leu Gly Gly Gly Gly Tyr Thr Ile Arg Asn
```

```
                         305                 310                 315
gtt gcg cgg tgt tgg tgc tat gag aca gga gtt gca ctt ggt cat gag    1068
Val Ala Arg Cys Trp Cys Tyr Glu Thr Gly Val Ala Leu Gly His Glu
320                 325                 330                 335 ctc act gac aag atg cct cca aat gag tat ttt gag tac ttt ggt cca    1116
Leu Thr Asp Lys Met Pro Pro Asn Glu Tyr Phe Glu Tyr Phe Gly Pro
                340                 345                 350 gat tat aca ctt cat gtt gca cca agt aac atg gag aac aaa aac aca    1164
Asp Tyr Thr Leu His Val Ala Pro Ser Asn Met Glu Asn Lys Asn Thr
            355                 360                 365 cgc cag cag ttg gat gat ata aga tca aga ctt ctt gat aat ctt tca    1212
Arg Gln Gln Leu Asp Asp Ile Arg Ser Arg Leu Leu Asp Asn Leu Ser
        370                 375                 380 aaa ctt cga cat gct cct agc gtc caa ttt caa gag cga ccc cct gag    1260
Lys Leu Arg His Ala Pro Ser Val Gln Phe Gln Glu Arg Pro Pro Glu
385                 390                 395 gct gag cta cct gag caa gat gaa gac caa gag gat cct gat gaa agg    1308
Ala Glu Leu Pro Glu Gln Asp Glu Asp Gln Glu Asp Pro Asp Glu Arg
400                 405                 410                 415 cac cat gct gat tct gat gtg gaa atg gat gat gtc aaa cct ttg gat    1356
His His Ala Asp Ser Asp Val Glu Met Asp Asp Val Lys Pro Leu Asp
                420                 425                 430 gac tca gga agg agg agc agt att cag aat gtg aga gtt aag aga gag    1404
Asp Ser Gly Arg Arg Ser Ser Ile Gln Asn Val Arg Val Lys Arg Glu
            435                 440                 445 tct gct gaa aca gat gcc gca gat cag gat ggt aat agg gtc gct gca    1452
Ser Ala Glu Thr Asp Ala Ala Asp Gln Asp Gly Asn Arg Val Ala Ala
        450                 455                 460 gag aac acc aag ggc aca gaa cct gcg gct gat gga gtt ggt tcc tcg    1500
Glu Asn Thr Lys Gly Thr Glu Pro Ala Ala Asp Gly Val Gly Ser Ser
465                 470                 475 aaa caa act gtt cct acc gat gca agt gcg atg gcc ata gac gaa cca    1548
Lys Gln Thr Val Pro Thr Asp Ala Ser Ala Met Ala Ile Asp Glu Pro
                480                 485                 490                 495 ggc tcc ctg aaa gtc gag cca gat aac tca aac aaa ttg caa gat caa    1596
Gly Ser Leu Lys Val Glu Pro Asp Asn Ser Asn Lys Leu Gln Asp Gln
            500                 505                 510 cca tcg gtg cac cag aag aca taatagttct ctctaccttaa aacttagta       1647
Pro Ser Val His Gln Lys Thr
                515 actgatgcca tctatcatcc attgattata ttggagaaac tcccaacttt gaagcagaga  1707 gttcatgcca taccaaaagt tatataccaa atttcgaatg gtatgtacac ctttcgaact  1767 ggtggtgttt tgtgcaatac atttatgcca ggctgactat tatgtggtat ctattattag  1827 ctttagtata aaaaaaaaaa aaaaaaa                                      1854

<210> SEQ ID NO 46
<211> LENGTH: 518
<212> TYPE: PRT
<213> ORGANISM: Oryza sativa

<400> SEQUENCE: 46

Met Asp Ala Ser Ala Gly Gly Gly Gly Asn Ser Leu Pro Thr Ala Gly
1               5                   10                  15

Ala Asp Gly Ala Lys Arg Arg Val Cys Tyr Phe Tyr Asp Ala Glu Val
                20                  25                  30

Gly Asn Tyr Tyr Tyr Gly Gln Gly His Pro Met Lys Pro His Arg Ile
            35                  40                  45

Arg Met Thr His Ala Leu Leu Ala His Tyr Gly Leu Leu Asp Gln Met
```

```
                50                  55                  60
Gln Val Leu Lys Pro His Pro Ala Arg Asp Arg Asp Leu Cys Arg Phe
 65                  70                  75                  80

His Ala Asp Asp Tyr Val Ala Phe Leu Arg Ser Val Thr Pro Glu Thr
                     85                  90                  95

Gln Gln Asp Gln Ile Arg Ala Leu Lys Arg Phe Asn Val Gly Glu Asp
                    100                 105                 110

Cys Pro Val Phe Asp Gly Leu Tyr Ser Phe Cys Gln Thr Tyr Ala Gly
                    115                 120                 125

Gly Ser Val Gly Gly Ala Val Lys Leu Asn His Gly His Asp Ile Ala
            130                 135                 140

Ile Asn Trp Ala Gly Leu His His Ala Lys Lys Cys Glu Ala Ser
145                 150                 155                 160

Gly Phe Cys Tyr Val Asn Asp Ile Val Leu Ala Ile Leu Glu Leu Leu
                    165                 170                 175

Lys Tyr His Gln Arg Val Leu Tyr Val Asp Ile Asp Ile His His Gly
                180                 185                 190

Asp Gly Val Glu Glu Ala Phe Tyr Thr Thr Asp Arg Val Met Thr Val
            195                 200                 205

Ser Phe His Lys Phe Gly Asp Tyr Phe Pro Gly Thr Gly Asp Ile Arg
210                 215                 220

Asp Ile Gly His Ser Lys Gly Lys Tyr Tyr Ser Leu Asn Val Pro Leu
225                 230                 235                 240

Asp Asp Gly Ile Asp Asp Glu Ser Tyr Gln Ser Leu Phe Lys Pro Ile
                245                 250                 255

Met Gly Lys Val Met Glu Val Phe Arg Pro Gly Ala Val Val Leu Gln
            260                 265                 270

Cys Gly Ala Asp Ser Leu Ser Gly Asp Arg Leu Gly Cys Phe Asn Leu
            275                 280                 285

Ser Ile Arg Gly His Ala Glu Cys Val Arg Phe Met Arg Ser Phe Asn
290                 295                 300

Val Pro Leu Leu Leu Leu Gly Gly Gly Gly Tyr Thr Ile Arg Asn Val
305                 310                 315                 320

Ala Arg Cys Trp Cys Tyr Glu Thr Gly Val Ala Leu Gly His Glu Leu
                325                 330                 335

Thr Asp Lys Met Pro Pro Asn Glu Tyr Phe Glu Tyr Phe Gly Pro Asp
                340                 345                 350

Tyr Thr Leu His Val Ala Pro Ser Asn Met Glu Asn Lys Asn Thr Arg
                355                 360                 365

Gln Gln Leu Asp Asp Ile Arg Ser Arg Leu Leu Asp Asn Leu Ser Lys
            370                 375                 380

Leu Arg His Ala Pro Ser Val Gln Phe Gln Glu Arg Pro Pro Glu Ala
385                 390                 395                 400

Glu Leu Pro Glu Gln Asp Glu Gln Glu Asp Pro Asp Glu Arg His
                    405                 410                 415

His Ala Asp Ser Asp Val Glu Met Asp Asp Val Lys Pro Leu Asp Asp
                420                 425                 430

Ser Gly Arg Arg Ser Ser Ile Gln Asn Val Arg Val Lys Arg Glu Ser
            435                 440                 445

Ala Glu Thr Asp Ala Ala Asp Gln Asp Gly Asn Arg Val Ala Ala Glu
            450                 455                 460

Asn Thr Lys Gly Thr Glu Pro Ala Ala Asp Gly Val Gly Ser Ser Lys
465                 470                 475                 480
```

```
Gln Thr Val Pro Thr Asp Ala Ser Ala Met Ala Ile Asp Glu Pro Gly
            485                 490                 495

Ser Leu Lys Val Glu Pro Asp Asn Ser Asn Lys Leu Gln Asp Gln Pro
        500                 505                 510

Ser Val His Gln Lys Thr
        515

<210> SEQ ID NO 47
<211> LENGTH: 1252
<212> TYPE: DNA
<213> ORGANISM: Glycine max
<220> FEATURE:
<221> NAME/KEY: CDS
<222> LOCATION: (4)..(1005)

<400> SEQUENCE: 47 ggg atg ctg aag cat gac acg ggc aat ggc gtg ttt gac acg ggg atg         48
    Met Leu Lys His Asp Thr Gly Asn Gly Val Phe Asp Thr Gly Met
    1               5                   10                  15 gat cca ggc ttc tta gag gtg ttg gag aag cac cct gaa aac tca gac         96
Asp Pro Gly Phe Leu Glu Val Leu Glu Lys His Pro Glu Asn Ser Asp
                20                  25                  30 aga gtg aaa aac cta gtg tct att ctc aaa agg ggt cct atc tcc cct        144
Arg Val Lys Asn Leu Val Ser Ile Leu Lys Arg Gly Pro Ile Ser Pro
            35                  40                  45 tac att tct tgg cac ctt ggt aca cct gca aaa atc cct gag ctt ttt        192
Tyr Ile Ser Trp His Leu Gly Thr Pro Ala Lys Ile Pro Glu Leu Phe
        50                  55                  60 tct ttt cac act cct gaa tac ata aat gaa ctg gta gaa gtt gat aaa        240
Ser Phe His Thr Pro Glu Tyr Ile Asn Glu Leu Val Glu Val Asp Lys
65                  70                  75 gaa ggg ggg aag cag ctt tgt ggt ggg aca ttt ttg aac cct gga tca        288
Glu Gly Gly Lys Gln Leu Cys Gly Gly Thr Phe Leu Asn Pro Gly Ser
80                  85                  90                  95 tgg gat gct gca ctt ctt gct gct ggg act aca cta tct gcg atg aag        336
Trp Asp Ala Ala Leu Leu Ala Ala Gly Thr Thr Leu Ser Ala Met Lys
                100                 105                 110 cat tta ctg aat ggg gat gga aaa gtt tcc tat gca ttg gtt agg ccc        384
His Leu Leu Asn Gly Asp Gly Lys Val Ser Tyr Ala Leu Val Arg Pro
            115                 120                 125 cct ggt cac cat gct cag cct tct ctg gcc gat ggc tac tgt ttc ctt        432
Pro Gly His His Ala Gln Pro Ser Leu Ala Asp Gly Tyr Cys Phe Leu
        130                 135                 140 aac aat gca ggt cta gct gtg caa ttg gct tta gat tcc ggc tgc aag        480
Asn Asn Ala Gly Leu Ala Val Gln Leu Ala Leu Asp Ser Gly Cys Lys
145                 150                 155 aag gtt gcg gtc ata gat att gat gtg cat tat gga aat gga acg gca        528
Lys Val Ala Val Ile Asp Ile Asp Val His Tyr Gly Asn Gly Thr Ala
160                 165                 170                 175 gag ggg ttt tat cga tct aat aag gtt ctt acc atc tct ctt cat atg        576
Glu Gly Phe Tyr Arg Ser Asn Lys Val Leu Thr Ile Ser Leu His Met
                180                 185                 190 aac cat gga tca tgg ggt cca tct cat ccg caa agt ggc tct gtt gat        624
Asn His Gly Ser Trp Gly Pro Ser His Pro Gln Ser Gly Ser Val Asp
            195                 200                 205 gag cta ggt gaa gga gaa ggt tat ggc ttt aac ttg aac ata cct cta        672
Glu Leu Gly Glu Gly Glu Gly Tyr Gly Phe Asn Leu Asn Ile Pro Leu
        210                 215                 220 cca aat gga act ggg gac aag gga tat gta cat gcc ttc aat gag ttg        720
Pro Asn Gly Thr Gly Asp Lys Gly Tyr Val His Ala Phe Asn Glu Leu
225                 230                 235
```

```
gtt gtt cca tcc atc caa aag ttt ggg cct gat atg ata gtt ttg gtt    768
Val Val Pro Ser Ile Gln Lys Phe Gly Pro Asp Met Ile Val Leu Val
240             245                 250                 255 ctt gga caa gac tct aat gca ttt gat ccc aat gga agg caa tgc tta    816
Leu Gly Gln Asp Ser Asn Ala Phe Asp Pro Asn Gly Arg Gln Cys Leu
                260                 265                 270 aca atg gag ggc tat aga gaa ata ggg cga att gtc cat ctt ctt gcg    864
Thr Met Glu Gly Tyr Arg Glu Ile Gly Arg Ile Val His Leu Leu Ala
            275                 280                 285 aaa agg cac agt gca gga cgc ctt cta att gtc cag gaa ggt gga tat    912
Lys Arg His Ser Ala Gly Arg Leu Leu Ile Val Gln Glu Gly Gly Tyr
        290                 295                 300 cat gtc aca tat tct gca tat tgt tta cat gca aca ctt gag ggg att    960
His Val Thr Tyr Ser Ala Tyr Cys Leu His Ala Thr Leu Glu Gly Ile
305                 310                 315 ctc aac cta cca atg cct cta cta gcg gat cct att gct ttt acc       1005
Leu Asn Leu Pro Met Pro Leu Leu Ala Asp Pro Ile Ala Phe Thr
320             325                 330 tagacgacga gacattttct gtccaagtta tagaagccat taagaattat caaaaagata  1065
aagtgtgcta gtggagaaac tcactagaca cttccttctg tgcgtgtgaa ataaatcttg  1125
atacttttca agaagggtta atatttatcg tgtaactatt gagggatttt caaggttatt  1185
ttaaataaat ttaatcttgt ccagttgatc ttttgattaa aaaaaaaaaa aaagagaacc  1245
gaacgca                                                            1252

<210> SEQ ID NO 48
<211> LENGTH: 334
<212> TYPE: PRT
<213> ORGANISM: Glycine max

<400> SEQUENCE: 48

Met Leu Lys His Asp Thr Gly Asn Gly Val Phe Asp Thr Gly Met Asp
1               5                   10                  15

Pro Gly Phe Leu Glu Val Leu Glu Lys His Pro Glu Asn Ser Asp Arg
            20                  25                  30

Val Lys Asn Leu Val Ser Ile Leu Lys Arg Gly Pro Ile Ser Pro Tyr
        35                  40                  45

Ile Ser Trp His Leu Gly Thr Pro Ala Lys Ile Pro Glu Leu Phe Ser
    50                  55                  60

Phe His Thr Pro Glu Tyr Ile Asn Glu Leu Val Glu Val Asp Lys Glu
65                  70                  75                  80

Gly Gly Lys Gln Leu Cys Gly Gly Thr Phe Leu Asn Pro Gly Ser Trp
                85                  90                  95

Asp Ala Ala Leu Leu Ala Ala Gly Thr Thr Leu Ser Ala Met Lys His
            100                 105                 110

Leu Leu Asn Gly Asp Gly Lys Val Ser Tyr Ala Leu Val Arg Pro Pro
        115                 120                 125

Gly His His Ala Gln Pro Ser Leu Ala Asp Gly Tyr Cys Phe Leu Asn
    130                 135                 140

Asn Ala Gly Leu Ala Val Gln Leu Ala Leu Asp Ser Gly Cys Lys Lys
145                 150                 155                 160

Val Ala Val Ile Asp Ile Asp Val His Tyr Gly Asn Gly Thr Ala Glu
                165                 170                 175

Gly Phe Tyr Arg Ser Asn Lys Val Leu Thr Ile Ser Leu His Met Asn
            180                 185                 190

His Gly Ser Trp Gly Pro Ser His Pro Gln Ser Gly Ser Val Asp Glu
        195                 200                 205
```

```
Leu Gly Glu Gly Glu Gly Tyr Gly Phe Asn Leu Asn Ile Pro Leu Pro
    210                 215                 220

Asn Gly Thr Gly Asp Lys Gly Tyr Val His Ala Phe Asn Glu Leu Val
225                 230                 235                 240

Val Pro Ser Ile Gln Lys Phe Gly Pro Asp Met Ile Val Leu Val Leu
                245                 250                 255

Gly Gln Asp Ser Asn Ala Phe Asp Pro Asn Gly Arg Gln Cys Leu Thr
            260                 265                 270

Met Glu Gly Tyr Arg Glu Ile Gly Arg Ile Val His Leu Leu Ala Lys
        275                 280                 285

Arg His Ser Ala Gly Arg Leu Leu Ile Val Gln Glu Gly Gly Tyr His
    290                 295                 300

Val Thr Tyr Ser Ala Tyr Cys Leu His Ala Thr Leu Glu Gly Ile Leu
305                 310                 315                 320

Asn Leu Pro Met Pro Leu Leu Ala Asp Pro Ile Ala Phe Thr
                325                 330

<210> SEQ ID NO 49
<211> LENGTH: 1723
<212> TYPE: DNA
<213> ORGANISM: Glycine max
<220> FEATURE:
<221> NAME/KEY: CDS
<222> LOCATION: (143)..(1429)

<400> SEQUENCE: 49
acatagagtg attaggctgg tagcaagcgc gacatggcac tgcagtgcag gttaagctca      60
caccattgat atcactagcc atattctcct ttcgctaatt cccgcaagct actactcttc     120
ttcaacgctc tctctgcaaa ag atg cgc tcc aag gac aga atc gct tac ttc     172
                         Met Arg Ser Lys Asp Arg Ile Ala Tyr Phe
                           1               5                  10 tac gac ggt gat gtc ggt agt gtt tac ttt ggg gcg aag cat ccg atg      220
Tyr Asp Gly Asp Val Gly Ser Val Tyr Phe Gly Ala Lys His Pro Met
             15                  20                  25 aag ccc cac cgg ctt tgc atg act cat cat ctt gtt ctc tca tac gat      268
Lys Pro His Arg Leu Cys Met Thr His His Leu Val Leu Ser Tyr Asp
         30                  35                  40 ctt cat aag aag atg gag att tat cgt cca cac aag gct tat cct gtt      316
Leu His Lys Lys Met Glu Ile Tyr Arg Pro His Lys Ala Tyr Pro Val
     45                  50                  55 gag ctt gcc cag ttt cat tca gct gat tat gtt gag ttt ttg aac agg      364
Glu Leu Ala Gln Phe His Ser Ala Asp Tyr Val Glu Phe Leu Asn Arg
 60                  65                  70 att aca cct gac act cag cac ttg ttc ttg aat gaa ctg aca aaa tat      412
Ile Thr Pro Asp Thr Gln His Leu Phe Leu Asn Glu Leu Thr Lys Tyr
 75                  80                  85                  90 aat ctt gga gaa gac tgc cct gta ttt gac aac tta ttt gaa ttt tgt      460
Asn Leu Gly Glu Asp Cys Pro Val Phe Asp Asn Leu Phe Glu Phe Cys
                 95                 100                 105 cag att tat gct ggt gga act ata gat gct gca cgt cga tta aac aat      508
Gln Ile Tyr Ala Gly Gly Thr Ile Asp Ala Ala Arg Arg Leu Asn Asn
            110                 115                 120 caa ctg tgt gat att gct atc aac tgg gcc ggt gga cta cat cat gcc      556
Gln Leu Cys Asp Ile Ala Ile Asn Trp Ala Gly Gly Leu His His Ala
        125                 130                 135 aag aaa tgc gag gca tct gga ttt tgt tac atc aat gac ttg gtt tta      604
Lys Lys Cys Glu Ala Ser Gly Phe Cys Tyr Ile Asn Asp Leu Val Leu
    140                 145                 150
```

```
gga atc ttg gag ctt ctt aaa tat cat gct cgt gtt tgt tat att gat      652
Gly Ile Leu Glu Leu Leu Lys Tyr His Ala Arg Val Leu Tyr Ile Asp
155                 160                 165                 170 ata gat gtg cac cat ggt gat ggt gta gaa gaa gcc ttc tac ttc act      700
Ile Asp Val His His Gly Asp Gly Val Glu Glu Ala Phe Tyr Phe Thr
                175                 180                 185 gac agg gtg atg act gtc agt ttt cac aag tat gga gat tcg ttc ttc      748
Asp Arg Val Met Thr Val Ser Phe His Lys Tyr Gly Asp Ser Phe Phe
            190                 195                 200 ccg ggt act ggc gat gct aag gaa ata gga gaa aga gaa gga aag ttt      796
Pro Gly Thr Gly Asp Ala Lys Glu Ile Gly Glu Arg Glu Gly Lys Phe
        205                 210                 215 tat gcc ata aat gtc cca ttg aag gat gga ata gat gac agt agc ttc      844
Tyr Ala Ile Asn Val Pro Leu Lys Asp Gly Ile Asp Asp Ser Ser Phe
    220                 225                 230 act cga ctt ttc aag act att att tcc aaa gta gtt gaa aca tat caa      892
Thr Arg Leu Phe Lys Thr Ile Ile Ser Lys Val Val Glu Thr Tyr Gln
235                 240                 245                 250 cct ggt gca ata gtt ctg cag tgt gga gca gat tcg ctt gct gga gat      940
Pro Gly Ala Ile Val Leu Gln Cys Gly Ala Asp Ser Leu Ala Gly Asp
                255                 260                 265 cgc ttg ggt tgc ttc aat ctc tct att gat ggt cat gct gaa tgt gtt      988
Arg Leu Gly Cys Phe Asn Leu Ser Ile Asp Gly His Ala Glu Cys Val
            270                 275                 280 agc ttc gta aag aga ttc aat ttg cca ttg ctg gtc act gga ggt ggg     1036
Ser Phe Val Lys Arg Phe Asn Leu Pro Leu Leu Val Thr Gly Gly Gly
        285                 290                 295 gga tac aca aaa gaa aat gtt gct cga tgt tgg act gtt gaa aca gga     1084
Gly Tyr Thr Lys Glu Asn Val Ala Arg Cys Trp Thr Val Glu Thr Gly
    300                 305                 310 gtt ctt cta gat aca gag ctt cca aat gag att ccg caa aat gat tat     1132
Val Leu Leu Asp Thr Glu Leu Pro Asn Glu Ile Pro Gln Asn Asp Tyr
315                 320                 325                 330 att aaa tac ttt gca cca gaa ttt tct ttg aag gtt cca aat ggg ccg     1180
Ile Lys Tyr Phe Ala Pro Glu Phe Ser Leu Lys Val Pro Asn Gly Pro
                335                 340                 345 ata gaa aat ttg aat agt aaa tca tat ctt agc acc att aaa atg caa     1228
Ile Glu Asn Leu Asn Ser Lys Ser Tyr Leu Ser Thr Ile Lys Met Gln
            350                 355                 360 gtc ttg gaa aat ctt cgt tgc atc cag cat gct cca agc gta cag atg     1276
Val Leu Glu Asn Leu Arg Cys Ile Gln His Ala Pro Ser Val Gln Met
        365                 370                 375 cag gag gtc cct cct gac ttc tac att cca gaa ttc gat gaa gat gag     1324
Gln Glu Val Pro Pro Asp Phe Tyr Ile Pro Glu Phe Asp Glu Asp Glu
    380                 385                 390 cag aac cct gat gaa cgc att gat cag cac act caa gac aag cac atc     1372
Gln Asn Pro Asp Glu Arg Ile Asp Gln His Thr Gln Asp Lys His Ile
395                 400                 405                 410 cag cgc gat gat gaa tat tat gat ggt gac aat gac aat gat caa atg     1420
Gln Arg Asp Asp Glu Tyr Tyr Asp Gly Asp Asn Asp Asn Asp Gln Met
                415                 420                 425 aat att tca tgaagtgcag ttgccgtttg cctttggcg ggggattgac              1469
Asn Ile Ser cgttttaaga gagaaggaaa atgttaatta gacaaacacc tagatgtatc aacaaagcgg    1529
tagtactagc ccaagaaact tgtatattta taagattttt attgttttca gttgctaata   1589
tatttgctca aagttacatt attaatgatg tttcttccct gtcattttt tgaatgaaaa    1649 tggacggtgt tagagcaact ctgacaacaa gagcttgcat aacattcttt ttacagaaaa   1709
aaaaaaaaaa aaaa                                                     1723
```

<210> SEQ ID NO 50
<211> LENGTH: 429
<212> TYPE: PRT
<213> ORGANISM: Glycine max

<400> SEQUENCE: 50

Met Arg Ser Lys Asp Arg Ile Ala Tyr Phe Tyr Asp Gly Asp Val Gly
1               5                   10                  15

Ser Val Tyr Phe Gly Ala Lys His Pro Met Lys Pro His Arg Leu Cys
            20                  25                  30

Met Thr His His Leu Val Leu Ser Tyr Asp Leu His Lys Lys Met Glu
        35                  40                  45

Ile Tyr Arg Pro His Lys Ala Tyr Pro Val Glu Leu Ala Gln Phe His
50                  55                  60

Ser Ala Asp Tyr Val Glu Phe Leu Asn Arg Ile Thr Pro Asp Thr Gln
65                  70                  75                  80

His Leu Phe Leu Asn Glu Leu Thr Lys Tyr Asn Leu Gly Glu Asp Cys
                85                  90                  95

Pro Val Phe Asp Asn Leu Phe Glu Phe Cys Gln Ile Tyr Ala Gly Gly
            100                 105                 110

Thr Ile Asp Ala Ala Arg Arg Leu Asn Asn Gln Leu Cys Asp Ile Ala
        115                 120                 125

Ile Asn Trp Ala Gly Gly Leu His His Ala Lys Lys Cys Glu Ala Ser
130                 135                 140

Gly Phe Cys Tyr Ile Asn Asp Leu Val Leu Gly Ile Leu Glu Leu Leu
145                 150                 155                 160

Lys Tyr His Ala Arg Val Leu Tyr Ile Asp Ile Asp Val His His Gly
                165                 170                 175

Asp Gly Val Glu Glu Ala Phe Tyr Phe Thr Asp Arg Val Met Thr Val
            180                 185                 190

Ser Phe His Lys Tyr Gly Asp Ser Phe Phe Pro Gly Thr Gly Asp Ala
        195                 200                 205

Lys Glu Ile Gly Glu Arg Glu Gly Lys Phe Tyr Ala Ile Asn Val Pro
210                 215                 220

Leu Lys Asp Gly Ile Asp Asp Ser Ser Phe Thr Arg Leu Phe Lys Thr
225                 230                 235                 240

Ile Ile Ser Lys Val Val Glu Thr Tyr Gln Pro Gly Ala Ile Val Leu
                245                 250                 255

Gln Cys Gly Ala Asp Ser Leu Ala Gly Asp Arg Leu Gly Cys Phe Asn
            260                 265                 270

Leu Ser Ile Asp Gly His Ala Glu Cys Val Ser Phe Val Lys Arg Phe
        275                 280                 285

Asn Leu Pro Leu Leu Val Thr Gly Gly Gly Gly Tyr Thr Lys Glu Asn
290                 295                 300

Val Ala Arg Cys Trp Thr Val Glu Thr Gly Val Leu Leu Asp Thr Glu
305                 310                 315                 320

Leu Pro Asn Glu Ile Pro Gln Asn Asp Tyr Ile Lys Tyr Phe Ala Pro
                325                 330                 335

Glu Phe Ser Leu Lys Val Pro Asn Gly Pro Ile Glu Asn Leu Asn Ser
            340                 345                 350

Lys Ser Tyr Leu Ser Thr Ile Lys Met Gln Val Leu Glu Asn Leu Arg
        355                 360                 365

Cys Ile Gln His Ala Pro Ser Val Gln Met Gln Glu Val Pro Pro Asp
370                 375                 380

```
Phe Tyr Ile Pro Glu Phe Asp Glu Asp Gln Asn Pro Asp Glu Arg
385                 390                 395                 400

Ile Asp Gln His Thr Gln Asp Lys His Ile Gln Arg Asp Asp Glu Tyr
            405                 410                 415

Tyr Asp Gly Asp Asn Asp Asn Asp Gln Met Asn Ile Ser
            420                 425

<210> SEQ ID NO 51
<211> LENGTH: 1498
<212> TYPE: DNA
<213> ORGANISM: Glycine max
<220> FEATURE:
<221> NAME/KEY: CDS
<222> LOCATION: (10)..(1260)

<400> SEQUENCE: 51 ctggtctcc atg cac ctt ctc aaa ttt cct cgc tct cca tct tcc ttc ggg         51
          Met His Leu Leu Lys Phe Pro Arg Ser Pro Ser Ser Phe Gly
          1               5                   10 aat gcg ttc ttt ctg gtg ggt cat cat gtt ttg gac ata aga gtg ttc           99
Asn Ala Phe Phe Leu Val Gly His His Val Leu Asp Ile Arg Val Phe
15              20                  25                  30 cgt aag aac cag aga tgt ttc aga gcg tcc ata tcg tgt tcg gct gtt          147
Arg Lys Asn Gln Arg Cys Phe Arg Ala Ser Ile Ser Cys Ser Ala Val
                35                  40                  45 agg aac ggt tct att gag caa cta agt gat gca cgg ctt ata tac tcc          195
Arg Asn Gly Ser Ile Glu Gln Leu Ser Asp Ala Arg Leu Ile Tyr Ser
            50                  55                  60 gtc gct cca tct atg ggc cac aac cag gag tct cat cca gaa tca cat          243
Val Ala Pro Ser Met Gly His Asn Gln Glu Ser His Pro Glu Ser His
65              70                  75 ttt aga gtt ccc gcg att gtc aat gct cta gaa gaa atg cag ctc act          291
Phe Arg Val Pro Ala Ile Val Asn Ala Leu Glu Glu Met Gln Leu Thr
            80                  85                  90 tcc aag ttc cgt ggc cca gag gta att gaa ctt caa cat ttt gag cct          339
Ser Lys Phe Arg Gly Pro Glu Val Ile Glu Leu Gln His Phe Glu Pro
95              100                 105                 110 gct tca gtt gat gat att gca agt gtg cat gca aga gcc tat gtt tct          387
Ala Ser Val Asp Asp Ile Ala Ser Val His Ala Arg Ala Tyr Val Ser
                115                 120                 125 ggg ctt gaa aag gtt atg gat caa gct gtg gag aaa ggc ctt att ttc          435
Gly Leu Glu Lys Val Met Asp Gln Ala Val Glu Lys Gly Leu Ile Phe
            130                 135                 140 ctt gat ggt tca gga cca aca tat gcc act gcc act acc ttc cag gag          483
Leu Asp Gly Ser Gly Pro Thr Tyr Ala Thr Ala Thr Thr Phe Gln Glu
            145                 150                 155 tca ata gtt gca gcc ggt gct gga tta gcc tta gtt gac tca gtg gtt          531
Ser Ile Val Ala Ala Gly Ala Gly Leu Ala Leu Val Asp Ser Val Val
160             165                 170 gca tgt tca aag ata aag gga gat gca ccc act ggt ttt gct ctg ata          579
Ala Cys Ser Lys Ile Lys Gly Asp Ala Pro Thr Gly Phe Ala Leu Ile
175             180                 185                 190 aga cca cca gga cat cac gca gtt cca caa gga cct atg gga ttc tgc          627
Arg Pro Pro Gly His His Ala Val Pro Gln Gly Pro Met Gly Phe Cys
                195                 200                 205 att ttt gga aat gtg gcc att gca gcc gtt tat tct cag cgt gtt cat          675
Ile Phe Gly Asn Val Ala Ile Ala Ala Arg Tyr Ser Gln Arg Val His
            210                 215                 220 gga ttg aag cgt gtg ttt ata att gac ttt gat gtt cat cat ggg aat          723
Gly Leu Lys Arg Val Phe Ile Ile Asp Phe Asp Val His His Gly Asn
            225                 230                 235
```

```
gga aca aat gat gct ttc tat gat gat cca gat gta ttt ttc ctt tca    771
Gly Thr Asn Asp Ala Phe Tyr Asp Asp Pro Asp Val Phe Phe Leu Ser
    240                 245                 250 ttt cac caa gat gga agc tat ccc ggt act ggt aaa ttt gat gaa gtt    819
Phe His Gln Asp Gly Ser Tyr Pro Gly Thr Gly Lys Phe Asp Glu Val
255                 260                 265                 270 gga agt gga gat ggt gaa gga acc aca tta aat ctg cct ctt cct gga    867
Gly Ser Gly Asp Gly Glu Gly Thr Thr Leu Asn Leu Pro Leu Pro Gly
                275                 280                 285 ggt tca ggt gat act gct att aga act gtg ttc gat gaa gtc att gta    915
Gly Ser Gly Asp Thr Ala Ile Arg Thr Val Phe Asp Glu Val Ile Val
            290                 295                 300 cca tgt gct caa aga ttt aaa cca gac atc att ctt gtt tct gct ggg    963
Pro Cys Ala Gln Arg Phe Lys Pro Asp Ile Ile Leu Val Ser Ala Gly
        305                 310                 315 tat gac ggc cac gtg ttg gat cca cta gct aat ctt caa tat aca act   1011
Tyr Asp Gly His Val Leu Asp Pro Leu Ala Asn Leu Gln Tyr Thr Thr
    320                 325                 330 gga aca tat tac atg cta gcg tcc agt atc aaa caa cta gcg aaa gat   1059
Gly Thr Tyr Tyr Met Leu Ala Ser Ser Ile Lys Gln Leu Ala Lys Asp
335                 340                 345                 350 tta tgt ggg ggc cga tgt gtg ttt ttc ttg gag gga gga tat aat ctg   1107
Leu Cys Gly Gly Arg Cys Val Phe Phe Leu Glu Gly Gly Tyr Asn Leu
                355                 360                 365 aag tct ctt tca tat tcc gtg gca gac aca ttc cgt gct ctt ctt ggg   1155
Lys Ser Leu Ser Tyr Ser Val Ala Asp Thr Phe Arg Ala Leu Leu Gly
            370                 375                 380 gac cga agc ttg gca tct gag ttt gat aac cct aac att ttg tac gaa   1203
Asp Arg Ser Leu Ala Ser Glu Phe Asp Asn Pro Asn Ile Leu Tyr Glu
        385                 390                 395 gag cca tct aca aaa gtt aag caa gct att cag aag ata aaa cac att   1251
Glu Pro Ser Thr Lys Val Lys Gln Ala Ile Gln Lys Ile Lys His Ile
    400                 405                 410 cat tcc ctg tgaggtcaaa atagaaactg acatgacaag catctaaatg           1300
His Ser Leu
415 tctagcatta ataatttcct tttctgtggg ttcaatctat aagtacatgt ctttacactc  1360 ttgggtgggc attctcccac ttatcacata gaagcaaaac cattgtacag gattgcttgt  1420 ggtctttgaa cgagtctcca gttacagttt ctatatgcca tgcagccatg catattgatc  1480 aaaaaaaaaa aaaaaaaa                                                1498

<210> SEQ ID NO 52
<211> LENGTH: 417
<212> TYPE: PRT
<213> ORGANISM: Glycine max

<400> SEQUENCE: 52

Met His Leu Leu Lys Phe Pro Arg Ser Pro Ser Phe Gly Asn Ala
1               5                   10                  15

Phe Phe Leu Val Gly His His Val Leu Asp Ile Arg Val Phe Arg Lys
                20                  25                  30

Asn Gln Arg Cys Phe Arg Ala Ser Ile Ser Cys Ser Ala Val Arg Asn
            35                  40                  45

Gly Ser Ile Glu Gln Leu Ser Asp Ala Arg Leu Ile Tyr Ser Val Ala
        50                  55                  60

Pro Ser Met Gly His Asn Gln Glu Ser His Pro Glu Ser His Phe Arg
65                  70                  75                  80
```

```
Val Pro Ala Ile Val Asn Ala Leu Glu Glu Met Gln Leu Thr Ser Lys
                85                  90                  95

Phe Arg Gly Pro Glu Val Ile Glu Leu Gln His Phe Glu Pro Ala Ser
            100                 105                 110

Val Asp Asp Ile Ala Ser Val His Ala Arg Ala Tyr Val Ser Gly Leu
        115                 120                 125

Glu Lys Val Met Asp Gln Ala Val Glu Lys Gly Leu Ile Phe Leu Asp
130                 135                 140

Gly Ser Gly Pro Thr Tyr Ala Thr Ala Thr Thr Phe Gln Glu Ser Ile
145                 150                 155                 160

Val Ala Ala Gly Ala Gly Leu Ala Leu Val Asp Ser Val Ala Cys
                165                 170                 175

Ser Lys Ile Lys Gly Asp Ala Pro Thr Gly Phe Ala Leu Ile Arg Pro
            180                 185                 190

Pro Gly His His Ala Val Pro Gln Gly Pro Met Gly Phe Cys Ile Phe
        195                 200                 205

Gly Asn Val Ala Ile Ala Ala Arg Tyr Ser Gln Arg Val His Gly Leu
    210                 215                 220

Lys Arg Val Phe Ile Ile Asp Phe Asp Val His His Gly Asn Gly Thr
225                 230                 235                 240

Asn Asp Ala Phe Tyr Asp Asp Pro Asp Val Phe Phe Leu Ser Phe His
                245                 250                 255

Gln Asp Gly Ser Tyr Pro Gly Thr Gly Lys Phe Asp Glu Val Gly Ser
            260                 265                 270

Gly Asp Gly Glu Gly Thr Thr Leu Asn Leu Pro Leu Pro Gly Gly Ser
        275                 280                 285

Gly Asp Thr Ala Ile Arg Thr Val Phe Asp Glu Val Ile Val Pro Cys
290                 295                 300

Ala Gln Arg Phe Lys Pro Asp Ile Ile Leu Val Ser Ala Gly Tyr Asp
305                 310                 315                 320

Gly His Val Leu Asp Pro Leu Ala Asn Leu Gln Tyr Thr Thr Gly Thr
                325                 330                 335

Tyr Tyr Met Leu Ala Ser Ser Ile Lys Gln Leu Ala Lys Asp Leu Cys
            340                 345                 350

Gly Gly Arg Cys Val Phe Phe Leu Glu Gly Gly Tyr Asn Leu Lys Ser
        355                 360                 365

Leu Ser Tyr Ser Val Ala Asp Thr Phe Arg Ala Leu Leu Gly Asp Arg
    370                 375                 380

Ser Leu Ala Ser Glu Phe Asp Asn Pro Asn Ile Leu Tyr Glu Glu Pro
385                 390                 395                 400

Ser Thr Lys Val Lys Gln Ala Ile Gln Lys Ile Lys His Ile His Ser
                405                 410                 415

Leu

<210> SEQ ID NO 53
<211> LENGTH: 2238
<212> TYPE: DNA
<213> ORGANISM: Triticum aestivum
<220> FEATURE:
<221> NAME/KEY: CDS
<222> LOCATION: (77)..(1633)

<400> SEQUENCE: 53
ccgagatacc gaaacccaaa cacagaggcg cgcaaacacg cggaggagag aaggcgcctc        60
ctccccccac gccgcg atg gac atc tcg gcc ggc ggc ggc ggc aac tcg ctg      112
               Met Asp Ile Ser Ala Gly Gly Gly Gly Asn Ser Leu
```

-continued

```
        1               5                   10
ccc acc acc ggc gcg gac ggc tcg aag cgc cgc gtc tgc tac ttc tac      160
Pro Thr Thr Gly Ala Asp Gly Ser Lys Arg Arg Val Cys Tyr Phe Tyr
            15              20                  25 gac gcg gag gtg ggc aac tac tac tac ggg cag ggc cac ccg atg aag      208
Asp Ala Glu Val Gly Asn Tyr Tyr Tyr Gly Gln Gly His Pro Met Lys
        30              35                  40 ccg cac cgc atc cgc atg acc cac gcc ctg ctc gcc cac tac ggc ctc      256
Pro His Arg Ile Arg Met Thr His Ala Leu Leu Ala His Tyr Gly Leu
45              50                  55                  60 ctc gac gag atg cag gtg ctc aag ccg cac ccc gcc cgc gac cgc gac      304
Leu Asp Glu Met Gln Val Leu Lys Pro His Pro Ala Arg Asp Arg Asp
                65                  70                  75 ctc tgc cgc ttc cac gcc gac gac tac gtc tcc ttc ctc cgc tcc gtc      352
Leu Cys Arg Phe His Ala Asp Asp Tyr Val Ser Phe Leu Arg Ser Val
                    80                  85                  90 acc ccg gag acg cag cag gac cag atc cgc gcc ctc aag cgc ttc aac      400
Thr Pro Glu Thr Gln Gln Asp Gln Ile Arg Ala Leu Lys Arg Phe Asn
                95                  100                 105 gtc ggc gag gac tgc ccc gtc ttc gac ggc ctc tac agc ttc tgc caa      448
Val Gly Glu Asp Cys Pro Val Phe Asp Gly Leu Tyr Ser Phe Cys Gln
110                 115                 120 acc tac gcc ggc ggc tcc gtc ggg ggc gcc gtc aag ctc aac cac ggc      496
Thr Tyr Ala Gly Gly Ser Val Gly Gly Ala Val Lys Leu Asn His Gly
125                 130                 135                 140 cac gac atc gcc atc aac tgg gcc ggc ggc ctc cac cac gcc aag aag      544
His Asp Ile Ala Ile Asn Trp Ala Gly Gly Leu His His Ala Lys Lys
                    145                 150                 155 tgc gag gcc tcc ggc ttc tgc tac gtc aac gac atc gtc ctc gcc atc      592
Cys Glu Ala Ser Gly Phe Cys Tyr Val Asn Asp Ile Val Leu Ala Ile
                160                 165                 170 ctc gag ctc ctc aaa tac cac cag cgt gtt ctg tat gtc gat atc gat      640
Leu Glu Leu Leu Lys Tyr His Gln Arg Val Leu Tyr Val Asp Ile Asp
                175                 180                 185 att cac cat ggg gac ggc gtg gag gag gcg ttt tac acc acg gac agg      688
Ile His His Gly Asp Gly Val Glu Glu Ala Phe Tyr Thr Thr Asp Arg
            190                 195                 200 gtg atg act gtc tca ttc cac aag ttt ggg gat tat ttc cca ggg aca      736
Val Met Thr Val Ser Phe His Lys Phe Gly Asp Tyr Phe Pro Gly Thr
205                 210                 215                 220 gga gac att cgt gac gtt ggg cac tcc aag ggg aag tat tat tcc ctg      784
Gly Asp Ile Arg Asp Val Gly His Ser Lys Gly Lys Tyr Tyr Ser Leu
                225                 230                 235 aat gtc ccg ttg gat gac ggc atc gac gac gag agc tat caa tcg ttg      832
Asn Val Pro Leu Asp Asp Gly Ile Asp Asp Glu Ser Tyr Gln Ser Leu
                240                 245                 250 ttc aag ccg atc atg ggt aaa gtt atg gag att ttc cgc ccc ggc gcg      880
Phe Lys Pro Ile Met Gly Lys Val Met Glu Ile Phe Arg Pro Gly Ala
                255                 260                 265 gtg gta ctc cag tgt gga gca gat tcc tta tcc ggt gac agg ttg ggc      928
Val Val Leu Gln Cys Gly Ala Asp Ser Leu Ser Gly Asp Arg Leu Gly
270                 275                 280 tgc ttc aac cta tcc att aag ggg cac gca gag tgc gtg aga ttc atg      976
Cys Phe Asn Leu Ser Ile Lys Gly His Ala Glu Cys Val Arg Phe Met
285                 290                 295                 300 agg tcc ttc aat gtt ccg gtg ttg ctg ctt ggt ggt ggt ggt tat acc      1024
Arg Ser Phe Asn Val Pro Val Leu Leu Leu Gly Gly Gly Gly Tyr Thr
                305                 310                 315 ata aga aat gtt gca cga tgt tgg tgc tat gag acg gga gtt gca ctt      1072
Ile Arg Asn Val Ala Arg Cys Trp Cys Tyr Glu Thr Gly Val Ala Leu
```

```
                  320                 325                 330
ggt cat gag cta act gac aag atg ccg cta aat gag cat tat gag tat     1120
Gly His Glu Leu Thr Asp Lys Met Pro Leu Asn Glu His Tyr Glu Tyr
        335                 340                 345 ttt ggc cca gat tat act ctt cat gtt gca cca agt aat atg gag aac     1168
Phe Gly Pro Asp Tyr Thr Leu His Val Ala Pro Ser Asn Met Glu Asn
350                 355                 360 aaa aac aca cac cgg cat ttg gat gaa ata aga tca aga ctt ctc gaa     1216
Lys Asn Thr His Arg His Leu Asp Glu Ile Arg Ser Arg Leu Leu Glu
365                 370                 375                 380 aat ctt aca aaa ctc cgg cat gct cct agt gtg cag ttt caa gag cga     1264
Asn Leu Thr Lys Leu Arg His Ala Pro Ser Val Gln Phe Gln Glu Arg
            385                 390                 395 cct cct gag gcc gag caa cca gag caa gat gag gat caa gag aat cct     1312
Pro Pro Glu Ala Glu Gln Pro Glu Gln Asp Glu Asp Gln Glu Asn Pro
            400                 405                 410 gat gaa agg cat cat gct gac tct gat gtg gaa atg gat gat gcc aag     1360
Asp Glu Arg His His Ala Asp Ser Asp Val Glu Met Asp Asp Ala Lys
            415                 420                 425 cct ctg gag gac tct gaa agg aga acc agt act cag ggt gcg aga gtt     1408
Pro Leu Glu Asp Ser Glu Arg Arg Thr Ser Thr Gln Gly Ala Arg Val
430                 435                 440 aag aga gaa tct gct gaa act gag gtg aca aca gat cag gat ggt aac     1456
Lys Arg Glu Ser Ala Glu Thr Glu Val Thr Thr Asp Gln Asp Gly Asn
445                 450                 455                 460 gga gta gct tca gaa caa gta agg ggc cca gaa cct gtg gct gat gga     1504
Gly Val Ala Ser Glu Gln Val Arg Gly Pro Glu Pro Val Ala Asp Gly
                465                 470                 475 gtt ggt tcc tca aaa caa aac cct cct att gat gca agt ccg atg gcc     1552
Val Gly Ser Ser Lys Gln Asn Pro Pro Ile Asp Ala Ser Pro Met Ala
            480                 485                 490 ata gac ggg cca gct gtt gtc agg gct gaa cca gag agg tca aac aaa     1600
Ile Asp Gly Pro Ala Val Val Arg Ala Glu Pro Glu Arg Ser Asn Lys
            495                 500                 505 tta cag gaa caa caa gca ttg cat cag aaa cca tgatcatcca ccttaacgta   1653
Leu Gln Glu Gln Gln Ala Leu His Gln Lys Pro
            510                 515 gcaactgatg catctgtgca gcccattgac tccattggac gagccaggac agtctgtaag   1713
ctgtagcata gttcaaacaa tctactgcac caacaagtta gctaccagaa tccaagatgg   1773
tccgtgtgcc ttgagagcag ttgaagcttt gtgcactata ttcgtgactt tgacacaaat   1833
gatagttgat tcgttaatgc cattttagc actaatttaa gtctgggcc tgtagagcaa     1893 ccaagttagt aatgcaatac attccaatca aatgcttccg gggagatgac ctggtgtatg   1953
tgacttagca gtgtatagct aggcgaaggc ttccttttgg ttggagctgt tttttctcat   2013
cgcataaggg tcttcttatg gtctgttagg aagaatgccg cttactgcgt tttcggtgtc   2073
aagtctgttc cattgaagaa aagttggatt cgtaatgtat tcccattgat ggattgtctc   2133
tttattgagt catcattgtt cttgtaacat tctagttggg gaaataattg tggcctttgt   2193
attgtaatgt tcaaacttga gaagactaaa aaaaaaaaaa aaaaa                   2238

<210> SEQ ID NO 54
<211> LENGTH: 519
<212> TYPE: PRT
<213> ORGANISM: Triticum aestivum

<400> SEQUENCE: 54

Met Asp Ile Ser Ala Gly Gly Gly Gly Asn Ser Leu Pro Thr Thr Gly
1               5                   10                  15
```

```
Ala Asp Gly Ser Lys Arg Arg Val Cys Tyr Phe Tyr Asp Ala Glu Val
            20                  25                  30

Gly Asn Tyr Tyr Tyr Gly Gln Gly His Pro Met Lys Pro His Arg Ile
            35                  40                  45

Arg Met Thr His Ala Leu Leu Ala His Tyr Gly Leu Leu Asp Glu Met
 50                  55                  60

Gln Val Leu Lys Pro His Pro Ala Arg Asp Arg Asp Leu Cys Arg Phe
 65                  70                  75                  80

His Ala Asp Asp Tyr Val Ser Phe Leu Arg Ser Val Thr Pro Glu Thr
                85                  90                  95

Gln Gln Asp Gln Ile Arg Ala Leu Lys Arg Phe Asn Val Gly Glu Asp
            100                 105                 110

Cys Pro Val Phe Asp Gly Leu Tyr Ser Phe Cys Gln Thr Tyr Ala Gly
            115                 120                 125

Gly Ser Val Gly Gly Ala Val Lys Leu Asn His Gly His Asp Ile Ala
130                 135                 140

Ile Asn Trp Ala Gly Gly Leu His His Ala Lys Lys Cys Glu Ala Ser
145                 150                 155                 160

Gly Phe Cys Tyr Val Asn Asp Ile Val Leu Ala Ile Leu Glu Leu Leu
                165                 170                 175

Lys Tyr His Gln Arg Val Leu Tyr Val Asp Ile Asp Ile His His Gly
            180                 185                 190

Asp Gly Val Glu Glu Ala Phe Tyr Thr Thr Asp Arg Val Met Thr Val
            195                 200                 205

Ser Phe His Lys Phe Gly Asp Tyr Phe Pro Gly Thr Gly Asp Ile Arg
210                 215                 220

Asp Val Gly His Ser Lys Gly Lys Tyr Tyr Ser Leu Asn Val Pro Leu
225                 230                 235                 240

Asp Asp Gly Ile Asp Asp Glu Ser Tyr Gln Ser Leu Phe Lys Pro Ile
                245                 250                 255

Met Gly Lys Val Met Glu Ile Phe Arg Pro Gly Ala Val Val Leu Gln
            260                 265                 270

Cys Gly Ala Asp Ser Leu Ser Gly Asp Arg Leu Gly Cys Phe Asn Leu
            275                 280                 285

Ser Ile Lys Gly His Ala Glu Cys Val Arg Phe Met Arg Ser Phe Asn
290                 295                 300

Val Pro Val Leu Leu Leu Gly Gly Gly Gly Tyr Thr Ile Arg Asn Val
305                 310                 315                 320

Ala Arg Cys Trp Cys Tyr Glu Thr Gly Val Ala Leu Gly His Glu Leu
                325                 330                 335

Thr Asp Lys Met Pro Leu Asn Glu His Tyr Glu Tyr Phe Gly Pro Asp
            340                 345                 350

Tyr Thr Leu His Val Ala Pro Ser Asn Met Glu Asn Lys Asn Thr His
            355                 360                 365

Arg His Leu Asp Glu Ile Arg Ser Arg Leu Leu Glu Asn Leu Thr Lys
370                 375                 380

Leu Arg His Ala Pro Ser Val Gln Phe Gln Glu Arg Pro Pro Glu Ala
385                 390                 395                 400

Glu Gln Pro Glu Gln Asp Glu Asp Gln Glu Asn Pro Asp Glu Arg His
                405                 410                 415

His Ala Asp Ser Asp Val Glu Met Asp Asp Ala Lys Pro Leu Glu Asp
            420                 425                 430

Ser Glu Arg Arg Thr Ser Thr Gln Gly Ala Arg Val Lys Arg Glu Ser
```

-continued

```
                435                 440                 445
Ala Glu Thr Glu Val Thr Thr Asp Gln Asp Gly Asn Gly Val Ala Ser
    450                 455                 460

Glu Gln Val Arg Gly Pro Glu Pro Val Ala Asp Gly Val Gly Ser Ser
465                 470                 475                 480

Lys Gln Asn Pro Pro Ile Asp Ala Ser Pro Met Ala Ile Asp Gly Pro
                485                 490                 495

Ala Val Val Arg Ala Glu Pro Glu Arg Ser Asn Lys Leu Gln Glu Gln
            500                 505                 510

Gln Ala Leu His Gln Lys Pro
            515
```